US010738052B2

(12) United States Patent
Zhuo et al.

(10) Patent No.: US 10,738,052 B2
(45) Date of Patent: *Aug. 11, 2020

(54) IMIDAZOTRIAINES AND IMIDAZOPYRIMIDINES AS KINASE INHIBITORS

(71) Applicants: Incyte Corporation, Wilmington, DE (US); Incyte Holdings Corporation, Wilmington, DE (US)

(72) Inventors: Jincong Zhuo, Boothwyn, PA (US); Meizhong Xu, Hockessin, DE (US); Chunhong He, Boothwyn, PA (US); Colin Zhang, Ambler, PA (US); Ding-Quan Qian, Newark, DE (US); David M. Burns, Philadelphia, PA (US); Yun-Long Li, Chadds Ford, PA (US); Brian Metcalf, Moraga, CA (US); Wenqing Yao, Kennett Square, PA (US)

(73) Assignees: INCYTE HOLDINGS CORPORATION, Wilmington, DE (US); INCYTE CORPORATION, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/925,996

(22) Filed: Mar. 20, 2018

(65) Prior Publication Data
US 2018/0282340 A1 Oct. 4, 2018

Related U.S. Application Data

(63) Continuation of application No. 15/016,841, filed on Feb. 5, 2016, now Pat. No. 9,944,645, which is a continuation of application No. 13/895,799, filed on May 16, 2013, now abandoned, which is a continuation of application No. 12/813,148, filed on Jun. 10, 2010, now Pat. No. 8,461,330, which is a continuation of application No. 11/942,130, filed on Nov. 19, 2007, now Pat. No. 7,767,675.

(60) Provisional application No. 60/957,236, filed on Aug. 22, 2007, provisional application No. 60/861,459, filed on Nov. 29, 2006, provisional application No. 60/860,840, filed on Nov. 22, 2006.

(51) Int. Cl.
| | | |
|---|---|---|
| *C07D 487/04* | (2006.01) | |
| *C07D 403/06* | (2006.01) | |
| *A61K 31/53* | (2006.01) | |
| *A61K 31/4709* | (2006.01) | |
| *A61P 35/00* | (2006.01) | |

(52) U.S. Cl.
CPC ........ *C07D 487/04* (2013.01); *A61K 31/4709* (2013.01); *A61K 31/53* (2013.01); *A61P 35/00* (2018.01); *C07D 403/06* (2013.01)

(58) Field of Classification Search
CPC .... C07D 487/04; C07D 403/06; A61K 31/53; A61K 31/4706; A61P 35/00
USPC .......................................... 544/184; 514/243
See application file for complete search history.

(56) References Cited

U.S. PATENT DOCUMENTS

| | | | |
|---|---|---|---|
| 1,411,859 A | 4/1922 | Marchand | |
| 2,837,520 A | 6/1958 | Fusco et al. | |
| 4,209,621 A | 6/1980 | Dusza et al. | |
| 4,405,619 A | 9/1983 | Heilman et al. | |
| 5,232,618 A | 8/1993 | Shiflett | |
| 5,236,917 A | 8/1993 | Dunlap et al. | |
| 5,254,548 A | 10/1993 | Wermuth et al. | |
| 6,784,297 B2 | 8/2004 | Purohit et al. | |
| 7,005,431 B2 | 2/2006 | Bettati et al. | |
| 7,176,203 B2 | 2/2007 | Chambers et al. | |
| 7,683,060 B2 | 3/2010 | Zhuo et al. | |
| 7,767,675 B2* | 8/2010 | Zhuo .................... | C07D 487/04 514/243 |
| 8,420,645 B2 | 4/2013 | Weng et al. | |
| 8,461,330 B2* | 6/2013 | Zhuo .................... | C07D 487/04 544/184 |
| 8,487,096 B2 | 7/2013 | Zhuo et al. | |
| 8,901,123 B2 | 12/2014 | Weng et al. | |
| 9,221,824 B2 | 12/2015 | Zhuo et al. | |
| 9,944,645 B2* | 4/2018 | Zhuo .................... | C07D 487/04 |
| 9,988,387 B2* | 6/2018 | Zhuo .................... | C07D 487/04 |
| 2003/0114468 A1 | 6/2003 | Wilde et al. | |
| 2004/0097506 A1 | 5/2004 | Thomas | |
| 2005/0075340 A1 | 4/2005 | Zhang et al. | |
| 2005/0085473 A1 | 4/2005 | Van Hirschheydt et al. | |
| 2005/0090498 A1 | 4/2005 | Samizu et al. | |

(Continued)

FOREIGN PATENT DOCUMENTS

| | | |
|---|---|---|
| CA | 1246568 A | 12/1988 |
| CA | 2158994 A1 | 9/1994 |

(Continued)

OTHER PUBLICATIONS

Cecil Textbook of Medicine, edited by Bennet, J.C., and Plum F., 20th edition,vol. 1, 1004-1010, 1996.*

(Continued)

*Primary Examiner* — Venkataraman Balasubramanian
(74) *Attorney, Agent, or Firm* — Brian C. Trinque; Lathrop GPM LLP

(57) ABSTRACT

The present invention is directed to imidazo[1,2-b][1,2,4]triazines and imidazo[1,2-a]pyrimidines, and pharmaceutical compositions thereof, which are inhibitors of kinases such as c-Met and are useful in the treatment of cancer and other diseases related to the dysregulation of kinase pathways.

18 Claims, No Drawings

(56) References Cited

U.S. PATENT DOCUMENTS

| | | |
|---|---|---|
| 2005/0165023 A1 | 7/2005 | Bettati et al. |
| 2005/0261297 A1 | 11/2005 | Igarashi et al. |
| 2005/0277650 A1 | 12/2005 | Venkataraman et al. |
| 2006/0046991 A1 | 3/2006 | Cui et al. |
| 2006/0058303 A1 | 3/2006 | Chambers et al. |
| 2006/0148801 A1 | 7/2006 | Hsieh et al. |
| 2006/0154915 A1 | 7/2006 | Corte et al. |
| 2007/0191376 A1 | 8/2007 | Zou et al. |
| 2008/0039457 A1 | 2/2008 | Zhuo et al. |
| 2008/0167287 A1 | 7/2008 | Zhuo et al. |
| 2009/0124609 A1 | 5/2009 | Albrecht et al. |
| 2009/0124612 A1 | 5/2009 | Albrecht et al. |
| 2009/0291956 A1 | 11/2009 | Weng et al. |
| 2011/0136781 A1 | 6/2011 | Zhuo et al. |
| 2013/0289036 A1 | 10/2013 | Weng et al. |
| 2013/0324515 A1 | 12/2013 | Zhuo et al. |
| 2013/0345224 A1 | 12/2013 | Zhuo et al. |
| 2015/0148348 A1 | 5/2015 | Weng et al. |
| 2016/0137650 A1 | 5/2016 | Zhuo et al. |

FOREIGN PATENT DOCUMENTS

| | | | |
|---|---|---|---|
| CA | | 2586259 A1 | 5/2006 |
| CN | | 1268137 A | 9/2000 |
| EP | | 0430385 A2 | 6/1991 |
| EP | | 0443453 B1 | 8/1991 |
| EP | | 1640010 A1 | 3/2006 |
| FR | | 2662163 A1 | 11/1991 |
| JP | | S63-037347 A | 2/1988 |
| JP | | S63-199347 A | 8/1988 |
| JP | | S63-310891 A | 12/1988 |
| JP | | H03-013934 A | 1/1991 |
| JP | | H04-251243 A | 9/1992 |
| JP | | H05-232618 A | 9/1993 |
| JP | | 2001-43978 A | 2/2001 |
| WO | WO 1983/000864 A1 | | 3/1983 |
| WO | WO 1999/006404 A1 | | 2/1999 |
| WO | WO 2002/072579 A1 | | 3/2001 |
| WO | WO 2002/079203 A1 | | 3/2001 |
| WO | WO 2001/034603 A2 | | 5/2001 |
| WO | WO 2001/034605 A1 | | 5/2001 |
| WO | | 01/72751 A1 | 10/2001 |
| WO | WO 2003/080621 A1 | | 3/2002 |
| WO | WO 2003/087026 A1 | | 4/2002 |
| WO | WO 2005/004607 A1 | | 7/2003 |
| WO | WO 2005/028475 A2 | | 9/2003 |
| WO | WO 2003/097641 A2 | | 11/2003 |
| WO | WO 2004/005290 A1 | | 1/2004 |
| WO | WO 2004/005291 A1 | | 1/2004 |
| WO | WO 2004/020438 A2 | | 3/2004 |
| WO | | 2004/056830 A1 | 7/2004 |
| WO | WO 2004/058769 A1 | | 7/2004 |
| WO | WO 2006/014325 A2 | | 7/2004 |
| WO | WO 2004/076412 A2 | | 9/2004 |
| WO | WO 2005/004808 A2 | | 1/2005 |
| WO | WO 2005/005378 A2 | | 1/2005 |
| WO | WO 2005/010005 A1 | | 2/2005 |
| WO | WO 2005/014598 A1 | | 2/2005 |
| WO | WO 2005/030140 A2 | | 4/2005 |
| WO | WO 2005/039586 A1 | | 5/2005 |
| WO | WO 2005/040154 A1 | | 5/2005 |
| WO | WO 2005/040345 A2 | | 5/2005 |
| WO | WO 2005/042537 A1 | | 5/2005 |
| WO | WO 2005/070891 A2 | | 8/2005 |
| WO | WO 2005/073224 A2 | | 8/2005 |
| WO | WO 2005/097800 A1 | | 10/2005 |
| WO | WO 2005/113494 A2 | | 12/2005 |
| WO | WO 2005/121125 A1 | | 12/2005 |
| WO | | 2006/012422 A1 | 2/2006 |
| WO | | 2006015123 A1 | 2/2006 |
| WO | | 2006/049339 A1 | 5/2006 |
| WO | WO 2006/124354 A2 | | 11/2006 |
| WO | WO 2007/008539 A2 | | 1/2007 |
| WO | WO 2007/013673 A1 | | 2/2007 |
| WO | WO 2007/015866 A2 | | 2/2007 |
| WO | WO 2007/025090 A2 | | 3/2007 |
| WO | WO 2008/144767 A1 | | 5/2007 |
| WO | WO 2007/064797 A2 | | 6/2007 |
| WO | WO 2007/075567 A1 | | 7/2007 |
| WO | WO 2007/096764 A2 | | 8/2007 |
| WO | WO 2005/077953 A1 | | 10/2007 |
| WO | WO 2008/008539 A2 | | 1/2008 |
| WO | WO 2008/051805 A2 | | 5/2008 |
| WO | WO 2008/058126 A2 | | 5/2008 |
| WO | WO 2008/064157 A1 | | 5/2008 |
| WO | WO 2009/091374 A2 | | 7/2009 |
| WO | WO 2009/143211 A2 | | 11/2009 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Jain et al., Nature Clinical Practice Oncology, 3(1), 24-40, 2006,.*
Gautschi et al., Clin. Cancer Res., 14(6), 1639-1648, 2008.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Pyne et al. Cancer Res 2011 ;71:6576-6582.*
Mountzios et al., Cancer Treatments Reviews, 34, 175-182, 2008.*
Ferrara, N, Oncology, 69 Suppl. 3, 11-16, 2005.*
Mo et al. Chronic Diseases and Translational Medicine 3 (2017) 148e153.*
Abdel-Rahman et al. (1993) "Synthesis of Some New Thioetheres of 1,2,4-Triazine-3-Hydrazones and Assays for Their Anticancer and Antihuman Immune Virus Activities," Farmaco. 48(3):397-406.
Acero-Alarcon et al. (1999) "Unusual Ring Closure Reaction of Amides with Pyrimidines: Novel Stereoselective Synthesis of Hexahydroimidazo[1,2-c]pyrimidines," Synthesis. 12:2124-2130.
Alarcon et al., "Unusual Ring Closure Reaction of Amides with Pyrimidines: Novel Stereoselective Synthesis of Hexahydroimidazo[1,2-c]pyrimidines." Synthesis, 12:2124-2130, 1999.
Balkovetz et al. (1999) "Hepatocyte Growth Factor and the Kidney: It Is Not Just for the Liver," Int. Rev. Cytol., vol. 186:225-260.
Banker et al: Eds. (1996) Modem Pharmaceutices. 3rd Ed. Marcel Dekker. New York, New York. pp. 451, 596.
Bennet et al.: Eds. (1996) Cecil: Textbook of Medicine. 20th Ed. vol. 1. pp. 1004-1010.
Berge et al. (1977) "Pharmaceutical Salts," Journal of Pharmaceutical Sciences. 66(1):1-19.
Birchmeier et al. (2003) "Met, Metastasis, Motility and More," Nature Reviews Molecular Cell Biology. 4(12):915-925.
Blom et al. (2004) "Preparative LC-MS Purification: Improved Compound-Specific Method Optimization," J. Comb. Chem. 6:874-883.
Blume-Jensen et al. (2001) "Oncogenic kinase signalling," Nature. 411(6835):355-365.
Boccaccio et al. (2006) "Invasive growth: a MET-driven genetic programme for cancer and stem cells," Nature Reviews Cancer. 6:637-645.
Bolen, J. (1993) "Nonreceptor tyrosine protein kinases," Oncogene. 8(8):2025-2031.
Brittain (1999) "Methods for the Characterization of Polymorphs and Solvates," In; Polymorphism in Pharmaceutical Solids. Marcel Dekker, Inc. New York, New York. vol. 95. Ch. 6. pp. 227-278.
Byrn et al. (1995) "Pharmaceutical Solids: A Strategic Approach to Regulatory Considerations," Pharmaceutical Research. 12(7):945-954.
Calic et al. (2005) "Flavonoids as Inhibitors of Lck and Fyn Kinases," Croatica Chemica Acta. 78(3):367-374.
Caplus, Accession No. 1959:39972, Rossi, Silvano et al., "Fluorescent pigment derivatives from 1,3,7,9-tetrazaindene".

(56) References Cited

OTHER PUBLICATIONS

Caplus, Accession No. 1985:45885, Povstyanoi, M.V. et al., "Synthesis and spectral characteristics of novel derivatives of imidazo[1,2-b]-1,2,4-triazine".
Caplus, Accession No. 1988:528957, Labouta, Ibrahim M. et al., "Synthesis of some substituted triazolo[4,3-b] [1,2,4] triazines as potential anticancer agents".
Caplus, Accession No. 1989-57624, Labouta, Ibrahim M. et al., "Potential antineoplastics: some substituted imidazo [1,2-b][1,2,4]triazines, triazino[4,3-b] [1,2,4]triazines, and imidazotriazino[5,6-b]indoles".
Caplus, Accession No. 1993:530910, Abdel-Rahman, R.M. et al., "Synthesis of some new thioethers of 1,2,4-triazine-3-hydrazones and assays for their anticancer and antihuman immune virus activities".
Caplus, Accession No. 1998:617972, Kruglenko, V.P. et al., "Condensed imidazo-1,2,4-azines. 28. Synthesis and transformations of 2-aroylmethyl-6, 7-diphenylimidazo[1,2-b]-1,2,4-triazin-4H-3-ones".
Caplus, Accession No. 2005:779142, Krayushkin, M.M. et al., "Synthesis and Structure of 5-Indolyl-6-thienyl-1,2,4-triazines".
Christensen et al. (2005) "c-Met as a target for human cancer and characterization of inhibitors for therapeutic intervention," Cancer Letters. 225:1-26.
Cohen (1999) "The development and therapeutic potential of protein kinase inhibitors," Current Opinion in Chemical Biology. 3:459-465.
Corso et al. (2005) "Cancer therapy: can the challenge be MET?" Trends in Molecular Medicine. 11(6):284-292.
Crestani et al. (2002) "Differential Role of Neutrophils and Alveolar Macrophages in Hepatocyte Growth Factor Production in Pulmonary Fibrosis," Lab. Invest. 82(8):1015-1022.
Dermer (1994) "Another Anniversary for the War on Cancer," BioTechnology. 12:320.
Druzhinin et al. (1993) "Acid-Base Reactions of Imidazo[1,2-b]-1,2,4-Triazines (Imitrines) with Proton Donors," Russian Journal of General Chemistry. 63(6, Part 2):953-958.
Druzhinin, S.U. et al., "Acid-Base Reactions of Imidazo[1,2-b]-1,2,4-Triazines (Imitrines) with Proton Donors," Russian Journal of General Chemistry, vol. 63(6, pt. 2):953-958 (1993).
Eguchi et al. (1999) "Changes in liver regenerative factors in a case of living-related liver transplantation," Clin. Transplantation. 13:536-544.
Fabbro et al. (2002) "Protein kinases as targets for anticancer agents: from inhibitors to useful drugs," Pharmacology & Therapeutics. 93:79-98.
Farmaco (1993), 48(3), 397-406, CODEN: FRMCE8; ISSN: 0014-827X.
Ferrara (2005) "VEGF as a therapeutic target in cancer," Oncology. 69(Suppl 3):11-16.
Freshney (1983) Culture of Animal Cells, A Manual of Basic Technique. Alan R. Liss, Inc. New York, New York. p. 4.
Fusco et al. (1955) "Studies on Asymmetric Triazines Synthesized from Tetraazaindene Derivatives," Rendiconti. 88:194-202.—with English translation.
Futamatsu et al. (2005) "Hepatocyte Growth Factor Ameliorates the Progression of Experimental Autoimmune Myocarditis. A Potential Role for Induction of T Helper 2 Cytokines," Circ. Res. 96:823-830.
Gautschi et al. (2008) "Aurora kinases as anticancer drug targets," Clin. Cancer Res. 14(6):1639-1648.
Gennaro: Ed. (1985) In; Remington's Pharmaceutical Sciences. 17th Ed. Mack Publishing Company. Easton, Pennsylvania. p. 1418.
Golub et al. (1999) "Molecular Classification of Cancer: Class Discovery and Class Prediction by Gene Expression Monitoring," Science. 286(5439):531-537.
Gould (1986) "Salt selection for basic drugs," International Journal of Pharmaceutics. 33(1):201-217.
Greene et al. (1991) Protective Groups in Organic Synthesis. 2nd Ed. Wiley & Sons.
Higuchi et al (1987) "Pro-drugs as Novel Drug Delivery Systems," In; The A.C.S. Symposium Series Bioreversible Carriers in Drug Design. vol. 14. Ed.: Roche. American Pharmaceutical Association and Pergamon Press.
Holla et al. (2003) "Synthesis and reactons of new N-bridged heterocycles derived from 3-substituted-4,5-diamino-1,2,4-tnazoles," Indian Journal of Chemistry. 42B:2054-2058.
International Preliminary Report on Patentability corresponding to International Patent Application No. PCT/US2007/075254, dated Feb. 10, 2009.
International Preliminary Report on Patentability corresponding to International Patent Application No. PCT/US2007/085100, dated May 26, 2009.
International Preliminary Report on Patentability corresponding to International Patent Application No. PCT/US2009/044622, dated Nov. 23, 2010.
International Preliminary Report on Patentability corresponding to International Patent Application No. PCT/US2011/023464, dated Aug. 7, 2012.
International Preliminary Report on Patentability for Application No. PCT/US2007/075254, dated Feb. 10, 2009.
International Preliminary Report on Patentability for Application No. PCT/US2007/085100, dated May 26, 2009.
International Preliminary Report on Patentability for PCT/US2007/075254, dated Feb. 10, 2009.
International Preliminary Report on Patentability for PCT/US2007/085100, dated Jun. 4, 2009.
International Search Report corresponding to International Patent Application No. PCT/US2007/075254, dated Jan. 18, 2008.
International Search Report corresponding to International Patent Application No. PCT/US2007/085100, dated Apr. 28, 2008.
International Search Report corresponding to International Patent Application No. PCT/US2009/044622, dated Jan. 18, 2010.
International Search Report corresponding to International Patent Application No. PCT/US2011/023464, dated Jul. 4, 2011.
Jain et al. (2006) "Lessons from phase III clinical trials on anti-VEGF therapy for cancer," Nature Clinical Practice Oncology. 3(1):24-40.
Koblish et al. (2008) "Preclinical in vivo characterization of INCB028060, a novel, potent and highly selective c-Met inhibitor," Journal of Clinical Oncology: ASCO Annual Meeting Proceedings. 26(15S):14561.
Koch et al. (1996) "Hepatocyte Growth Factor. A Cytokine Mediating Endothelial Migration in Inflammatory Arthritis," Arthritis & Rheumatism. 39(9):1566-1575.
Krayushkin et al. (2005) "Synthesis and Structure of 5-Indoly1-6-thien1-1,2,4-triazines," Russian Journal of Organic Chemistry. 40(6):875-883.
Kruglenko et al. (1998) "Condensed Imidazo-1,2,4-Azines. 28. Synthesis adn Transformations of 2-Aroylmethy1-6,7-Diphenyllimidazo-[1,2-b]-1,2,4-Triazin-4H-3-Ones," Chemistry of Heterocyclic Compounds. 34(2):232-236.
Labouta et al. (1987) "Potential antineoplastics: Some substituted imidazo[1,2-b][1,2,4]triazines, triazino[4,3-b][1,2,4]triazines and imidazotriazino[5,6-b]indoles," J. Serb. Chem. Soc. 52(9):523-527.
Labouta et al. (1988) "Synthesis of some substituted triazolo[4,3-b][1,2,4]triazines as potential anticancer agents," Monatshefte fuer Chemie. 119(5):591-596.
Labouta et al., Journal of the Serbian Chemical Society (1987), 52(9), 523-7; CA 110:57624, 1989 (CAPLUS Abstract provided).
Liu (2002) "Hepatocyte growth factor and the kidney," Cuff. Opin. Nephrol. Hypertens. 11:23-30.
Liu (2008) "INCB028060. A Novel, Potent and Selective c-MET RTK Inhibitor for Cancer Treatment," In; GTC Bio: The 4th Modem Drug Discovery & Development Summit.
Liu (Apr. 12-16, 2008) "Discovery and Characterization of INCB028060. A Novel, Potent and Selective MET RTK Inhibitor for Cancer Treatment," In; The AACR Annual Meeting, 2008.
Liu et al. (2008) "Targeting the c-MET signaling pathway for cancer therapy," Expert Opin. Investig. Drug. 17(7):997-1011.
Ma et al. (2002) "Hepatocyte growth factor is a survival factor for endothelial cells and is expressed in human atherosclerotic plaques," Atherosclerosis. 164:79-87.

(56) References Cited

OTHER PUBLICATIONS

Madhusudan et al. (2004) "Tyrosine kinase inhibitors in cancer therapy," Clinical Biochemistry. 37:618-635.
Manning et al. (2002) "The Protein Kinase Complement of the Human Genome," Science. 298(5600):1912-1934.
Mass (2004) "The HER Receptor Family: A Rich Target for Therapeutic Development," Int. J. Radiation Oncology Biol. Phys. 58(3):932-940.
Matsumoto et al. (2001) "Hepatocyte growth factor: Renotropic role and potential therapeutics for renal diseases," Kidney International. 59:2023-2038.
McMahon (2000) "VEGF receptor signaling in tumor angiogenesis," The Oncologist. 5(Suppl 1):3-10.
Miyazawa et al. (1998) "Protection of Hippocampal Neurons From Ischemia-Induced Delayed Neuronal Death by Hepatocyte Growth Factor: A Novel Neurotrophic Factor," Journal of Cerebral Blood Flow and Metabolism. 18:345-348.
Monatshefte fuer Chemie (1988), 119(5), 591-6, CODEN: MOCMB7; ISSN: 0026-9247.
Morishita et al. (2002) "Hepatocyte Growth Factor as Cardiovascular Hormone: Role of HGF in the Pathogenesis of Cardiovascular Disease," Endocrine Journal. 49(3):273-284.
Morishita et al. (2004) "Therapeutic Angiogenesis using Hepatocyte Growth Factor (HGF)," Current Gene Therapy. 4:199-206.
Mountzios et al. (2008) "Aurora kinases as targets for cancer therapy," Cancer Treatments Reviews. 34:175-182.
Pinedo et al. (2000) "Introduction translational research: the role of VEGF in tumor angiogenesis," The Oncologist. 5(Suppl 1):1-2.
Povstyanoi et al. (1984) "Synthesis and spectral characteristics of novel derivatives of imidazo[1,2-13]1,2,4-triazine," Izvestiya Timiryazevskoi Sel'skokhozyaistvennoi Akademii 5:155-159.— CAPLUS Abstract provided.
Pyne et al. (2011) "Sphingosine kinase inhibitors and cancer: seeking the golden sword of Hercules," Cancer Res. 71:6576-6582.
Qiu (2000) "Signaling network of the Btk family kinases," Oncogene. 19:5651-5661.
Ravin (1985) "Preformulation," Ch. 76 In; Remington's Pharmaceutical Sciences. 17th Ed. Mack Publishing Company. Easton, Pennsylvania. pp. 1409-1423.
Remington's Pharmaceutical Sciences, 17.sup.th ed., Mack Publishing Company, Easton, PA., 1985, p. 1418.
Rossi et al. (1958) "Fluorescent pigments derived from 1,4,7,9-tetraazaindene," La Chimica E L'Industria. 40(10):827-830—with English translation.
Rossi, Silvan et al. (Oct. 1958) "Pigmenti Fluorescenti derivati dall'1,4,7,9—tetraziandene." La Chimica E L'Industria. 40(10):827-830 (English translation).
Russian Journal of Organic Chemistry (2005), 41(6), 875-883, CODEN: RJOCEQ; ISSN: 1070-4280.
Segura-Flores et al. (2004) "Factor de crecimiento de hepatocitos (HGF) y sus aplicaciones terapeuticas," Revista de Gastroenterologia de Mexico. 69(4):243-250.—English summary.
Simone, Joseph V., "Introduction," Cecil Textbook of Medicine, 20th Edition, vol. 1, J.C. Bennett and F. Plum (Eds.), W.B. Saunders Company, pp. 1004-1010 (1996).

STN Search dated Jul. 26, 2006.
STN Search dated Nov. 1, 2006.
STN Search dated Oct. 16, 2006.
STN Search dated Oct. 19, 2006.
Higuchi, T. et al., "Pro-drugs as Novel Delivery Systems," vol. 14 of the A.C.S. Symposium Series Bioreversible Carriers in Drug Design, ed. Edward B. Roche, American Pharmaceutical Association and Pergamon Press, 1987.
Tomchin (1982) "Heterocyclic Semicarbazones and Thiosemicarbazones. XLV. 1,2,4-Triazinoindole Derivatives with a Condensed Imidazole, Thiazole, or Triazole Ring," Zhurnal Organicheskoi Khimii. 18(6):1272-1280.
Vidal et al. (2001) "Effect of imidazo[1,2-a]pyrimidine derivatives on leukocyte function," Inflamm. Res. 50:317-320.
Wang et al. (2003) "Potent and selective inhibitors of the Met [hepatocyte growth factor/scatter factor (HGF/SF) receptor] tyrosine kinase block HGF/SF-induced tumor cell growth and invasion," Molecular Cancer Therapeutics. 2:1085-1092.
Wermuth (1996) "Molecular Variations Based on Isosteric Replacements," Ch. 13 In; The Practice of Medicinal Chemistry. Academic Press Limited. pp. 203-237.
Wolff: Ed. (1995) Burger's Medicinal Chemistry. 5th Ed. Part 1. John Wiley & Sons. pp. 975-977.
Yap et al. (2010) "Targeting the HGF/c-Met Axis: State of Play," Mol. Cancer Ther. 9(5):1077-1079.
U.S. Appl. No. 15/016,841 2016-0326178 U.S. Pat. No. 9,944,645, filed Feb. 5, 2016 Nov. 10, 2016 Apr. 17, 2018, Jincong Zhuo.
U.S. Appl. No. 13/895,799 2013-0324515, filed May 16, 2013 Dec. 5, 2013, Jincong Zhuo.
U.S. Appl. No. 12/813,148 2011-0136781 U.S. Pat. No. 8,461,330, filed Jun. 10, 2010 Jun. 9, 2011 Jun. 11, 2013, Jincong Zhuo.
U.S. Appl. No. 11/942,130 2008-0167287 U.S. Pat. No. 7,767,675, filed Nov. 19, 2007 Jul. 10, 2008 Aug. 3, 2010, Jincong Zhuo.
U.S. Appl. No. 12/469,360 2009-0291956 U.S. Pat. No. 8,420,645, filed May 20, 2009 Nov. 26, 2009 Apr. 16, 2013, Lingkai Weng.
U.S. Appl. No. 13/793,864 2013-0289036 U.S. Pat. No. 8,901,123, filed Mar. 11, 2013 Oct. 31, 2013 Dec. 2, 2014, Lingkai Weng.
U.S. Appl. No. 14/525,381 2015-0148348, filed Oct. 28, 2014 May 28, 2015, Lingkai Weng.
U.S. Appl. No. 15/355,630 2017-0258800, filed Nov. 18, 2016 Sep. 14, 2017, Lingkai Weng.
PCT/US09/44622 WO 2009/143211, May 20, 2009 Nov. 26, 2009, Lingkai Weng.
U.S. Appl. No. 13/019,718 2011-0212967 U.S. Pat. No. 8,487,096, filed Feb. 2, 2011 Sep. 1, 2011 Jul. 16, 2013, Jincong Zhuo.
U.S. Appl. No. 13/915,702 2013-0345224 U.S. Pat. No. 9,221,824, filed Jun. 12, 2013 Dec. 26, 2013 Dec. 29, 2015, Jincong Zhuo.
U.S. Appl. No. 14/918,879 2016-0137650 U.S. Pat. No. 9,988,387, filed Oct. 21, 2015 May 19, 2016 Jun. 5, 2018, Jincong Zhuo.
U.S. Appl. No. 15/969,519, filed May 2, 2018, Jincong Zhuo.
PCT/US11/23464 WO 2011/162835, Feb. 2, 2011 Dec. 29, 2011, Jincong Zhuo.
Notice of Opposition to a European Patent for European Patent No. EP2300455, dated Apr. 18, 2018.
Extended European Search Report for European Application No. 18182215.6, dated Jan. 22, 2019.

* cited by examiner

IMIDAZOTRIAINES AND IMIDAZOPYRIMIDINES AS KINASE INHIBITORS

CROSS REFERENCE TO RELATED APPLICATIONS

This application is a continuation of U.S. application Ser. No. 15/016,841, filed on Feb. 5, 2016, which is a continuation of U.S. application Ser. No. 13/895,799, filed May 16, 2013, now abandoned, which is a continuation of U.S. application Ser. No. 12/813,148, filed Jun. 10, 2010, now U.S. Pat. No. 8,461,330, which is a continuation of U.S. application Ser. No. 11/942,130, filed Nov. 19, 2007, now U.S. Pat. No. 7,767,675, which claims the benefit of U.S. Ser. Nos. 60/860,840, filed Nov. 22, 2006, 60/861,459, filed Nov. 29, 2006, and 60/957,236, filed Aug. 22, 2007, the disclosures of each of which are incorporated herein by reference in their entireties.

FIELD OF THE INVENTION

The present invention is directed to imidazo[1,2-b][1,2,4]triazines and imidazo[1,2-a]pyrimidines, and pharmaceutical compositions thereof, which are inhibitors of kinases such as c-Met and are useful in the treatment of cancer and other diseases related to the dysregulation of kinase pathways.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

Protein kinases can be categorized as receptor type and non-receptor type. Receptor tyrosine kinases (RTKs) have an extracellular portion, a transmembrane domain, and an intracellular portion, while non-receptor tyrosine kinases are entirely intracellular. RTK mediated signal transduction is typically initiated by extracellular interaction with a specific growth factor (ligand), typically followed by receptor dimerization, stimulation of the intrinsic protein tyrosine kinase activity, and receptor transphosphorylation. Binding sites are thereby created for intracellular signal transduction molecules and lead to the formation of complexes with a spectrum of cytoplasmic signaling molecules that facilitate the appropriate cellular response such as cell division, differentiation, metabolic effects, and changes in the extracellular microenvironment At present, at least nineteen (19) distinct RTK subfamilies have been identified. One RTK subfamily, designated the HER subfamily, includes EGFR, HER2, HER3 and HER4, and bind such ligands as epithelial growth factor (EGF), TGF-α, amphiregulin, HB-EGF, betacellulin and heregulin. A second family of RTKs, designated the insulin subfamily, includes the INS-R, the IGF-1R and the IR-R. A third family, the "PDGF" subfamily, includes the PDGF alpha and beta receptors, CSFIR, c-kit and FLK-II. Another subfamily of RTKs, referred to as the FLK subfamily, encompasses the Kinase insert Domain-Receptor fetal liver kinase-1 (KDR/FLK-1), the fetal liver kinase 4 (FLK-4) and the fins-like tyrosine kinase 1 (fit-1). Two other subfamilies of RTKs have been designated as the FGF receptor family (FGFR1, FGFR2, FGFR3 and FGFR4) and the Met subfamily (c-Met, Ron and Sea). For a detailed discussion of protein kinases, see for example, Blume-Jensen, P. et al., Nature. 2001, 411(6835):355-365, and Manning, G. et al., Science. 2002, 298(5600):1912-1934.

The non-receptor type of tyrosine kinases is also composed of numerous subfamilies, including Src, Btk, Abl, Fak, and Jak. Each of these subfamilies can be further subdivided into multiple members that have been frequently linked to oncogenesis. The Src family, for example, is the largest and includes Src, Fyn, Lck and Fgr among others. For a detailed discussion of these kinases, see Bolen JB. Non-receptor tyrosine protein kinases. Oncogene. 1993, 8(8): 2025-31.

A significant number of tyrosine kinases (both receptor and nonreceptor) are associated with cancer (see Madhusudan S, Ganesan TS. Tyrosine kinase inhibitors in cancer therapy. Clin. Biochem. 2004, 37(7):618-35.). Clinical studies suggest that overexpression or dysregulation of tyrosine kinases may also be of prognostic value. For example, members of the HER family of RTKs have been associated with poor prognosis in breast, colorectal, head and neck and lung cancer. Mutation of c-Kit tyrosine kinase is associated with decreased survival in gastrointestinal stromal tumors. In acute myelogenous leukemia, Flt-3 mutation predicts shorter disease free survival. VEGFR expression, which is important for tumor angiogenesis, is associated with a lower survival rate in lung cancer. Tie-1 kinase expression inversely correlates with survival in gastric cancer. BCR-Abl expression is an important predictor of response in chronic myelogenous leukemia and Src tyrosine kinase is an indicator of poor prognosis in all stages of colorectal cancer.

c-Met, a proto-oncogene, is a member of a distinct subfamily of heterodimeric receptor tyrosine kinases which include Met, Ron, and Sea (Birchmeier, C. et al., Nat. Rev. Mol. Cell Biol. 2003, 4(12):915-925; Christensen, J. G. et al., Cancer Lett. 2005, 225(1):1-26). The only high affinity ligand for c-Met is the hepatocyte growth factor (HGF), also known as scatter factor (SF). Binding of HGF to c-Met induces activation of the receptor via autophosphorylation resulting in an increase of receptor dependent signaling. Both c-Met and HGF are widely expressed in a variety of organs, but their expression is normally confined to the cells of epithelial and mesenchymal origin, respectively. The biological functions of c-Met (or c-Met signaling pathway) in normal tissues and human malignancies such as cancer have been well documented (Christensen, J. G. et al., Cancer Lett. 2005, 225(1):1-26; Corso, S. et al., Trends in Mol. Med. 2005, 11(6):284-292).

HGF and c-Met are each required for normal mammalian development, and abnormalities reported in both HGF- and c-Met-null mice are consistent with proximity of embryonic expression and epithelial-mesenchymal transition defects during organ morphogenesis (Christensen, J. G. et al., Cancer Lett. 2005, 225(1):1-26). Consistent with these findings, the transduction of signaling and subsequent biological effects of HGF/c-Met pathway have been shown to be important for epithelial-mesenchymal interaction and regulation of cell migration, invasion, cell proliferation and survival, angiogenesis, morphogenesis and organization of three-dimensional tubular structures (e.g. renal tubular cells, gland formation) during development. The specific consequences of c-Met pathway activation in a given cell/tissue are highly context-dependent.

Dysregulated c-Met pathway plays important and sometimes causative (in the case of genetic alterations) roles in tumor formation, growth, maintenance and progression (Birchmeier, C. et al., Nat. Rev. Mol. Cell. Biol. 2003, 4(12):915-925; Boccaccio, C. et al., Nat. Rev. Cancer 2006, 6(8):637-645; Christensen, J. G. et al., Cancer Lett. 2005, 225(1):1-26). HGF and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistance to chemotherapy and radiotherapy. In addition to the abnormal HGF/c-Met expression, c-Met receptor can also be activated in cancer patients through genetic mutations (both germline and somatic) and gene amplification. Although gene amplification and mutations are the most common genetic alterations that have been reported in patients, the receptor can also be activated by deletions, truncations, gene rearrangement, as well as abnormal receptor processing and defective negative regulatory mechanisms.

The various cancers in which c-Met is implicated include, but are not limited to: carcinomas (e.g., bladder, breast, cervical, cholangiocarcinoma, colorectal, esophageal, gastric, head and neck, kidney, liver, lung, nasopharygeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

The notion that the activated c-Met pathway contributes to tumor formation and progression and could be a good target for effective cancer intervention has been further solidified by numerous preclinical studies (Birchmeier, C. et al., Nat. Rev. Mol. Cell Biol. 2003, 4(12):915-925; Christensen, J. G. et al., Cancer Lett. 2005, 225(1):1-26; Corso, S. et al., Trends in Mol. Med. 2005, 11(6):284-292). For example, studies showed that the tpr-met fusion gene, overexpression of c-met and activated c-met mutations all caused oncogenic transformation of various model cell lines and resulted in tumor formation and metastasis in mice. More importantly, significant anti-tumor (sometimes tumor regression) and anti-metastasis activities have been demonstrated in vitro and in vivo with agents that specifically impair and/or block HGF/c-Met signaling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al., Cancer Lett. 2005, 225(1):1-26).

In addition to the established role in cancer, abnormal HGF/c-Met signaling is also implicated in atherosclerosis, lung fibrosis, renal fibrosis and regeneration, liver diseases, allergic disorders, inflammatory and autoimmune disorders, cerebrovascular diseases, cardiovascular diseases, conditions associated with organ transplantation (Ma, H. et al., Atherosclerosis. 2002, 164(1):79-87; Crestani, B. et al., Lab. Invest. 2002, 82(8):1015-1022; Sequra-Flores, A. A. et al., Rev. Gastroenterol. Mex. 2004, 69(4)243-250; Morishita, R. et al., Curr. Gene Ther. 2004, 4(2)199-206; Morishita, R. et al., Endocr. J. 2002, 49(3)273-284; Liu, Y., Curr. Opin. Nephrol. Hypertens. 2002, 11(1):23-30; Matsumoto, K. et al., Kidney Int. 2001, 59(6):2023-2038; Balkovetz, D. F. et al., Int. Rev. Cytol. 1999, 186:225-250; Miyazawa, T. et al., J. Cereb. Blood Flow Metab. 1998, 18(4)345-348; Koch, A. E. et al., Arthritis Rheum. 1996, 39(9):1566-1575; Futamatsu, H. et al., Circ. Res. 2005, 96(8)823-830; Eguchi, S. et al., Clin. Transplant. 1999, 13(6)536-544).

Despite the important/causative roles that the c-Met pathway plays in the above described human diseases including cancer, there are no c-Met inhibitors or antagonists that are currently available for treating these human disorders that associate with abnormal HGF/c-Met signaling. Therefore, there is a clear unmet medical need to develop new compounds as inhibitors of c-Met and other kinases. The compounds, compositions, and pharmaceutical methods provided herein help meet this need.

SUMMARY OF THE INVENTION

The present invention provides, inter alia, compounds that are inhibitors of kinases, including receptor tyrosine kinases such as those of the Met subfamily, having Formula I:

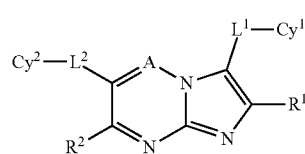

or pharmaceutically acceptable salts thereof or prodrugs thereof, wherein constituent members are defined herein.

The present invention further provides compositions comprising a compound of Formula I, or pharmaceutically acceptable salt thereof, and at least one pharmaceutically acceptable carrier.

The present invention further provides methods of inhibiting activity of a receptor or non-receptor tyrosine kinase comprising contacting the kinase with a compound of Formula I, or pharmaceutically acceptable salt thereof.

The present invention further provides methods of inhibiting the HGF/c-Met kinase signaling pathway in a cell comprising contacting the cell with a compound of Formula I, or pharmaceutically acceptable salt thereof.

The present invention further provides methods of inhibiting the proliferative activity of a cell comprising contacting the cell with a compound of Formula I, or pharmaceutically acceptable salt thereof.

The present invention further provides methods of inhibiting tumor growth in a patient comprising administering to the patient a therapeutically effective amount of a compound of Formula I, or pharmaceutically acceptable salt thereof.

The present invention further provides methods of inhibiting tumor metastasis in a patient comprising administering to the patient a therapeutically effective amount of a compound of Formula I, or pharmaceutically acceptable salt thereof.

The present invention further provides methods of treating a disease in a patient, wherein said disease is associated with dysregulation of the HGF/c-MET signaling pathway, comprising administering to the patient a therapeutically effective amount of a compound of Formula I, or pharmaceutically acceptable salt thereof.

The present invention further provides methods of treating cancer in a patient comprising administering to the patient a therapeutically effective amount of a compound of Formula I, or pharmaceutically acceptable salt thereof.

DETAILED DESCRIPTION

The present invention provides, inter alia, compounds that are inhibitors of kinases, including receptor tyrosine kinases such as those of the Met subfamily, having Formula I:

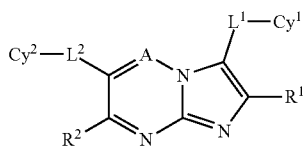

or pharmaceutically acceptable salts thereof or prodrugs thereof, wherein:

A is N or $CR^3$;

$Cy^1$ is aryl, heteroaryl, cycloalkyl, or heterocycloalkyl, each optionally substituted by 1, 2, 3, 4, or 5 —W—X—Y—Z;

$Cy^2$ is aryl, heteroaryl, cycloalkyl, or heterocycloalkyl, each optionally substituted by 1, 2, 3, 4, or 5 —W'—X'—Y'—Z';

$L^1$ is $(CR^4R^5)_m$, $(CR^4R^5)_p$-(cycloalkylene)-$(CR^4R^5)_q$, $(CR^4R^5)_p$-(arylene)-$(CR^4R^5)_q$, $(CR^4R^5)_p$—(heterocycloalkylene)-$(CR^4R^5)_q$, $(CR^4R^5)_p$-(heteroarylene)-$(CR^4R^5)_q$, $(CR^4R^5)_pO(CR^4R^5)_q$, $(CR^4R^5)_pS(CR^4R^5)_q$, $(CR^4R^5)_pC(O)(CR^4R^5)_q$, $(CR^4R^5)_pC(O)NR^6(CR^4R^5)_q$, $(CR^4R^5)_pC(O)O(CR^4R^5)_q$, $(CR^4R^5)_pOC(O)(CR^4R^5)_q$, $(CR^4R^5)_pOC(O)NR^6(CR^4R^5)_q$, $(CR^4R^5)_pNR^6(CR^4R^5)_q$, $(CR^4R^5)_pNR^6C(O)NR^6(CR^4R^5)_q$, $(CR^4R^5)_pS(O)(CR^4R^5)_q$, $(CR^4R^5)_pS(O)NR^6(CR^4R^5)_q$, $(CR^4R^5)_pS(O)_2(CR^4R^5)_q$, or $(CR^4R^5)_pS(O)_2NR^6(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^e)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

$L^2$ is $(CR^7R^8)_r$, $(CR^7R^8)_s$-(cycloalkylene)-$(CR^7R^8)_t$, $(CR^7R^8)_s$-(arylene)-$(CR^7R^8)_t$, $(CR^7R^8)_s$-(heterocycloalkylene)-$(CR^7R^8)_t$, $(CR^7R^8)_s$-(heteroarylene)-$(CR^7R^8)_t$, $(CR^7R^8)_sO(CR^7R^8)_t$, $(CR^7R^8)_sS(CR^7R^8)_t$, $(CR^7R^8)_sC(O)(CR^7R^8)_t$, $(CR^7R^8)_sC(O)NR^9(CR^7R^8)_t$, $(CR^7R^8)_sC(O)O(CR^7R^8)_t$, $(CR^7R^8)_sOC(O)(CR^7R^8)_t$, $(CR^7R^8)_sOC(O)NR^9(CR^7R^8)_t$, $(CR^7R^8)_sNR^9(CR^7R^8)_t$, $(CR^7R^8)_sNR^9C(O)NR^9(CR^8R^9)_t$, $(CR^7R^8)_sS(O)(CR^7R^8)_t$, $(CR^7R^8)_sS(O)NR^7(CR^7R^8)_t$, $(CR^7R^8)_sS(O)_2(CR^7R^8)_t$, or $(CR^7R^8)_sS(O)_2NR^9(CR^7R^8)_t$, wherein said cycloalkylene, arylene, heterocycloalkylene, or heteroarylene is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$ $NR^{c1}C(O)NR^{c1}R^{d1}$, $NR^{c1}C(O)OR^{a1}$, $C(=NR^g)NR^{c1}R^{d1}$, $NR^{c1}(=NR^g)NR^{c1}R^{d1}$, $P(R^{f1})_2$, $P(OR^{c1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^1$ is H or —W"—X"—Y"—Z";

$R^2$ is H, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, or $S(O)_2NR^CR^D$;

$R^3$ is H, cycloalkyl, aryl, heterocycloalkyl, heteroaryl, halo, $C_{1-6}$ alkyl, $C_{2-6}$ alkenyl, $C_{2-6}$ alkynyl, 5 $C_{1-6}$ haloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, and $S(O)_2NR^CR^D$; wherein said cycloalkyl, aryl, heterocycloalkyl, heteroaryl, or $C_{1-6}$ alkyl is optionally substituted with 1, 2, or 3 substituents independently selected from $Cy^5$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

or $R^2$ and $-L^2-Cy^2$ are linked together to form a group of formula:

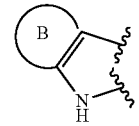

wherein ring B is a fused aryl or fused heteroaryl ring, each optionally substituted with 1, 2, or 3-W'—X'—Y'—Z';

$R^4$ and $R^5$ are independently selected from H, halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;

or $R^4$ and $R^5$ together with the C atom to which they are attached form a 3, 4, 5, 6, or 7-membered cycloalkyl or heterocycloalkyl ring, each optionally substituted by 1, 2, or 3 substituents independently selected from halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;

$R^6$ is H, $C_{1-6}$ alkyl, $C_{2-6}$ alkenyl, or $C_{2-6}$ alkynyl;

$R^7$ and $R^8$ are independently selected from H, halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

or $R^7$ and $R^8$ together with the C atom to which they are attached form a 3, 4, 5, 6, or 7-membered cycloalkyl or heterocycloalkyl ring, each optionally substituted by 1, 2, or 3 substituent independently selected from halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

$R^9$ is H, $C_{1-6}$ alkyl, $C_{2-6}$ alkenyl, or $C_{2-6}$ alkynyl;

W, W', and W" are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$ and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

X, X', and X" are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, NO$_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, C(O)OR$^j$, C(O)NR$^h$R$^i$, amino, $C_{1-6}$ alkylamino, and $C_{2-8}$ dialkylamino;

Y, Y', and Y" are independently absent or independently selected from $C_{1-6}$ alkylene, $C_{2-6}$ alkenylene, $C_{2-6}$ alkynylene, O, S, NR$^h$, CO, COO, CONR$^h$, SO, SO$_2$, SONR$^h$, and NR$^h$CONR$^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z, Z', and Z" are independently selected from H, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{e2}$R$^{d2}$, NR$^{e2}$R$^{d2}$, NR$^{c2}$C(O)R$^{b2}$, NR$^{c2}$C(O)NR$^{c2}$R$^{d2}$, NR$^{c2}$C(O)OR$^{a2}$, C(=NR$^g$)NR$^{c2}$R$^{d2}$, NR$^{e2}$C(=NR)NR$^{c2}$R$^{d2}$, P(R)$_2$, P(OR$^{e2}$)$_2$, P(O)R$^{e2}$R$^{f2}$, P(O)OR$^{e2}$OR, S(O)R$^{b2}$, S(O)NR$^{c2}$R$^{d2}$, S(O)$_2$R$^{b2}$ NR$^{e2}$S(O)$_2$R$^{b2}$, S(O)$_2$NR$^{c2}$R$^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{e2}$R$^{d2}$, NR$^{e2}$R$^{d2}$, NR$^{e2}$C(O)R$^{b2}$, NR$^{e2}$C(O)NR$^{e2}$R$^{d2}$, NR$^{e2}$C(O)OR$^{a2}$, C(=NR$^g$)NR$^{c2}$R$^{d2}$, NR$^{c2}$C(=NR$^g$)NR$^{e2}$R$^{d2}$, P(R$^{f2}$)$_2$, P(OR$^{e2}$)$_2$, P(O)R$^{e2}$R$^{f2}$)$_2$, P(O)OR$^{e2}$OR, S(O)R$^{b2}$, S(O)NR$^{e2}$R$^{d2}$, S(O)$_2$R$^{b2}$, NR$^{e2}$S(O)$_2$R$^{b2}$, and S(O)$_2$NR$^{e2}$R$^{d2}$;

wherein two adjacent —W—X—Y—Z, together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^g$)NR$^{c3}$R$^{d3}$ NR$^{c3}$C(=NR$^g$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, S(O)$_2$NR$^{c3}$R$^{d3}$, aryl, cycloalkyl, heteroaryl, and heterocycloalkyl;

wherein two adjacent —W'—X'—Y'—Z', together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^g$)NR$^{c3}$R$^{d3}$, NR$^3$C(=NR$^g$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, S(O)$_2$NR$^{c3}$R$^{d3}$ aryl, cycloalkyl, heteroaryl, and heterocycloalkyl;

Cy$^3$, Cy$^4$, and Cy$^5$ are independently selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^g$)NR$^{c4}$R$^{d4}$, NR$^{c4}$C(=NR$^g$) NR$^{c4}$R$^{d4}$, P(R$^{f4}$)$_2$, P(OR$^{c4}$)$_2$, P(O)R$^{e4}$R$^{f4}$, P(O)OR$^{e4}$OR$^{f4}$, S(O)R$^{b4}$, S(O)NR$^{c4}$R$^{d4}$, S(O)$_2$R$^{b4}$, NR$^{c4}$S(O)$_2$R$^{b4}$, and S(O)$_2$ NR$^{c4}$R$^{d4}$;

R$^A$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, $C_{2-4}$ alkynyl, cycloalkyl, heterocycloalkyl, aryl or heteroaryl is optionally substituted with 1, 2, or 3 substituents independently selected from OH, CN, amino, halo, and $C_{1-4}$ alkyl;

R$^B$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, or $C_{2-4}$ alkynyl, cycloalkyl, heterocycloalkyl, aryl, or heteroaryl is optionally substituted with 1, 2, or 3 substituents independently selected from OH, CN, amino, halo, and $C_{1-4}$ alkyl;

R$^C$ and R$^D$ are independently selected from H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

or R$^C$ and R$^D$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, and $C_{1-4}$ alkyl;

R$^a$, R$^{a1}$, R$^{a2}$, R$^{a3}$, and R$^{a4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

R$^b$, R$^{b1}$, R$^{b2}$, R$^{b3}$, and R$^{b4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

R$^c$ and R$^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or R$^c$ and R$^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c3}$ and $R^{d3}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c4}$ and $R^{d4}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^e$, $R^{e1}$, $R^{e2}$, and $R^{e4}$ are independently selected from H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, and heterocycloalkylalkyl;

$R^f$, $R^{f1}$, $R^{f2}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl;

$R^g$ is H, CN, and $NO_2$;

$R^h$ and $R^i$ are independently selected from H and $C_{1-6}$ alkyl;

$R^j$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl;

m is 0, 1, 2, 3, 4, 5, or 6;
p is 0, 1, 2, 3, or 4;
q is 0, 1, 2, 3, or 4;
r is 0, 1, 2, 3, 4, 5, or 6;
s is 0, 1, 2, 3, or 4; and
t is 0, 1, 2, 3, or 4.

In some embodiments, when A is CH, then $L^1$ is other than CO or $(CR^4R^5)_u$ wherein u is 1.

In some embodiments, when A is CH, then $L^1$ is other than $(CR^4R^5)_pC(O)(CR^4R^5)_q$ or $(CR^4R^5)_v$ wherein v is 1, 2, 3, 4, 5, or 6.

In some embodiments, when A is CH, then $L^1$ is $(CR^4R^5)_p$-(cycloalkylene)-$(CR^4R^5)_q$, $(CR^4R^5)_p$-(arylene)-$(CR^4R^5)_q$, $(CR^4R^5)_p$-(heterocycloalkylene)-$(CR^4R^5)_q$, $(CR^4R^5)_p$-(heteroarylene)-$(CR^4R^5)_q$, $(CR^4R^5)_pO(CR^4R^5)_q$, $(CR^4R^5)_pS(CR^4R^5)_q$, $(CR^4R^5)_pC(O)NR^6(CR^4R^5)_q$, $(CR^4R^5)_pC(O)O(CR^4R^5)_q$, $(CR^4R^5)_pOC(O)(CR^4R^5)_q$, $(CR^4R^5)_pOC(O)NR^6(CR^4R^5)_q$, $(CR^4R^5)_pNR^6(CR^4R^5)_q$, $(CR^4R^5)_pNR^6C(O)NR^6(CR^4R^5)_q$, $(CR^4R^5)_pS(O)(CR^4R^5)_q$, $(CR^4R^5)_pS(O)NR^6(CR^4R^5)_q$, $(CR^4R^5)_pS(O)_2(CR^4R^5)_q$, or $(CR^4R^5)_pS(O)_2NR^6(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

In some embodiments, when A is CH, then $L^1$ is $(CR^4R^5)_p$-(cycloalkylene)-$(CR^4R^5)_q$, p is 0, q is 0.

In some embodiments, when A is N, then $L^1$ is $(CR^4R^5)_p$-(cycloalkylene)-$(CR^4R^5)_q$, p is 0, q is 0.

In some embodiments, A is N.

In some embodiments, A is $CR^3$.

In some embodiments, A is CH.

In some embodiments, $Cy^1$ is aryl or heteroaryl, each optionally substituted by 1, 2, 3, 4, or 5 —W—X—Y—Z.

In some embodiments, $Cy^1$ is aryl optionally substituted by 1, 2, 3, 4, or 5 —W—X—Y—Z.

In some embodiments, $Cy^1$ is heteroaryl optionally substituted by 1, 2, 3, 4, or 5 —W—X—Y—Z.

In some embodiments, $Cy^2$ is aryl or heteroaryl, each optionally substituted by 1, 2, 3, 4, or 5 —W'—X'—Y'—Z'.

In some embodiments, $Cy^2$ is aryl or heteroaryl, each optionally substituted by 1, 2, 3, 4, or 5 —W'—X'—Y'—Z' wherein at least one of said —W'—X'—Y'—Z' is C(O)NR$^{c2}$R$^{d2}$.

In some embodiments, $Cy^2$ is aryl optionally substituted by 1, 2, 3, 4, or 5 —W'—X'—Y'—Z'.

In some embodiments, $Cy^2$ is heteroaryl optionally substituted by 1, 2, 3, 4, or 5 —W'—X'—Y'—Z'.

In some embodiments, $Cy^1$ is quinonlinyl optionally substituted by 1, 2, 3, 4, or 5 —W—X—Y—Z.

In some embodiments, $Cy^1$ is quinolinyl.

In some embodiments, $L^1$ is $(CR^4R^5)_m$, $(CR^4R^5)_p$-(cycloalkylene)-$(CR^4R^5)_q$, $(CR^4R^5)_p$-(arylene)-$(CR^4R^5)_q$, $(CR^4R^5)_p$-(heterocycloalkylene)-$(CR^4R^5)_q$, $(CR^4R^5)_p$-(heteroarylene)-$(CR^4R^5)_q$, $(CR^4R^5)_pO(CR^4R^5)_q$, or $(CR^4R^5)_pS(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, $L^1$ is $(CR^4R^5)_m$, $(CR^4R^5)_p$-(cycloalkylene)-$(CR^4R^5)_q$, $(CR^4R^5)_p$-(arylene)-$(CR^4R^5)_q$, $(CR^4R^5)_p$-(heterocycloalkylene)-$(CR^4R^5)_q$, $(CR^4R^5)_p$-(heteroarylene)-$(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^W$R$^d$, NR$^c$C(=NR$^g$)NR$^c$R$^d$, P(R)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, $L^1$ is $(CR^4R^5)_m$ or $(CR^4R^5)_p$-(cycloalkylene)-$(CR^4R^5)_q$ wherein said cycloalkylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, $L^1$ is CH$_2$ or CH$_2$CH$_2$ or cycloalkylene.

In some embodiments, $L^1$ is CH$_2$ or cyclopropylene.

In some embodiments, $L^1$ is $(CR^4R^5)_p$-(cycloalkylene)-$(CR^4R^5)_q$, $(CR^4R^5)_p$-(arylene)-$(CR^4R^5)_q$, $(CR^4R^5)_p$-(heterocycloalkylene)-$(CR^4R^5)_q$, or $(CR^4R^5)_p$-(heteroarylene)-$(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, L is $(CR^4R^5)_p$-(cycloalkylene)-$(CR^4R^5)_q$ wherein said cycloalkylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$.

In some embodiments, L is cycloalkylene.

In some embodiments, L is cyclopropylene.

In some embodiments, L is $(CR^4R^5)_pO(CR^4R^5)_q$ or $(CR^4R^5)_pS(CR^4R^5)_q$.

In some embodiments, L is O or S.

In some embodiments, $L^2$ is $(CR^7R^8)_r$.

In some embodiments, $L^2$ is $(CR^7R^8)_r$, and r is 0.

In some embodiments, $L^2$ is $(CR^7R^8)_r$, $(CR^7R^8)_s$-(cycloalkylene)-$(CR^7R^8)_t$, $(CR^7R^8)_s$-(arylene)-$(CR^7R^8)_t$, $(CR^7R^8)_s$-(heterocycloalkylene)-$(CR^7R^8)_t$, or $(CR^7R^8)_s$-(heteroarylene)-$(CR^7R^8)_t$, wherein said cycloalkylene, arylene, heterocycloalkylene, or heteroarylene is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{e1}$C(O)OR$^{a1}$, C(=NR$^g$)NR$^{c1}$R$^{d1}$, NR$^{c1}$C(=NR$^g$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{e1}$R$^{d1}$.

In some embodiments, $L^2$ is $(CR^7R^8)_r$, $(CR^7R^8)_s$-(cycloalkylene)-$(CR^7R^8)_t$, or $(CR^7R^8)_s$-(arylene)-$(CR^7R^8)_t$, wherein said cycloalkylene or arylene, is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{e1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, $L^2$ is $(CR^7R^8)_s$-(cycloalkylene)-$(CR^7R^8)_t$ or $(CR^7R^8)_s$-(arylene)-$(CR^7R^8)_t$, wherein said cycloalkylene or arylene, is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, NO$_2$, N$_3$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$.

In some embodiments, $L^2$ is cycloalkylene or arylene.

In some embodiments, $L^2$ is arylene.

In some embodiments, $Cy^2$ is aryl optionally substituted by 1, 2, 3, 4, or 5 —W'—X'—Y'—Z'.

In some embodiments, $Cy^2$ is heteroaryl optionally substituted by 1, 2, 3, 4, or 5 —W'—X'—Y'—Z'.

In some embodiments, $Cy^2$ is cycloalkyl optionally substituted by 1, 2, 3, 4, or 5 —W'—X'—Y'—Z'.

In some embodiments, $Cy^2$ is heterocycloalkyl optionally substituted by 1, 2, 3, 4, or 5 —W'—X'—Y'—Z'.

In some embodiments, $R^1$ is H.

In some embodiments, $R^2$ is H.

In some embodiments, $R^3$ is H.

In some embodiments, $R^4$ is H.

In some embodiments, $R^5$ is H.
In some embodiments, $R^6$ is H.
In some embodiments, $R^7$ is H.
In some embodiments, $R^8$ is H.
In some embodiments, $R^9$ is H.

In some embodiments, —W—X—Y—Z is halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$ $NR^{c2}R^{d2}$, $NR^{c2}C(O)R^b2$, $NR^{c2}C(O)NR^{c2}R^{d2}$, $NR^{c2}C(O)OR^{a}2$, $C(=NR^g)NR^{c2}R^{d2}$, $NR^{c2}C(=NR^g)NR^{c2}R^{d2}$, $P(R)_2$, $P(OR^{e2})_2$, $P(O)R^{e2}R^2$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$ $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR)NR^{c2}R^{d2}$, $NR^{c2}C(=NR^g)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, —W—X—Y—Z is halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$ $NR^{c2}R^{d2}$, $NR^{c2}C(O)R^b2$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R^{f2})_2$, $P(OR^{e2})_2$, $P(O)R^{e2}R^f$, $P(O)OR^{e2}OR^{f2}$, $S(O)R^{b2}$, $S(O)NR^{c2}R^{d2}$, $S(O)_2R^{b2}$, $NR^2S(O)_2R^{b2}$, or $S(O)_2NR^{c2}R^{d2}$.

In some embodiments, —W—X—Y—Z is halo, $C_{1-6}$ alkyl, $C_{1-6}$ haloalkyl, CN, $NO_2$, $N_3$, or $OR^{a2}$.

In some embodiments, —W—X—Y—Z is $OR^{a2}$.

In some embodiments, —W—X—Y—Z is methoxy.

In some embodiments, —W'—X'—Y'—Z' is halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$ $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R)_2$, $P(OR^{e2})_2$, $P(O)R^{e2}R^{f2}$, $P(O)OR^{e2}OR$, $S(O)R^{b2}$, $S(O)NR^{c2}R^{d2}$, $S(O)_2R^{b2}$, $NR^{c2}S(O)_2R^{b2}$ $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$ $NR^{c2}R^{d2}$, $NR^{c2}C(O)R^b2$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$.

In some embodiments, —W'—X'—Y'—Z' is halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$ $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR)NR^{c2}R^{d2}$, $NR^{c2}C(=NR^g)NR^{c2}R^{d2}$, $P(R^{f1})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, or $S(O)_2NR^{c2}R^{d2}$.

In some embodiments, —W'—X'—Y'—Z' is halo, $C_{1-6}$ alkyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $S(O)R^{b2}$, $S(O)NR^{c2}R^{d2}$, $S(O)_2R^{b2}$, $NR^{c2}S(O)_2R^{b2}$, or $S(O)_2NR^{c2}R^{d2}$.

In some embodiments, —W'—X'—Y'—Z' is halo, $C_{1-6}$ alkyl, $C_{1-6}$ haloalkyl, CN, $NO_2$, $N_3$, $OR^{a2}$, or $C(O)NR^{c2}R^{d2}$.

In some embodiments, —W'—X'—Y'—Z' is halo, $C_{1-6}$ alkyl, $C_{1-6}$ haloalkyl, CN, $NO_2$, $N_3$, or $OR^{a2}$.

In some embodiments, —W'—X'—Y'—Z' is halo or $C(O)NR^{c2}R^{d2}$.

In some embodiments, —W'—X'—Y'—Z' is $C(O)NR^{c2}R^{d2}$.

In some embodiments, m is 1, 2, 3, 4, 5, or 6.

In some embodiments, the compounds of the invention have Formula IIa or IIb:

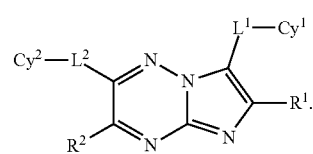

IIa

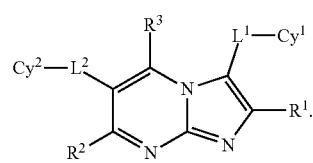

IIb

In some embodiments, the compounds of the invention have Formula III:

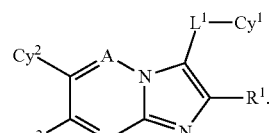

III

In some embodiments, the compounds of the invention have Formula VI:

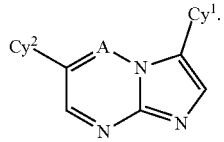

VI

In some embodiments, the compounds of the invention have Formula VIIa:

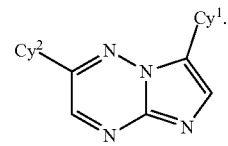

VIIa

In some embodiments, the compounds of the invention have Formula VIIb:

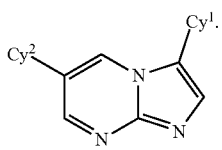

VIIb

In some embodiments, the compounds of the invention have Formula VIII:

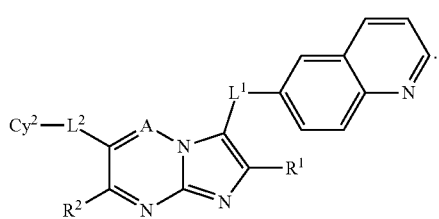

VIII

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkylyene" refers to a linking alkyl group.

As used herein, "alkenyl" refers to an alkyl group having one or more double carbon-carbon bonds. Example alkenyl groups include ethenyl, propenyl, and the like.

As used herein, "alkenylene" refers to a linking alkenyl group.

As used herein, "alkynyl" refers to an alkyl group having one or more triple carbon-carbon bonds. Example alkynyl groups include ethynyl, propynyl, and the like.

As used herein, "alkynylene" refers to a linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, "cycloalkylene" refers to a linking cycloalkyl group.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. Also included in the definition of heterocycloalkyl are moieties where one or more ring-forming atoms is substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylene" refers to a linking heterocycloalkyl group.

As used herein, "arylcycloalkyl" refers to cycloalkyl group substituted by an aryl group.

As used herein, "arylheterocycloalkyl" refers to a heterocycloalkyl group substituted by an aryl group.

As used herein, "arylheteroaryl" refers to a heteroaryl group substituted by an aryl group.

As used herein, "biaryl" refers to an aryl group substituted by another aryl group.

As used herein, "heteroarylcycloalkyl" refers to a cycloalkyl group substituted by a heteroaryl group.

As used herein, "heteroarylheterocycloalkyl" refers to a heterocycloalkyl group substituted by a heteroaryl group.

As used herein, "heteroarylaryl" refers to an aryl group substituted by a heteroaryl group.

As used herein, "biheteroaryl" refers to a heteroaryl group substituted by another heteroaryl group.

As used herein, "halo" or "halogen" includes fluoro, chloro, bromo, and iodo.

As used herein, "halosulfanyl" refers to a sulfur group having one or more halogen substituents. Example halosulfanyl groups include pentahalosulfanyl groups such as SF$_5$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "hydroxyalkyl" refers to an alkyl group substituted by OH.

As used herein, "cyanoalkyl" refers to an alkyl group substituted by CN.

As used herein, "alkoxyalkyl" refers to an alkyl group substituted by an alkoxy group.

As used herein, "alkoxyalkoxy" refers to an alkoxy group substituted by alkoxy.

As used herein, "haloalkoxy" refers to an —O-(haloalkyl) group.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to NH$_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which is was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the invention can be prepared, for example, using the reaction pathways and techniques as described below.

A series of imidazo[1,2-b][1,2,4]triazine derivatives of formula 10 can be prepared by the methods outlined in Scheme 1. Alkylations of ester 1 with haloalkyl ($R^4X$ or $R^5X$, X=Cl, Br, I) using a suitable base such as, but not limit to, NaH, lithium diisopropylamine (LDA), sodium bis(trimethylsilyl)amide (NaHMDS), or lithium bis(trimethylsilyl)amide (LiHMDS) can give the corresponding ester 2 which can be hydrolyzed to the acid 3 with alkaline solution such as lithium hydroxide, sodium hydroxide, or potassium hydroxide. Coupling of the acid 3 with N,O-dimethylamine hydrochloride in the presence of benzotriazol-1-yloxytris-(dimethylamino)-phosphonium hexafluorophosphate (BOP), or N-(3-dimethylaminopropyl)-N'-ethylcarbodiimide hydrochloride (EDCI), or N,N,N',N'-tetramethyl-O-(7-azabenzotriazol-1-yl)uronium hexafluorophosphate (HATU), or O-(benzotriazol-1-yl)-N,N,N',N'-tetramethyluronium hexafluorophosphate (HBTU), or N,N'-dicyclohexylcarbodiimide (DCC) can produce the amide 4 which is reduced to the aldehyde 5 by lithium tetrahydroaluminate (LAH). Wittig's reaction of the aldehyde 5 with (methoxymethyl)(triphenyl)phosphonium bromide and a suitable base such as NaH, lithium sodium bis(trimethylsilyl)amide (NaHMDS), or lithium bis(trimethylsilyl)amide (LiHMDS) can give a methoxyethene derivative 6 which can be converted to the aldehyde 7 by treatment with aqueous HCl solution. Reaction of chloro-aldehyde 8 which can be obtained from the aldehyde 7 by treatment with NCS with 2-aminotriazine 9 provide imidazo[1,2-b][1,2,4]triazine derivatives 10.

Scheme 1

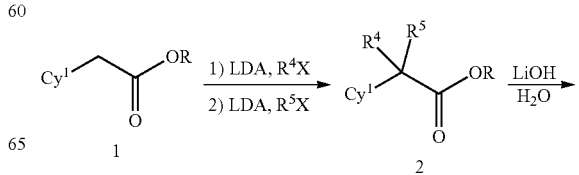

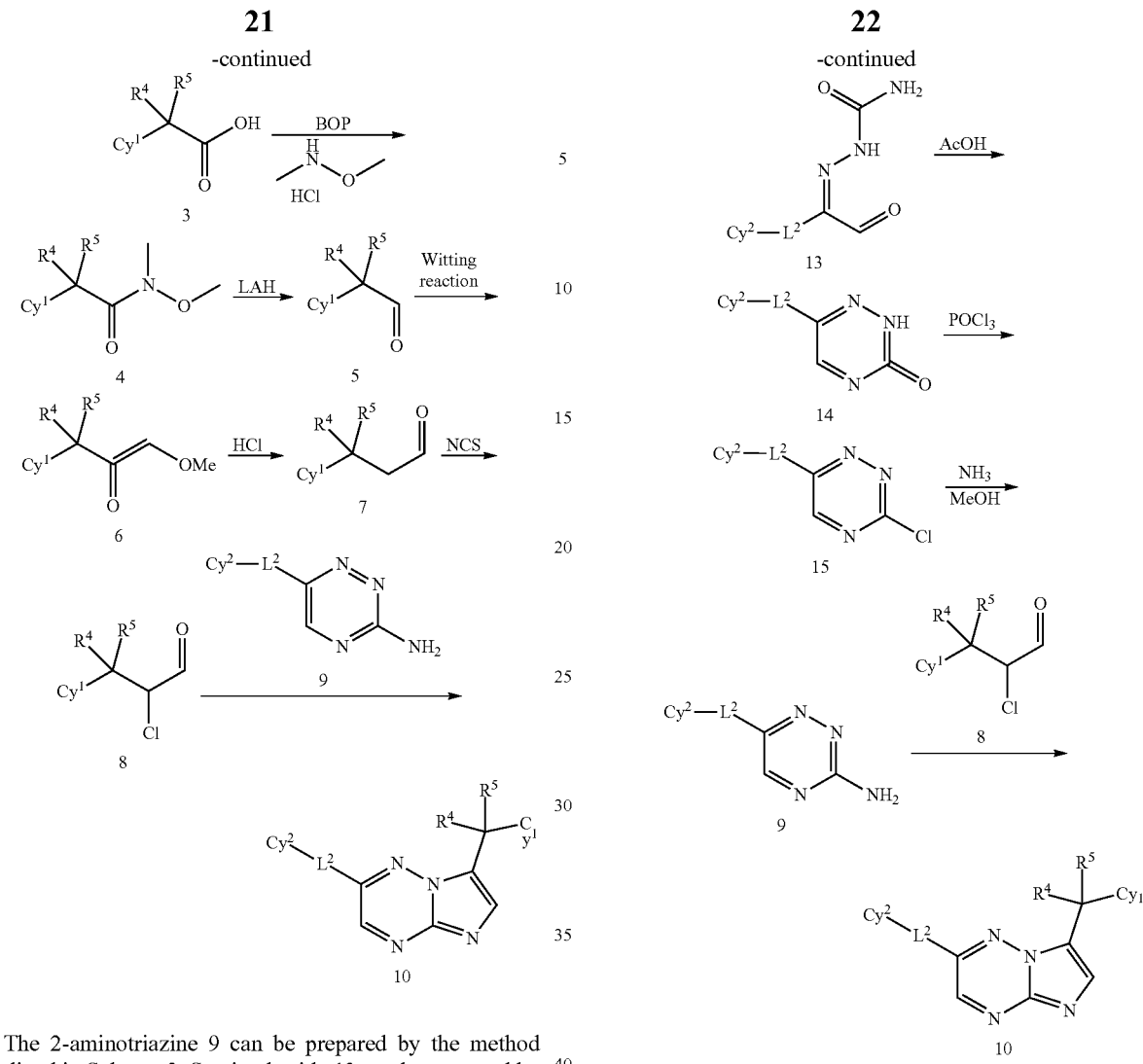

The 2-aminotriazine 9 can be prepared by the method outlined in Scheme 2. Semicarbazide 13 can be prepared by reaction of the semicarbazide hydrochloride with oxo-acetal 12 which, in turn, can be obtained from oxo-acetaldehyde 11 by treatment with triethylformate. Intramolecular ring closure of 13 can afford the triazinone 14 which can be converted to the corresponding chloride 15 by reflux with $POCl_3$ in an inert solvent such as chloroform, 1,2-dichloroethane, or toluene in the presence of a catalytic amount of dimethylformamide (DMF). Replacement of the chlorine in 15 with ammonia can yield 2-aminotriazine 9 which can be converted to 10 by reaction with the chloride 8.

Alternatively, the triazinone 14 can be prepared according to the procedure outlined in Scheme 3. The oxo-acetaldehyde 11 can be transformed to the corresponding oxo-oxime 16. Reaction of 16 with semicarbazide can give the compound 17. Hydrolysis of the oxime in 17 followed by intramolecular ring closure can afford compound 14.

Scheme 2

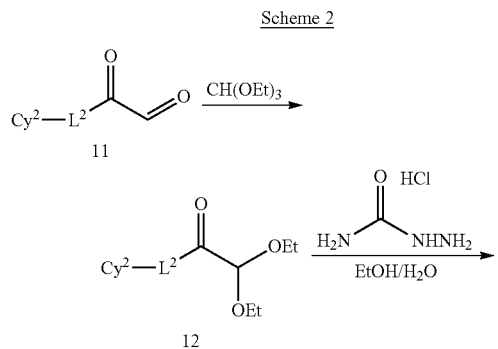

Scheme 3

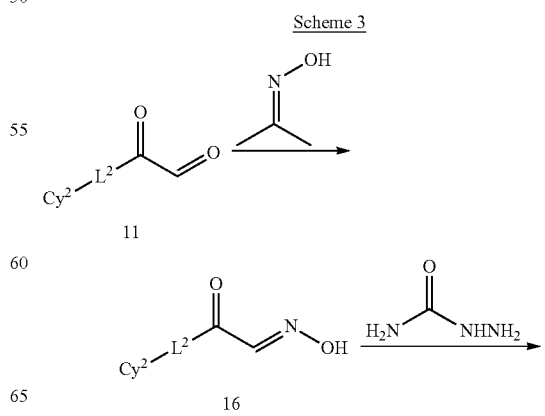

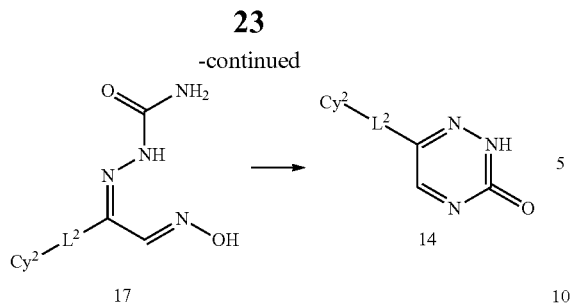

Further alternatively, compound 14 can be prepared according to the procedure outlined in Scheme 4. The acid ester 18 can be converted to alpha-halo ketone 20 by treatment with dimethylsulfoxonium methylide, generated by refluxing of trimethylsulfoxonium chloride with potassium tert-butoxide in THF, followed by a cleavage reaction with anhydrous hydrogen chloride at about 65° C. N-alkylation of α-halo ketone 20 with the sodium salt of 2,4-thiazolidinedione can produce the N-substituted 2,4-thiazolidinedione 22 which can be converted to dihydrotriazinone 23. Oxidation of 23 with suitable oxidants such sodium 3-nitrobenzenesulfonate or tert-butylhypochlorite or DDQ can yield the triazinone 14.

In a similar manner, the triazine 3 can be prepared by the methods outline in Scheme 5. Amide 25, obtained by coupling of the acid 24 with N,O-dimethylhydroxylamine in the presence of BOP or DCC, can be converted to the corresponding ketone 27 by reaction with lithium agent 26 which can be produced by treatment of 1,3-dithiane with n-butyl lithium at low temperature. Reflux of the ketone 27 with thiosemicarbazide in an inert solvent such as ethanol or toluene in the presence of an acid such as 4-toluenesulfonic acid can afford the compound 28. Alkylation of compound 28 with methyl iodide in the presence of a suitable base such as cesium carbonate, potassium carbonate, sodium carbonate or sodium hydroxide can give triazine 29 which can be transformed to the compound 9. The triazine 3 can be prepared from 9 as previously described.

Scheme 4

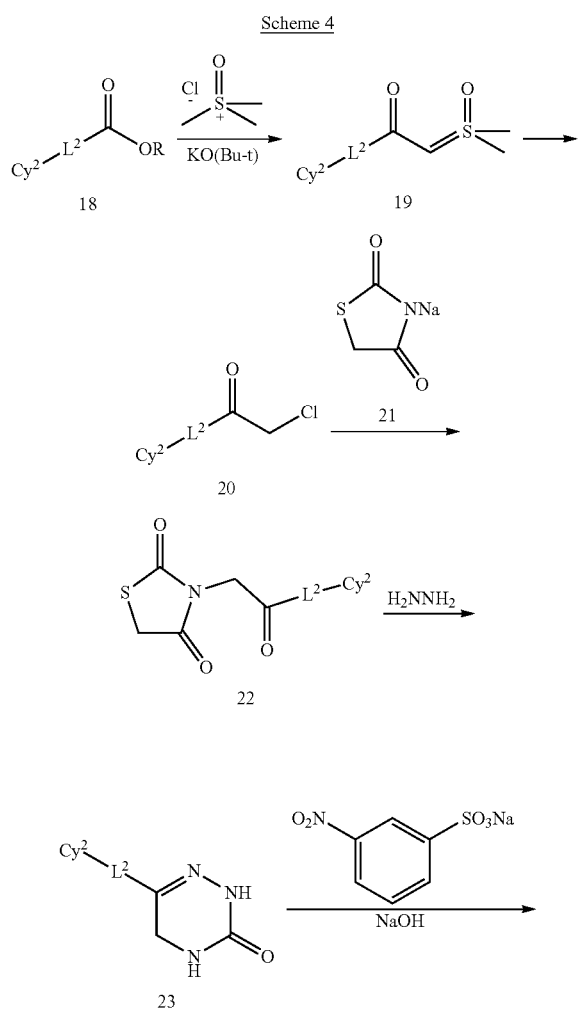

Scheme 5

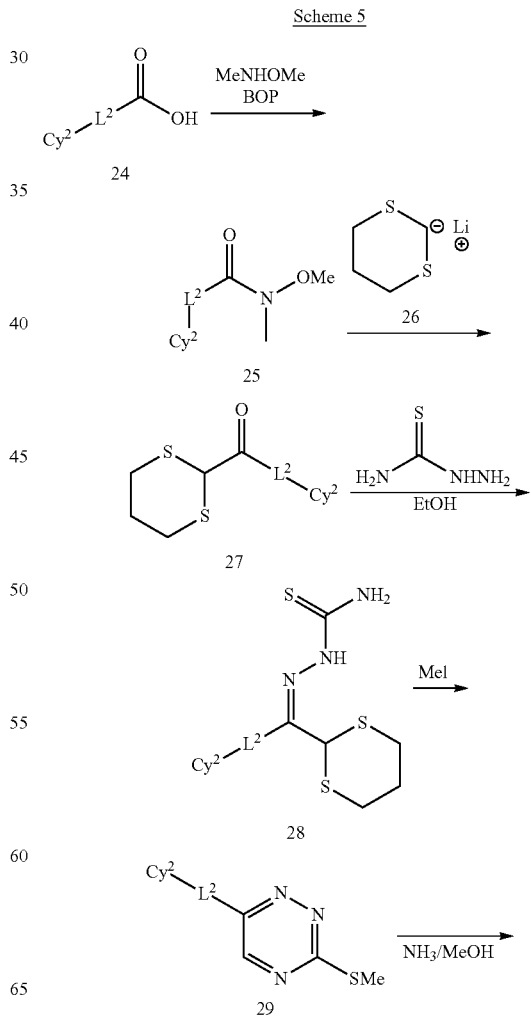

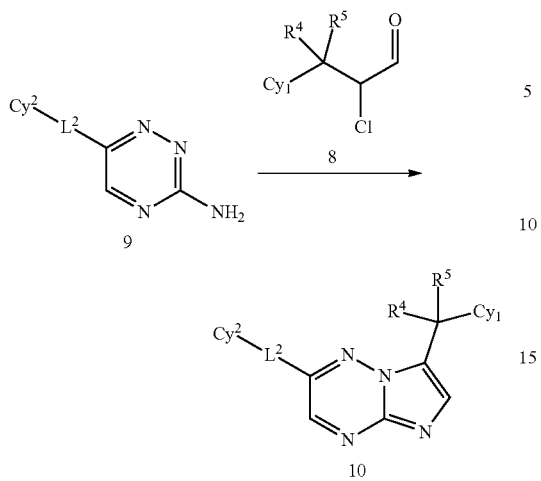

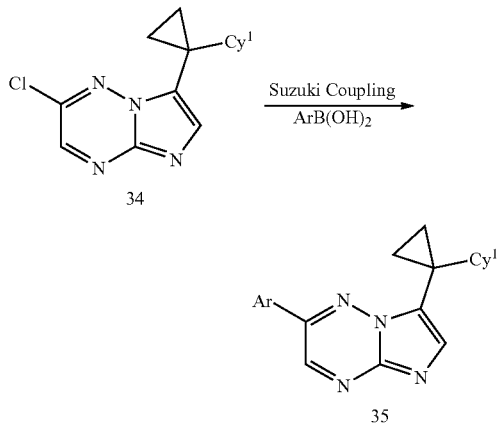

A series of triazine derivatives of formula 35 can be prepared according to the procedures outlined in Scheme 6. Amine derivative 32 can be obtained from the chloride 30 by treatment with ethyl hydrazinecarbimidothioate hydrobromide followed by replacement with hydrazine. Reaction of 32 with acid chloride 8 can produce the triazinone 33 which can be transformed to the corresponding chloride 34. Suzuki Coupling of 34 with ArB(OH)$_2$ give the triazine derivative 35.

A series of triazine derivatives of formula 42 can be prepared according to the procedures outlined in Scheme 7. Treatment of the acid 36 with thiosemicarbazide in the presence of base such as sodium carbonate, potassium carbonate, sodium hydroxide, potassium hydroxide, or the like can give the compound 37 which can convert to compound 38 by alkylation with methyl iodide. Triazinone 40 can be obtained from 38 by replacement with ammonia followed by reaction with the chloride 8. Compound 40 can be transformed to the corresponding chloride 41 by treatment with POCl$_3$ or SOCl$_2$. Reaction of 41 with an appropriate amine can afford the triazine derivative 42.

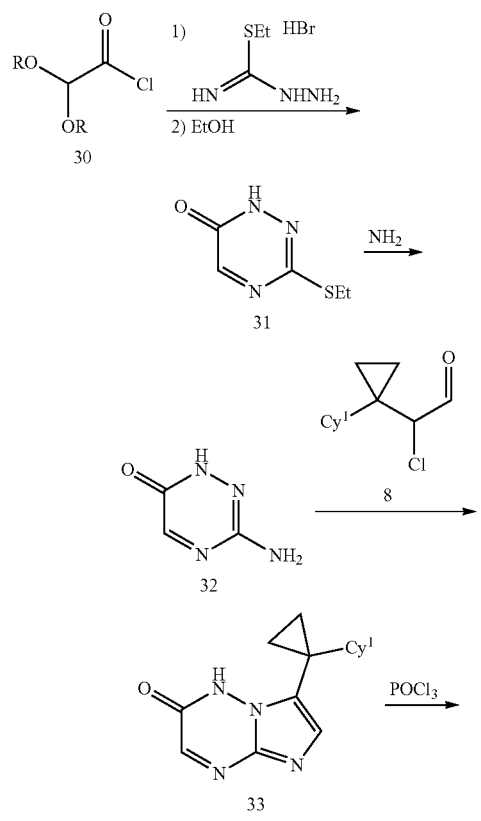

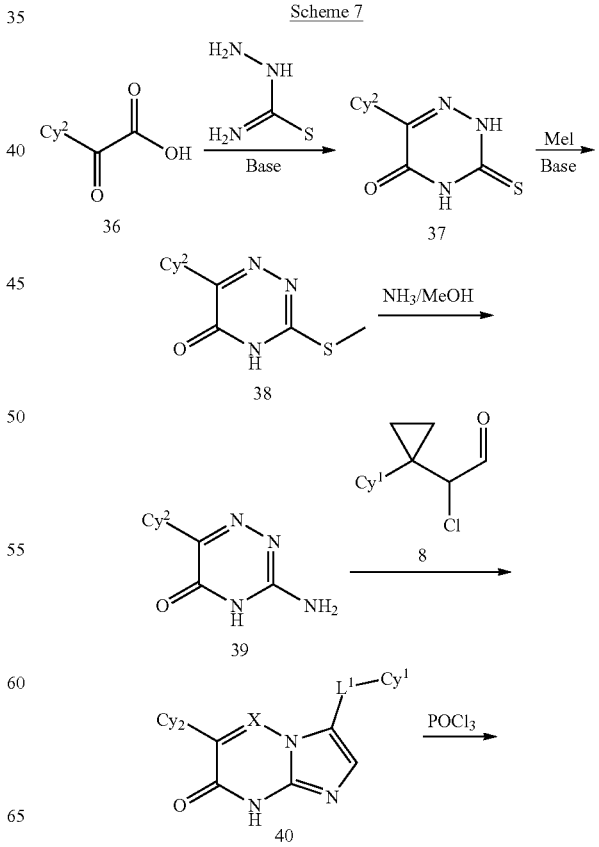

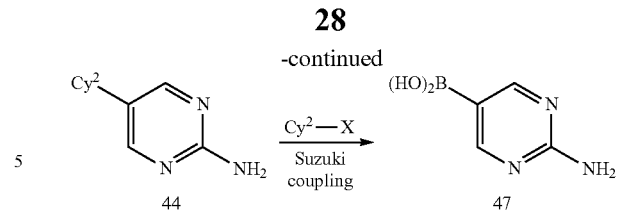

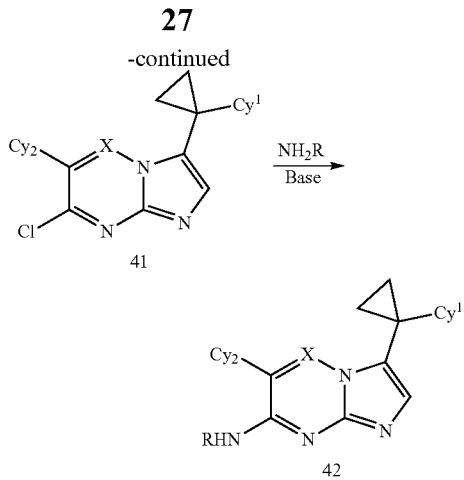

A series of triazine derivatives of formula 45 can be prepared according to the procedures outlined in Scheme 8. Suzuki coupling of bromopyrimidine 43 with an arylboronic acid ArB(OH)$_2$ can give 2-aminotriazine 44 which can react with chloro-aldehyde 8 to provide the triazine derivative 45.

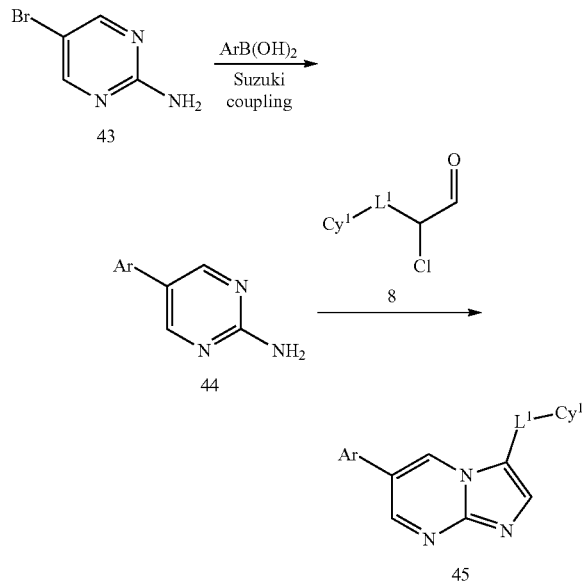

The 2-aminotriazine 44 can be prepared by the method outlined in Scheme 9. The 2-aminopyrimidine 44 can be obtained by heating a mixture of an enaminaldehyde 46 with guanine hydrochloride. Alternatively, Suzuki coupling of aminopyrimidinyl boronic acid 47 with aromatic halide Cy$^2$-X (Cy$^2$ is an aromatic moiety and X=Cl, Br, I) provides the 2-aminopyrimidine 44.

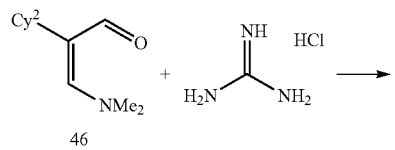

A series of cycloalkylcarboxylic acids formula 51 can be prepared by the method outlined in Scheme 10. Monoalkylation of alpha-substituted methyl 48 with an alkylenedihalide such as ethylene dibromide, 1,3-dibromopropane, and 1,4-dibromobutane can provide mono-alkylated product 49, followed by treatment with either 1) sodium hydride in dimethylsuloxide (DMSO) or DMF or 2) lithium diisopropylamide (LDA) in THF can provide the cycloalkylcarboxylic acid esters 50. Hydrolysis of 50 in presence of base such as lithium hydroxide, sodium hydroxide, potassium hydroxide, or the like can give the corresponding acid 51.

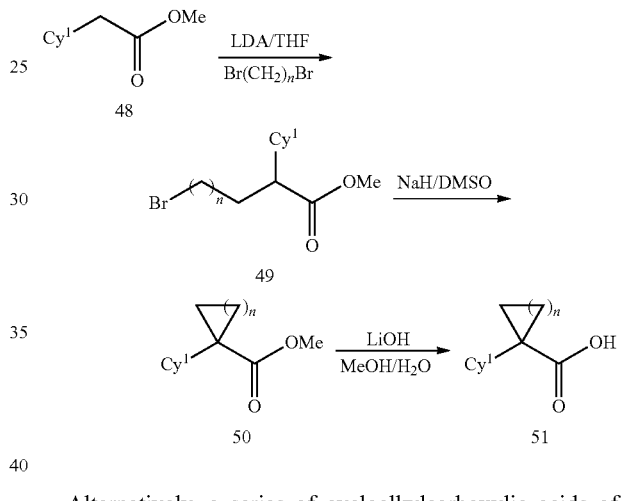

Alternatively, a series of cycloalkylcarboxylic acids of formula 51 can be prepared from the corresponding nitrile 52 as shown in Scheme 12. Alpha-substituted acetonitrile 52 can be treated with potassium hydroxide and alkylenedihalides such as ethylene dibromide, 1,3-dibromopropane, 1,4-dibromobutane, and the like to provide substituted cycloalkylcarbonitriles 53, which can be followed by hydrolysis to afford the desired cycloalkylcarboxylic acid 51.

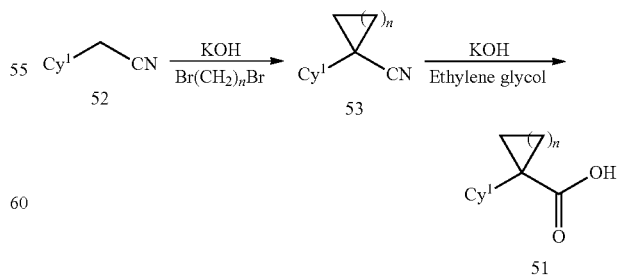

Methods of Use

Compounds of the invention can modulate activity of protein kinases. Example protein kinases modulated by the compounds of the invention include RTKs of the HER subfamily (e.g., EGFR, HER2, HER3 and HER4), of the insulin subfamily (e.g., INS-R, the IGF-1R and the IR-R), of the PDGF subfamily (e.g., the PDGF alpha and beta receptors, CSFIR, c-kit and FLK-II), of the FLK subfamily (e.g., Kinase insert Domain-Receptor fetal liver kinase-1 (KDR/FLK-1), the fetal liver kinase 4 (FLK-4) and the fms-like tyrosine kinases 1 and 3 (flt-1 and fit-3)), of the FGF receptor family (e.g., FGFR1, FGFR2, FGFR3 and FGFR4), of the Met subfamily (e.g., c-Met, Ron amd Sea), and of the Src, Abl, and Jak (e.g., Jak1, Jak2, and Jak3) subfamilies. In some embodiments, the compounds of the invention modulate activity of c-Met.

The term "modulate" is meant to refer to an ability to increase or decrease activity of an enzyme or receptor. Modulation can occur in vitro or in vivo. Modulation can further occur in a cell. Accordingly, compounds of the invention can be used in methods of modulating a protein kinase, such as an RTK, by contacting the enzyme (or cell or sample containing the enzyme) with any one or more of the compounds or compositions described herein.

In some embodiments, compounds of the present invention can act as inhibitors of one or more protein kinases. In some further embodiments, compounds of the invention can be used in methods of inhibiting an RTK of the Met or FLK subfamilies. In yet further embodiments, the compounds of the invention can be used in methods of inhibiting c-Met, KDR, or fit-3 kinase. In yet further embodiments, the compounds of the invention can be used as inhibitors c-Met. In yet further embodiments, the compounds of the invention are selective inhibitors of c-Met.

Treatment of a cell (in vitro or in vivo) that expresses a protein kinase with a compound of the invention can result in inhibiting the ligand/kinase signaling pathway and inhibiting downstream events related to the signaling pathway such as cellular proliferation and increased cell motility. For example, the compounds of the invention can block and/or impair the biochemical and biological processes resulting from c-Met pathway activation, including, but not limited to, c-Met kinase activation (e.g. c-Met phosphorylation) and signaling (activation and recruitment of cellular substrates such as Gab 1, Grb2, She and c-Cb1 and subsequent activation of a number of signal transducers including PI-3 kinase, PLC-γ, STATs, ERK1/2 and FAK), cell proliferation and survival, cell motility, migration and invasion, metastasis, angiogenesis, and the like. Thus, the present invention further provides methods of inhibiting a ligand/kinase signaling pathway such as the HGF/c-Met kinase signaling pathway in a cell by contacting the cell with a compound of the invention. The present invention further provides methods of inhibiting proliferative activity of a cell or inhibiting cell motility by contacting the cell with a compound of the invention.

The present invention further provides methods of treating diseases associated with a dysregulated kinase signaling pathway, including abnormal activity and/or overexpression of the protein kinase, in an individual (e.g., patient) by administering to the individual in need of such treatment a therapeutically effective amount or dose of a compound of the present invention or a pharmaceutical composition thereof. In some embodiments, the dysregulated kinase is of the Met family (e.g., c-Met, Ron, or Sea). In some embodiments, the dysregulated kinase is overexpressed in the diseased tissue of the patient. In some embodiments, the dysregulated kinase is abnormally active in the diseased tissue of the patient. Dysregulation of c-Met and the HGF/c-Met signaling pathway is meant to include activation of the enzyme through various mechanisms including, but not limited to, HGF-dependent autocrine and paracrine activation, c-met gene overexpression and amplification, point mutations, deletions, truncations, rearrangement, as well as abnormal c-Met receptor processing and defective negative regulatory mechanisms.

In some embodiments, the compounds of the invention are useful in treating diseases such as cancer, atherosclerosis, lung fibrosis, renal fibrosis and regeneration, liver disease, allergic disorder, inflammatory disease, autoimmune disorder, cerebrovascular disease, cardiovascular disease, or condition associated with organ transplantation. In further embodiments, the compounds of the invention can be useful in methods of inhibiting tumor growth or metastasis of a tumor in a patient.

Example cancers treatable by the methods herein include bladder cancer, breast cancer, cervical cancer, cholangiocarcinoma cancer, colorectal cancer, esophageal cancer, gastric cancer, head and neck cancer, cancer of the kidney, liver cancer, lung cancer, nasopharygeal cancer, ovarian cancer, pancreatic cancer, prostate cancer, thyroid cancer, osteosarcoma, synovial sarcoma, rhabdomyosarcoma, MFH/fibrosarcoma, leiomyosarcoma, Kaposi's sarcoma, multiple myeloma, lymphoma, adult T cell leukemia, acute myelogenous leukemia, chronic myeloid leukemia. glioblastoma, astrocytoma, melanoma, mesothelioma, or Wilm's tumor, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a compound of the invention with a protein kinase includes the administration of a compound of the present invention to an individual or patient, such as a human, as well as, for example, introducing a compound of the invention into a sample containing a cellular or purified preparation of the protein kinase.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapy

One or more additional pharmaceutical agents or treatment methods such as, for example, chemotherapeutics, anti-cancer agents, cytotoxic agents, or anti-cancer therapies (e.g., radiation, hormone, etc.), can be used in combination with the compounds of the present invention for treatment of the diseases, disorders or conditions described herein. The agents or therapies can be administered together with the compounds of the invention (e.g., combined into a single dosage form), or the agents or therapies can be administered simultaneously or sequentially by separate routes of administration.

Suitable anti-cancer agents include kinase inhibiting agents including trastuzumab (Herceptin), imatinib (Gleevec), gefitinib (Iressa), erlotinib hydrochloride (Tarceva), cetuximab (Erbitux), bevacizumab (Avastin), sorafenib (Nexavar), sunitinib (Sutent), and RTK inhibitors described in, for example, WO 2005/004808, WO 2005/004607, WO 2005/005378, WO 2004/076412, WO 2005/121125, WO 2005/039586, WO 2005/028475, WO 2005/040345, WO 2005/039586, WO 2003/097641, WO 2003/087026, WO 2005/040154, WO 2005/030140, WO 2006/014325, WO 2005/070891, WO 2005/073224, WO 2005/113494, and US Pat. App. Pub. Nos. 2005/0085473, 2006/0046991, and 2005/0075340.

Suitable chemotherapeutic or other anti-cancer agents further include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents further include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxycoformycin, mitomycin-C, L-asparaginase, interferons (especially IFN-a), etoposide, and teniposide.

Other cytotoxic agents include navelbene, CPT-11, anastrazole, letrozole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.). Further antibody therapeutics include antibodies to tyrosine kinases and/or their ligands such as anti-HGF antibodies and/or anti-c-Met antibodies. The term "antibody" is meant to include whole antibodies (e.g., monoclonal, polyclonal, chimeric, humanized, human, etc.) as well as antigen-binding fragments thereof.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Other anti-cancer agents include anti-cancer vaccines such as dendritic cells, synthetic peptides, DNA vaccines and recombinant viruses.

Methods for the safe and effective administration of most of the above agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which is a combination of a compound of the invention and a pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral adminstration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents, vaccines, antibodies, immune enhancers, immune suppressants, anti-inflammatory agents and the like.

Labeled Compounds and Assay Methods

Another aspect of the present invention relates to fluorescent dye, spin lable, heavy metal or radio-labeled compounds of the invention that would be useful not only in imaging but also in assays, both in vitro and in vivo, for localizing and quantitating the protein kinase target in tissue samples, including human, and for identifying kinase ligands by inhibition binding of a labeled compound. Accordingly, the present invention includes kinase enzyme assays that contain such labeled compounds.

The present invention further includes isotopically-labeled compounds of the compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro IDO enzyme labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the enzyme. Accordingly, the ability of a test compound to compete with the radio-labeled compound for binding to the enzyme directly correlates to its binding affinity.

Kits

The present invention also includes pharmaceutical kits useful, for example, in the treatment or prevention of diseases, such as cancer and other diseases referred to herein, which include one or more containers containing a pharmaceutical composition comprising a therapeutically effective amount of a compound of the invention, or pharmaceutically acceptable salt thereof. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples were found to be inhibitors of c-Met according to one or more of the assays provided herein.

EXAMPLES

Experimentals for compounds of the invention are provided below. In some instances, the crude product is a mixture of regioisomers. Typically, these isomers are separated on a preparative scale by high performance liquid chromatography (HPLC) or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: 0.1% TFA in acetonitrile; the flow rate is 30 ml/m, the separating gradient is optimized for each compound using the Compound Specific Method Optimization protocol as described in the literature ["Preparative LCMS Purification: Improved Compound Specific Method Optimization", K. Blom, B. Glass, R. Sparks, A. Combs, *J. Comb. Chem.*, 6, 874-883 (2004)].

pH=10 purifications: Waters XBridge $C_{18}$ 5 µm, 19×100 mm column, eluting with mobile phase A: 0.15% $NH_4OH$ in water and mobile phase B: 0.15% $NH_4OH$ in acetonitrile; the flow rate was 30 ml/m, the separating gradient is optimized for each compound using the Compound Specific Method Optimization protocol as described in the literature ["Preparative LCMS Purification: Improved Compound Specific Method Optimization", K. Blom, B. Glass, R. Sparks, A. Combs, *J. Comb. Chem.*, 6, 874-883 (2004)].

The separated isomers are typically subjected to analytical liquid chromatography mass spectrometry (LCMS) for purity under the following conditions: Instrument; Agilent 1100 series, LC/MSD, Column: Waters Sunfire™ $C_{18}$ 5 µm, 2.1×5.0 mm, Buffers: mobile phase A: 0.025% TFA in water and mobile phase B: 0.025% TFA in acetonitrile; gradient 2% to 80% of B in 3 min with flow rate 1.5 mL/min. Retention time ($R_t$) data in the Examples refer to these analytical LC/MS conditions unless otherwise specified.

Example 1: 2-(4-Fluorophenyl)-7-(4-methoxybenzyl)imidazo[1,2-b][1,2,4]triazine

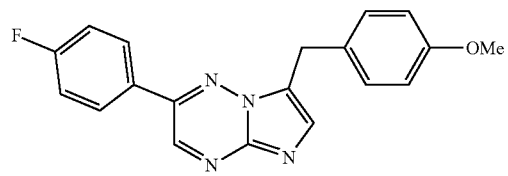 [SMILES: COc1ccc(Cc2cnc3ncc(-c4ccc(F)cc4)nn23)cc1]

Step 1. 2,2-Diethoxy-1-(4-fluorophenyl)ethanone

A mixture of 1-(4-fluorophenyl)-2,2-dihydroxyethanone (4.0 g, 0.024 mol), ethyl orthoformate (7.3 g, 49 mmol), and p-toluenesulfonic acid monohydrate (200 g, 1.05 mol) in dichloromethane (50 mL) was refluxed for 40 min. After cooling to room temperature (RT), the mixture was concentrated under reduced pressure. The residue was purified by flash chromatography eluting with dichloromethane to give the desired product (5.2 g). $^1$H-NMR (300 MHz, CDCl$_3$): 8.18-8.25 (m, 2H), 7.08-7.16 (m, 2H), 5.18 (s, 1H), 3.58-3.82 (m, 4H), 1.25 (t, J=7.0 Hz, 6H).

Step 2. 6-(4-Fluorophenyl)-1,2,4-triazin-3(2H)-one

A mixture of 2,2-diethoxy-1-(4-fluorophenyl)ethanone (5.2 g, 23 mmol), semicarbazide hydrochloride (2.6 g, 24 mmol) in ethanol (50 mL) was stirred overnight at ambient temperature and then heated to 80° C. for 5 hours. The reaction mixture was concentrated and the resulting residue was dissolved in acetic acid (50 mL) which was heated to 130° C. for 6 h. After cooling, the mixture was concentrated under reduced pressure. The residue was triturated with ethyl ether, filtered, and washed with diethyl ether and then hexanes. The crystalline material was collected and dried under high vacuum to give the desired product. (4.2 g, 96%) LCMS: (M+H)=192.1.

Step 3. 3-Chloro-6-(4-fluorophenyl)-1,2,4-triazine

A mixture of 6-(4-fluorophenyl)-1,2,4-triazin-3(2H)-one (1.0 g, 5.23 mmol) and phosphoryl chloride (8.0 mL) in chloroform (5.0 mL) was heated under reflux conditions overnight. After cooling, the volatiles were removed under reduced pressure. The residue was dissolved in dichloromethane (60 mL) and was poured into ice with stirring. The mixture was neutralized with aqueous 2N potassium carbonate and filtered through a pad of Celite. The organic layer was separated and the aqueous layer was extracted with dichloromethane (3×20 mL). The combined organic extracts were dried over magnesium sulfate, filtered, and concentrated under reduced pressure. The residue was purified by flash chromatography to give the desired product. (600 mg, 54.6%) $^1$H-NMR (300 MHz, CDCl$_3$): 8.88 (s, 1H), 8.06-8.12 (m, 2H), 7.06-7.14 (m, 2H). LCMS: (M+H)= 210.1/212.1.

Step 4. 6-(4-Fluorophenyl)-1,2,4-triazin-3-amine

Ammonia gas was bubbled through a solution of 3-chloro-6-(4-fluorophenyl)-1,2,4-triazine (600 mg, 0.0029 mol) in tetrahydrofuran (8 mL) for 5 min at −40° C. The reaction mixture was sealed and heated at 50° C. for 2 hours. The mixture was concentrated under reduced pressure to yield the desired product (550 mg) which was directly used in the next step without further purification. LCMS: (M+H)= 209.1.

Step 5. 3-(4-Methoxyphenyl)propanal

A solution of dimethyl sulfoxide (5.1 mL) in dichloromethane (10 ml) was added to a stirred solution of oxalyl chloride (3.0 mL, 36 mmol) in dichloromethane (40 mL) at −78° C. over 30 min. Upon completion of the addition, the mixture was stirred at −78° C. for 5 min, followed by addition of a solution of 4-methoxybenzenepropanol (3.0 g, 18 mmol) in dichloromethane (20 ml) at −78° C. over 30 min. The resulting mixture was stirred at −78° C. for 40 min. Next, triethylamine (15 mL, 110 mmol) was added dropwise over 10 min. The resulting mixture was allowed to warm to 0° C. and stirred at this temperature for 1 hour. It was diluted with dichloromethane (30 mL) and quenched with water (15 mL). The organic extracts were separated, washed with water and brine, dried over magnesium sulfate, filtered, and concentrated under reduced pressure. The residue was purified by flash chromatography eluting with ethyl acetate in hexanes (gradient: 3 min: 0/100 to 23 min: 20/80) to afford the desired product (1.50 g, 51%).

Step 6. 2-Chloro-3-(4-methoxyphenyl)propanal

N-Chlorosuccinimide (980 mg, 0.0073 mol) was added to a mixture of 3-(4-methoxyphenyl)propanal (1.0 g, 6.1 mmol) and D-proline (40 mg, 0.3 mmol) in dichloromethane (10 mL, 200 mmol) at 0° C. The reaction mixture was warmed to RT after 1 h, quenched with water, and extracted with dichloromethane. The organic extracts were washed with brine, dried over magnesium sulfate, filtered, and concentrated under reduced pressure. The residue was purified by flash chromatography eluting with ethyl acetate in hexanes to give the desired product (860 mg). $^1$H NMR (400 MHz, CDCl$_3$): 9.52 (s, 1H), 7.18 (dd, 2H), 6.84 (dd, 2H), 4.36 (m, 1H), 3.80 (s, 3H), 3.32 (m, 1H), 3.02 (m, 1H).

Step 7. 2-(4-Fluorophenyl)-7-(4-methoxybenzyl) imidazo[1,2-b][1,2,4]triazine A mixture of 6-(4-fluorophenyl)-1,2,4-triazin-3-amine hydrochloride (50 mg, 0.2 mmol) and 2-chloro-3-(4-methoxyphenyl)propanal (48 mg, 0.24 mmol) in tert-amyl alcohol (1 mL) was heated at 130° C. for 4 h. After cooling, the mixture was purified by preparative HPLC to afford the desired product. (7.1 mg) LCMS: (M+H)=335.1.

Example 2: 2-(4-Fluorophenyl)-7-[1-(4-methoxyphenyl)cyclopropyl]imidazo[1,2-b]-[1,2,4]-triazine

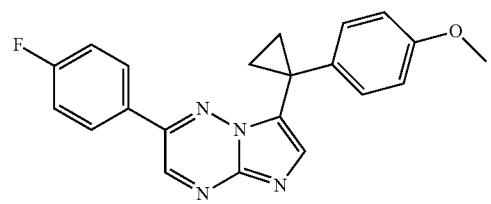 [SMILES: COc1ccc(C2(c3cnc4ncc(-c5ccc(F)cc5)nn34)CC2)cc1]

Step 1. 1-Methoxy-4-1-[(E)-2-methoxyvinyl]cyclopropylbenzene 1.0 M of Potassium tert-butoxide in tetrahydrofuran (THF) (6.8 mL, 6.8 mmol) was slowly added to a suspension of chloro(methoxymethyl)triphenylphosphorane (2.3 g, 6.8 mmol) in THF (6.0 mL, 74 mmol) at −10° C., and then the mixture was stirred at ambient temperature for 1 h. 1-(4-methoxyphenyl)cyclopropanecarbaldehyde (300 mg, 1.7 mmol) in THF (2.0 mL) was then added dropwise to the reaction mixture at 0° C., and stirred at RT for 1 hour. The mixture was filtered through a pad of silica gel eluting with dichloromethane. The filtrate was concentrated under reduced pressure. The residue was purified by flash chromatography eluting with ethyl acetate in hexanes (0-10%) to afford the desired product.

Step 2. [1-(4-Methoxyphenyl)cyclopropyl]acetaldehyde

1N HCl (3.0 mL) was added to a solution of 1-methoxy-4-1-[(E)-2-methoxyvinyl]cyclopropylbenzene (350 mg, 1.7 mmol) in tetrahydrofuran (5.0 mL). The mixture was stirred at ambient temperature for 6 hours, and then concentrated hydrochloric acid (0.2 mL) was added. The mixture was stirred overnight, diluted with water, and extracted with ethyl acetate. The organic layer was dried over magnesium sulfate, filtered, and concentrated under reduced pressure. The residue was purified by flash chromatography eluting with ethyl acetate in hexanes (0-10%) to afford the desired product. LCMS: (M+H)=190.9.

Step 3. Chloro[1-(4-methoxyphenyl)cyclopropyl]acetaldehyde

L-Proline (10 mg, 0.1 mmol) was added to a solution of [1-(4-methoxyphenyl)cyclopropyl]acetaldehyde (100 mg, 0.53 mmol) in chloroform (1 mL) at 0° C. followed by addition of N-chlorosuccinimide (84 mg, 0.63 mmol). The reaction mixture was stirred at ambient temperature for 2 h. The mixture was diluted with hexanes and filtered. The filtrate was concentrated under reduced pressure and the residue was purified by flash chromatography eluting with ethyl acetate in hexanes (0-10%) to afford the desired product.

Step 4. 2-(4-Fluorophenyl)-7-[1-(4-methoxyphenyl)cyclopropyl]imidazo[1,2-b]-[1,2,4]-triazine A mixture of 6-(4-fluorophenyl)-1,2,4-triazin-3-amine (20.1 mg, 0.106 mmol) and chloro[1-(4-methoxyphenyl)cyclopropyl]acetaldehyde (53 mg, 0.24 mmol) in isopropyl alcohol (0.6 mL) was heated to 90° C. overnight. After cooling, the mixture was diluted with methanol and was purified by mass-guided RP-HPLC to afford the desired product. LCMS: (M+H)=361.1.

Example 3: 6-(1-(2-(4-Fluorophenyl)imidazo[1,2-b][1,2,4]triazin-7-yl)cyclopropyl)quinoline

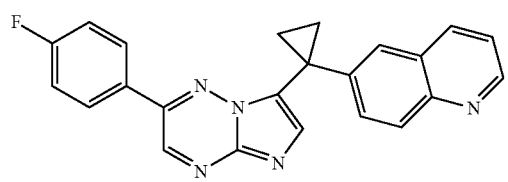 [SMILES: Fc1ccc(-c2cnc3ncc(C4(c5ccc6ncccc6c5)CC4)n3n2)cc1]

This compound was prepared using procedures analogous to those for Example 2. LCMS: (M+H)=382.0.

Example 4: 6-(4-Fluorophenyl)-3-(4-methoxybenzyl)imidazo[1,2-a]pyrimidine

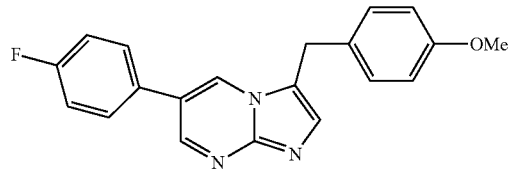 [SMILES: COc1ccc(Cc2cnc3ncc(-c4ccc(F)cc4)cn23)cc1]

Step 1. 2-Chloro-5-(4-fluorophenyl)pyrimidine

A mixture of 5-bromo-2-chloropyrimidine (500 mg, 2 mmol), 4-fluorophenylboronic acid (430 mg, 3.1 mmol), [1,1'-bis(diphenylphosphino)ferrocene]dichloropalladium(II) dichloromethane complex (1:1) (210 mg, 0.26 mmol) and potassium carbonate (1.8 g, 13 mmol) in 1,4-dioxane (6 mL) was irradiated under microwave at 120° C. for 30 min. After cooling, the solvent was evaporated. The residue was purified by flash chromatography eluting with ethyl acetate in hexanes to give the desired product. (376 mg) LCMS: (M+H)=209.0.

Step 2. 5-(4-Fluorophenyl)pyrimidin-2-amine

2-Chloro-5-(4-fluorophenyl)pyrimidine (376 mg) in 7M of ammonia in methanol (10 mL) in a sealed tube was heated at 50° C. overnight. After concentration, the product was obtained (360 g) which was used in the next reaction step without further purification. LCMS: (M+H)=190.1.

Step 3. 6-(4-Fluorophenyl)-3-(4-methoxybenzyl)imidazo[1,2-a]pyrimidine

A mixture of 5-(4-fluorophenyl)pyrimidin-2-amine (50 mg, 0.3 mmol), 2-chloro-3-(4-methoxyphenyl)propanal (52 mg, 0.26 mmol) in tert-amyl alcohol (1.0 mL) in a sealed reaction vial was heated at 130° C. for 3 hours. After cooling, the mixture was purified by preparative HPLC to afford the desired product. LCMS: (M+H)=334.0.

Example 5: 6-(4-Fluorophenyl)-3-(1-(4-methoxyphenyl)cyclopropyl)imidazo[1,2-a]pyrimidine

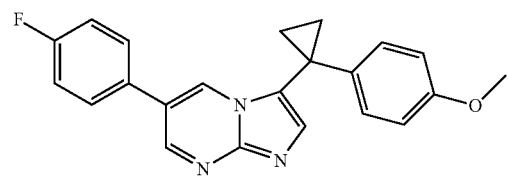 [SMILES: COc1ccc(C2(c3cnc4ncc(-c5ccc(F)cc5)cn34)CC2)cc1]

This compound was prepared using procedures analogous to those for Example 4. LCMS: (M+H)$^+$=360.1.

Example 6: 6-(1-(6-(4-Fluorophenyl)imidazo[1,2-a]pyrimidin-3-yl)cyclopropyl)quinoline

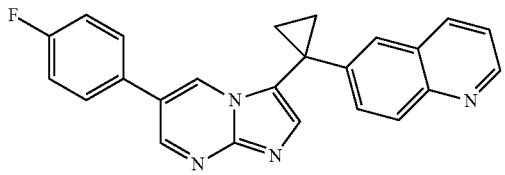 [SMILES: Fc1ccc(-c2cnc3ncc(C4(c5ccc6ncccc6c5)CC4)n3c2)cc1]

This compound was prepared using procedures analogous to those for Example 4. LCMS: (M+H)$^+$=381.0.

Example 7: 2-Fluoro-N-methyl-4-[7-(quinolin-6-ylmethyl)imidazo[1,2-b][1,2,4]triazin-2-yl]benzamide

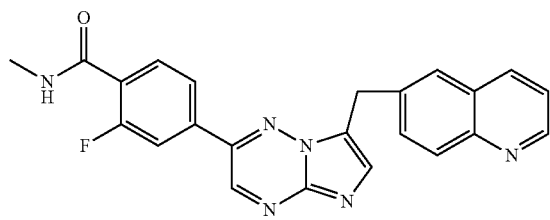 [SMILES: CNC(=O)c1ccc(-c2cnc3ncc(Cc4ccc5ncccc5c4)n3n2)cc1F]

Step 1. 4-Bromo-3-fluoro-N-methoxy-N-methylbenzamide

Oxalyl chloride (38.1 mL, 450 mmol) was slowly added to a mixture of 4-bromo-3-fluorobenzoic acid (49.3 g, 225 mmol) in dichloromethane (300 mL). Subsequently, N,N'-dimethylformamide (1.0 mL) was added and the reaction mixture was stirred at ambient temperature for 2 h. The reaction mixture was concentrated under reduced pressure and co-evaporated with toluene 3 times. The residue was then dissolved in dichloromethane (100 mL). The solution was added dropwise to a mixture of N,O-dimethylhydroxylamine hydrochloride (30.7 g, 315 mmol) and potassium carbonate (120 g, 900 mmol) in dichloromethane (300 mL) and water (300 mL). The reaction mixture was stirred at ambient temperature for 2 hours. The organic layer was separated. The aqueous layer was extracted with dichloromethane (2×50 mL). The combined organic extracts were washed with brine, dried over magnesium sulfate, filtered and concentrated under reduced pressure to give the product. (58.5 g) LCMS: (M+H)=261.9/263.9.

Step 2. 1-(4-Bromo-3-fluorophenyl)ethanone

To a solution of 4-bromo-3-fluoro-N-methoxy-N-methylbenzamide (58.5 g, 223 mmol) in tetrahydrofuran (500 mL) was added 3M of methylmagnesium chloride in THF (125 mL, 380 mmol) at 0° C. The reaction mixture was stirred for 1 hour at 0° C., and was quenched with cold aqueous ammonium chloride solution (150 mL). The organic layer was separated and concentrated under reduced pressure. The residue was redissolved in ethyl acetate (100 mL). The aqueous layer was diluted with water (100 mL) and was extracted with ethyl acetate (3×50 mL). The organic extracts were combined, washed with brine, and dried over magnesium sulfate. Filtration and concentration under reduced pressure gave the product (48.4 g) which was used in the next reaction step without further purification.

Step 3. (4-Bromo-3-fluorophenyl)(oxo)acetaldehyde and 1-(4-bromo-3-fluorophenyl)-2,2-dihydroxyethanone To a solution of 1-(4-bromo-3-fluorophenyl)ethanone (9.0 g, 41 mmol) in dimethyl sulfoxide (40 mL) was added slowly a 48% aqueous solution of hydrogen bromide. (14 mL) The reaction mixture was stirred at 60° C. overnight and then cooled to ambient temperature, poured into ice water. The precipitate was filtered and washed with water and the solid was dried under vacuum overnight to obtain 8.1 g of desired product. The aqueous layer was extracted with ethyl acetate 3 times. The combined extracts were washed with water, brine, dried, filtered, and concentrated to give an additional 2.2 g of the desired product. (10.3 g total).

Step 4. 1-(4-bromo-3-fluorophenyl)-2,2-diethoxyethanone

To a mixture of 1-(4-bromo-3-fluorophenyl)-2,2-dihydroxyethanone or 4-bromo-3-fluorophenyl)(oxo)acetaldehyde (7.0 g, 28 mmol) in toluene (50 mL) was added ethyl orthoformate (12 mL, 70 mmol) and p-toluenesulfonic acid (200 mg, 1 mmol). The reaction mixture was refluxed for 4 h. The reaction mixture was cooled to RT, diluted with ethyl acetate, washed with aqueous sodium bicarbonate, water, brine, and dried over magnesium sulfate. Concentration under reduced pressure gave the desired product which was used in the next step without further purification.

Step 5. 6-(4-Bromo-3-fluorophenyl)-1,2,4-triazin-3-amine

A mixture of 1-(4-bromo-3-fluorophenyl)-2,2-diethoxyethanone (15.2 g, 50 mmol), aminoguanidine bicarbonate (10.2 g, 75 mmol) and potassium hydroxide (6.6 g, 100 mmol) in ethanol (200 mL) and water (4 mL) was refluxed overnight. The solvent was evaporated under reduced pressure and the residue was washed with acetonitrile and filtered. The filtrate was concentrated under reduced pressure. The residue was dissolved in dichloromethane (100 mL), washed with water, brine, and concentrated under reduced pressure. The residue was dissolved in ethanol (50 mL). To the solution was added 0.2N hydrochloric acid (50 mL). The resultant mixture was heated to 110° C. for 8 h, and cooled with an ice-water bath. The precipitate that formed was collected by filtration and washed with isopropanol to give the desired product. (5.5 g, 41%) LCMS: (M+H)=286.8/288.8. $^1$H-NMR (400 MHz, CDCl$_3$): 8.60 (s, 1H), 7.79 (dd, J=8.6, 2.0 Hz, 1H), 7.68 (dd, J=8.3, 7.0 Hz, 1H), 7.61 (dd, J=8.3, 2.0 Hz, 1H), 5.43 (s, 2H).

Step 6. 3-quinolin-6-ylpropanal

Tris(dibenzylideneacetone)dipalladium (480 mg, 0.52 mmol) and tri-tert-butyl-phosphonium tetrafluoroborate (300 mg, 1.0 mmol) in a flask was evacuated and refilled with nitrogen (2 times). 1,4-dioxane (31 mL) was added followed by consecutive addition of 6-bromoquinoline (7.2 g, 35 mmol), 2-propen-1-ol (4.7 mL, 69 mmol) and N-cyclohexyl-N-methyl-cyclohexanamine (8.9 mL, 42 mmol). The reaction vessel was evacuated and refilled with nitrogen (2 times). The reaction mixture was stirred at 30° C. for 24 h. Diethyl ether (30 mL) was added to the reaction mixture and then filtered and washed with diethyl ether. The organic extract was concentrated under reduced pressure. The residue was purified by flash chromatography eluting with ethyl acetate in hexanes (0-50%) to afford the desired product. (~55%) LCMS: (M+H)=186.0; (M+H$_2$O+H)$^+$=204.0.

Step 7. 2-chloro-3-quinolin-6-ylpropanal

L-Proline (410 mg, 3.5 mmol) was added to a solution of 3-quinolin-6-ylpropanal (3.27 g, 17.6 mmol) in chloroform (39 mL) at 0° C. followed by addition of N-chlorosuccinimide (2.48 g, 18.5 mmol) and the reaction mixture was slowly warmed to ambient temperature and stirred for 1 h, monitoring by LCMS. The solvent was concentrated under reduced pressure and the residue was purified on a silica gel column with ethyl acetate in hexane (0-50%) to give the desired product. (95%) LCMS: (M+H+H$_2$O)=237.9/239.9.

Step 8. 6-[2-(4-Bromo-3-fluorophenyl)imidazo[1,2-b][1,2,4]triazin-7-yl]methyl-quinoline A mixture of 6-(4-bromo-3-fluorophenyl)-1,2,4-triazin-3-amine (800 mg, 2.97 mmol) and 2-chloro-3-quinolin-6-ylpropanal (784 mg, 3.57 mmol) in isopropyl alcohol (10.0 mL) in a sealed tube was heated at 110° C. for 48 h. After the reaction mixture was cooled to ambient temperature, the product was precipitated and collected by filtration. The mother liquor was concentrated and the residue was dissolved in ethyl acetate, washed with aqueous sodium bicarbonate, water, brine, dried over magnesium sulfate, and concentrated under reduced pressure. The residue was purified on a silica gel column with methanol in dichloromethane (0-6%) to give the desired product. (65%) LCMS: (M+H)=434.0/436.0.

Step 9. 2-Fluoro-4-[7-(quinolin-6-ylmethyl)imidazo[1,2-b][1,2,4]triazin-2-yl]benzo-nitrile Zinc cyanide (131 mg, 1.11 mmol), tris(dibenzylideneacetone)dipalladium(0) (35 mg, 0.038 mmol), (9,9-dimethyl-9H-xanthene-4,5-diyl)bis(diphenylphosphine) (78.5 mg, 0.136 mmol), and N,N,N',N'-Tetramethylethylenediamine (0.22 mL, 1.4 mmol) were added successively to a mixture of 6-[2-(4-bromo-3-fluorophenyl)imidazo[1,2-b][1,2,4]-triazin-7-yl]methylquinoline (480 mg, 1.10 mmol) in N,N-dimethylformamide (8.7 mL) in a microwave tube. The tube was sealed and degassed three times and heated to 160° C. under microwave irradiation for 500 s. Most of the solvent was removed under reduced pressure and the residue was dissolved in ethyl acetate, washed with aqueous sodium bicarbonate, water and brine, and dried over magnesium sulfate. Filtration and concentration afforded a residue which was purified on a silica gel column with methanol in dichloromethane (0-6%) to give the desired product. (90%) LCMS: (M+H)=381.0.

Step 10. 2-Fluoro-4-[7-(quinolin-6-ylmethyl)imidazo[1,2-b][1,2,4]triazin-2-yl]benzoic acid 2-Fluoro-4-[7-(quinolin-6-ylmethyl)imidazo[1,2-b][1,2,4]triazin-2-yl]benzonitrile (750 mg, 2 mmol) in a concentrated solution of hydrochloric acid (5.0 mL, 53 mmol) and water (1.0 mL) was stirred at 105° C. overnight. The solvent was removed under reduced pressure and the resultant residue was washed with water and filtered to provide the crude product which was directly used in next reaction step without further purification. LCMS: (M+H)=400.0.

Step 11. 2-Fluoro-N-methyl-4-[7-(quinolin-6-ylmethyl)imidazo[1,2-b][1,2,4]triazin-2-yl]benzamide 2-Fluoro-4-[7-(quinolin-6-ylmethyl)imidazo[1,2-b][1,2,4]triazin-2-yl]benzoic acid (0.350 µg, 0.876 mmol) and (benzotriazol-1-yloxy)tripyrrolidinophosphonium hexafluorophosphate (540 mg, 1.0 mmol) in N,N-dimethylformamide (5.0 mL) were stirred at ambient temperature for 3 min. A solution of 2M methylamine in THF (3.0 mL) was slowly added at 0° C. followed by triethylamine (0.61 mL, 4.4 mmol) and the reaction mixture was stirred for 2 h at ambient temperature. The reaction mixture was concentrated under reduced pressure to afford a yellow solid. Water (1.0 mL) was added and the solid was filtered and washed with acetonitrile and water. The yellow solid (260 mg) was shown to be the desired product by LCMS as the free base. The solid was then treated with 1.05 equivalents of hydrochloric acid to form the hydrochloric acid salt. The mother liquor was further purified by preparative HPLC to give another batch of the product. (~90%) LCMS: (M+H)=413.0.

Example 8: 2-(4-Bromo-3-fluorophenyl)-7-[(4-methoxyphenyl)thio]imidazo[1,2-b][1,2,4]triazine

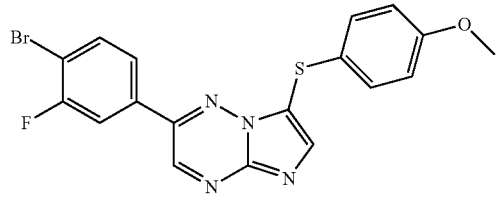

Step 1. 1-[(2,2-dimethoxyethyl)thio]-4-methoxybenzene

To an ice cooled solution of sodium ethoxide (3.26 g, 48.0 mmol) in ethanol (25.0 mL) was slowly added 4-methoxybenzenethiol (6.73 g, 48.0 mmol). The reaction mixture was stirred for 15 min. 2-Bromo-1,1-dimethoxyethane (5.64 mL, 48.0 mmol) was added, and the reaction mixture was refluxed for 2 h. After the precipitate was isolated by filtration, the mother liquor was evaporated under reduced pressure. The resultant residue was diluted with diethyl ether (100 mL) and washed with water and brine, dried over sodium sulfate, filtered, and concentrated to give the desired crude product (11.0 g) which was directly used in next step reaction without further purification. $^1$H-NMR (400 MHz, CDCl$_3$): 7.40 (m, 2H), 6.85 (m, 2H), 4.47 (t, J=5.6 Hz, 1H), 3.80 (s, 3H), 3.34 (s, 6H), 3.01 (d, J=5.6 Hz, 2H).

Step 2. [(4-methoxyphenyl)thio]acetaldehyde

1-[(2,2-Dimethoxyethyl)thio]-4-methoxybenzene (11.0 g) was dissolved in 1% aqueous hydrochloric acid (60 mL) and acetone (30 mL). The reaction mixture was refluxed for 2 h. Acetone was removed under reduced pressure and the residue was neutralized with aqueous sodium bicarbonate and extracted with ethyl acetate. The organic layer was dried over sodium sulfate, filtered, and concentrated under reduced pressure. The residue was purified by flash chromatography on silica gel with 20% ethyl acetate in hexanes to afford the desired product (8.5 g, 97%). ¹H-NMR (400 MHz, CDCl₃): 9.55 (t, J=4.2 Hz, 1H), 7.36 (m, 2H), 6.84 (m, 2H), 3.79 (s, 3H), 3.40 (d, J=4.2 Hz, 2H).

Step 3. 2-(4-bromo-3-fluorophenyl)-7-[(4-methoxyphenyl)thio]imidazo[1,2-b][1,2,4]triazine To a cooled (0° C.) reaction mixture of [(4-methoxyphenyl)thio]acetaldehyde (36.4 mg, 0.2 mmol) and D-proline (4.6 mg, 0.04 mmol) in chloroform (1.2 mL) was added N-chlorosuccinimide. (26.7 mg, 0.2 mmol). The reaction mixture was stirred at 0° C. for 30 min, then gradually warmed to RT for 2 h. To the reaction mixture was added [6-(4-bromo-3-fluorophenyl)-1,2,4-triazin-3-amine (26.9 mg, 0.1 mmol). The reaction mixture was stirred for 1 h. The solvent was removed under reduced pressure. The residue was dissolved in isopropanol (2 mL) and heated at 100° C. overnight. After cooling, the reaction mixture was filtered and the filtrate was purified by RP-HPLC (pH=10) to afford the desired product. LCMS: (M+H)⁺=431.0.

Example 9: 2-Fluoro-4-(3-[(4-methoxyphenyl)thio]imidazo[1,2-a]pyrimidin-6-yl)-N-methylbenzamide

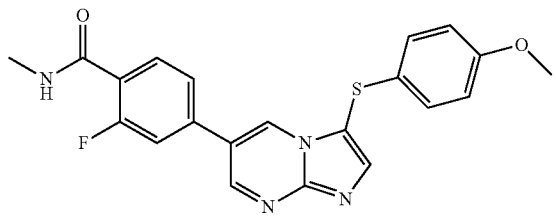

Step 1. 4-(2-aminopyrimidin-5-yl)-2-fluoro-N-methylbenzamide

A mixture of 4-bromo-2-fluoro-N-methylbenzamide (900 mg, 3.9 mmol), 5-(4,4,5,5-tetramethyl-1,3,2-dioxaborolan-2-yl)pyrimidin-2-amine (710 mg, 3.2 mmol), tetrakis(triphenylphosphine)palladium (100 mg, 0.1 mmol) and potassium carbonate (1.3 g, 9.7 mmol) in toluene (6.0 mL) and ethanol (3.0 mL) and water (3.0 mL) was heated at 110° C. for 2 hours. After cooling to RT, the reaction mixture was quenched with water and extracted with diethyl ether. The solid was filtered and washed with water and diethyl ether to afford the desired product (720 mg).

Step 2. 2-fluoro-4-(3-[(4-methoxyphenyl)thio]imidazo[1,2-a]pyrimidin-6-yl)-N-methylbenzamide This compound was prepared using procedures analogous to those for Example 8. LCMS: (M+H)=409.0.

Example 10: 2-chloro-4-3-[(4-methoxyphenyl)thio]imidazo[1,2-a]pyrimidin-6-yl-N-methylbenzamide

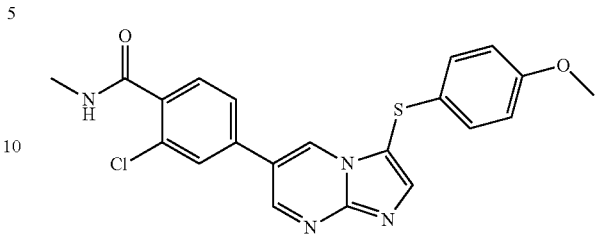

This compound was prepared using procedures analogous to those for Example 8. LCMS: (M+H)=425.0/427.0.

Example 11: 2-Fluoro-N-methyl-4-[3-(quinolin-6-ylthio)imidazo[1,2-a]pyrimidin-6-yl]benzamide

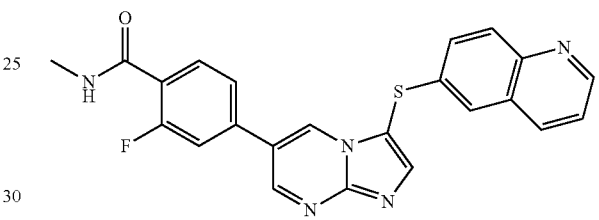

Step 1. 2-fluoro-4-imidazo[1,2-a]pyrimidin-6-yl-N-methylbenzamide

A mixture of 4-(2-aminopyrimidin-5-yl)-2-fluoro-N-methylbenzamide (123 mg, 0.5 mmol) and chloroacetaldehyde (0.318 mL, 2.5 mmol) in isopropyl alcohol (4 mL) was stirred at 90° C. for 4 h. The solvent was removed under vacuum and the residue was triturated with ethyl acetate and hexanes. The solid formed was collected and dried under reduced pressure to give the desired product (120 mg, 88.8%). LCMS: (M+H)=271.0.

Step 2. 4-(3-bromoimidazo[1,2-a]pyrimidin-6-yl)-2-fluoro-N-methylbenzamide

Bromine (17.4 μL, 0.338 mmol) was added to a mixture of sodium acetate (40.3 mg, 0.491 mmol) and 2-fluoro-4-imidazo[1,2-a]pyrimidin-6-yl-N-methylbenzamide (83.0 mg, 0.307 mmol) in acetic acid (2.6 mL) and the reaction mixture was stirred at ambient temperature for 30 min. The solvent was removed under reduced pressure. The residue was dissolved in ethyl acetate and washed with saturated sodium bicarbonate and brine, dried over sodium sulfate, filtered, and concentrated. The residue was purified by chromatography on silica gel with ethyl acetate in dichloromethane (0-50%) to afford the desired product (95 mg, 88.6%). LCMS: (M+H)=348.8/350.9.

Step 3. quinoline-6-thiol

To a solution of 6-bromoquinoline (0.81 g, 3.89 mmol) in N,N-dimethylacetamide (4 mL) was added sodium methyl mercaptide (2.0 g, 28.5 mmol). The mixture was heated at 150° C. for 2 h. After cooling, the mixture was diluted with ethyl acetate, and neutralized with aqueous 1N hydrochloric acid. The organic layer was separated and the aqueous layer was extracted with ethyl acetate. The combined organic extracts were washed with water and brine, dried over magnesium sulfate, filtered, and concentrated under reduced pressure. The residue was directly used in the next step without further purification. (0.50 g, 79%) LCMS: (M+H)+=161.9.

Step 4. 2-fluoro-N-methyl-4-[3-(quinolin-6-ylthio)imidazo[1,2-a]pyrimidin-6-yl]benzamide N,N-Diisopropylethylamine (70 µL, 0.4 mmol), tris(dibenzylideneacetone)-dipalladium(0) (4.58 mg, 0.0050 mmol) and (9,9-dimethyl-9H-xanthene-4,5-diyl)bis(diphenylphosphine) (5.79 mg, 0.010 mmol) was added successively to a solution of 4-(3-bromoimidazo[1,2-a]pyrimidin-6-yl)-2-fluoro-N-methylbenzamide (69.8 mg, 0.2 mmol) and quinoline-6-thiol (32.2 mg, 0.2 mmol) in 1,4-dioxane (0.42 mL) in a microwave tube. The tube was sealed and degassed three times, and heated to 100° C. overnight. After cooling, the reaction mixture was diluted with methanol, and filtered. The filtrate was purified by RP-HPLC (pH 10) to give the desired product. LCMS: (M+H)=430.0.

Example 12: 2-chloro-N-methyl-4-[3-(quinolin-6-ylthio)imidazo[1,2-a]pyrimidin-6-yl]benzamide

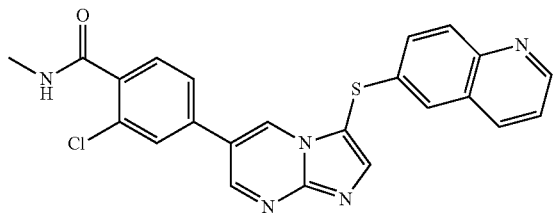 [SMILES: CNC(=O)c1ccc(-c2cnc3ncc(Sc4ccc5ncccc5c4)n3c2)cc1Cl]

This compound was prepared using procedures analogous to those for Example 11. LCMS: (M+H)=446.0

Example 13: Methyl 2-fluoro-4-[7-(quinolin-6-ylthio)imidazo[1,2-b][1,2,4]triazin-2-yl]benzoate

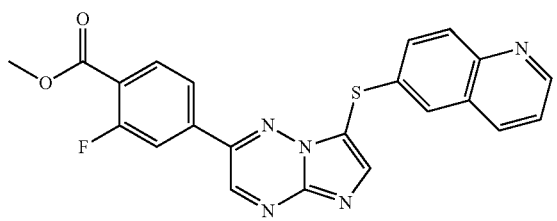 [SMILES: COC(=O)c1ccc(-c2cnc3ncc(Sc4ccc5ncccc5c4)n3n2)cc1F]

Step 1. 6-[(2,2-dimethoxyethyl)thio]quinoline

To a solution of 6-bromoquinoline (0.832 g, 4.0 mmol) in N,N-dimethylacetamide (4.0 mL) was added sodium methyl mercaptide (0.841 g, 12.0 mmol). The reaction mixture was heated at 150° C. for 2 h. After cooling, 2-bromo-1,1-dimethoxyethane (1.41 mL, 12.0 mol) was then added, and the reaction mixture was diluted with ethanol (5 mL), and heated at 80° C. for 1 h. After the precipitated salt was isolated by filtration, the mother liquor was evaporated under reduced pressure. The residue was diluted with diethyl ether (50 mL), washed with water, brine, dried over sodium sulfate, filtered, and concentrated. The residue was directly used in the next reaction step without further purification. LCMS: (M+H)=249.9.

Step 2. (quinolin-6-ylthio)acetaldehyde

6-[(2,2-Dimethoxyethyl)thio]quinoline (1.0 g) was dissolved in aqueous 1N hydrochloric acid (6 mL) and acetone (3 mL). The reaction mixture was refluxed for 3 h. Acetone was removed under reduced pressure. The aqueous layer was neutralized with saturated sodium bicarbonate and extracted with ethyl acetate. The organic extracts were dried over sodium sulfate, filtered, and concentrated. The residue was purified by chromatography on silica gel with 20% ethyl acetate in hexanes to afford the desired product. LCMS: (M+H)=204.0; (M+H$_2$O)=221.9; (M+MeOH)=236.0.

Step 3. 4-acetyl-2-fluorobenzonitrile

N,N,N',N'-Tetramethylethylenediamine (0.667 mL, 4.42 mmol), zinc cyanide (1.46 g, 12.4 mmol), tris(dibenzylideneacetone)dipalladium(0) (54.05 mg, 0.059 mmol) and (9,9-dimethyl-9H-xanthene-4,5-diyl)bis(diphenylphosphine) (124.3 mg, 0.215 mmol) was added successively to a solution of 1-(4-bromo-3-fluorophenyl)ethanone (4.34 g, 20.0 mmol) in N,N-dimethylformamide (15 mL) in a microwave tube. The tube was sealed and degassed three times, and heated to 160° C. under microwave irradiation with a 240 s hold time, and 300 Watt maximum power input. After cooling, the reaction mixture was filtered through a pad of Celite with a thin layer of silica gel in the middle using dichloromethane as the eluant. The combined filtrates were concentrated under reduced pressure. The residue was purified by chromatography on silica gel with ethyl acetate in hexanes (0-40%) to give the desired product. (3.20 g, 98.1%).

Step 4. 4-acetyl-2-fluorobenzoic acid

A suspension of 4-acetyl-2-fluorobenzonitrile (2.42 g, 14.8 mmol) in aqueous hydrochloric acid (20%, 100 mL) was refluxed (oil bath temperature: 110° C.) overnight. After cooling, the crystals formed were collected by filtration and dried to give the desired product (2.16 g). The mother liquor was concentrated under reduced pressure. The residue was washed with water and filtered to give 300 mg of the desired product. (2.46 g, 91%) LCMS (M+H)=182.9.

Step 5. methyl 4-acetyl-2-fluorobenzoate

4-Acetyl-2-fluorobenzoic acid (46.1 mmol, 0.0461 mol) in dichloromethane (30 mL) was treated with oxalyl chloride (7.8 mL, 92 mmol) and N,N-dimethylformamide (0.2 mL) at 0° C. The reaction mixture was stirred at ambient temperature for 3 h. The reaction mixture was concentrated under reduced pressure and the residue was dissolved in dichloromethane (50 mL, 0.78 mol) and cooled to 0° C. A solution of methanol (4.7 mL) and triethylamine (16 mL, 120 mmol) was added. The reaction mixture was stirred at ambient temperature for 1 h, washed with water aqueous 1N hydrochloric acid, and brine. The organic extracts were dried over magnesium sulfate, filtered, and concentrated under reduced pressure. The residue was purified by flash chromatography eluting with 20% ethyl acetate in hexanes to afford the desired product. (5.64 g, 62.4%).

Step 6. methyl 2-fluoro-4-(oxoacetyl)benzoate

A mixture of methyl 4-acetyl-2-fluorobenzoate (1.6 g, 8.2 mmol) and 8.8M hydrogen bromide in water (2.8 mL) in dimethyl sulfoxide (20 mL) was stirred at 60° C. overnight. After cooling, the mixture was poured into ice-water. The reaction mixture was extracted with diethyl ether. The combined organic extracts were washed with brine, dried over sodium sulfate, filtered and concentrated to yield the desired product which was used in the next reaction step without further purification. (1.60 g, 93.3%).

Step 7. methyl 4-(diethoxyacetyl)-2-fluorobenzoate

A mixture of methyl 2-fluoro-4-(oxoacetyl)benzoate (6.0 g, 0.028 mol), ethyl orthoformate (12.0 mL, 0.071 mol), and p-toluenesulfonic acid monohydrate (200 mg) in toluene (60 mL) was heated under reflux for 4 h. After cooling, the reaction mixture was concentrated under reduced pressure to give the desired product which was used in the next step without further purification.

Step 8. methyl 2-fluoro-4-[3-(methylthio)-1,2,4-triazin-6-yl]benzoate

Methyl 4-(diethoxyacetyl)-2-fluorobenzoate (3.0 g, 0.01 mol) was dissolved in ethanol (30 mL). Thiosemicarbazide (1.2 g, 0.013 mol) and p-toluenesulfonic acid monohydrate (100 mg) were added to the reaction mixture. The reaction mixture was heated at 90° C. for 2 h. After cooling, the reaction mixture to ambient temperature methyl iodide (3 mL, 0.05 mol) was added. The reaction mixture was stirred at RT for 2 h, and then concentrated under reduced pressure. The residue was dissolved in acetic acid (50 mL), and heated at 60° C. for 2 h. The reaction mixture was concentrated under reduced pressure. The residue was taken up in methanol and the precipitate was collected by filtration and dried under reduced pressure to give the desired product. (1.2 g, 41%).

Step 9. methyl 4-(3-amino-1,2,4-triazin-6-yl)-2-fluorobenzoate

To a solution of methyl 2-fluoro-4-[3-(methylthio)-1,2,4-triazin-6-yl]benzoate (1.2 g, 4.3 mmol) in dichloromethane (90 mL) at 0° C. was added slowly a solution of m-chloroperbenzoic acid (1.5 g, 6.4 mmol) in dichloromethane. (5.0 ml) The reaction mixture was stirred at 0° C. for 2 h, and quenched with saturated aqueous sodium thiosulfate. The organic layer was separated, washed with saturated aqueous sodium bicarbonate, water, brine, dried over sodium sulfate, filtered, and concentrated under reduced pressure to yield the desired intermediate. LCMS: 295.9 (M+H).

A mixture of the above intermediate and a 2M solution of ammonia in isopropyl alcohol (20 mL) was stirred at ambient temperature for 2 h. The solid formed was collected by filtration and washed with isopropanol to provide the desired product. (700 mg, 60%) LCMS: 248.9, 267.0.

Step 10. methyl 2-fluoro-4-[7-(quinolin-6-ylthio)imidazo[1,2-b][1,2,4]triazin-2-yl]benzoate To a cooled (0° C.) mixture of (quinolin-6-ylthio)acetaldehyde (40.6 mg, 0.2 mmol) and D-proline (4.6 mg, 0.04 mmol) in chloroform (1.0 mL) was added N-chlorosuccinimide (26.7 mg, 0.2 mmol) with stirring. The mixture was stirred at 0° C. for 30 min, then gradually warmed to ambient temperature for 2 h. To the mixture was added methyl 4-(3-amino-1,2,4-triazin-6-yl)-2-fluorobenzoate (24.8 mg, 0.1 mmol). The reaction mixture was stirred for 1 h. The solvent was removed under reduced pressure. The residue was dissolved in isopropanol (2 mL) and heated to 100° C. overnight. After cooling, the mixture was filtered and the filtrate was purified by RP-HPLC (pH 10) to afford the desired product. LCMS: (M+H)=432.3.

Example 14: 2-(4-Bromo-3-fluorophenyl)-7-(4-methoxyphenoxy)imidazo[1,2-b][1,2,4]triazine

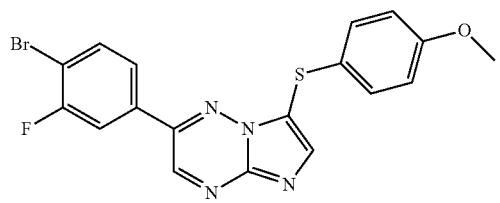 [SMILES: COc1ccc(Sc2cnc3ncc(-c4ccc(Br)c(F)c4)nn23)cc1]

Step 1. (4-methoxyphenoxy)acetaldehyde 1-(2,2-Diethoxyethoxy)-4-methoxybenzene (4.8 g, 20 mmol) was dissolved in 1% aqueous HCl (30 mL) and acetone (15 mL). The reaction mixture was heated under refluxed for 2 h. Acetone was removed under reduced pressure. The aqueous mixture was neutralized with saturated sodium bicarbonate, and extracted with ethyl acetate. The organic layer was dried over sodium sulfate, filtered, and concentrated. The residue was dried under reduced pressure to afford the desired product which was used in the next step without further purification. (3.30 g, 99.3%).

Step 2. 2-(4-bromo-3-fluorophenyl)-7-(4-methoxyphenoxy)imidazo[1,2-b][1,2,4]triazine To a cooled (0° C.) mixture of (4-methoxyphenoxy)acetaldehyde (33.2 mg, 0.2 mmol) and D-proline (4.6 mg, 0.04 mmol) in chloroform (1.0 mL) was added N-chlorosuccinimide (26.7 mg, 0.2 mmol) with stirring. The mixture was stirred at 0° C. for 30 min, then gradually warmed to ambient temperature for 2 h. To the reaction mixture was added 6-(4-bromo-3-fluorophenyl)-1,2,4-triazin-3-amine (26.9 mg, 0.1 mmol). The reaction mixture was stirred for 1 h and then the solvent was removed under reduced pressure. The residue was dissolved in isopropanol (2 mL) and heated to 100° C. overnight. After cooling, the mixture was filtered and the filtrate was purified by RP-HPLC (pH 10) to afford the desired product. LCMS: (M+H)=415.0/416.9.

Example 15: 3-(4-Methoxyphenoxy)-6-(4-methyl-1H-pyrazol-1-yl)imidazo[1,2-a]pyrimidine

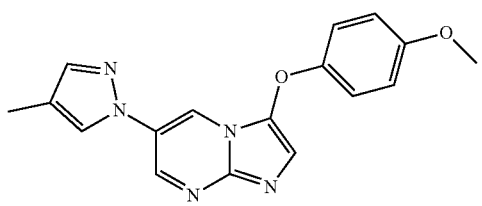

Step 1. 5-(4-methyl-1H-pyrazol-1-yl)pyrimidin-2-amine

A suspension of 4-methyl-1H-pyrazole (0.72 g, 0.0088 mol), 5-bromopyrimidin-2-amine (1.3 g, 7.3 mmol), copper (I) iodide (58.2 mg, 0.306 mmol), N,N'-dimethylcyclohexane-1,2-diamine (0.193 mL, 1.22 mmol), potassium carbonate (1.77 g, 12.8 mmol) in N,N-dimethylformamide (5.0 mL) was irradiated under microwave at 180° C. for 1 h. After cooling, the mixture was purified by chromatography on silica gel with methanol in methylene chloride (0-10%) to afford the desired product. LCMS: (M+H)=176.0.

Step 2. 3-(4-methoxyphenoxy)-6-(4-methyl-1H-pyrazol-1-yl)imidazo[1,2-a]pyrimidine This compound was prepared using procedures analogous to those for Example 14. LCMS: (M+H)=322.0.

Example 16: 6-(4-Bromophenyl)-3-(4-methoxyphenoxy)imidazo[1,2-a]pyrimidine

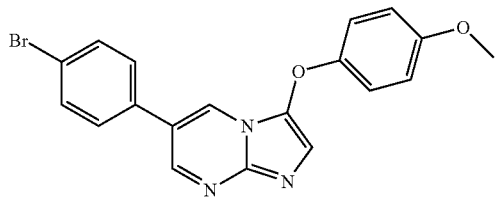 [SMILES: COc1ccc(Sc2cnc3ncc(-c4ccc(Br)cc4)cn23)cc1]

Step 1. (2Z)-2-(4-bromophenyl)-3-(dimethylamino)acrylaldehyde

Phosphoryl chloride (55.0 mL, 590 mmol) was added dropwise to N,N-dimethylformamide (80.0 mL) at 0° C. The reaction mixture was stirred at 0° C. for an additional 30 min after which 4-bromophenylacetic acid (43.0 g, 200 mmol) was added portion wise. The resulting mixture was heated at 70° C. overnight. After cooling, the reaction mixture was added slowly to a mixture of ice and water with external cooling. Ice was added intermittently to keep the temperature <10° C. When the quenching was complete, potassium carbonate and ice were added slowly until pH 11 was achieved. Small quantities of ethanol were added to control frothing. To the alkaline mixture was added toluene (120 mL), and the reaction mixture was refluxed for 1.5 hours and cooled to ambient temperature. The aqueous layer was extracted with toluene (2×50 mL). The combined organic extracts were washed with water, dried over sodium sulfate, filtered, and concentrated under reduced pressure. The residue was recrystallized from dichloromethane/hexanes to give the desired product. (26.5 g, 52%) LCMS: (M+H)=281.0/283.0.

Step 2. 5-(4-bromophenyl)pyrimidin-2-amine

A mixture of (Z)-2-(4-bromophenyl)-3-(dimethylamino)acrylaldehyde (1.27 g, 5 mmol), guanidine hydrochloride (0.525 g, 5.5 mmol) and potassium carbonate (1.38 g, 10 mmol) in ethanol (10 mL) was heated at 80° C. overnight. After cooling, the reaction mixture was filtered, washed with methanol and water, and dried under high vacuum to give the desired product (1.2 g, 96%). LCMS: (M+H)=249.9/251.9.

Step 3. 6-(4-bromophenyl)-3-(4-methoxyphenoxy)imidazo[1,2-a]pyrimidine

This compound was prepared using procedures analogous to those for Example 14. LCMS: (M+H)=395.9/397.9.

Example 17: 2-chloro-N-methyl-4-[3-(quinolin-6-yloxy)imidazo[1,2-a]pyrimidin-6-yl]benzamide

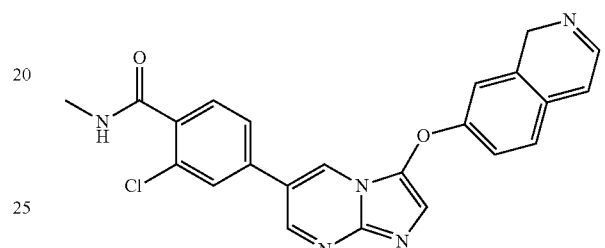

Step 1. 6-(2,2-dimethoxyethoxy)quinoline

To a cooled (0° C.) solution of quinolin-6-ol (5.81 g, 40 mmol) in N,N-dimethylformamide (30 mL) was slowly added a 1M solution of sodium hexamethyldisilazane in THF (40 mL, 40 mmol). The mixture was stirred for 15 min after which 2-bromo-1,1-dimethoxyethane (5.18 mL, 44 mmol) was added. The reaction mixture was then refluxed conditions for 6 h. The solvent was evaporated under reduced pressure. The residue was diluted with diethyl ether (100 mL) and washed with water, brine, dried over sodium sulfate, filtered, and concentrated. The residue was purified by flash chromatography eluting with ethyl acetate in hexanes. (0-50%) to give the desired product. (9 g, 96%) LCMS: (M+H)$^+$=233.9.

Step 2. 2-(quinolin-6-yloxy)acetaldehyde 6-(2,2-dimethoxyethoxy)quinoline (9.0 g) was dissolved in aqueous 1N hydrochloric acid (60 mL) and acetone (30 mL). The reaction mixture was heated under reflux for 3 h. Acetone was removed under reduced pressure. To the residue was added ethyl acetate, and the solution was neutralized with aqueous 1N NaOH. The organic layer was washed with brine, dried over sodium sulfate, filtered, and concentrated to afford the desired product which was used in the next step without further purification. (4.8 g) LCMS: (M+H$_2$O)=205.9, and (M+MeOH)=219.9.

Step 3. 2-chloro-N-methyl-4-[3-(quinolin-6-yloxy)imidazo[1,2-a]pyrimidin-6-yl]benzamide This compound was prepared using procedures analogous to those for Example 14. LCMS: (M+H)=430.0/432.0

Example 18: 2-Fluoro-N-methyl-4-[3-(1-quinolin-6-ylcyclopropyl)imidazo[1,2-a]pyrimidin-6-yl]benzamide

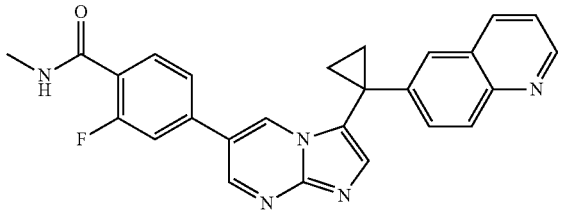

Step 1. quinolin-6-ylacetonitrile

To a mixture of (9,9-dimethyl-9H-xanthene-4,5-diyl)bis(diphenylphosphine) (6.7 g, 12 mmol), tris(dibenzylideneacetone)dipalladium(0) (10 g, 12 mmol), 6-bromoquinoline (120 g, 577 mmol) in N,N-dimethylformamide (360 mL) in a 3-neck round bottom flask with stirring under positive nitrogen pressure was added (trimethylsilyl)acetonitrile (98.7 mL, 721 mmol), followed by zinc difluoride (42 g, 400 mmol). The flask was sealed under an atmosphere of nitrogen. The reaction mixture was stirred at 105° C. for 20 h. After cooling the solution to RT, the reaction mixture was quenched with an aqueous ammonia solution and extracted with ethyl acetate (3×500 mL). The combined organic extracts were washed with brine, dried over sodium sulfate, filtered, and concentrated under reduced pressure. The residue was purified under flash chromatography eluting with ethyl acetate in hexanes (0-65%) to afford the desired product. (70 g, 72.1%) LCMS: (M+H)=168.9.

Step 2. 1-quinolin-6-ylcyclopropanecarbonitrile 60 mL of 50% aqueous sodium hydroxide was added to a mixture of 1-bromo-2-chloroethane (22.0 mL, 265 mmol), quinolin-6-ylacetonitrile (16.0 g, 66.6 mmol), and benzyltriethylammonium chloride (990 mg, 4.3 mmol) at 50° C. The reaction mixture was stirred at 50° C. for 3 h. After cooling to RT, the reaction mixture was poured into 100 mL water, and extracted with dichloromethane (3×100 mL). The combined organic extracts were dried over sodium sulfate, filtered through a pad of silica gel eluting with 20% ethyl acetate in dichloromethane. The filtrate was concentrated to give the desired product which was used in the next step without further purification. (12.4 g, 96%).

Step 3. 1-quinolin-6-ylcyclopropanecarbaldehyde

Diisobutylaluminum hydride (1M in THF, 96 mL, 96 mmol) was added to a solution of 1-quinolin-6-ylcyclopropanecarbonitrile (12.4 g, 63.9 mmol) in toluene (120 mL) at −78° C. under an atmosphere of nitrogen. The reaction mixture was allowed to warm to −5 to 0° C., and stirred at that temperature for 3 h. The reaction mixture was cooled to −60° C. Isopropyl alcohol (10 mL) was carefully added dropwise. After stirring for 30 min, the reaction mixture was warmed to −5 to 0° C. The reaction mixture was diluted with ethyl acetate, quenched with water and extracted with ethyl acetate. The combined organic extracts were washed with water, brine, dried over sodium sulfate, filtered through a pad of silica gel eluting with 40% ethyl acetate in hexanes. The filtrate was concentrated to yield the desired product. (12 g, 95.1%).

Step 4. 6-1-[(E)-2-methoxyvinyl]cyclopropylquinoline

To a suspension of chloro(methoxymethyl)triphenylphosphorane (3.5 g, 10 mmol) in tetrahydrofuran (10 mL) at −10° C. was added dropwise a solution of 1.0 M potassium tert-butoxide in tetrahydrofuran (10 mL). After the reaction mixture was stirred at RT for 1 hour, the reaction mixture was cooled to 0° C. and a solution of 1-quinolin-6-ylcyclopropanecarbaldehyde (500 mg, 2.5 mmol) in THF (5 mL) was added. The mixture was stirred at ambient temperature for 1 h. The reaction mixture was filtered through a pad of silica gel eluting with dichloromethane. The solution was concentrated and the residue was purified by flash chromatography eluting with ethyl acetate in hexanes (0-30% in 17 min) to afford the desired product. (450 mg, 78.8%) LCMS: (M+H)=226.3.

Step 5. (1-quinolin-6-ylcyclopropyl)acetaldehyde

To a solution of 6-1-[(E)-2-methoxyvinyl]cyclopropylquinoline (450 mg, 2.0 mmol) in THF (30 mL) was added 3 ml of 10% aqueous HCl solution at ambient temperature with stirring. The reaction mixture was stirred at ambient temperature for 2 h, and then neutralized with saturated sodium bicarbonate. The mixture was extracted with ethyl acetate. The organic extract was washed with brine, dried over sodium sulfate, filtered, and concentrated to yield the desired product which was used in the next reaction step without further purification. (410 mg, 97.2%) LCMS: (M+H)=212.2; (M+H$_2$O+H)=230.2.

Step 6. chloro(1-quinolin-6-ylcyclopropyl)acetaldehyde

To a mixture of (1-quinolin-6-ylcyclopropyl)acetaldehyde (410 mg, 1.94 mmol), D-proline (45 mg, 0.39 mmol) in dichloromethane (10 mL) cooled (0° C.) was added N-chlorosuccinimide (311 mg, 2.33 mmol) with stirring. The reaction mixture was stirred at 0° C. for 1 h, then gradually warmed to RT. The reaction mixture was quenched with water, extracted with dichloromethane. The combined organic extracts were concentrated and the residue purified by flash chromatography eluting with ethyl acetate in hexanes (0-25% in 18 min) to afford the desired product. (320 mg, 67.1%) LCMS: (M+H)=246.2; (M+H$_2$O+H)=264.2.

Step 7. 2-fluoro-N-methyl-4-[3-(1-quinolin-6-ylcyclopropyl) imidazo[1,2-a]pyrimidin-6-yl]benzamide A mixture of 4-(2-aminopyrimidin-5-yl)-2-fluoro-N-methylbenzamide (0.72 g, 2.9 mmol) and 1-[2-chloro-1-hydroxy-2-(1-quinolin-6-ylcyclopropyl)ethyl]pyrrolidine-2,5-dione (1.0 g, 2.9 mmol) in ethanol (20 mL) was stirred at 105° C. overnight. After cooling, the reaction mixture was purified by RP-HPLC (pH=2) to afford the desired product as the trifluoroacetic acid salt. (1.0 g, 43.9%) LCMS: (M+H)=438.0.

Example 19: 6-(4-bromophenyl)-3-[(4-methoxyphenyl)thio]imidazo[1,2-a]pyrimidine

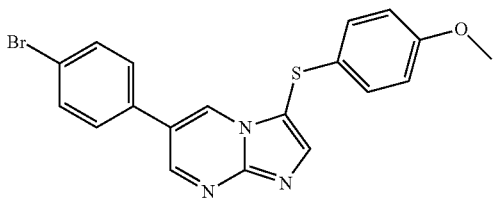

This compound was prepared using procedures analogous to those for Example 8. LCMS: (M+H)=412.0/414.0; ¹H-NMR (400 MHz, CDCl₃): 8.83 (d, J=2.5 Hz, 1H), 8.61 (d, J=2.5 Hz, 1H), 8.18 (s, 1H), 7.65 (m, 2H), 7.39 (m, 2H), 7.14 (m, 2H), 6.80 (m, 2H), 3.75 (s, 3H).

Example 20: 2-(4-fluorophenyl)-7-[(4-methoxyphenyl)thio]imidazo[1,2-b][1,2,4]triazine

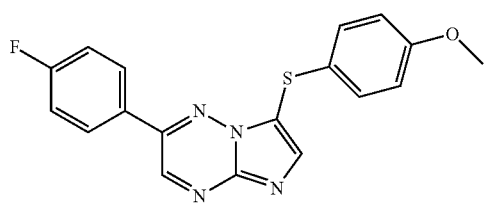 [SMILES: COc1ccc(Sc2cnc3ncc(-c4ccc(F)cc4)nn23)cc1]

This compound was prepared using procedures analogous to those for Example 8. LCMS: (M+H)=353.0; ¹H-NMR (400 MHz, CDCl₃): 8.88 (s, 1H), 8.16 (s, 1H), 7.96-8.01 (m, 4H), 7.45 (m, 2H), 6.82 (m, 2H), 3.76 (s, 3H).

Example 21: 6-(1-{6-[3-Fluoro-4-(1-methyl-2-oxo-2-pyrrolidin-1-ylethoxy)phenyl]imidazo[1,2-a]pyrimidin-3-yl}cyclopropyl)quinoline

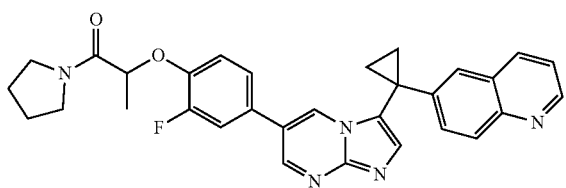 [SMILES: CC(Oc1ccc(-c2cnc3ncc(C4(c5ccc6ncccc6c5)CC4)n3c2)cc1F)C(=O)N1CCCC1]

Step 1. 4-(2-aminopyrimidin-5-yl)-2-fluorophenol

A mixture of 5-bromopyrimidin-2-amine (3.3 g, 19 mmol), (3-fluoro-4-hydroxyphenyl)boronic acid (2.7 g, 17 mmol), tetrakis(triphenylphosphine)palladium (0.6 g, 0.5 mmol), sodium carbonate (18.3 g, 172 mmol) in ethanol (15 mL), water (5 mL) and toluene (15 mL) was heated at 120° C. for 3 h. The volatiles were removed under reduced pressure. The residue was diluted with EtOAc, washed with water and brine, dried over MgSO₄, filtered, and concentrated to obtain the desired product which was directly used in the next step.

Step 2. tert-butyl 2-[4-(2-aminopyrimidin-5-yl)-2-fluorophenoxy]propionate

To a solution of triphenylphosphine (0.315 g, 1.2 mmol) in tetrahydrofuran (THF, 5.0 mL) was added diethyl azodicarboxylate (0.19 mL, 1.2 mmol) and tert-butyl (S)-2-hydroxypropanoate (292 mg, 2 mmol) followed by 4-(2-aminopyrimidin-5-yl)-2-fluorophenol (0.20 g, 1.0 mmol) at RT (RT) under nitrogen. The mixture was stirred overnight at RT, evaporated and the residue was purified by chromatography on silica gel to afford the desired product (0.24 g, 72%). LCMS: (M+H)=334.1.

Step 3. tert-butyl 2-{2-fluoro-4-[3-(1-quinolin-6-ylcyclopropyl)imidazo[1,2-a]pyrimidin-6-yl]phenoxy}propanoate A mixture of tert-butyl 2-[4-(2-aminopyrimidin-5-yl)-2-fluorophenoxy]propanoate (0.33 g, 1.0 mmol) and chloro(1-quinolin-6-ylcyclopropyl)acetaldehyde (0.24 g, 1.0 mmol) in isopropanol was heated at 100° C. overnight. After cooling to RT, the mixture was purified by RP-HPLC (pH 2.0) to afford the desired product (0.22 g, 42%). LCMS: (M+H)=525.2.

Step 4. 2-{2-fluoro-4-[3-(1-quinolin-6-ylcyclopropyl)imidazo[1,2-a]pyrimidin-6-yl]phenoxy}propanoic acid tert-Butyl-2-{2-fluoro-4-[3-(1-quinolin-6-ylcyclopropyl)imidazo[1,2-a]pyrimidin-6-yl]phenoxy}propanoate (100 mg, 0.2 mmol) was dissolved in a mixed solvent of methylene chloride (5.0 mL) and trifluoroacetic acid (5.0 mL). The solution was stirred at RT for 2 h. The volatiles were evaporated under reduced pressure. The residue was co-evaporated with toluene three times, and was directly used in next step. LCMS: (M+H)=469.1.

Step 5. 6-(1-{6-[3-fluoro-4-(1-methyl-2-oxo-2-pyrrolidin-1-ylethoxy)phenyl]imidazo[1,2-a]pyrimidin-3-yl}cyclopropyl)quinoline To a solution of 2-{2-fluoro-4-[3-(1-quinolin-6-ylcyclopropyl)imidazo[1,2-a]pyrimidin-6-yl]phenoxy}propanoic acid (59.1 mg, 0.126 mmol) in N,N-dimethylformamide (1.0 mL) was added benzotriazol-1-yloxytris(dimethylamino)phosphonium hexafluorophosphate (56 mg, 0.126 mmol), pyrrolidine (9.0 mg, 0.13 mmol) and N,N-diisopropylethylamine (0.1 mL) at RT. The mixture was stirred at RT for 3 h, and then purified by RP-HPLC (pH 10) to afford the desired product. LCMS: (M+H)=522.0.

Example 22: 6-{1-[6-(1H-Pyrazol-1-yl)imidazo[1,2-a]pyrimidin-3-yl]cyclopropyl}quinoline

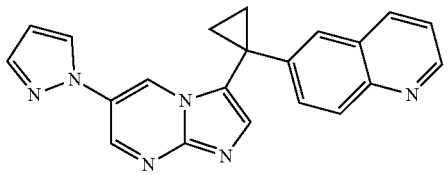 [SMILES: c1cnc2ccc(C3(c4cnc5ncc(-n6cccn6)cn45)CC3)cc2c1]

Step 1. 5-(1H-pyrazol-1-yl)pyrimidin-2-amine

A suspension of 1H-pyrazole (0.42 g, 0.0061 mol), 5-bromopyrimidin-2-amine (1.3 g, 7.3 mmol), copper(I) iodide (58.2 mg, 0.306 mmol), N,N'-dimethylcyclohexane-1,2-diamine (0.193 mL, 1.22 mmol), potassium carbonate (1.77 g, 12.8 mmol) in N,N-dimethylformamide (5.00 mL) was irradiated under microwave at 180° C. for 1 h. After cooling, the mixture was purified by chromatography on silica gel with methanol in methylene chloride (0-10%) to afford the desired product. LCMS: (M+H)=162.1.

Step 2. 6-{1-[6-(1H-pyrazol-1-yl)imidazo[1,2-a]pyrimidin-3-yl]cyclopropyl}quinoline A mixture of 5-(1H-pyrazol-1-yl)pyrimidin-2-amine (0.08 g, 0.5 mmol) and chloro(1-quinolin-6-ylcyclopropyl)acetaldehyde (0.1 g, 0.5 mmol) in isopropanol (15 mL) was heated at 90° C. overnight. After cooling, the mixture was purified by RP-HPLC (pH 10) to afford the desired product. LCMS: (M+H)=353.1.

Example 23: 6-{1-[6-(4-Methyl-1H-pyrazol-1-yl)imidazo[1,2-a]pyrimidin-3-yl]cyclopropyl}quinoline

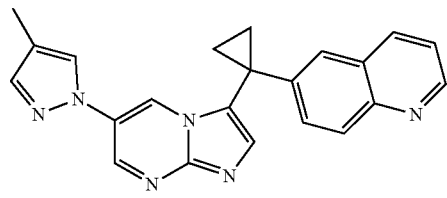 [SMILES: Cc1cnn(-c2cnc3ncc(C4(c5ccc6ncccc6c5)CC4)n3c2)c1]

This compound was prepared from 4-methyl-1H-pyrazole using procedures analogous to those for Example 22. LCMS: (M+H)=367.1.

Example 24: N,N-Dimethyl-1-[3-(1-quinolin-6-ylcyclopropyl)imidazo[1,2-a]pyrimidin-6-yl]-1H-pyrazole-4-carboxamide

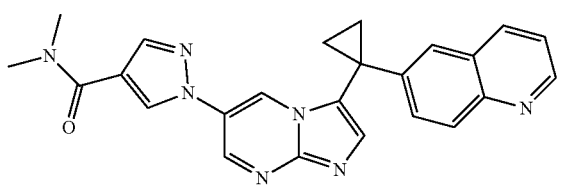 [SMILES: CN(C)C(=O)c1cnn(-c2cnc3ncc(C4(c5ccc6ncccc6c5)CC4)n3c2)c1]

Step 1. ethyl 1-[3-(1-quinolin-6-ylcyclopropyl)imidazo[1,2-a]pyrimidin-6-yl]-1H-pyrazole-3-carboxylate This compound was prepared from ethyl 1H-pyrazole-3-carboxylate using procedures analogous to those for Example 22, Steps 1 and 2. LCMS: (M+H)=425.1.

Step 2. 1-[3-(1-quinolin-6-ylcyclopropyl)imidazo[1,2-a]pyrimidin-6-yl]-1H-pyrazole-4-carboxylic acid Ethyl 1-[3-(1-quinolin-6-ylcyclopropyl)imidazo[1,2-a]pyrimidin-6-yl]-1H-pyrazole-4-carboxylate (0.42 g, 1.0 mmol) was dissolved in methanol (10 mL), and was treated with an aqueous solution of lithium hydroxide (0.048 g, 2.0 mmol) in water (5 mL). The mixture was stirred at 50° C. for 2 h, cooled to RT, neutralized with 1N HCl (2 mL). The volatiles were removed under reduced pressure. The residue was co-evaporated with toluene (3×), and dried to afford the desired product which was directly used in next step. LCMS: (M+H)=397.1.

Step 3. N,N-dimethyl-1-[3-(1-quinolin-6-ylcyclopropyl)imidazo[1,2-a]pyrimidin-6-yl]-1H-pyrazole-4-carboxamide To a solution of 1-[3-(1-quinolin-6-ylcyclopropyl)imidazo[1,2-a]pyrimidin-6-yl]-1H-pyrazole-4-carboxylic acid (50 mg, 0.13 mmol) in N,N-dimethylformamide (1.0 mL) was added benzotriazol-1-yloxytris(dimethylamino)phosphonium hexafluorophosphate (65 mg, 0.15 mmol), dimethylamine (2M in THF, 0.10 mL, 0.2 mmol) and N,N-diisopropylethylamine (0.10 mL). The mixture was stirred at RT for 2 h, and purified by RP-HPLC (pH 10) to afford the desired product. LCMS: (M+H)=424.1.

Example 25: N-[1-(4-Methyl-1,3-thiazol-2-yl)ethyl]-1-[3-(1-quinolin-6-ylcyclopropyl)imidazo[1,2-a]pyrimidin-6-yl]-1H-pyrazole-4-carboxamide

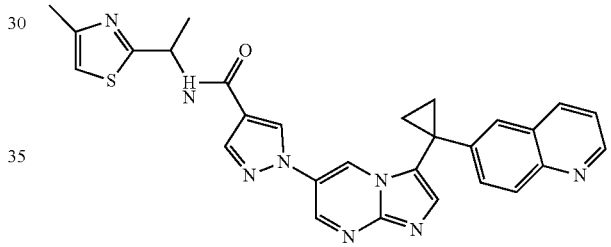

This compound was prepared from 1-[3-(1-quinolin-6-ylcyclopropyl)imidazo[1,2-a]pyrimidin-6-yl]-1H-pyrazole-4-carboxamide acid using procedure analogous to those for Example 24. LCMS: (M+H)=521.0.

Example 26: N-Cyclohexyl-3-(1-quinolin-6-ylcyclopropyl)imidazo[1,2-a]pyrimidine-6-carboxamide

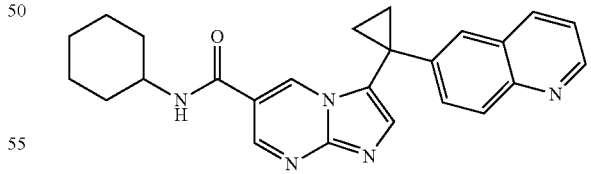

Step 1. methyl 3-(1-quinolin-6-ylcyclopropyl)imidazo[1,2-a]pyrimidine-6-carboxylate A mixture of methyl 2-aminopyrimidine-5-carboxylate (153 mg, 1.0 mmol) and chloro(1-quinolin-6-ylcyclopropyl)acetaldehyde (270 mg, 1.1 mmol) in isopropyl alcohol (3 mL) was heated at 100° C. for 4 h. After cooling to RT, the mixture was diluted with methanol (3 mL) and subjected to preparative RP-HPLC to afford the two regioisomers:

methyl 3-(1-quinolin-6-ylcyclopropyl)imidazo[1,2-a]pyrimidine-6-carboxylate (Isomer-I, 45 mg, R, =1.763 min.) and methyl 3-(1-quinolin-6-ylcyclopropyl)imidazo[1,2-a]pyrimidine-7-carboxylate (Isomer-II, 89 mg, R, =1.001 min.). LCMS: (M+H)=345.1.

Step 2. 3-(1-quinolin-6-ylcyclopropyl)imidazo[1,2-a]pyrimidine-6-carboxylic acid A mixture of methyl 3-(1-quinolin-6-ylcyclopropyl)imidazo[1,2-a]pyrimidine-6-carboxylate (14 mg, 0.040 mmol, isomer-I from Step 1), 1M lithium hydroxide in water (0.16 mL), and methanol (1.0 mL) was stirred overnight at RT. The mixture was neutralized with 1N HCl (0.16 mL) and concentrated under reduced pressure. The residue was dried to yield the desired product which was directly used in next step. LCMS: (M+H)=331.0.

Step 3. N-cyclohexyl-3-(1-quinolin-6-ylcyclopropyl)imidazo[1,2-a]pyrimidine-6-carboxamide Triethylamine (13.9 µL, 0.1 mmol) was added to a mixture of 3-(1-quinolin-6-ylcyclopropyl)imidazo[1,2-a]pyrimidine-6-carboxylic acid (8.26 mg, 0.025 mmol), (benzotriazol-1-yloxy)tripyrrolidinophosphonium hexafluorophosphate (14.3 mg, 0.0275 mmol) and cyclohexanamine (5.7 µL, 0.05 mmol) in N,N-dimethylformamide (0.5 mL) at RT. The mixture was stirred at RT for 2 h, and diluted with methanol (1.3 mL). The resulting solution was purified by RP-HPLC to give the desired product. LCMS: (M+H)=412.1.

Example 27: 3-(1-Quinolin-6-ylcyclopropyl)-N-(tetrahydrofuran-2-ylmethyl)imidazo[1,2-a]pyrimidine-6-carboxamide

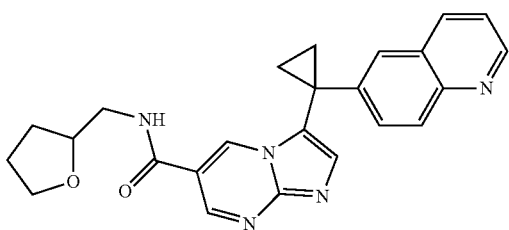 [SMILES: O=C(NCC1CCCO1)c1cnc2ncc(C3(c4ccc5ncccc5c4)CC3)n2c1]

This compound was prepared from 3-(1-quinolin-6-ylcyclopropyl)imidazo[1,2-a]pyrimidine-6-carboxylic acid using procedure analogous to those for Example 26. LCMS: (M+H)=414.1.

Example 28: N-Cyclobutyl-4-[3-(1-quinolin-6-ylcyclopropyl)imidazo[1,2-a]pyrimidin-6-yl]benzamide

Step 1. tert-butyl 4-(2-aminopyrimidin-5-yl)benzoate

Sodium carbonate (0.636 g, 6.0 mmol) in water (2.0 mL) was added to a mixture of 5-bromopyrimidin-2-amine (0.348 g, 2.0 mmol), [4-(tert-butoxycarbonyl)phenyl]boronic acid (0.533 g, 2.4 mmol) and tetrakis(triphenylphosphine)palladium (69 mg, 0.06 mmol) in ethanol (3 mL) and toluene (3 mL). The mixture was heated at 120° C. for 3 h. After cooling to RT, the mixture was diluted with EtOAc and washed with water and brine. The organic layer was dried over $Na_2SO_4$, filtered and concentrated under reduced pressure to afford the desired product (470 mg, 86.6%) which was directly used in next step. LCMS: (M+H)=272.1.

Step 2. tert-butyl 4-[3-(1-quinolin-6-ylcyclopropyl)imidazo[1,2-a]pyrimidin-6-yl]benzoate A mixture of tert-butyl 4-(2-aminopyrimidin-5-yl)benzoate (0.144 g, 0.531 mmol) and chloro(1-quinolin-6-ylcyclopropyl)acetaldehyde (0.156 g, 0.637 mmol) in isopropyl alcohol (3 mL) was heated at 90° C. overnight. The mixture was adjusted to pH=9 using triethylamine, solvent was removed and the residue was purified by chromatography on silica gel using MeOH in methylene chloride (0-5%) to afford the desired product (125 mg, 50.9%). LCMS: (M+H)= 463.1.

Step 3. 4-[3-(1-quinolin-6-ylcyclopropyl)imidazo[1,2-a]pyrimidin-6-yl]benzoic acid tert-Butyl-4-[3-(1-quinolin-6-ylcyclopropyl)imidazo[1,2-a]pyrimidin-6-yl]benzoate (0.125 g, 0.27 mmol) was treated with 4M HCl in 1,4-dioxane (1.5 mL) at RT for 3 h. The mixture was decanted. The solid was washed with ether and dried to give the desired product as HCl salt (129 mg, 99.5%) which was directly used in next step without further purification. LCMS: (M+H)=407.1.

Step 4. N-cyclobutyl-4-[3-(1-quinolin-6-ylcyclopropyl)imidazo[1,2-a]pyrimidin-6-yl]benzamide N,N-Diisopropylethylamine (30.0 µL, 0.172 mmol) was added to a mixture of 4-[3-(1-quinolin-6-ylcyclopropyl)imidazo[1,2-a]pyrimidin-6-yl]benzoic acid dihydrochloride (18.5 mg, 0.0386 mmol), cyclobutanamine (4.12 mg, 0.0579 mmol) and benzotriazol-1-yloxytris(dimethylamino)phosphonium hexafluorophosphate (20.5 mg, 0.0463 mmol) in N,N-dimethylformamide (1 mL). The mixture was stirred at RT for 3 h, and diluted with methanol (0.8 mL). The resulting solution was purified by RP-HPLC (pH 10) to give the desired product. LCMS: (M+H)=460.1.

Example 29: 6-(1-{6-[4-(Azetidin-1-ylcarbonyl)phenyl]imidazo[1,2-a]pyrimidin-3-yl}cyclopropyl)quinoline

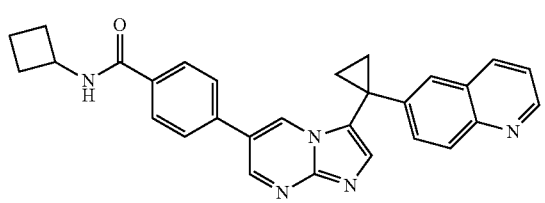 [SMILES: O=C(NC1CCC1)c1ccc(-c2cnc3ncc(C4(c5ccc6ncccc6c5)CC4)n3c2)cc1]

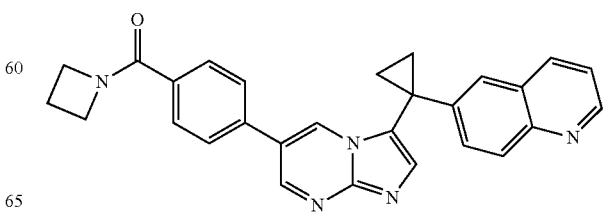

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=446.1.

Example 30: N,N-Dimethyl-4-[3-(1-quinolin-6-ylcyclopropyl)imidazo[1,2-a]pyrimidin-6-yl]benzamide

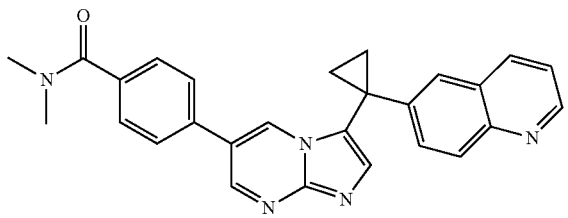 [SMILES: CN(C)C(=O)c1ccc(-c2cnc3ncc(C4(c5ccc6ncccc6c5)CC4)n3c2)cc1]

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=434.1.

Example 31: 4-[3-(1-Quinolin-6-ylcyclopropyl)imidazo[1,2-a]pyrimidin-6-yl]-N-(tetrahydrofuran-2-ylmethyl)benzamide

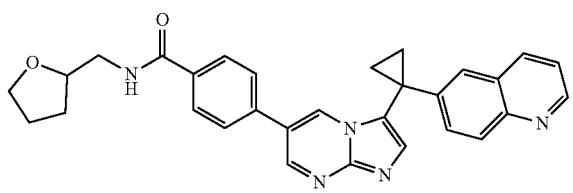 [SMILES: O=C(NCC1CCCO1)c1ccc(-c2cnc3ncc(C4(c5ccc6ncccc6c5)CC4)n3c2)cc1]

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=490.1.

Example 32: N-(1-Benzylpyrrolidin-3-yl)-N-methyl-4-[3-(1-quinolin-6-ylcyclopropyl)imidazo[1,2-a]pyrimidin-6-yl]benzamide

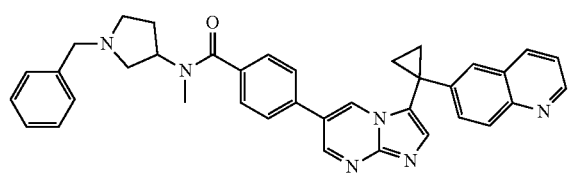 [SMILES: CN(C(=O)c1ccc(-c2cnc3ncc(C4(c5ccc6ncccc6c5)CC4)n3c2)cc1)C1CCN(Cc2ccccc2)C1]

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=579.2.

Example 33: N-(1-Pyridin-2-ylpiperidin-4-yl)-4-[3-(1-quinolin-6-ylcyclopropyl)imidazo[1,2-a]pyrimidin-6-yl]benzamide

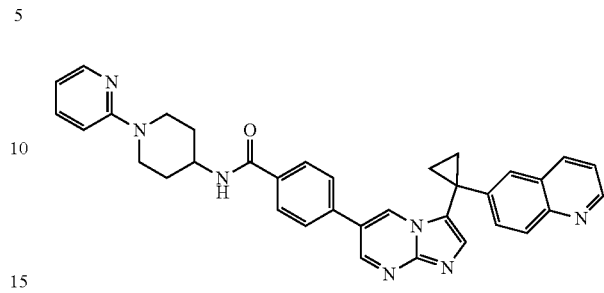

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=566.2.

Example 34: N-(1-Pyridin-2-ylethyl)-4-[3-(1-quinolin-6-ylcyclopropyl)imidazo[1,2-a]pyrimidin-6-yl]benzamide

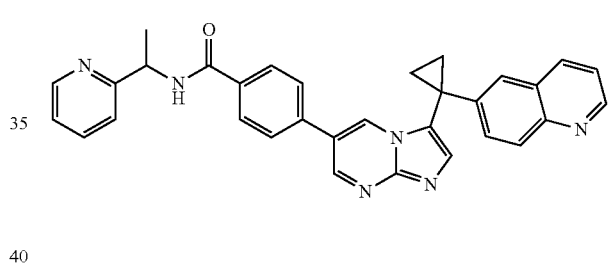

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=511.1.

Example 35: 6-{1-[6-(4-[(3S)-3-Fluoropyrrolidin-1-yl]carbonylphenyl)imidazo[1,2-a]pyrimidin-3-yl]cyclopropyl}quinoline

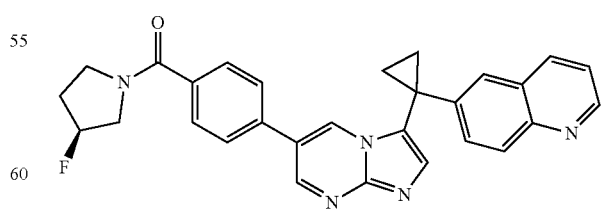

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=478.1.

Example 36: N-[1-(Methoxymethyl)cyclobutyl]-4-[3-(1-quinolin-6-ylcyclopropyl)imidazo[1,2-a]pyrimidin-6-yl]benzamide

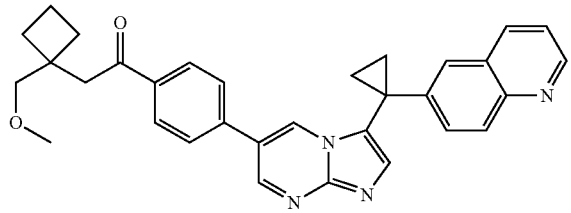 [SMILES: COCC1(CC(=O)c2ccc(-c3cnc4ncc(C5(c6ccc7ncccc7c6)CC5)n4c3)cc2)CCC1]

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=504.1

Example 37: N-(1-Pyridin-2-ylpyrrolidin-3-yl)-4-[3-(1-quinolin-6-ylcyclopropyl)imidazo[1,2-a]pyrimidin-6-yl]benzamide

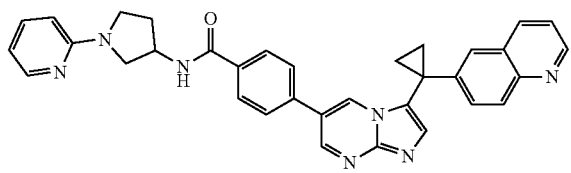 [SMILES: O=C(NC1CCN(c2ccccn2)C1)c1ccc(-c2cnc3ncc(C4(c5ccc6ncccc6c5)CC4)n3c2)cc1]

Step 1. tert-butyl (1-pyridin-2-ylpyrrolidin-3-yl)carbamate

A mixture of 2-fluoropyridine (1.0 g, 10.3 mmol) and tert-butyl pyrrolidin-3-ylcarbamate (1.80 g, 9.66 mmol) was heated at 120° C. for 5 h. After cooling to RT, the solid formed was treated with ether, filtered, and washed with ether. The solid was collected and dried to give the desired product (2.50 g, 98.2%). LCMS: (M+H)=264.1.

Step 2. 1-(pyridin-2-yl)pyrrolidin-3-amine dihydrochloride tert-Butyl (1-pyridin-2-ylpyrrolidin-3-yl)carbamate (2.5 g) was dissolved in methanol (4 mL) and was treated with 4M hydrogen chloride in 1,4-dioxane (8 mL). The mixture was stirred overnight at RT. The solvents were evaporated under reduced pressure. The residue was washed with ether and dried to give the desired product (2.1 g, 92%). LCMS: (M+H)=164.1.

Step 3. N-(1-pyridin-2-ylpyrrolidin-3-yl)-4-[3-(1-quinolin-6-ylcyclopropyl)imidazo[1,2-a]pyrimidin-6-yl]benzamide This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=552.2.

Example 38: 6-[1-(6-{4-[(3-Pyridin-2-ylpyrrolidin-1-yl)carbonyl]phenyl}imidazo[1,2-a]pyrimidin-3-yl)cyclopropyl]quinoline

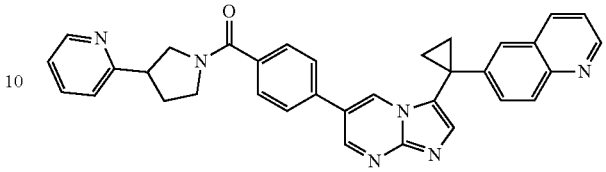

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=537.2.

Example 39: 6-{1-[6-(4-[(3S)-3-(Pyridin-2-yloxy)pyrrolidin-1-yl]carbonylphenyl)imidazo[1,2-a]pyrimidin-3-yl]cyclopropyl}quinoline

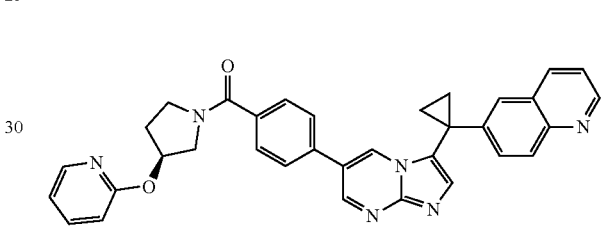

Step 1. (S)-2-(pyrrolidin-3-yloxy)pyridine dihydrochloride

To a solution of tert-butyl (S)-3-hydroxypyrrolidine-1-carboxylate (0.936 g, 5.0 mmol) in N,N-dimethylformamide (5 mL) was added sodium hydride (0.3 g, 7.5 mmol). The mixture was stirred at RT for 30 min followed by addition of 2-fluoropyridine (0.5 g, 5.15 mmol). The mixture was heated at 80° C. overnight. After cooling to RT, the mixture was poured into ice-water, and extracted with EtOAc (3×20 mL). The combined organic layers were washed with brine, dried over $Na_2SO_4$, filtered, and concentrated to give the crude product. LCMS: (M+56)=209.1.

The above product was treated with 4M of hydrogen chloride in 1,4-dioxane (4.0 mL) and stirred at RT for 1 h. Ether (10 mL) was added and the solvent was decanted. The solid was washed with ether and dried to give the desired product (1.07 g, 90.2%).

Step 2. 6-{1-[6-(4-[(3S)-3-(pyridin-2-yloxy)pyrrolidin-1-yl]carbonylphenyl)imidazo[, 2-a]pyrimidin-3-yl]cyclopropyl}quinoline This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=553.2.

Example 40: N-[2-(Pyridin-2-yloxy)ethyl]-4-[3-(1-quinolin-6-ylcyclopropyl)imidazo[1,2-a]pyrimidin-6-yl]benzamide

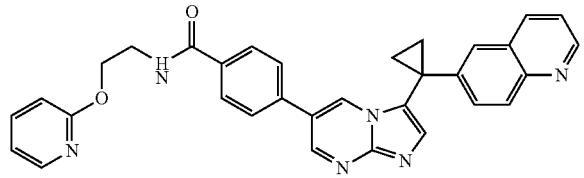 [SMILES: O=C(NCCOc1ccccn1)c1ccc(-c2cnc3ncc(C4(c5ccc6ncccc6c5)CC4)n3c2)cc1]

Step 1. tert-butyl [2-(pyridin-2-yloxy)ethyl]carbamate

Diethyl azodicarboxylate (630 μL, 4.00 mmol) was added to a mixture of 2-hydroxypyridine (0.380 g, 4.0 mmol), tert-butyl (2-hydroxyethyl)carbamate (0.322 g, 2.0 mmol) and triphenylphosphine (1.05 g, 4.0 mmol) in THF (6.0 mL). The mixture was stirred overnight at RT, and concentrated. The residue was chromatographed on silica gel with EtOAc in hexanes to give the product (0.353 g, 74.1%). LCMS: (M+H)=239.2.

Step 2. 2-(pyridin-2-yloxy)ethanamine dihydrochloride tert-Butyl 2-(pyridin-2-yloxy)ethylcarbamate (0.353 g) was treated with 4M of hydrogen chloride in 1,4-dioxane (0.6 mL) at RT for 1 h. The solvent was evaporated under reduced pressure. The residue was washed with ether, and dried to give the desired product (0.30 g, 96.8%).

Step 3. N-[2-(pyridin-2-yloxy)ethyl]-4-[3-(1-quinolin-6-ylcyclopropyl)imidazo[1,2-a]pyrimidin-6-yl]benzamide This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=527.1

Example 41: N-[1-Methyl-2-(pyridin-2-yloxy)ethyl]-4-[3-(1-quinolin-6-ylcyclopropyl)imidazo[1,2-a]pyrimidin-6-yl]benzamide

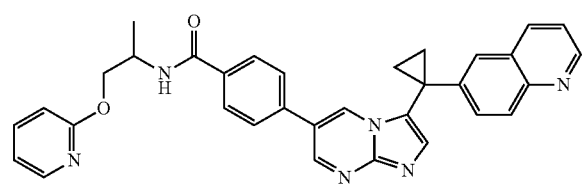 [SMILES: CC(COc1ccccn1)NC(=O)c1ccc(-c2cnc3ncc(C4(c5ccc6ncccc6c5)CC4)n3c2)cc1]

This compound was prepared from tert-butyl (2-hydroxypropyl)carbamate using procedures analogous to those for Example 40. LCMS: (M+H)=541.1.

Example 42: N-(2-Phenoxyethyl)-4-[3-(1-quinolin-6-ylcyclopropyl)imidazo[1,2-a]pyrimidin-6-yl]benzamide

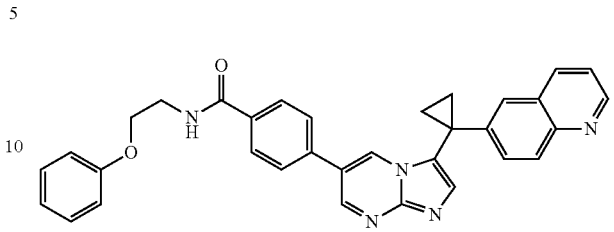

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=526.2.

Example 43: N-(1S)-2,2-Dimethyl-1-[(methylamino)carbonyl]propyl-4-[3-(1-quinolin-6-ylcyclopropyl)imidazo[1,2-a]pyrimidin-6-yl]benzamide

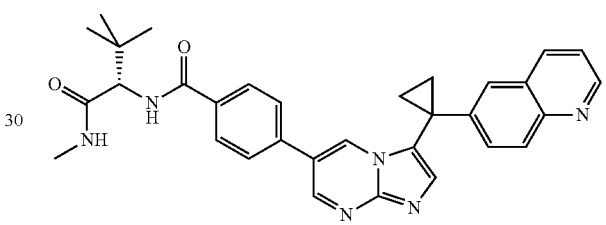

Step 1. (2S)-3,3-dimethyl-2-({4-[3-(1-quinolin-6-ylcyclopropyl)imidazo[1,2-a]pyrimidin-6-yl]benzoyl}amino)butanoic acid dihydrochloride Triethylamine (230 μL) was added to a mixture of 4-[3-(1-quinolin-6-ylcyclopropyl)imidazo[1,2-a]pyrimidin-6-yl]benzoic acid dihydrochloride (162 mg, 0.339 mmol), tert-butyl (2S)-2-amino-3,3-dimethylbutanoate hydrochloride (75.8 mg, 0.339 mmol) and benzotriazol-1-yloxytris(dimethylamino)phosphonium hexafluorophosphate (165 mg, 0.373 mmol) in methylene chloride (10 mL). The mixture was stirred at RT for 3 h, washed with NaHCO$_3$ (7.5%) and brine, dried over Na$_2$SO$_4$, filtered, and concentrated. The residue [LCMS: (M+H)=576.2] was treated with HCl in 1,4-dioxane (4M, 1.0 mL) at RT for 3 h. The solvent was evaporated. The residue was washed with ether and dried to give the desired product.

Step 2. N-(1S)-2,2-dimethyl-1-[(methylamino)carbonyl]propyl-4-[3-(1-quinolin-6-ylcyclopropyl)imidazo[1,2-a]pyrimidin-6-yl]benzamide N,N-Diisopropylethylamine (30.0 μL, 0.172 mmol) was added to a mixture of (2S)-3,3-dimethyl-2-(4-[3-(1-quinolin-6-ylcyclopropyl)imidazo[1,2-a]pyrimidin-6-yl]benzoylamino)butanoic acid dihydrochloride (15.4 mg, 0.0260 mmol), benzotriazol-1-yloxytris(dimethylamino)phosphonium hexafluorophosphate (12.6 mg, 0.0286 mmol) and methylamine (2M in THF, 0.020 mL) in N,N-dimethylformamide (1.0 mL). The mixture was stirred at RT for 3 h, and diluted with methanol (0.8 mL). The resulting solution was purified by RP-HPLC (pH=10) to give the desired product. LCMS: (M+H)=533.2.

Example 44: N-(1S)-1-[(Dimethylamino)carbonyl]-2,2-dimethylpropyl-4-[3-(1-quinolin-6-ylcyclopropyl)imidazo[1,2-a]pyrimidin-6-yl]benzamide

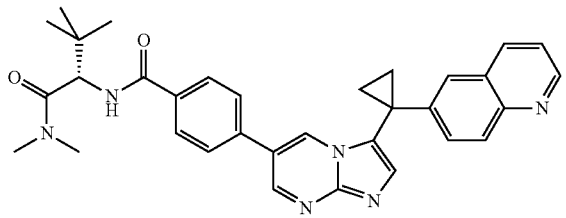 [SMILES: CN(C)C(=O)[C@@H](NC(=O)c1ccc(-c2cnc3ncc(C4(c5ccc6ncccc6c5)CC4)n3c2)cc1)C(C)(C)C]

This compound was prepared from (2S)-3,3-dimethyl-2-(4-[3-(1-quinolin-6-ylcyclopropyl)imidazo[1,2-a]pyrimidin-6-yl]benzoylamino)butanoic acid dihydrochloride using procedures analogous to those for Example 43. LCMS: (M+H)=547.2.

Example 45: N-[(1S)-1-(Azetidin-1-ylcarbonyl)-2,2-dimethylpropyl]-4-[3-(1-quinolin-6-ylcyclopropyl)imidazo[1,2-a]pyrimidin-6-yl]benzamide

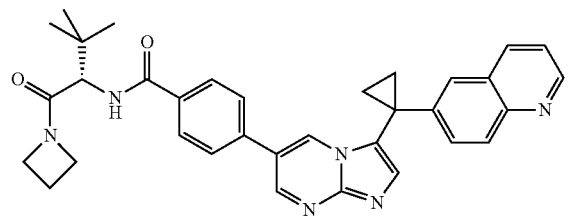

This compound was prepared from (2S)-3,3-dimethyl-2-(4-[3-(1-quinolin-6-ylcyclopropyl)imidazo[1,2-a]pyrimidin-6-yl]benzoylamino)butanoic acid dihydrochloride using procedures analogous to those for Example 43. LCMS: (M+H)=559.2.

Example 46: N-Cyclopropyl-3-[3-(1-quinolin-6-ylcyclopropyl)imidazo[1,2-a]pyrimidin-6-yl]benzamide

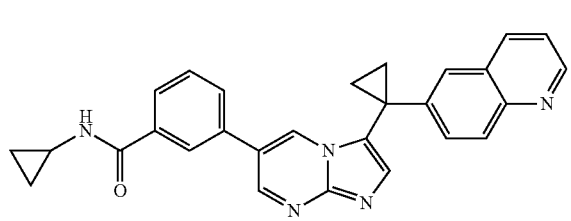 [SMILES: O=C(NC1CC1)c1cccc(-c2cnc3ncc(C4(c5ccc6ncccc6c5)CC4)n3c2)c1]

Step 1. tert-butyl 3-(2-aminopyrimidin-5-yl)benzoate

Sodium carbonate (0.636 g, 6.0 mmol) in water (2.0 mL) was added to a mixture of 5-bromopyrimidin-2-amine (0.348 g, 2.0 mmol), [3-(tert-butoxycarbonyl)phenyl]boronic acid (0.533 g, 2.4 mmol) and tetrakis(triphenylphosphine)palladium (69 mg, 0.06 mmol) in ethanol (3.0 mL) and toluene (3.0 mL). The resulting mixture was heated at 120° C. for 3 h. The mixture was diluted with EtOAc and washed with water and brine. The organic layer was dried over Na₂SO₄, filtered, and concentrated under reduced pressure. The residue was treated with methanol. The precipitate was filtered and dried to give the product (399 mg, 73.5%). 272.1.

Step 2. 3-[3-(1-(quinolin-6-yl)cyclopropyl)imidazo[1,2-a]pyrimidin-6-yl]benzoic acid A mixture of tert-butyl 3-(2-aminopyrimidin-5-yl)benzoate (167 mg, 0.616 mmol) and chloro(1-quinolin-6-ylcyclopropyl)acetaldehyde (151 mg, 0.616 mmol) in isopropyl alcohol (3 mL, 40 mmol) was heated at 90° C. overnight. The solvent was evaporated and the residue was treated with 50% TFA in methylene chloride (2.0 mL) at RT for 2 h. The solvents were evaporated and the residue was washed with ether, and dried to give the desired product as a TFA salt (0.36 g) which was directly used in next step without further purification. LCMS: (M+H)+=407.1.

Step 3. N-cyclopropyl-3-[3-(1-quinolin-6-ylcyclopropyl)imidazo[1,2-a]pyrimidin-6-yl]benzamide N,N-Diisopropylethylamine (194 µL, 1.11 mmol) was added to a mixture of 3-[3-(1-quinolin-6-ylcyclopropyl)imidazo[1,2-a]pyrimidin-6-yl]benzoic acid TFA salt (126.9 mg, 0.2 mmol), cyclopropylamine (17.1 mg, 0.3 mmol) and benzotriazol-1-yloxytris(dimethylamino)phosphonium hexafluorophosphate (97.3 mg, 0.22 mmol) in N,N-dimethylformamide (1.0 mL). The mixture was stirred at RT for 3 h, and was diluted with methanol (0.8 mL). The resulting solution was purified by RP-HPLC (pH=10) to give the desired product. LCMS: (M+H)=446.1.

Example 47: N-(Pyridin-2-ylmethyl)-3-[3-(1-quinolin-6-ylcyclopropyl)imidazo[1,2-a]pyrimidin-6-yl]benzamide

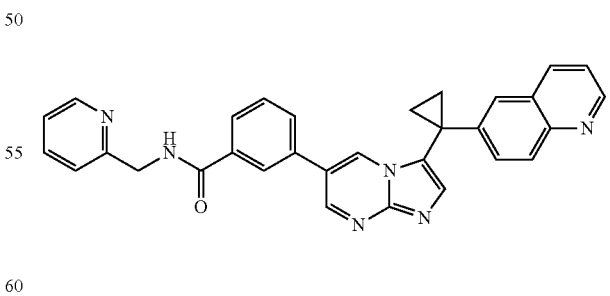

This compound was prepared from 3-[3-(1-quinolin-6-ylcyclopropyl)imidazo[1,2-a]pyrimidin-6-yl]benzoic acid TFA salt using procedures analogous to those for Example 46. LCMS: (M+H)=497.1.

Example 48: N,N-Dimethyl-3-[3-(1-quinolin-6-yl-cyclopropyl)imidazo[1,2-a]pyrimidin-6-yl]benzamide

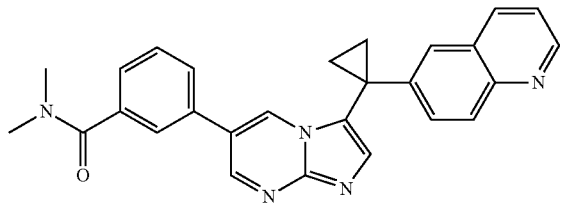 [SMILES: CN(C)C(=O)c1cccc(-c2cnc3ncc(C4(c5ccc6ncccc6c5)CC4)n3c2)c1]

This compound was prepared from 3-[3-(1-quinolin-6-ylcyclopropyl)imidazo[1,2-a]pyrimidin-6-yl]benzoic acid TFA salt using procedures analogous to those for Example 46. LCMS: (M+H)=434.1.

Example 49: N-Methyl-3-[3-(1-quinolin-6-ylcyclopropyl)imidazo[1,2-a]pyrimidin-6-yl]benzamide

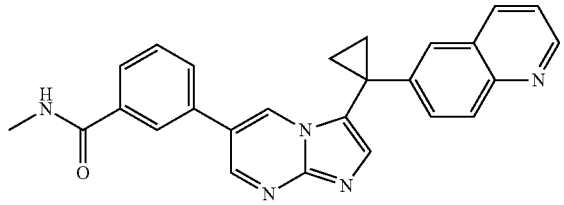 [SMILES: CNC(=O)c1cccc(-c2cnc3ncc(C4(c5ccc6ncccc6c5)CC4)n3c2)c1]

This compound was prepared from 3-[3-(1-quinolin-6-ylcyclopropyl)imidazo[1,2-a]pyrimidin-6-yl]benzoic acid TFA salt using procedures analogous to those for Example 46. LCMS: (M+H)=420.1.

Example 50: N-[(1S)-1-Methyl-2-(methylamino)-2-oxoethyl]-4-[3-(1-quinolin-6-ylcyclopropyl)imidazo[1,2-a]pyrimidin-6-yl]benzamide

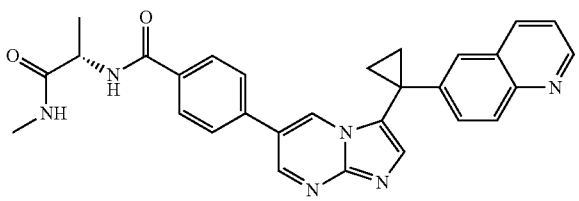 [SMILES: CNC(=O)[C@H](C)NC(=O)c1ccc(-c2cnc3ncc(C4(c5ccc6ncccc6c5)CC4)n3c2)cc1]

This compound was prepared from 4-[3-(1-quinolin-6-ylcyclopropyl)imidazo[1,2-a]pyrimidin-6-yl]benzoic acid dihydrochloride using procedures analogous to those for Example 43. LCMS: (M+H)=491.1.

Example 51: N-[(1R)-1-Methyl-2-(methylamino)-2-oxoethyl]-4-[3-(1-quinolin-6-ylcyclopropyl)imidazo[1,2-a]pyrimidin-6-yl]benzamide

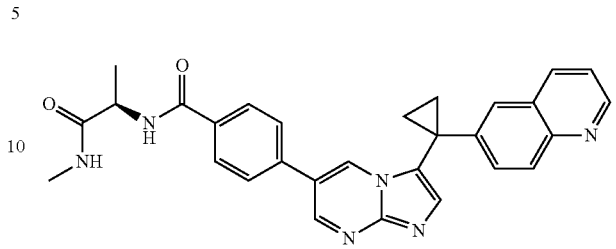

This compound was prepared from 4-[3-(1-quinolin-6-ylcyclopropyl)imidazo[1,2-a]pyrimidin-6-yl]benzoic acid dihydrochloride using procedures analogous to those for Example 43. LCMS: (M+H)=491.1.

Example 52: (3R)-1-{4-[3-(1-Quinolin-6-ylcyclopropyl)imidazo[1,2-a]pyrimidin-6-yl]benzoyl}pyrrolidine-3-carbonitrile

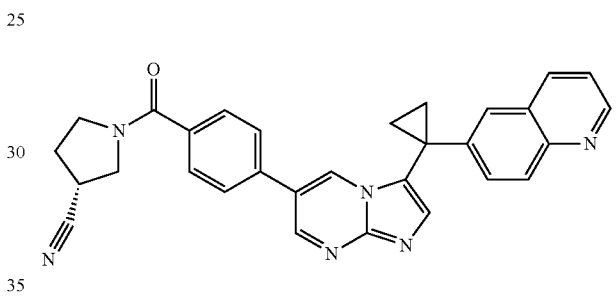

This compound was prepared from 4-[3-(1-quinolin-6-ylcyclopropyl)imidazo[1,2-a]pyrimidin-6-yl]benzoic acid dihydrochloride using procedures analogous to those for Example 28. LCMS: (M+H)=485.1.

Example 53: Methyl 4-{5-[3-(1-quinolin-6-ylcyclopropyl)imidazo[1,2-a]pyrimidin-6-yl]pyridin-2-yl}piperazine-1-carboxylate

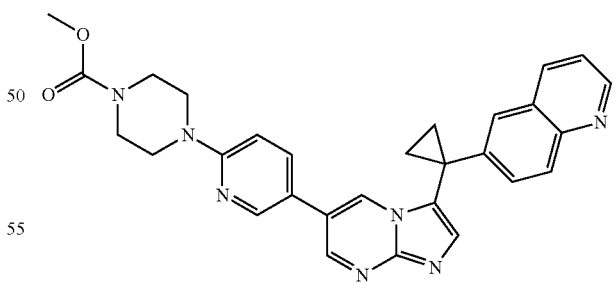

Step 1. tert-butyl 4-[5-(2-aminopyrimidin-5-yl)pyridin-2-yl]piperazine-1-carboxylate Sodium carbonate (1.59 g) in water (6.0 mL) was added to a mixture of tert-butyl 4-[5-(4,4,5,5-tetramethyl-1,3,2-dioxaborolan-2-yl)pyridin-2-yl]piperazine-1-carboxylate (0.205 g, 0.526 mmol), 5-bromopyrimidin-2-amine (0.0940 g, 0.54 mmol) and tetrakis(triphenylphosphine)palladium (35 mg, 0.03 mmol) in ethanol (6.0 mL) and toluene (6.0 mL). The resulting mixture was heated at 120° C. for 1 h. The mixture was diluted with EtOAc and water. The precipitate was collected by filtration to give the desired product (120 mg, 63.9%). LCMS: (M+H)=357.1.

Step 2. tert-butyl 4-{5-[3-(1-quinolin-6-ylcyclopropyl) imidazo[1,2-a]pyrimidin-6-yl]pyridin-2-yl}piperazine-1-carboxylate A mixture of tert-butyl 4-[5-(2-aminopyrimidin-5-yl)pyridin-2-yl]piperazine-1-carboxylate (0.120 g, 0.337 mmol) and chloro(1-quinolin-6-ylcyclopropyl)acetaldehyde (0.0827 g, 0.337 mmol) in isopropyl alcohol (2.0 mL) was heated at 100° C. overnight. The mixture was diluted with methanol and purified by RP-HPLC (pH 10.0) to give the desired product (80 mg, 43.4%). LCMS: (M+H)=548.2.

Step 3. 6-{1-[6-(6-piperazin-1-ylpyridin-3-yl) imidazo[1,2-a]pyrimidin-3-yl]cyclopropyl}quinoline tert-butyl 4-{5-[3-(1-quinolin-6-ylcyclopropyl)imidazo[1,2-a]pyrimidin-6-yl]pyridin-2-yl}piperazine-1-carboxylate (80.0 mg, 0.146 mmol) in methylene chloride (1.0 mL) was treated with trifluoroacetic acid (1.0 mL) at RT for 2 h. The volatiles were evaporated and the residue was co-evaporated with acetonitrile to give the desired product (125 mg) as a TFA salt which was directly used in next step without further purification. LCMS: (M+H)=448.1.

Step 4. methyl 4-{5-[3-(1-quinolin-6-ylcyclopropyl) imidazo[1,2-a]pyrimidin-6-yl]pyridin-2-yl}piperazine-1-carboxylate 4-Methylmorpholine (19.3 µL, 0.175 mmol) was added to a solution of 6-{1-[6-(6-piperazin-1-ylpyridin-3-yl)imidazo[1,2-a]pyrimidin-3-yl]cyclopropyl}quinoline TFA salt (25.0 mg, 0.0292 mmol) in acetonitrile (0.8 mL), followed by addition of methyl chloroformate (3.39 µL, 0.0438 mmol). The mixture was stirred at RT for 30 min, and was diluted with methanol (1.0 mL). The resulting solution was purified by RP-HPLC (pH=10) to give the desired product. LCMS: (M+H)=506.1.

Example 54: 6-[1-(6-{6-[4-(Methylsulfonyl)piperazin-1-yl]pyridin-3-yl}imidazo[1,2-a]pyrimidin-3-yl)cyclopropyl]quinoline

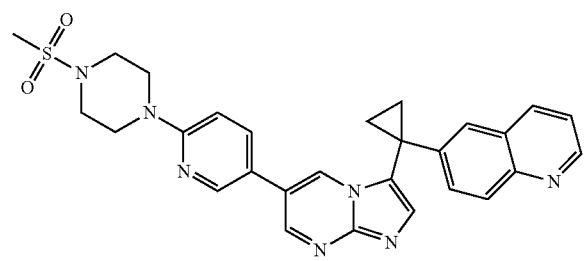 [SMILES: CS(=O)(=O)N1CCN(c2ccc(-c3cnc4ncc(C5(c6ccc7ncccc7c6)CC5)n4c3)cn2)CC1]

This compound was prepared from 6-{1-[6-(6-piperazin-1-ylpyridin-3-yl)imidazo[1,2-a]pyrimidin-3-yl] cyclopropyl}quinoline TFA salt using procedures analogous to those for Example 53. LCMS: (M+H)=526.1.

Example 55: N,N-Dimethyl-4-{5-[3-(1-quinolin-6-ylcyclopropyl)imidazo[1,2-a]pyrimidin-6-yl]pyridin-2-yl}piperazine-1-carboxamide

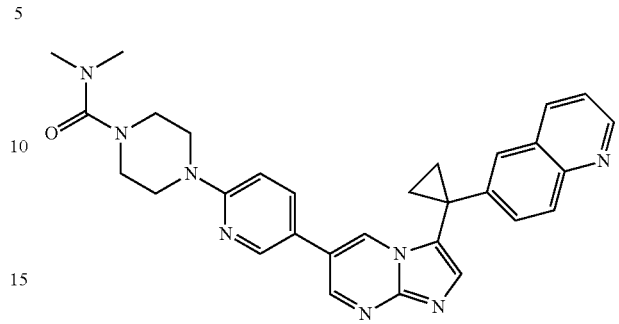

This compound was prepared from 6-{1-[6-(6-piperazin-1-ylpyridin-3-yl)imidazo[1,2-a]pyrimidin-3-yl] cyclopropyl}quinoline TFA salt using procedures analogous to those for Example 53. LCMS: (M+H)=519.2.

Example 56: N-(1S)-1-[(Dimethylamino)carbonyl]-2-methylpropyl-4-[3-(1-quinolin-6-ylcyclopropyl) imidazo[1,2-a]pyrimidin-6-yl]benzamide

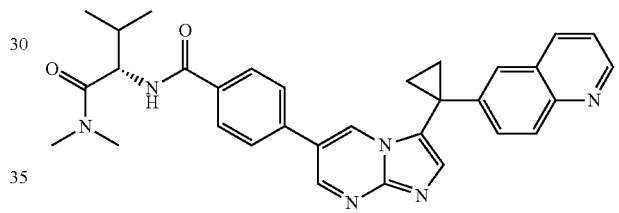

Step 1. tert-butyl (1S)-1-[(dimethylamino)carbonyl]-2-methylpropylcarbamate

N,N-Diisopropylethylamine (1.0 mL, 5.74 mmol) was added to a mixture of (2S)-2-[(tert-butoxycarbonyl)amino]-3-methylbutanoic acid (0.217 g, 1.0 mmol), N-(3-dimethylaminopropyl)-N'-ethylcarbodiimide hydrochloride (0.211 g, 1.1 mmol) and dimethylamine in THF (2M, 1.0 mL) in methylene chloride (10 mL). The mixture was stirred overnight at RT. The mixture was washed with water, saturated NaHCO₃ solution, brine, dried over Na₂SO₄, filtered, and concentrated. The residue was chromatographed on silica gel to give the desired product (131 mg, 53.6%).

Step 2. (2S)-2-amino-N,N, 3-trimethylbutanamide hydrochloride tert-Butyl (1S)-1-[(dimethylamino)carbonyl]-2-methylpropylcarbamate (131 mg) was treated with 4M of hydrogen chloride in 1,4-dioxane (1.0 mL) at RT for 2 h. The solvent was evaporated under reduced pressure. The residue was dried to give the desired product (96 mg).

Step 3. N-(1S)-1-[(dimethylamino)carbonyl]-2-methylpropyl-4-[3-(1-quinolin-6-ylcyclopropyl)imidazo[1,2-a]pyrimidin-6-yl]benzamide N,N-Diisopropylethylamine (40.0 µL, 0.23 mmol) was added to a mixture of 4-[3-(1-quinolin-6-ylcyclopropyl)

imidazo[1,2-a]pyrimidin-6-yl]benzoic acid dihydrochloride (21 mg, 0.044 mmol), (2S)-2-amino-N,N,3-trimethylbutanamide hydrochloride (11.9 mg, 0.0657 mmol) and benzotriazol-1-yloxytris(dimethylamino)phosphonium hexafluorophosphate (23.2 mg, 0.0526 mmol) in N,N-dimethylformamide (1.0 mL). The mixture was stirred at RT for 3 h, and was diluted with methanol (0.8 mL). The resulting solution was purified by RP-HPLC (pH 10) to give the desired product. LCMS: (M+H)=533.2.

Example 57: N-1-[(Dimethylamino)carbonyl]cyclobutyl-4-[3-(1-quinolin-6-ylcyclopropyl)imidazo[1,2-a]pyrimidin-6-yl]benzamide

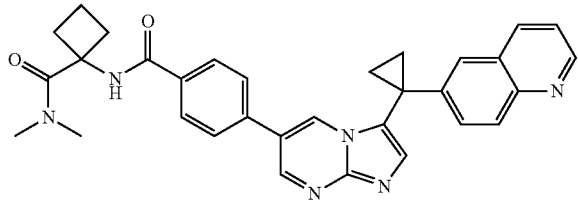 [SMILES: CN(C)C(=O)C1(NC(=O)c2ccc(-c3cnc4ncc(C5(c6ccc7ncccc7c6)CC5)n4c3)cc2)CCC1]

This compound was prepared from 1-(tert-butoxycarbonylamino)cyclobutanecarboxylic acid using procedures analogous to those for Example 56. LCMS: (M+H)=531.2.

Example 58: N-[(1S)-1-(Azetidin-1-ylcarbonyl)-2,2-dimethylpropyl]-5-[3-(1-quinolin-6-ylcyclopropyl)imidazo[1,2-a]pyrimidin-6-yl]pyridine-2-carboxamide

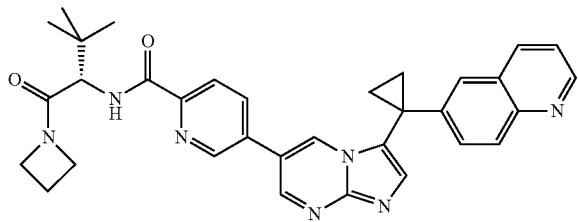 [SMILES: CC(C)(C)[C@H](NC(=O)c1ccc(-c2cnc3ncc(C4(c5ccc6ncccc6c5)CC4)n3c2)cn1)C(=O)N1CCC1]

Step 1. 5-(2-aminopyrimidin-5-yl)picolinic acid

Sodium carbonate (0.636 g, 6.0 mmol) in water (2.0 mL) was added to a mixture of 5-(4,4,5,5-tetramethyl-1,3,2-dioxaborolan-2-yl)pyrimidin-2-amine (0.442 µg, 2.0 mmol), 5-bromopyridine-2-carboxylic acid methyl ester (0.518 g, 2.4 mmol) and tetrakis(triphenylphosphine)palladium (69 mg, 0.06 mmol) in ethanol (3.0 mL) and toluene (3.0 mL). The resulting mixture was heated at 120° C. for 3 h. The organic solvents were removed under reduced pressure. The residue was diluted with water, and adjusted with 1N HCl to pH=4. The precipitates were collected by filtration, washed with water and EtOAc, and dried to give the desired product (0.25 g, 58%). LCMS: (M+H)=217.0.

Step 2. tert-butyl (2S)-2-([5-(2-aminopyrimidin-5-yl)pyridin-2-yl]carbonylamino)-3,3-dimethylbutanoate N,N-Diisopropylethylamine (1.13 mL, 6.48 mmol) was added to a mixture of tert-butyl (2S)-2-amino-3,3-dimethylbutanoate hydrochloride (0.250 g, 1.12 mmol), and 5-(2-aminopyrimidin-5-yl)pyridine-2-carboxylic acid (0.242 g, 1.12 mmol) in N,N-dimethylformamide (10 mL). The mixture was stirred at RT for 3 h, and filtered. The filtrate was diluted with methanol (10 mL). The resulting solution was purified by RP-HPLC (pH 10) to give the desired product (182 mg, 42.3%). LCMS: (M+H)=386.2.

Step 3. (2S)-3,3-dimethyl-2-[({5-[3-(1-quinolin-6-ylcyclopropyl)imidazo[1,2-a]pyrimidin-6-yl]pyridin-2-yl}carbonyl)amino]butanoic acid A mixture of tert-butyl (2S)-2-([5-(2-aminopyrimidin-5-yl)pyridin-2-yl]carbonylamino)-3,3-dimethylbutanoate (0.182 g, 0.472 mmol) and chloro(1-quinolin-6-ylcyclopropyl)acetaldehyde (0.128 g, 0.519 mmol) in isopropyl alcohol (2 mL) was heated at 90° C. overnight. The mixture was adjusted to pH 9 by adding triethylamine, and the solvent was removed. The residue was purified by chromatography on silica gel using MeOH in methylene chloride (0-5%) to give the tert-butyl ester (0.21 g, 77.1%). LCMS: (M+H)=577.2.

The above tert-butyl ester (0.21 g) was treated with 4M of hydrogen chloride in 1,4-dioxane (1.0 mL) at RT for 3 h. The ether (3 mL) was added. The solvent was decanted. The residue was washed with ether, and dried to give the desired product as a HCl salt (0.229 g). LCMS: (M+H)=521.3.

Step 4. N-[(1S)-1-(azetidin-1-ylcarbonyl)-2,2-dimethylpropyl]-5-[3-(1-quinolin-6-ylcyclopropyl)imidazo[1,2-a]pyrimidin-6-yl]pyridine-2-carboxamide N,N-Diisopropylethylamine (30 µL, 0.172 mmol) was added to a mixture of (2S)-3,3-dimethyl-2-[(5-[3-(1-quinolin-6-ylcyclopropyl)imidazo[1,2-a]pyrimidin-6-yl]pyridin-2-ylcarbonyl)amino]butanoic acid trihydrochloride (16.4 mg, 0.026 mmol), benzotriazol-1-yloxytris(dimethylamino) phosphonium hexafluorophosphate (12.6 mg, 0.0286 mmol) and azetidine hydrochloride (3.65 mg, 0.039 mmol) in N,N-dimethylformamide (1.0 mL). The mixture was stirred at RT for 3 h, and was diluted with methanol (0.8 mL). The resulting solution was purified by RP-HPLC (pH 10) to give the desired product. LCMS: (M+H)=560.2.

Example 59: N-(1S)-2,2-Dimethyl-1-[(methylamino)carbonyl]propyl-5-[3-(1-quinolin-6-ylcyclopropyl)imidazo[1,2-a]pyrimidin-6-yl]pyridine-2-carboxamide

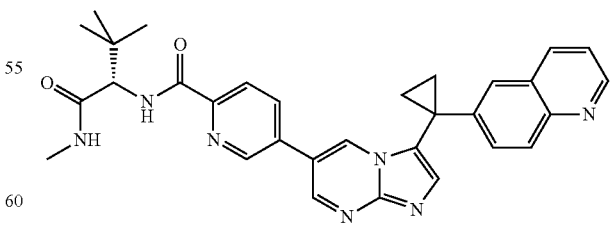

This compound was prepared from (2S)-3,3-dimethyl-2-[(5-[3-(1-quinolin-6-ylcyclopropyl)imidazo[1,2-a]pyrimidin-6-yl]pyridin-2-ylcarbonyl)amino]butanoic acid trihydrochloride using procedures analogous to those for Example 58. LCMS: (M+H)=534.2.

Example 60: N-(1S)-1-[(Cyclopropylamino)carbonyl]-2,2-dimethylpropyl-5-[3-(1-quinolin-6-ylcyclopropyl)imidazo[1,2-a]pyrimidin-6-yl]pyridine-2-carboxamide

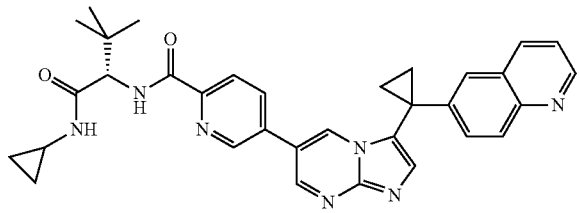 [SMILES: CC(C)(C)[C@H](NC(=O)c1ccc(-c2cnc3ncc(C4(c5ccc6ncccc6c5)CC4)n3c2)cn1)C(=O)NC1CC1]

This compound was prepared from (2S)-3,3-dimethyl-2-[(5-[3-(1-quinolin-6-ylcyclopropyl)imidazo[1,2-a]pyrimidin-6-yl]pyridin-2-ylcarbonyl)amino]butanoic acid trihydrochloride using procedures analogous to those for Example 58. LCMS: (M+H)=560.2.

Example 61: N-[(1S)-2-(Dimethylamino)-1-methyl-2-oxoethyl]-5-[3-(1-quinolin-6-ylcyclopropyl)imidazo[1,2-a]pyrimidin-6-yl]pyridine-2-carboxamide

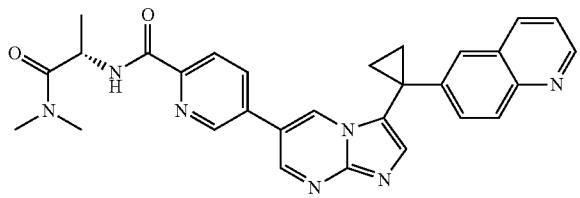 [SMILES: C[C@H](NC(=O)c1ccc(-c2cnc3ncc(C4(c5ccc6ncccc6c5)CC4)n3c2)cn1)C(=O)N(C)C]

This compound was prepared from (2S)-3,3-dimethyl-2-[(5-[3-(1-quinolin-6-ylcyclopropyl)imidazo[1,2-a]pyrimidin-6-yl]pyridin-2-ylcarbonyl)amino]butanoic acid trihydrochloride using procedures analogous to those for Example 58. LCMS: (M+H)=506.2.

Example 62: N-[(1R)-2-(Dimethylamino)-1-methyl-2-oxoethyl]-5-[3-(1-quinolin-6-ylcyclopropyl)imidazo[1,2-a]pyrimidin-6-yl]pyridine-2-carboxamide

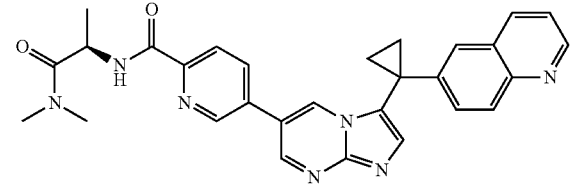 [SMILES: C[C@@H](NC(=O)c1ccc(-c2cnc3ncc(C4(c5ccc6ncccc6c5)CC4)n3c2)cn1)C(=O)N(C)C]

This compound was prepared from (2S)-3,3-dimethyl-2-[(5-[3-(1-quinolin-6-ylcyclopropyl)imidazo[1,2-a]pyrimidin-6-yl]pyridin-2-ylcarbonyl)amino]butanoic acid trihydrochloride using procedures analogous to those for Example 58. LCMS: (M+H)=506.1.

Example 63: 6-(1-{6-[4-(2-Oxo-2-pyrrolidin-1-ylethoxy)phenyl]imidazo[1,2-a]pyrimidin-3-yl}cyclopropyl)quinoline

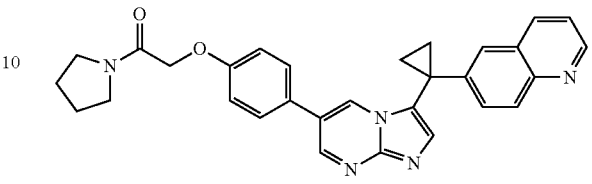

Step 1. 1-[(4-bromophenoxy)acetyl]pyrrolidine

Oxalyl chloride (0.5 mL, 5.9 mmol) was added to a suspension of (4-bromophenoxy)acetic acid (0.462 g, 2.0 mmol) in methylene chloride (10 mL) and 2 drops of N,N-dimethylformamide. The mixture was stirred at RT for 2 h. The solvent was evaporated under reduced pressure. The residue was diluted with methylene chloride (10 mL), cooled with ice-water bath, and 1M of sodium hydroxide aqueous solution (3.0 mL) was added. To the mixture was added pyrrolidine (167 µL, 2.0 mmol). The mixture was stirred and allowed to warm to RT. The organic layer was separated, washed with water and brine, dried over $Na_2SO_4$, filtered, and concentrated. The residue was directly used in next step without further purification (550 mg, 96.7%). LCMS: (M+H)=286.0/284.0

Step 2. 5-[4-(2-oxo-2-pyrrolidin-1-ylethoxy)phenyl]pyrimidin-2-amine

Sodium carbonate (0.318 g, 3.0 mmol) in water (2.0 mL) was added to a mixture of 5-(4,4,5,5-tetramethyl-1,3,2-dioxaborolan-2-yl)pyrimidin-2-amine (0.221 µg, 1.0 mmol), 1-[(4-bromophenoxy)acetyl]pyrrolidine (0.341 g, 1.2 mmol) and tetrakis(triphenylphosphine)palladium (35 mg, 0.03 mmol) in ethanol (1.5 mL) and toluene (1.5 mL). The resulting mixture was heated at 120° C. for 3 h. The mixture was diluted with EtOAc and washed with water and brine. The organic layer was dried over $Na_2SO_4$, filtered, and concentrated under reduced pressure. The residue (0.29 g) was directly used in next step without further purification. LCMS: (M+H)=299.1.

Step 3. 6-(1-{6-[4-(2-oxo-2-pyrrolidin-1-ylethoxy)phenyl]imidazo[1,2-a]pyrimidin-3-yl}cyclopropyl)quinoline A mixture of 5-[4-(2-oxo-2-pyrrolidin-1-ylethoxy)phenyl]pyrimidin-2-amine (23.9 mg, 0.08 mmol) and chloro(1-quinolin-6-ylcyclopropyl)acetaldehyde (19.6 mg, 0.08 mmol) in isopropyl alcohol (0.4 mL) was heated at 90° C. overnight. The mixture was diluted with methanol, and purified by RP-HPLC (pH 10) to give the desired product. LCMS: (M+H)=490.1.

Example 64: 1-{4-[3-(1-Quinolin-6-ylcyclopropyl)imidazo[1,2-a]pyrimidin-6-yl]phenyl}cyclopropanecarbonitrile

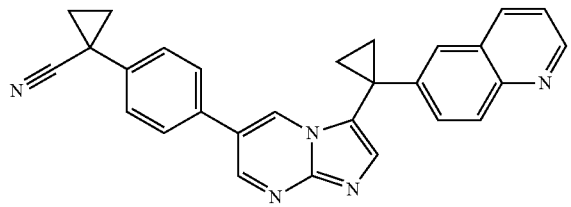 [SMILES: N#CC1(c2ccc(-c3cnc4ncc(C5(c6ccc7ncccc7c6)CC5)n4c3)cc2)CC1]

This compound was prepared from 1-(4-bromophenyl)cyclopropanecarbonitrile using procedures analogous to those for Example 63, Steps 2 and 3. LCMS: (M+H)=428.1.

Example 65: N,N-Dimethyl-4-[3-(1-quinolin-6-ylcyclopropyl)imidazo[1,2-a]pyrimidin-6-yl]benzenesulfonamide

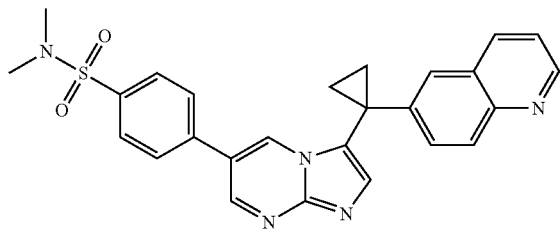 [SMILES: CN(C)S(=O)(=O)c1ccc(-c2cnc3ncc(C4(c5ccc6ncccc6c5)CC4)n3c2)cc1]

Sodium carbonate (79.5 mg) in water (0.5 mL) was added to a mixture of N,N-dimethyl-4-(4,4,5,5-tetramethyl-1,3,2-dioxaborolan-2-yl)benzenesulfonamide (93.4 mg, 0.3 mmol), 5-bromopyrimidin-2-amine (43.5 mg, 0.25 mmol) and tetrakis(triphenylphosphine)palladium (8.7 mg, 0.0075 mmol) in ethanol (1.0 mL) and toluene (1.0 mL). The resulting mixture was heated at 120° C. for 2 h. The mixture was diluted with water, filtered, and washed with water. The solid was collected and dried. Chloro(1-quinolin-6-ylcyclopropyl)acetaldehyde (45.0 mg, 0.183 mmol) in isopropanol (1.0 mL) was added to the above solid. The mixture was heated at 90° C. overnight. After cooling to RT, the mixture was diluted with methanol, and purified by RP-HPLC (pH 10) to give the desired product. LCMS: (M+H)=470.1.

Example 66: Methyl 2-fluoro-4-[3-(1-quinolin-6-ylcyclopropyl)imidazo[1,2-a]pyrimidin-6-yl]benzylcarbamate

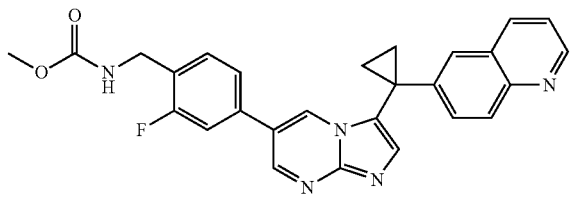 [SMILES: COC(=O)NCc1ccc(-c2cnc3ncc(C4(c5ccc6ncccc6c5)CC4)n3c2)cc1F]

Step 1. methyl (4-bromo-2-fluorobenzyl)carbamate

Methyl chloroformate (85.0 µL, 1.1 mmol) was added to a solution of 1-(4-bromo-2-fluorophenyl)methanamine (0.204 g, 1.0 mmol) and triethylamine (148.1 µL, 1.1 mmol) in methylene chloride (5 mL) at 0° C. After 10 min, the ice-water bath was removed. The mixture was stirred at RT for 1 h, washed with water, and brine. The organic layer was dried over $Na_2SO_4$, filtered, and concentrated under reduced pressure. The residue (220 mg, 83.9%) was directly used in next step without further purification. LCMS: (M+H)=263.9/261.8.

Step 2. methyl 2-fluoro-4-[3-(1-quinolin-6-ylcyclopropyl)imidazo[1,2-a]pyrimidin-6-yl]benzylcarbamate This compound was prepared from methyl (4-bromo-2-fluorobenzyl)carbamate using procedures analogous to those for Example 63, Steps 2 and 3. LCMS: (M+H)=468.1.

Example 67: N'-2-Fluoro-4-[3-(1-quinolin-6-ylcyclopropyl)imidazo[1,2-a]pyrimidin-6-yl]benzyl-N,N-dimethylurea

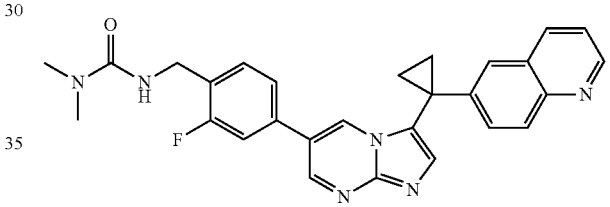

Step 1. N'-(4-bromo-2-fluorobenzyl)-N,N-dimethylurea

N,N-Dimethylcarbamoyl chloride (101 µL, 1.1 mmol) was added to a solution of 1-(4-bromo-2-fluorophenyl)methanamine (0.204 g, 1.0 mmol) and triethylamine (148.1 µL, 1.10 mmol) in methylene chloride (5 mL) at 0° C., followed by 4-dimethylaminopyridine (0.012 g, 0.1 mmol). After 10 min, the ice-water bath was removed and the mixture was stirred overnight at RT. The mixture was washed with water and brine. The organic layer was dried over $Na_2SO_4$, filtered, and concentrated under reduced pressure. The residue (253 mg, 91.9%) was directly used in next step without further purification. LCMS: (M+H)=276.9/274.9.

Step 2. N'-2-fluoro-4-[3-(1-quinolin-6-ylcyclopropyl)imidazo[, 2-a]pyrimidin-6-yl]benzyl-N,N-dimethylurea This compound was prepared from N'-(4-bromo-2-fluorobenzyl)-N,N-dimethylurea using procedures analogous to those for Example 63, Steps 2 and 3. LCMS: (M+H)=481.1.

Example 68: (3R)-1-{2-Fluoro-4-[3-(1-quinolin-6-ylcyclopropyl)imidazo[1,2-a]pyrimidin-6-yl]benzyl}pyrrolidin-3-ol

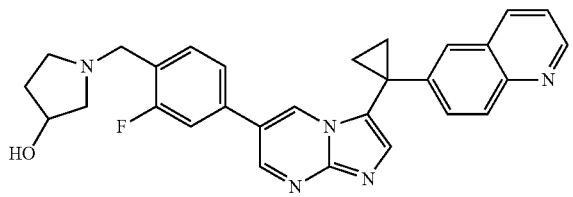 [SMILES: OC1CCN(Cc2ccc(-c3cnc4ncc(C5(c6ccc7ncccc7c6)CC5)n4c3)cc2F)C1]

Step 1. (3R)-1-(4-bromo-2-fluorobenzyl)pyrrolidin-3-ol 4-bromo-2-fluorobenzaldehyde (203.0 mg, 1.0 mmol) was mixed with (3R)-pyrrolidin-3-ol (87.1 mg, 1.0 mmol) in 1,2-dichloroethane (10 mL). The mixture was stirred at RT for 5 min, and then was treated with sodium triacetoxyborohydride (318 mg, 1.5 mmol). The mixture was stirred at RT for 2 h, and quenched by adding 1N NaOH. The organic phase was separated. The aqueous phase was extracted with methylene chloride. The combined organic phases were washed with brine, dried over $Na_2SO_4$, filtered, and concentrated to give the crude product (252 mg, 91.9%) which was directly used in next step without further purification. LCMS: (M+H)=275.9/273.9.

Step 2. (3R)-1-{2-fluoro-4-[3-(1-quinolin-6-ylcyclopropyl)imidazo[1,2-a]pyrimidin-6-yl]benzyl}pyrrolidin-3-ol This compound was prepared from (3R)-1-(4-bromo-2-fluorobenzyl)pyrrolidin-3-ol using procedures analogous to those for Example 63, Step 2 and 3. LCMS: (M+H)=480.1.

Example 69: 6-(1-{6-[3-Fluoro-4-(1H-pyrazol-1-ylmethyl)phenyl]imidazo[1,2-a]pyrimidin-3-yl}cyclopropyl)quinoline

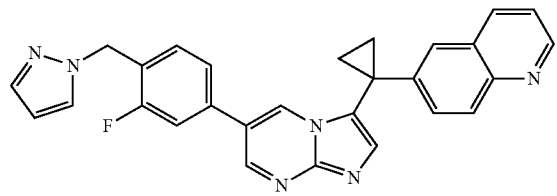 [SMILES: Fc1cc(-c2cnc3ncc(C4(c5ccc6ncccc6c5)CC4)n3c2)ccc1Cn1cccn1]

Step 1. 1-(4-bromo-2-fluorobenzyl)-1H-pyrazole

A mixture of 4-bromo-1-(bromomethyl)-2-fluorobenzene (0.268 g, 1.0 mmol), 1H-pyrazole (0.0681 g, 1.0 mmol) and cesium carbonate (0.489 g, 1.5 mmol) in N,N-dimethylformamide (1.0 mL) was heated at 90° C. for 3 h. After cooling to RT, the mixture was diluted with EtOAc, and filtered. The filtrate was washed with water and brine. The organic layer was dried over $Na_2SO_4$, filtered, and concentrated under reduced pressure. The residue (210 mg, 82.3%) was directly used in next step without further purification. LCMS: (M+H)= 256.9/254.9.

Step 2. 6-(1-{6-[3-fluoro-4-(1H-pyrazol-1-ylmethyl)phenyl]imidazo[1,2-a]pyrimidin-3-yl}cyclopropyl)quinoline This compound was prepared from 1-(4-bromo-2-fluorobenzyl)-1H-pyrazole using procedures analogous to those for Example 63, Step 2 and 3. LCMS: (M+H)=461.0.

Example 70: 3-{2-Fluoro-4-[3-(1-quinolin-6-ylcyclopropyl)imidazo[1,2-a]pyrimidin-6-yl]benzyl}-1,3-oxazolidin-2-one

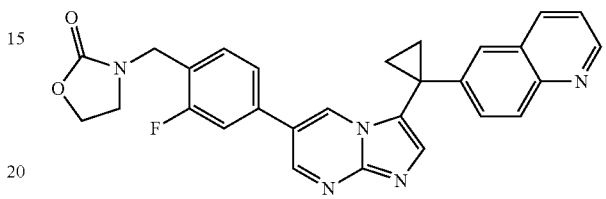

Step 1. 3-(4-bromo-2-fluorobenzyl)-1,3-oxazolidin-2-one 2-chloroethyl chloridocarbonate (114 µL, 1.1 mmol) was added to a mixture of 1-(4-bromo-2-fluorophenyl)methanamine hydrochloride (0.240 g, 1.0 mmol) and triethylamine (293 µL, 2.1 mmol). The mixture was stirred at RT for 3 h, and then 1M of potassium tert-butoxide in THF (1.2 mL) was added. The mixture was stirred overnight at RT, diluted with methylene chloride, washed with water and brine, dried over $Na_2SO_4$, filtered, and concentrated under reduced pressure to give the desired product which was directly used in next step without further purification. LCMS: (M+H)= 275.9/273.9.

Step 2. 3-{2-fluoro-4-[3-(1-quinolin-6-ylcyclopropyl)imidazo[1,2-a]pyrimidin-6-yl]benzyl}-1,3-oxazolidin-2-one This compound was prepared from 3-(4-bromo-2-fluorobenzyl)-1,3-oxazolidin-2-one using procedures analogous to those for Example 63, Step 2 and 3. LCMS: (M+H) =480.0.

Example 71: 2-Fluoro-N-methyl-4-[7-(quinoxalin-6-ylmethyl)imidazo[1,2-b][1,2,4]triazin-2-yl]benzamide

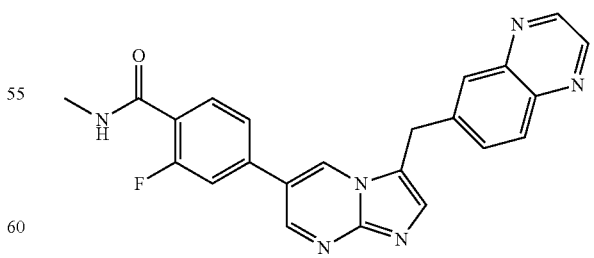

Step 1. 3-quinoxalin-6-ylpropanal

A mixture of 6-bromoquinoxaline (0.40 g, 1.9 mmol), 2-propen-1-ol (0.260 mL, 3.8 mmol), tris(dibenzylideneacetone)dipalladium (26 mg, 0.029 mmol), tri-tert-butylphosphonium tetrafluoroborate (16 mg, 0.057 mmol) and N-cyclohexyl-N-methyl-cyclohexanamine (0.49 mL, 2.3 mmol) in 1,4-dioxane (3.0 mL) was stirred at 40° C. overnight. After cooling to RT, the mixture was filtered, washed with methylene chloride and the filtrate was concentrated. The crude material was purified by chromatography on silica gel with EtOAc in Hexane (0-40%) to afford the desired product (195 mg). LCMS: (M+H)=187.3.

Step 2. 2-chloro-3-quinoxalin-6-ylpropanal

To a cooled (0° C.) solution of 3-quinoxalin-6-ylpropanal (0.195 g, 0.00105 mol) in chloroform (3 mL) was added D-proline (24 mg, 0.00021 mol) followed by N-chlorosuccinimide (147 mg, 0.00110 mol). The mixture was stirred at 0° C. for 2 h, and then at RT overnight. The mixture was diluted with methylene chloride. The solution was washed with water, brine, dried over $Na_2SO_4$, filtered, and concentrated to yield the desired product (220 mg, 95%). LCMS: (M+H)=221.3.

Step 3. 6-[2-(4-bromo-3-fluorophenyl) imidazo[1,2-b][1,2,4]triazin-7-yl]methylquinoxaline A mixture of 2-chloro-3-quinoxalin-6-ylpropanal (110 mg, 0.52 mmol), and 6-(4-bromo-3-fluorophenyl)-1,2,4-triazin-3-amine (140 mg, 0.52 mmol) in tert-butyl alcohol (4 mL) was stirred at 110° C. overnight. After cooling to RT, it was concentrated and purified by chromatography on silica gel with EtOAc in Hexane (0-40%) to afford the desired product (140 mg, 62%). LCMS: (M+H)=435.2.

Step 4. 2-fluoro-4-[7-(quinoxalin-6-ylmethyl)imidazo[1,2-b][1,2,4]triazin-2-yl]benzonitrile A mixture of 6-[2-(4-bromo-3-fluorophenyl)imidazo[1,2-b][1,2,4]triazin-7-yl]methylquinoxaline (120 mg, 0.28 mmol), tris(dibenzylideneacetone)dipalladium (8.8 mg, 0.0096 mmol), (9,9-dimethyl-9H-xanthene-4,5-diyl)bis(diphenylphosphine) (11 mg, 0.019 mmol), zinc cyanide (20.1 mg, 0.171 mmol), and N,N,N',N'-tetramethylethylenediamine (49.9 μL, 0.331 mmol) in N,N-dimethylformamide (0.2 mL) was irradiated under microwave at 160° C. for 10 min. After cooling to RT, the mixture was concentrated and the residue was purified by chromatography on silica gel with MeOH in methylene chloride (0-5%) to afford the desired product (65 mg, 62%). LCMS: (M+H)=382.0.

Step 5. 2-fluoro-4-[7-(quinoxalin-6-ylmethyl)imidazo[1,2-b][1,2,4]triazin-2-yl]benzoic acid A mixture of 2-fluoro-4-[7-(quinoxalin-6-ylmethyl)imidazo[1,2-b][1,2,4]triazin-2-yl]benzonitrile (65 mg, 0.17 mmol) in 10M of hydrogen chloride aqueous solution (0.8 mL) and water (20 μL) was stirred at 105° C. for 3 h. After cooling to RT, the mixture was concentrated to yield the desired product. LCMS: (M+H)=401.3.

Step 6. 2-fluoro-N-methyl-4-[7-(quinoxalin-6-ylmethyl)imidazo[, 2-b][1,2,4]triazin-2-yl]benzamide A mixture of 2-fluoro-4-[7-(quinoxalin-6-ylmethyl)imidazo[1,2-b][1,2,4]triazin-2-yl]benzoic acid (20 mg, 0.05 mmol), methylamine (2M in THF, 37 μL), benzotriazol-1-yloxytris(dimethylamino)phosphonium hexafluorophosphate (23.2 mg, 0.0524 mmol), and N,N-diisopropylethylamine (26 μL, 0.15 mmol) in 1,4-dioxane (0.5 mL) was stirred at RT for 4 h. The mixture was diluted with methanol and purified by RP-HPLC (pH 2) to give the desired product as a TFA salt. LCMS: (M+H)=414.4.

Example 72: 6-{1-[6-(4-Chloro-1H-pyrazol-1-yl) imidazo[1,2-a]pyrimidin-3-yl]cyclopropyl}quinoline

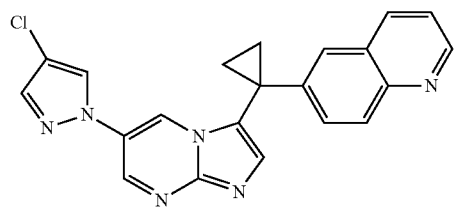 [SMILES: Clc1cnn(-c2cnc3ncc(C4(c5ccc6ncccc6c5)CC4)n3c2)c1]

This compound was prepared from 4-chloro-1H-pyrazole using procedures analogous to those for Example 22. LCMS: (M+H)+=387.0.

Example 73: 6-{1-[6-(2-Methyl-1,3-thiazol-4-yl) imidazo[1,2-a]pyrimidin-3-yl]cyclopropyl}quinoline

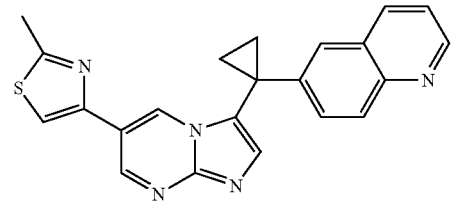 [SMILES: Cc1nc(-c2cnc3ncc(C4(c5ccc6ncccc6c5)CC4)n3c2)cs1]

This compound was prepared using procedures analogous to those for Example 63, Step 2 and 3. LCMS: (M+H)= 384.0.

Example 74: 6-{1-[6-(1,3-Thiazol-4-yl)imidazo[1,2-a]pyrimidin-3-yl]cyclopropyl}quinoline

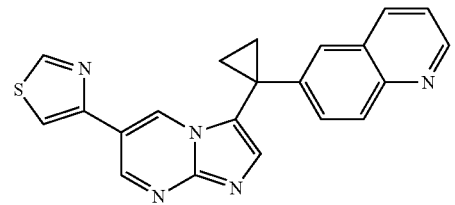 [SMILES: c1cnc2ccc(C3(c4cnc5ncc(-c6cscn6)cn45)CC3)cc2c1]

This compound was prepared using procedures analogous to those for Example 63, Step 2 and 3. LCMS: (M+H)= 370.0.

Example 75: 3-Fluoro-N-methyl-4-[3-(1-quinolin-6-ylcyclopropyl)imidazo[1,2-a]pyrimidin-6-yl]benzamide

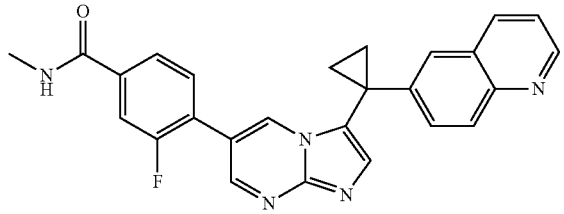 [SMILES: CNC(=O)c1ccc(-c2cnc3ncc(C4(c5ccc6ncccc6c5)CC4)n3c2)c(F)c1]

Step 1: methyl 3-fluoro-4-[3-(1-quinolin-6 ylcyclopropyl)imidazo[1,2-a]pyrimidin-6-yl]benzoate This compound was prepared from 4-bromo-3-fluorobenzoic acid using procedures analogous to those for Example 63, Step 2 and 3. LCMS: (M+H)=439.0.

Step 2. 3-fluoro-4-(3-(1-(quinolin-6-yl)cyclopropyl)imidazo[1,2-a]pyrimidin-6-yl)benzoic acid To a solution of methyl 3-fluoro-4-[3-(1-quinolin-6-ylcyclopropyl)imidazo[1,2-a]pyrimidin-6-yl]benzoate (100 mg, 0.2 mmol) in 5 ml of THF-MeOH—H$_2$O (3:1:1) was added 2M of lithium hydroxide in water (0.23 mL) at 0° C. under N$_2$. The solution was stirred for 10 min at 0° C., and 1.5 h at RT. The reaction solution was concentrated to dryness to give the desired product which was directly used in next step without further purification.

Step 3. 3-fluoro-N-methyl-4-[3-(1-quinolin-6-ylcyclopropyl) imidazo[1,2-a]pyrimidin-6-yl]benzamide 3-Fluoro-4-(3-(1-(quinolin-6-yl)cyclopropyl)imidazo[1,2-a]pyrimidin-6-yl)benzoic acid obtained from Step 2 was dissolved in N,N-dimethylformamide (1 mL). To this solution was added methylamine (2M in THF, 0.2 mL), benzotriazol-1-yloxytris(dimethylamino)phosphonium hexafluorophosphate (110 mg, 0.25 mmol) and N,N-diisopropylethylamine (0.12 mL, 0.68 mmol). The solution was stirred overnight at RT, diluted with MeOH, and purified by RP-HPLC (pH 10) to afford the desired compound. LCMS (M+H): m/z=438.0.

Example 76: (3S)-1-{3-Fluoro-4-[3-(1-quinolin-6-ylcyclopropyl)imidazo[1,2-a]pyrimidin-6-yl]benzoyl}pyrrolidin-3-ol

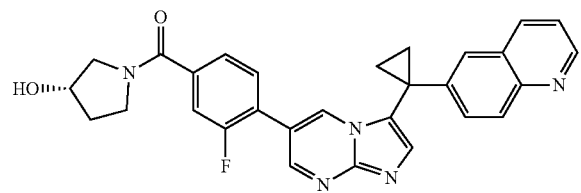 [SMILES: O=C(c1ccc(-c2cnc3ncc(C4(c5ccc6ncccc6c5)CC4)n3c2)c(F)c1)N1CC[C@H](O)C1]

This compound was prepared from 3-fluoro-4-(3-(1-(quinolin-6-yl)cyclopropyl)imidazo[1,2-a]pyrimidin-6-yl)benzoic acid using procedures analogous to those for Example 75. LCMS: (M+H)=494.1.

Example 77: 2,5-Difluoro-N-methyl-4-[3-(1-quinolin-6-ylcyclopropyl)imidazo[1,2-a]pyrimidin-6-yl]benzamide

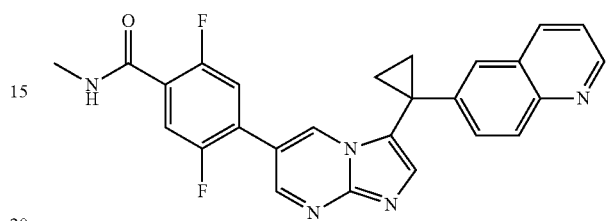

This compound was prepared from 2,5-difluoro-4-(3-(1-(quinolin-6-yl)cyclopropyl)imidazo[1,2-a]pyrimidin-6-yl)benzoic acid which was prepared from 4-chloro-2,5-difluorobenzoic acid using procedures analogous to those for Example 75. LCMS: (M+H)=456.0.

Example 78: 2,5-Difluoro-4-[3-(1-quinolin-6-ylcyclopropyl)imidazo[1,2-a]pyrimidin-6-yl]benzamide

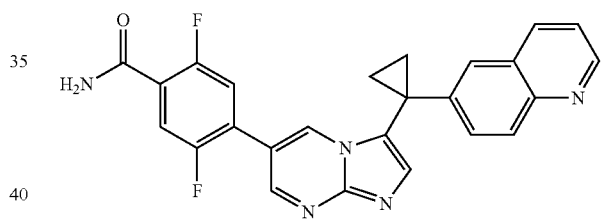

This compound was prepared from 2,5-difluoro-4-(3-(1-(quinolin-6-yl)cyclopropyl)imidazo[1,2-a]pyrimidin-6-yl)benzoic acid using procedures analogous to those for Example 75. LCMS: (M+H)=442.0.

Example 79: N-Cyclopropyl-2,5-difluoro-4-[3-(1-quinolin-6-ylcyclopropyl)imidazo[1,2-a]pyrimidin-6-yl]benzamide

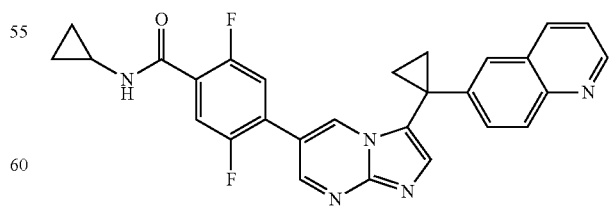

This compound was prepared from 2,5-difluoro-4-(3-(1-(quinolin-6-yl)cyclopropyl)imidazo[1,2-a]pyrimidin-6-yl)benzoic acid using procedures analogous to those for Example 75. LCMS: (M+H)=482.0.

Example 80: 2,5-Difluoro-N-(trans-4-hydroxycyclohexyl)-4-[3-(1-quinolin-6-ylcyclopropyl)imidazo[1,2-a]pyrimidin-6-yl]benzamide

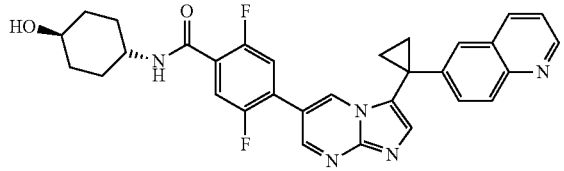

This compound was prepared from 2,5-difluoro-4-(3-(1-(quinolin-6-yl)cyclopropyl)imidazo[1,2-a]pyrimidin-6-yl)benzoic acid using procedures analogous to those for Example 75. LCMS: (M+H)=540.2.

Example 81: 1-{2-Fluoro-4-[3-(1-quinolin-6-ylcyclopropyl)imidazo[1,2-a]pyrimidin-6-yl]phenyl}pyrrolidin-2-one

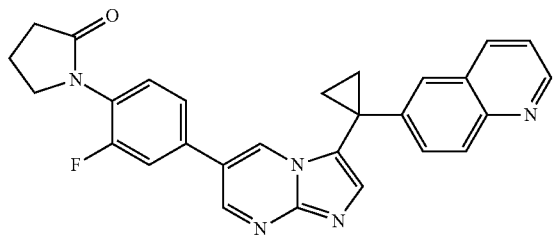 [SMILES: O=C1CCCN1c1ccc(-c2cnc3ncc(C4(c5ccc6ncccc6c5)CC4)n3c2)cc1F]

To a solution of 6-{1-[6-(4-bromo-3-fluorophenyl)imidazo[1,2-a]pyrimidin-3-yl]cyclopropyl}quinoline (20 mg, 0.04 mmol) in 1,4-dioxane (1 mL) was added 2-pyrrolidinone (5.7 mg, 0.067 mmol), (1S,2S)—N,N'-dimethylcyclohexane-1,2-diamine (1 mg, 0.009 mmol), copper(I) iodide (0.8 mg, 0.004 mmol), and potassium carbonate (13 mg, 0.095 mmol). The mixture was irradiated at under microwave 150° C. for 1 h. After cooling to RT, the solution was purified by RP-HPLC (pH=10) to afford the desired compound. LCMS: (M+H)+=464.1.

Example 82: 3-{2-Fluoro-4-[3-(1-quinolin-6-ylcyclopropyl)imidazo[1,2-a]pyrimidin-6-yl]phenyl}-1,3-oxazolidin-2-one

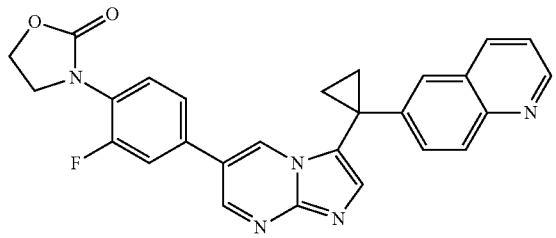 [SMILES: O=C1OCCN1c1ccc(-c2cnc3ncc(C4(c5ccc6ncccc6c5)CC4)n3c2)cc1F]

This compound was prepared from 6-{1-[6-(4-bromo-3-fluorophenyl)imidazo[1,2-a]pyrimidin-3-yl]cyclopropyl}quinoline using procedures analogous to those for Example 81. LCMS: (M+H)=466.0.

Example 83: Ethyl 4-{4-[3-(1-quinolin-6-ylcyclopropyl)imidazo[1,2-a]pyrimidin-6-yl]-1H-pyrazol-1-yl}piperidine-1-carboxylate

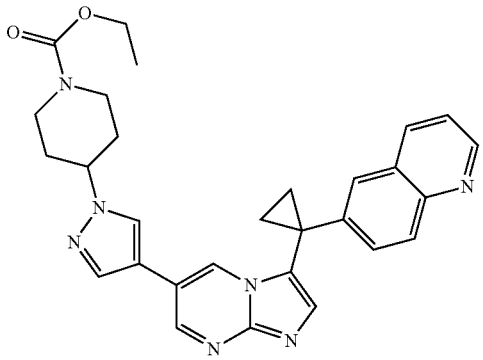 [SMILES: CCOC(=O)N1CCC(n2cc(-c3cnc4ncc(C5(c6ccc7ncccc7c6)CC5)n4c3)cn2)CC1]

Step 1. 6-{1-[6-(1-piperidin-4-yl-1H-pyrazol-4-yl)imidazo[1,2-a]pyrimidin-3-yl]cyclopropyl}quinoline tert-Butyl 4-{4-[3-(1-quinolin-6-ylcyclopropyl)imidazo[1,2-a]pyrimidin-6-yl]-1H-pyrazol-1-yl}piperidine-1-carboxylate, which was prepared using a procedure that was analogous to that described for the synthesis of Example 88 Steps 1-4, was treated with TFA in methylene chloride to afford the desired product. LCMS: (M+H)=436.1.

Step 2. ethyl 4-{4-[3-(1-quinolin-6-ylcyclopropyl)imidazo[1,2-a]pyrimidin-6-yl]-1H-pyrazol-1-yl}piperidine-1-carboxylate 6-{1-[6-(1-piperidin-4-yl-1H-pyrazol-4-yl)imidazo[1,2-a]pyrimidin-3-yl]cyclopropyl}) quinoline (4 mg, 0.0092 mmol) was dissolved in N,N-dimethylformamide (0.5 mL) and cooled to 0° C. followed by the addition of ethyl chloroformate (1.0 μL, 0.01 mmol) and N,N-diisopropylamine (4.0 μL, 0.023 mmol). The solution was allowed to gradually warm to RT over 2 h. The reaction mixture was purified by RP-HPLC (pH 2) to afford the desired product as a TFA salt. LCMS: (M+H)=508.2.

Example 84: 2-(4-{2-Fluoro-4-[3-(1-quinolin-6-ylcyclopropyl)imidazo[1,2-a]pyrimidin-6-yl]phenyl}-1H-pyrazol-1-yl)-N,N-dimethylacetamide

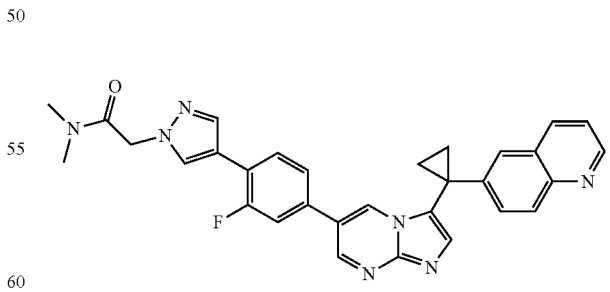

Step 1: tert-butyl [4-(4,4,5,5-tetramethyl-1,3,2-dioxaborolan-2-yl)-1H-pyrazol-1-yl]acetate To a solution of 4-(4,4,5,5-tetramethyl-1,3,2-dioxaborolan-2-yl)-1H-pyrazole (1.5 g, 7.7 mmol) in N,N-dimethylformamide (25 mL) was added tert-butyl 2-bromoacetate (1.2 mL, 8.5 mmol) and cesium carbonate (3.8 g, 0.012 mol). The suspension was stirred overnight at RT and partitioned with EtOAc and water. The organic phase was washed with brine, dried with MgSO₄, filtered, and concentrated to afford the desired compound which was directly used in next step. LCMS: (M+H)=309.4.

Step 2: tert-butyl [4-(4-bromo-2-fluorophenyl)-1H-pyrazol-1-yl]acetate

To a solution of 4-bromo-2-fluoro-1-iodobenzene (380 mg, 1.3 mmol) in THF (10 mL) was added tert-butyl [4-(4,4,5,5-tetramethyl-1,3,2-dioxaborolan-2-yl)-1H-pyrazol-1-yl]acetate (390 mg, 1.3 mmol), 2M sodium carbonate in water (2.5 mL) and tetrakis(triphenylphosphine)palladium (40 mg, 0.04 mmol). The solution was degassed with N₂, and heated at 80° C. overnight. The mixture was cooled to RT, poured into water, extracted with EtOAc, washed with brine, dried over MgSO₄, filtered, and concentrated. The residue was purified by flash chromatograph on a silica gel column with EtOAc in Hexanes (30%) to afford the desired compound. LCMS: (M+57)=299.0.

Step 3: tert-butyl 4-[4-(2-aminopyrimidin-5-yl)-2-fluorophenyl]-1H-pyrazol-1-ylacetate To a solution of tert-butyl [4-(4-bromo-2-fluorophenyl)-1H-pyrazol-1-yl]acetate (400 mg, 0.001 mol) in 1,4-dioxane (3 mL) was added 5-(4,4,5,5-tetramethyl-1,3,2-dioxaborolan-2-yl)pyrimidin-2-amine (270 mg, 1.2 mmol), potassium phosphate (640 mg, 3.0 mmol) and tetrakis(triphenylphosphine)palladium (70 mg, 0.06 mmol). The solution was degassed with N₂, and heated at 120° C. for 3 h. The solution was cooled to RT, poured into water, extracted with EtOAc, washed with brine, dried over MgSO₄, filtered, and concentrated. The residue was purified by flash chromatograph on a silica gel column with EtOAc in Hexanes (50%) to afford the desired compound. LCMS: (M+H)=370.1.

Step 4: tert-butyl (4-2-fluoro-4-[3-(1-quinolin-6-ylcyclopropyl) imidazo[1,2-a]pyrimidin-6-yl]phenyl-1H-pyrazol-1-yl)acetate A mixture of tert-butyl 4-[4-(2-aminopyrimidin-5-yl)-2-fluorophenyl]-1H-pyrazol-1-ylacetate (100 mg, 0.27 mmol) and chloro(1-quinolin-6-ylcyclopropyl)acetaldehyde (67.2 mg, 0.273 mmol) in ethanol (2 mL) was stirred at 100° C. overnight. The solution was concentrated and the residue was purified by chromatography on silica gel with EtOAc in CH₂Cl₂ (0-90%) to afford the desired compound. LCMS: (M+H)=561.1.

Step 5: 2-(4-{2-fluoro-4-[3-(1-quinolin-6-ylcyclopropyl)imidazo[, 2-a]pyrimidin-6-yl]phenyl}-1H-pyrazol-1-yl)-N,N-dimethylacetamide To a solution of tert-butyl (4-2-fluoro-4-[3-(1-quinolin-6-ylcyclopropyl)imidazo[1,2-a]pyrimidin-6-yl]phenyl-1H-pyrazol-1-yl)acetate (20 mg, 0.04 mmol) in CH₂Cl₂ (2 mL) was added TFA (1 mL) and the solution was stirred at RT for 2 h. The volatiles were removed under reduced pressure. The residue was dissolved in N,N-dimethylformamide (0.5 mL). treated with 2M dimethylamine in THF (0.036 mL), benzotriazol-1-yloxytris(dimethylamino)phosphonium hexafluorophosphate (24 mg, 0.054 mmol), and N,N-diisopropylethylamine (19 μL, 0.11 mmol). The solution was stirred at RT for 3 h, and purified by RP-HPLC (pH 10) to afford the desired compound. LCMS: (M+H)=532.0.

Example 85: 5-{2-Fluoro-4-[3-(1-quinolin-6-ylcyclopropyl)imidazo[1,2-a]pyrimidin-6-yl]phenyl}-N-methylpyridine-2-carboxamide

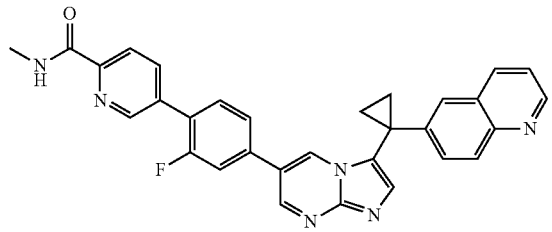 [SMILES: CNC(=O)c1ccc(-c2ccc(-c3cnc4ncc(C5(c6ccc7ncccc7c6)CC5)n4c3)cc2F)cn1]

Step 1:
5-(4-bromo-3-fluorophenyl)pyrimidin-2-amine

To a solution of 5-bromopyrimidin-2-amine (2.1 g, 0.012 mol) in 1,4-dioxane (30 mL) was added (4-bromo-3-fluorophenyl)boronic acid (2.0 g, 0.0091 mol), potassium phosphate (6.4 g, 0.030 mol) and tetrakis(triphenylphosphine) palladium (700 mg, 0.6 mmol), water (5 mL). The solution was degassed with N₂, and heated at 120° C. for 4 h. The mixture was cooled to RT, poured into water, and extracted with EtOAc. The combined organic layers were washed with brine, dried with MgSO₄, filtered, and concentrated. The residue was purified by chromatography on silica gel with EtOAc in CH₂Cl₂ (0-30%) to afford the desired compound. LCMS: (M+H)=267.9.

Step 2: 6-{1-[6-(4-bromo-3-fluorophenyl)imidazo[1,2-a]pyrimidin-3-yl]cyclopropyl}quinoline A mixture of 5-(4-bromo-3-fluorophenyl)pyrimidin-2-amine (0.50 g, 1.9 mmol) and chloro(1-quinolin-6-ylcyclopropyl)acetaldehyde (0.463 g, 1.88 mol) in ethanol (20 mL) was stirred at 100° C. overnight. The solution was concentrated and the residue was purified by chromatography on silica gel with MeOH in CH₂Cl₂ (0-6%) to afford the desired compound. LCMS: (M+H)=458.9.

Step 3: 5-{2-fluoro-4-[3-(1-quinolin-6-ylcyclopropyl)imidazo[1,2-a]pyrimidin-6-yl]phenyl}-N-methylpyridine-2-carboxamide To a solution of 6-{1-[6-(4-bromo-3-fluorophenyl)imidazo[1,2-a]pyrimidin-3-yl]cyclopropyl}quinoline (20 mg, 0.04 mmol) in 1,4-dioxane (1 mL) was added N-methyl-5-(4,4,5,5-tetramethyl-1,3,2-dioxaborolan-2-yl)pyridine-2-carboxamide (17 mg, 0.065 mmol), tetrakis(triphenylphosphine)palladium (3 mg, 0.003 mmol), and potassium phosphate (28 mg, 0.13 mol). The mixture was heated at 120° C. overnight. After cooling to RT, the solution was purified by RP-HPLC (pH 2) to afford the desired compound as a TFA salt. LCMS: (M+H)=515.0.

Example 86: 5-{2-Fluoro-4-[3-(1-quinolin-6-ylcyclopropyl)imidazo[1,2-a]pyrimidin-6-yl]phenyl}-N,N-dimethylpyridine-2-carboxamide

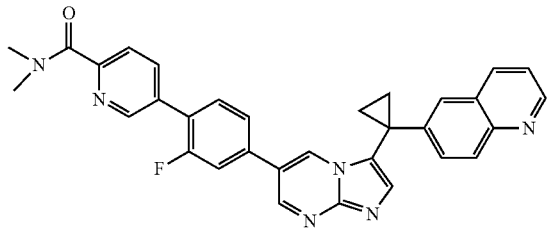 [SMILES: CN(C)C(=O)c1ccc(-c2ccc(-c3cnc4ncc(C5(c6ccc7ncccc7c6)CC5)n4c3)cc2F)cn1]

This compound was prepared as a TFA salt starting from 6-{1-[6-(4-bromo-3-fluorophenyl)imidazo[1,2-a]pyrimidin-3-yl]cyclopropyl}quinoline using procedures analogous to those for Example 85. LCMS: (M+H)=529.0.

Example 87: 6-(1-{6-[3-Fluoro-4-(1-methyl-1H-pyrazol-4-yl)phenyl]imidazo[1,2-a]pyrimidin-3-yl}cyclopropyl)quinoline

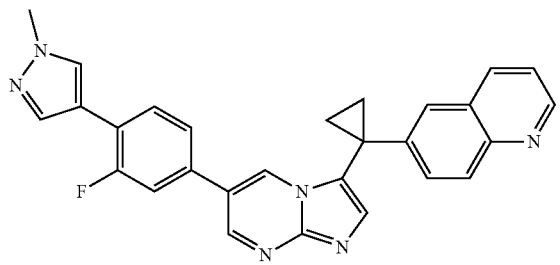 [SMILES: Cn1cc(-c2ccc(-c3cnc4ncc(C5(c6ccc7ncccc7c6)CC5)n4c3)cc2F)cn1]

This compound was prepared as a TFA salt starting from 6-{1-[6-(4-bromo-3-fluorophenyl)imidazo[1,2-a]pyrimidin-3-yl]cyclopropyl}quinoline using procedures analogous to those for Example 85. LCMS: (M+H)=461.1.

Example 88: 6-(1-{6-[1-(Tetrahydrofuran-3-yl)-1H-pyrazol-4-yl]imidazo[1,2-a]pyrimidin-3-yl}cyclopropyl)quinoline

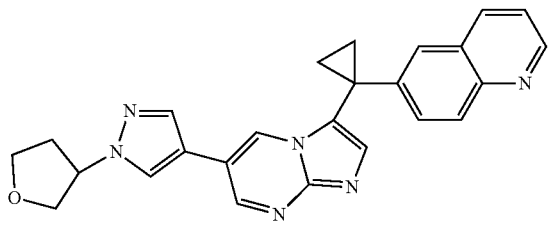 [SMILES: c1cnc2ccc(C3(c4cnc5ncc(-c6cnn(C7CCOC7)c6)cn45)CC3)cc2c1]

Step 1. tetrahydrofuran-3-yl methanesulfonate

3-Hydroxytetrahydrofuran (83.3 µL, 1.03 mmol) was dissolved in methylene chloride (anhydrous, 2 mL) and cooled to 0° C. followed by the addition of triethylamine (166 µL, 1.2 mmol) and methanesulfonyl chloride (88 µL, 1.14 mmol). The reaction mixture was stirred for 16 h while gradually warming to ambient temperature. The reaction was quenched with water, diluted with methylene chloride (20 mL), and the resulting layers were separated. The organic layer was washed with water (2×2 mL) and the combined aqueous phases were extracted with methylene chloride (2×3 mL). The combined organic phases were washed with brine (2×2 mL), dried over Na₂SO₄, filtered, and concentrated. The crude product was used directly in the next step.

Step 2. 1-(tetrahydrofuran-3-yl)-4-(4,4,5,5-tetramethyl-1,3,2-dioxaborolan-2-yl)-1H-pyrazole Tetrahydrofuran-3-yl methanesulfonate was dissolved in N,N-dimethylformamide (0.5 mL) and added to a pre-stirred solution of 4-(4,4,5,5-tetramethyl-1,3,2-dioxaborolan-2-yl)-1H-pyrazole (100 mg, 0.52 mmol) and sodium hydride (25 mg, 1.1 mmol) in N,N-dimethylformamide (1 mL). The mixture was heated to 60° C. for 2 d, cooled to RT, and purified by RP-HPLC to afford the desired product. LCMS: (M+H)=265.1.

Step 3. 5-[1-(tetrahydrofuran-3-yl)-1H-pyrazol-4-yl]pyrimidin-2-amine

To a solution of 1-(Tetrahydrofuran-3-yl)-4-(4,4,5,5-tetramethyl-1,3,2-dioxaborolan-2-yl)-1H-pyrazole (110 mg, 0.42 mmol) in 1,4-dioxane (3 mL) was added EtOH (1 mL) and water (0.4 mL). The following reagents were added successively: 5-bromopyrimidin-2-amine (75 mg, 0.43 mmol), potassium carbonate (180 mg, 1.3 mmol), and [1,1'-bis(diphenylphosphino)ferrocene]dichloropalladium (II), complex with dichloromethane (1:1) (20 mg, 0.02 mmol). The vessel was purged several times with N₂ and heated to 100° C. for 4 h. The reaction mixture was filtered through a pad of Celite, concentrated, and purified by chromatography on silica gel (40 g column, 0-15% MeOH/methylene chloride) to afford the desired product. LCMS: (M+H)=232.0.

Step 4. 6-(1-{6-[1-(tetrahydrofuran-3-yl)-1H-pyrazol-4-yl]imidazo[1,2-a]pyrimidin-3-yl}cyclopropyl)quinoline The title compound was prepared as a TFA salt from the condensation of 5-[1-(tetrahydrofuran-3-yl)-1H-pyrazol-4-yl]pyrimidin-2-amine and chloro(1-quinolin-6-ylcyclopropyl) acetaldehyde using a procedure analogous to that described for the synthesis of Example 7, Step 8. LCMS: (M+H)=423.1.

Example 89: 6-(1-{6-[1-(1-Benzylpyrrolidin-3-yl)-1H-pyrazol-4-yl]imidazo[1,2-a]pyrimidin-3-yl}cyclopropyl)quinoline

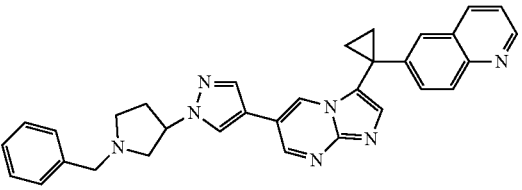 [SMILES: c1ccc(CN2CCC(n3cc(-c4cnc5ncc(C6(c7ccc8ncccc8c7)CC6)n5c4)cn3)C2)cc1]

This compound was prepared as a TFA salt using a procedure that was analogous to that described for the synthesis of Example 88, Steps 1-4 to afford the desired product. LCMS: (M+H)=512.2.

Example 90: 6-{1-[6-(1-Methyl-1H-pyrazol-4-yl)imidazo[1,2-a]pyrimidin-3-yl]cyclopropyl}quinoline

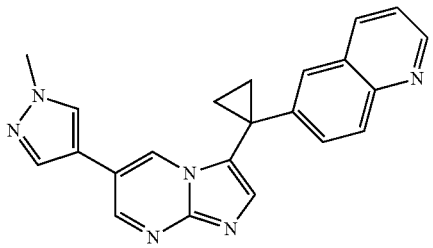 [SMILES: Cn1cc(-c2cnc3ncc(C4(c5ccc6ncccc6c5)CC4)n3c2)cn1]

Step 1. 6-{1-[6-(1H-pyrazol-4-yl)imidazo[1,2-a]pyrimidin-3-yl]cyclopropyl}quinoline This compound was prepared using a procedure analogous to that described for the synthesis of Example 88, Steps 3-4 starting from 4-(4,4,5,5-tetramethyl-1,3,2-dioxaborolan-2-yl)-1-trityl-1H-pyrazole. The trityl group of 6-{1-[6-(1-trityl-1H-pyrazol-4-yl)imidazo[1,2-a]pyrimidin-3-yl]cyclopropyl}quinoline was removed upon treatment with ~1% TFA in acetonitrile and was purified by RP-HPLC. LC/MS 353.1 (M+1H)

Step 2. 6-{1-[6-(1-methyl-1H-pyrazol-4-yl)imidazo[1,2-a]pyrimidin-3-yl]cyclopropyl}quinoline To a solution of 6-{1-[6-(1H-pyrazol-4-yl)imidazo[1,2-a]pyrimidin-3-yl]cyclopropyl}) quinoline (6 mg, 0.017 mmol) in N,N-dimethylformamide (200 µL) was added potassium carbonate (4.0 mg, 0.029 mmol) and methyl iodide (3 µL, 0.048 mmol). After stirring at RT for 16 h, the reaction mixture was purified by RP-HPLC to afford the desired product. LCMS: (M+H)=367.0.

Example 91: N,N-Dimethyl-4-{4-[3-(1-quinolin-6-ylcyclopropyl)imidazo[1,2-a]pyrimidin-6-yl]-1H-pyrazol-1-yl}piperidine-1-carboxamide

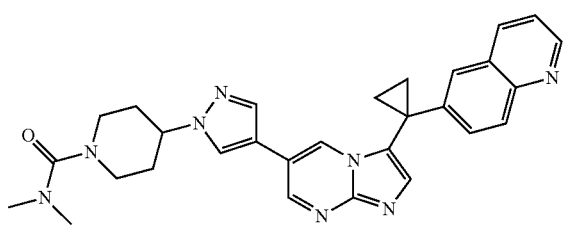 [SMILES: CN(C)C(=O)N1CCC(n2cc(-c3cnc4ncc(C5(c6ccc7ncccc7c6)CC5)n4c3)cn2)CC1]

This compound was prepared using a procedure that was analogous to that described for the synthesis of Example 83 using methylene chloride as a solvent and N,N-dimethylcarbamoyl chloride as the acylating agent in Step 2 to afford the desired product as a TFA salt. LCMS: (M+H)=507.2.

Example 92: 4-{4-[3-(1-Quinolin-6-ylcyclopropyl)imidazo[1,2-a]pyrimidin-6-yl]-1H-pyrazol-1-yl}cyclohexanol

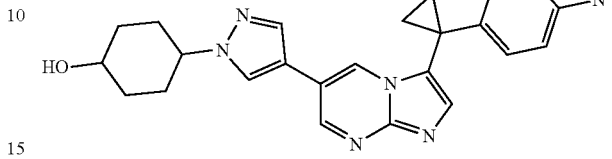

Step1. 4-{4-[3-(1-quinolin-6-ylcyclopropyl)imidazo[1,2-a]pyrimidin-6-yl]-1H-pyrazol-1-yl}cyclohexanone The crude reaction mixture containing 6-(1-{2-[1-(1,4-dioxaspiro[4.5]dec-8-yl)-1H-pyrazol-4-yl]imidazo[1,2-b][1,2,4]triazin-7-yl}cyclopropyl)quinoline (~30 mg, 0.07 mmol), prepared using a procedure analogous to that described for the synthesis of Example 88 starting from 1,4-dioxaspiro[4.5]decan-8-ol, was concentrated and treated directly with AcOH (1 mL), water (100 µL) and heated to 100° C. for 1 h to afford the desired product, which was purified by RP-HPLC. LCMS: (M+H)=449.2.

Step 2. 4-{4-[3-(1-quinolin-6-ylcyclopropyl)imidazo[1,2-a]pyrimidin-6-yl]-1H-pyrazol-1-yl}cyclohexanol 4-{4-[3-(1-Quinolin-6-ylcyclopropyl)imidazo[1,2-a]pyrimidin-6-yl]-1H-pyrazol-1-yl}cyclohexanone (16 mg, 0.036 mmol) was dissolved in MeOH (1 mL) and cooled to about −20° C. followed by the addition of sodium tetrahydroborate (3.0 mg, 0.079 mmol). The reaction mixture was allowed to gradually warm to ambient temperature and stirred for 2 h. The reaction mixture was purified by RP-HPLC (pH 2) to afford the desired product as a TFA salt. LCMS: (M+H)=451.1.

Example 93: {4-[3-(1-Quinolin-6-ylcyclopropyl)imidazo[1,2-a]pyrimidin-6-yl]-1H-pyrazol-1-yl}acetonitrile

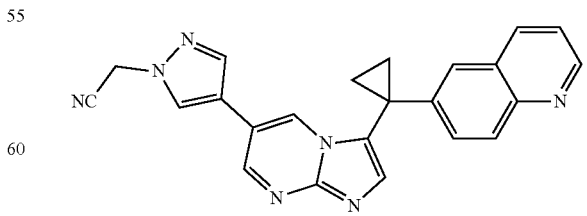

This compound was prepared as a TFA salt using a procedure analogous to those for Example 88, Steps 2-4. LCMS: (M+H)=392.1.

Example 94: N-Methyl-5-{4-[7-(1-quinolin-6-ylcyclopropyl)imidazo[1,2-b][1,2,4]triazin-2-yl]phenyl}pyridine-2-carboxamide

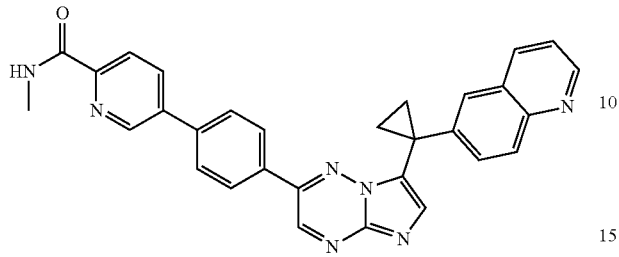

Step 1. 6-(4-bromophenyl)-1,2,4-triazin-3-amine

This compound was prepared using procedures analogous to those described for the synthesis of Example 7, Steps 3-5 starting from 4-bromoacetophenone. LCMS: (M+H$_2$O+H)= 269.0/271.0.

Step 2. 6-{1-[2-(4-bromophenyl) imidazo[1,2-b][1,2,4]triazin-7-yl]cyclopropyl}quinoline This compound was prepared from the condensation of 6-(4-bromophenyl)-1,2,4-triazin-3-amine and chloro(1-quinolin-6-ylcyclopropyl)acetaldehyde using a procedure analogous to that described for the synthesis of Example 7, Step 8. LCMS: (M+H)=442.3/444.2.

Step 3. N-methyl-5-{4-[7-(1-quinolin-6-ylcyclopropyl)imidazo[1,2-b][1,2,4]triazin-2-yl]phenyl}pyridine-2-carboxamide To a solution of 6-{1-[2-(4-bromophenyl)imidazo[1,2-b][1,2,4]triazin-7-yl]cyclopropyl}quinoline (10.0 mg, 0.0226 mmol) in 1,4-dioxane (1 mL), EtOH (0.2 mL) and water (0.2 mL) was added N-methyl-5-(4,4,5,5-tetramethyl-1,3,2-dioxaborolan-2-yl)pyridine-2-carboxamide (12 mg, 0.045 mmol), cesium carbonate (15 mg, 0.045 mmol), and [1,1'-bis(diphenylphosphino)ferrocene]dichloropalladium(II), complex with dichloromethane (1:1) (1.8 mg, 0.0023 mmol). The reaction vessel was purged with N$_2$ and then heated in a sealed tube at 120° C. for 1 h. LCMS and HPLC data indicated that the reaction was complete. The mixture was purified by RP-HPLC (pH 2) to give the desired product as a TFA salt. LCMS: (M+H)=498.1.

Example 95: 6-{1-[2-(4-Pyrimidin-5-yl-phenyl)imidazo[1,2-b][1,2,4]triazin-7-yl]cyclopropyl}quinoline

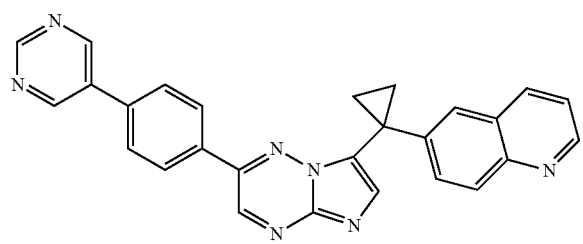 [SMILES: c1cnc2ccc(C3(c4cnc5ncc(-c6ccc(-c7cncnc7)cc6)nn45)CC3)cc2c1]

This compound was prepared as a TFA salt starting from 6-{1-[2-(4-bromophenyl)imidazo[1,2-b][1,2,4]triazin-7-yl]cyclopropyl}quinoline using procedures analogous to those for Example 94. LCMS: (M+H)=442.1.

Example 96: 6-(1-{2-[4-(1-Acetyl-1,2,3,6-tetrahydropyridin-4-yl)phenyl]imidazo[1,2-b][1,2,4]triazin-7-yl}cyclopropyl)quinoline

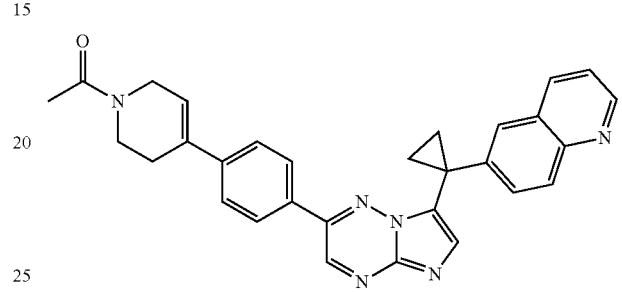

Step 1. tert-butyl 4-{4-[7-(1-quinolin-6-ylcyclopropyl)imidazo[1,2-b][1,2,4]triazin-2-yl]phenyl}-3,6-dihydropyridine-1 (2H)-carboxylate This compound was prepared using procedures analogous to those for Example 94. LCMS: (M+H)=545.2.

Step 2. 6-(1-{2-[4-(1,2,3,6-tetrahydropyridin-4-yl)phenyl]imidazo[1,2-b][1,2,4]triazin-7-yl}cyclopropyl)quinoline hydrochloride tert-Butyl 4-{4-[7-(1-quinolin-6-ylcyclopropyl)imidazo[1,2-b][1,2,4]triazin-2-yl]phenyl})-3,6-dihydropyridine-1 (2H)-carboxylate (36.0 mg, 0.0661 mmol) was dissolved in 4M of hydrogen chloride in 1,4-dioxane (5.0 mL) and stirred at RT for 2 h. The volatiles were removed under vacuum and the residue was azeotropically washed with acetonitrile. The crude material was used in the next step. LCMS: (M+H)=445.0.

Step 3. 6-(1-{2-[4-(1-acetyl-1,2,3,6-tetrahydropyridin-4-yl)phenyl]imidazo[1,2-b][1,2,4]triazin-7-yl}cyclopropyl)quinoline To a solution of 6-(1-{2-[4-(1,2,3,6-Tetrahydropyridin-4-yl)phenyl]imidazo[1,2-b][1,2,4]triazin-7-yl}) cyclopropyl)quinoline hydrochloride (12 mg) in N,N-dimethylformamide (1 mL) and acetonitrile (1 mL) was added N,N-diisopropylethylamine (23.0 µL, 0.132 mmol; ~5 equiv.) and acetyl chloride (3.8 µL, 0.053 mmol; ~2.0 equiv.). The resulting solution was stirred at RT for 1 h, quenched with MeOH and purified directly by RP-HPLC (pH 2) to afford the desired product as a TFA salt. LCMS: (M+H)=487.1.

Example 97: 6-[1-(2-{4-[1-(Methylsulfonyl)-1,2,3,6-tetrahydropyridin-4-yl]phenyl}imidazo[1,2-b][1,2,4]triazin-7-yl)cyclopropyl]quinoline

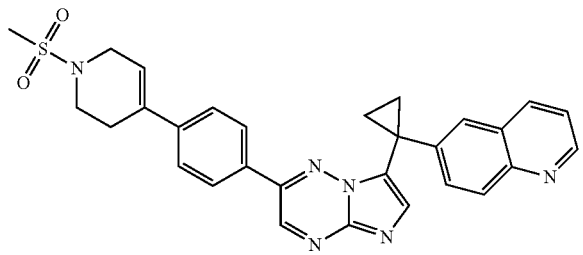 [SMILES: CS(=O)(=O)N1CC=C(c2ccc(-c3cnc4ncc(C5(c6ccc7ncccc7c6)CC5)n4n3)cc2)CC1]

This compound was prepared as a TFA salt starting from 6-(1-{2-[4-(1,2,3,6-tetrahydropyridin-4-yl)phenyl]imidazo[1,2-b][1,2,4]triazin-7-yl}cyclopropyl)quinoline hydrochloride using procedures analogous to those for Example 96. LCMS: (M+H)=523.2.

Example 98: N,N-Dimethyl-5-{4-[7-(1-quinolin-6-ylcyclopropyl)imidazo[1,2-b][1,2,4]triazin-2-yl]phenyl}pyridine-2-carboxamide

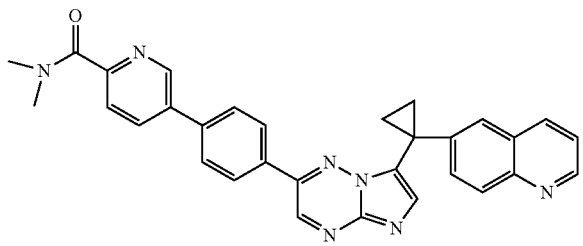 [SMILES: CN(C)C(=O)c1ccc(-c2ccc(-c3cnc4ncc(C5(c6ccc7ncccc7c6)CC5)n4n3)cc2)cn1]

This compound was prepared as a TFA salt starting from 6-{1-[2-(4-bromophenyl)imidazo[1,2-b][1,2,4]triazin-7-yl]cyclopropyl}quinoline using procedures analogous to those for Example 94. LCMS: (M+H)=512.3

Example 99: 6-(1-{2-[4-(1H-Imidazol-1-yl)phenyl]imidazo[1,2-b][1,2,4]triazin-7-yl}cyclopropyl)-quinoline

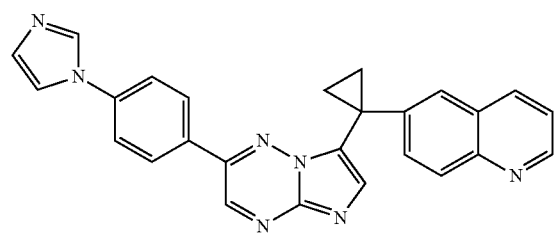 [SMILES: c1cnc2ccc(C3(c4cnc5ncc(-c6ccc(-n7ccnc7)cc6)nn45)CC3)cc2c1]

To a solution of 6-{1-[2-(4-bromophenyl)imidazo[1,2-b][1,2,4]triazin-7-yl]cyclopropyl}quinoline (15 mg, 0.034 mmol) and 1H-imidazole (2.77 mg, 0.0407 mmol) in 1,4-dioxane (0.50 mL) was added (1S,2S)—N,N'-dimethylcyclohexane-1,2-diamine (0.96 mg, 0.0068 mmol), copper(I) iodide (0.64 mg), and potassium carbonate (9.84 mg). The mixture was refluxed overnight. After cooling to RT, the mixture was purified by RP-HPLC (pH 2) to afford the desired product as a TFA salt. LCMS: (M+H)=430.4.

Example 100: 2-Fluoro-N-(trans-4-hydroxycyclohexyl)-4-[7-(1-quinolin-6-ylcyclopropyl)imidazo[1,2-b][1,2,4]triazin-2-yl]benzamide

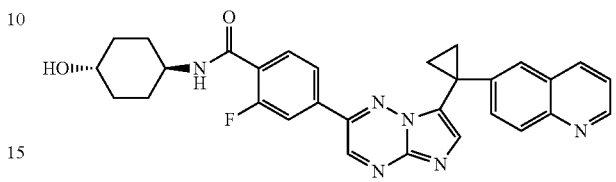

Step 1. 6-{1-[2-(4-Bromo-3-fluorophenyl)imidazo[1,2-b][1,2,4]triazin-7-yl]cyclopropyl}quinoline A mixture of 6-(4-bromo-3-fluorophenyl)-1,2,4-triazin-3-amine (80.0 mg, 0.297 mmol, Example 7, Steps 1-5) and chloro(1-quinolin-6-ylcyclopropyl)acetaldehyde (0.088 g, 0.36 mmol) in isopropyl alcohol (3 mL) and a drop of water was heated at 110° C. for 48 h. The mixture was adjusted to pH 9 with triethylamine. The volatiles were removed under reduced pressure. The residue was purified by chromatography on silica gel with EtOAc in CH$_2$Cl$_2$ (0-60%) to afford the desired product. LCMS: (M+H)=459.9/461.9.

Step 2. 2-Fluoro-4-[7-(1-quinolin-6-ylcyclopropyl)imidazo[1,2-b][1,2,4]triazin-2-yl]benzonitrile A mixture of 6-1-[2-(4-bromo-3-fluorophenyl)imidazo[1,2-b][1,2,4]triazin-7-yl]cyclopropylquinoline (0.060 g, 0.13 mmol), potassium hexacyanoferrate(II) trihydrate (0.02 g, 0.05 mmol), sodium carbonate (0.016 g, 0.16 mmol) and palladium acetate (0.001 g, 0.006 mmol) in N,N-dimethylacetamide (1.0 mL, 11 mmol) was stirred at 120° C. for 2 h. The reaction mixture was diluted with EtOAc, washed with water and brine, dried over Na$_2$SO$_4$, filtered, and concentrated. The residue was purified by chromatography on silica gel with MeOH in CH$_2$Cl$_2$ (0-5%) to afford the desired product. LCMS: (M+H)=407.1.

Step 3. 2-Fluoro-4-[7-(1-quinolin-6-ylcyclopropyl)imidazo[1,2-b][1,2,4]triazin-2-yl]benzoic acid 2-Fluoro-4-[7-(1-quinolin-6-ylcyclopropyl)imidazo[1,2-b][1,2,4]triazin-2-yl]benzonitrile (40.0 mg, 0.0984 mmol) in concentrated hydrochloric acid (0.6 mL, 0.006 mol) was stirred at 110° C. overnight. The volatiles were removed under reduced pressure. The residue was co-evaporated with toluene, and dried to give the desired product. LCMS: (M+H)=426.0.

Step 4. 2-Fluoro-N-(trans-4-hydroxycyclohexyl)-4-[7-(1-quinolin-6-ylcyclopropyl)imidazo[1,2-b][1,2,4]triazin-2-yl]benzamide N,N-Diisopropylethylamine (6.4 μL, 0.037 mmol) was added to a mixture of 2-fluoro-4-[7-(1-quinolin-6-ylcyclopropyl)imidazo[1,2-b][1,2,4]triazin-2-yl]benzoic acid (5.2 mg, 0.012 mmol), trans-4-aminocyclohexanol hydrochloride, and benzotriazol-1-yloxytris(dimethylamino)phosphonium hexafluorophosphate (8.1 mg, 0.018 mmol) in N,N-

Example 101: N-Cyclopropyl-2-fluoro-4-[7-(1-quinolin-6-ylcyclopropyl)imidazo[1,2-b][1,2,4]triazin-2-yl]benzamide

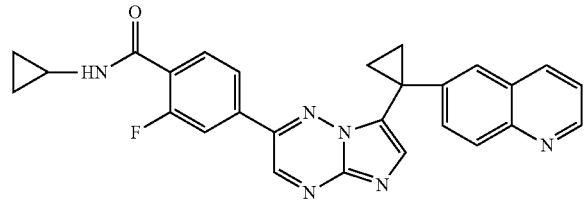 [SMILES: O=C(NC1CC1)c1ccc(-c2cnc3ncc(C4(c5ccc6ncccc6c5)CC4)n3n2)cc1F]

This compound was prepared as a TFA salt starting from 2-fluoro-4-[7-(1-quinolin-6-ylcyclopropyl)imidazo[1,2-b][1,2,4]triazin-2-yl]benzoic acid using procedures analogous to those for Example 100. LCMS: (M+H)=465.0

Example 102: 2-Fluoro-N-methyl-4-[7-(1-quinolin-6-ylcyclopropyl)imidazo[1,2-b][1,2,4]triazin-2-yl]benzamide

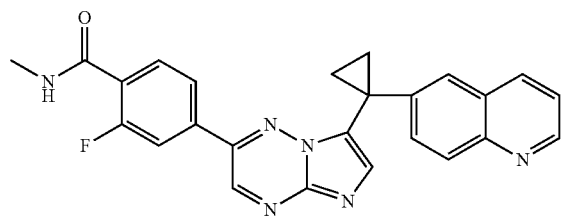 [SMILES: CNC(=O)c1ccc(-c2cnc3ncc(C4(c5ccc6ncccc6c5)CC4)n3n2)cc1F]

This compound was prepared as a TFA salt starting from 2-fluoro-4-[7-(1-quinolin-6-ylcyclopropyl)imidazo[1,2-b][1,2,4]triazin-2-yl]benzoic acid using procedures analogous to those for Example 100. LCMS: (M+H)=439.1.

Example 103: 2-Fluoro-N-[1-(methoxymethyl)cyclopropyl]-4-[7-(1-quinolin-6-ylcyclopropyl)imidazo[1,2-b][1,2,4]triazin-2-yl]benzamide

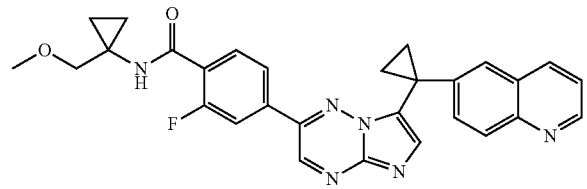 [SMILES: COCC1(NC(=O)c2ccc(-c3cnc4ncc(C5(c6ccc7ncccc7c6)CC5)n4n3)cc2F)CC1]

This compound was prepared as a TFA salt starting from 2-fluoro-4-[7-(1-quinolin-6-ylcyclopropyl)imidazo[1,2-b][1,2,4]triazin-2-yl]benzoic acid using procedures analogous to those for Example 100. LCMS: (M+H)=509.1.

Example 104: 2-Fluoro-4-(7-(1-(quinolin-6-yl)cyclopropyl)imidazo[1,2-b][1,2,4]triazin-2-yl)benzamide

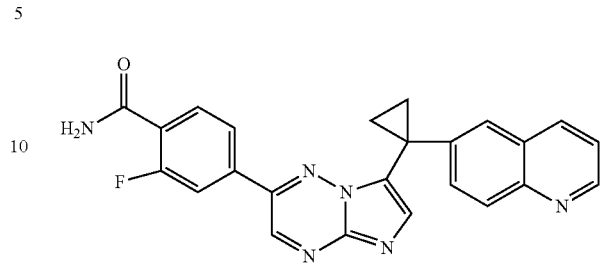

This compound was prepared as a TFA salt starting from 2-fluoro-4-[7-(1-quinolin-6-ylcyclopropyl)imidazo[1,2-b][1,2,4]triazin-2-yl]benzoic acid using procedures analogous to those for Example 100. LCMS: (M+H)=425.1.

Example 105: 4-[7-(1-Quinolin-6-ylcyclopropyl)imidazo[1,2-b][1,2,4]triazin-2-yl]-N-(tetrahydrofuran-2-ylmethyl)benzamide

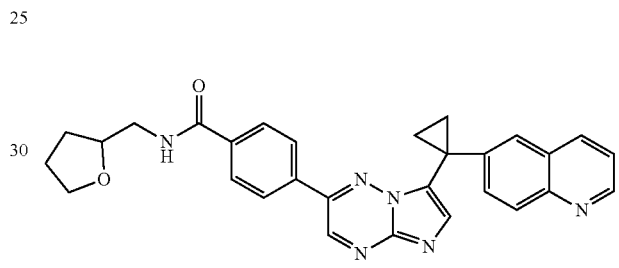

Step 1. Methyl 4-(oxoacetyl)benzoate

To a solution of 4-acetylbenzoic acid methyl ester (25 g, 0.14 mol) in dimethyl sulfoxide (300 mL) was added slowly a solution of hydrogen bromide in water (48%, 48 mL) at RT with stirring. The mixture was stirred at 60° C. overnight. After cooling to RT, it was poured into ice-water. The precipitate was filtered and dried to afford the desired product (15.6 g, 79%).

Step 2. Methyl 4-(diethoxyacetyl)benzoate

A mixture of methyl 4-(oxoacetyl)benzoate (13.5 g, 0.0702 mol), ethyl orthoformate (29 mL, 0.18 mol), p-toluenesulfonic acid monohydrate (0.7 g) in toluene (150 mL) was refluxed for 2 h. After cooling to RT, the solvent was removed under reduced pressure. The crude material was chromatographed on silica gel to afford the desired product (15.4 g, 82%). LCMS: (M+Na)=289.0.

Step 3. Methyl 4-(3-oxo-2,3-dihydro-1,2,4-triazin-6-yl)benzoate

A mixture of methyl 4-(diethoxyacetyl)benzoate (15.4 g, 0.0578 mol), semicarbazide hydrochloride (7.1 g, 0.064 mol), N,N-diisopropylethylamine (12 mL, 0.069 mol) in 1,2-dichloroethane (150 mL), and methanol (2 mL) was heated at 95° C. for 4 h. To the mixture was added an additional 0.1 equivalents of semicarbazide hydrochloride. The mixture was stirred at 95° C. for 1 h. After cooling to RT, the mixture was diluted with methylene chloride and

--- dimethylformamide (0.6 mL) at 0° C. and was stirred overnight at RT. The mixture was diluted with methanol and purified by RP-HPLC (pH 2) to afford the desired product as a TFA salt. LCMS: (M+H)=523.0.

washed with water, brine, dried over Na₂SO₄, filtered, and concentrated. The residue was refluxed with acetic acid (100 mL) and water (1.0 mL) overnight. The mixture was concentrated to yield quantitative crude material which was directly used in the next step.

Step 4. Methyl 4-(3-chloro-1,2,4-triazin-6-yl)benzoate

A mixture of methyl 4-(3-oxo-2,3-dihydro-1,2,4-triazin-6-yl)benzoate (13.4 g, 0.0580 mol), phosphoryl chloride (30 mL, 0.3 mol) in chloroform (50 mL) was refluxed (oil-bath temperature about 100° C.) for 2 h. After cooling to RT, the mixture was concentrated to remove excess phosphoryl chloride. The residue was dissolved in methylene chloride and poured into ice-water, and carefully neutralized with K₂CO₃. The organic layer was separated and the aqueous solution was extracted with methylene chloride. The combined organic phases were dried over Na₂SO₄, concentrated, and further purified by chromatography to afford the desired product (2.5 g, 17%). LCMS: (M+H)=249.9. ¹H NMR (300 MHz, CDCl₃): δ in ppm, 3.98 (s, 3H), 8.18 (d, 2H), 8.24 (d, 2H), 8.96 (s, 1H).

Step 5. methyl 4-(3-amino-1,2,4-triazin-6-yl)benzoate

A solution of methyl 4-(3-chloro-1,2,4-triazin-6-yl)benzoate (180 mg, 0.721 mmol) and 2M of ammonia in isopropyl alcohol (5 ml, 10 mmol) was stirred at 25° C. for 3 h. The reaction was diluted with water, and the precipitate was filtered to give the desired product. LCMS: (M+H₂O+H)=249.0.

Step 6. methyl 4-[7-(1-quinolin-6-ylcyclopropyl)imidazo[1,2-b][1,2,4]triazin-2-yl]benzoate A mixture of methyl 4-(3-amino-1,2,4-triazin-6-yl)benzoate (160 mg, 0.70 mmol) and chloro(1-quinolin-6-ylcyclopropyl)acetaldehyde (200 mg, 0.83 mmol) in isopropyl alcohol (6 mL) was heated at 110° C. for 24 h. The mixture was adjusted to pH 9 by adding triethylamine and then the volatiles were removed under reduced pressure. The residue was purified by chromatography on silica gel with EtOAc in CH₂Cl₂ (0-60%) to afford the desired product (130 mg, 44%). LCMS: (M+H)=421.1.

Step 7. 4-[7-(1-quinolin-6-ylcyclopropyl)imidazo[1,2-b][1,2,4]triazin-2-yl]benzoic acid Lithium hydroxide monohydrate (14 mg, 0.34 mmol) was added to a solution of methyl 4-[7-(1-quinolin-6-ylcyclopropyl)imidazo[1,2-b][1,2,4]triazin-2-yl]benzoate (30.0 mg, 0.07 mmol) in THF (0.3 mL), methanol (0.3 mL), and water (0.2 mL). The mixture was stirred at RT for 2 h and adjusted to pH 2 with conc. HCl. The volatiles were removed under reduced pressure and the residue was dried to provide the crude product which was directly used in the next step without further purification. LCMS: (M+H)=408.1.

Step 8. 4-[7-(1-quinolin-6-ylcyclopropyl)imidazo[1,2-b][1,2,4]triazin-2-yl]-N-(tetrahydrofuran-2-ylmethyl)benzamide N,N-Diisopropylethylamine (13 μL, 0.074 mmol) was added to the mixture of 4-[7-(1-quinolin-6-ylcyclopropyl)imidazo[1,2-b][1,2,4]triazin-2-yl]benzoic acid (10.0 mg, 0.0245 mmol), (tetrahydrofuran-2-yl)methanamine (8.0 mg) and benzotriazol-1-yloxytris(dimethylamino)phosphonium hexafluorophosphate (16 mg, 0.037 mmol) in N,N-dimethylformamide (0.5 mL) at 0° C. The mixture was stirred at RT for 3 h, and purified by RP-HPLC (pH 2) to afford the desired product as a TFA salt. LCMS: (M+H)=491.1.

Example 106: N-(Pyridin-2-ylmethyl)-4-[7-(1-quinolin-6-ylcyclopropyl)imidazo[1,2-b][1,2,4]triazin-2-yl]benzamide

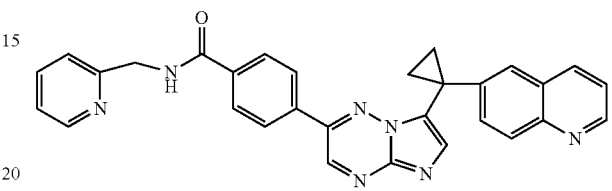

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=498.1.

Example 107: N-Cyclopropyl-4-[7-(1-quinolin-6-ylcyclopropyl)imidazo[1,2-b][1,2,4]triazin-2-yl]benzamide

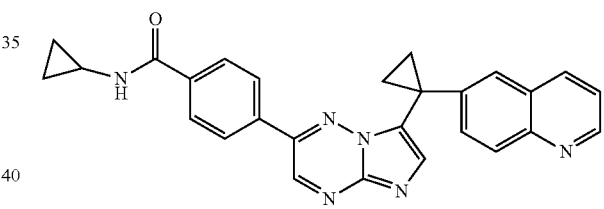

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=447.1.

Example 108: N-Cyclobutyl-4-[7-(1-quinolin-6-ylcyclopropyl)imidazo[1,2-b][1,2,4]triazin-2-yl]benzamide

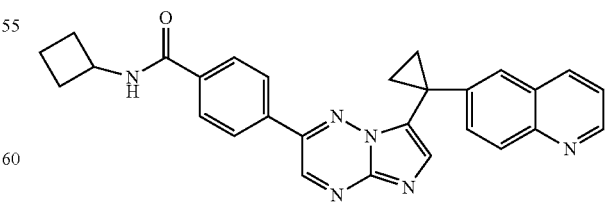

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=461.1.

Example 109: N-(1-Pyridin-2-ylcyclopropyl)-4-[7-(1-quinolin-6-ylcyclopropyl)imidazo[1,2-b][1,2,4]triazin-2-yl]benzamide

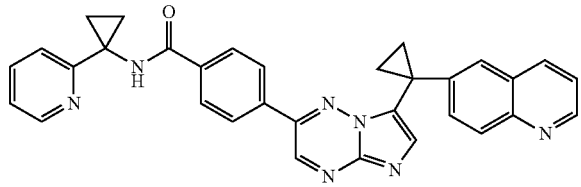 [SMILES: O=C(NC1(c2ccccn2)CC1)c1ccc(-c2cnc3ncc(C4(c5ccc6ncccc6c5)CC4)n3n2)cc1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=524.1.

Example 110: N-(2-Hydroxy-1,1-dimethylethyl)-4-[7-(1-quinolin-6-ylcyclopropyl)imidazo[1,2-b][1,2,4]triazin-2-yl]benzamide

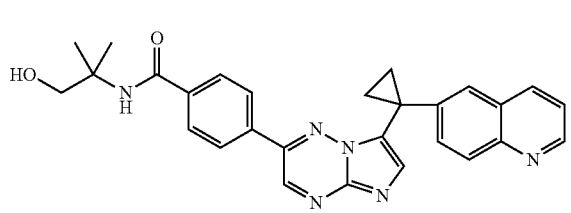 [SMILES: CC(C)(CO)NC(=O)c1ccc(-c2cnc3ncc(C4(c5ccc6ncccc6c5)CC4)n3n2)cc1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=479.1.

Example 111: N-[(1S)-1-Benzyl-2-hydroxyethyl]-4-[7-(1-quinolin-6-ylcyclopropyl)imidazo[1,2-b][1,2,4]triazin-2-yl]benzamide

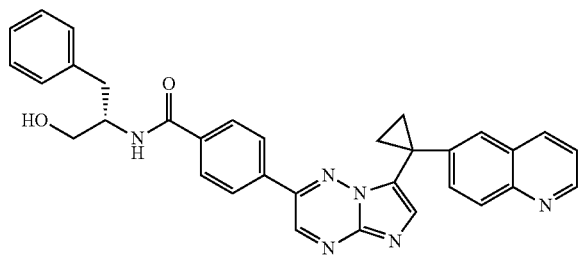 [SMILES: O=C(N[C@H](CO)Cc1ccccc1)c1ccc(-c2cnc3ncc(C4(c5ccc6ncccc6c5)CC4)n3n2)cc1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=541.1.

Example 112: (3R)-1-{4-[7-(1-quinolin-6-ylcyclopropyl)imidazo[1,2-b][1,2,4]triazin-2-yl]benzoyl}pyrrolidin-3-ol

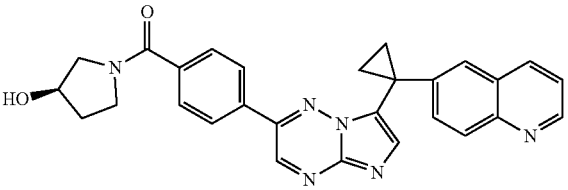 [SMILES: O=C(c1ccc(-c2cnc3ncc(C4(c5ccc6ncccc6c5)CC4)n3n2)cc1)N1CC[C@@H](O)C1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=477.1.

Example 113: 4-(7-(1-(Quinolin-6-yl)cyclopropyl)imidazo[1,2-b][1,2,4]triazin-2-yl)-N-(tetrahydro-2H-pyran-4-yl)benzamide

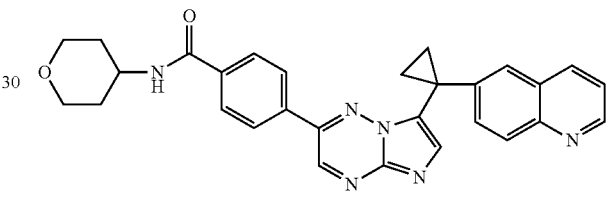

This compound was prepared as a TFA salt starting from 4-[7-(1-quinolin-6-ylcyclopropyl)imidazo[1,2-b][1,2,4]triazin-2-yl]benzoic acid using procedures analogous to those for Example 105. LCMS: (M+H)=491.1.

Example 114: N-Cyclopropyl-N-methyl-4-[7-(1-quinolin-6-ylcyclopropyl)imidazo[1,2-b][1,2,4]triazin-2-yl]benzamide

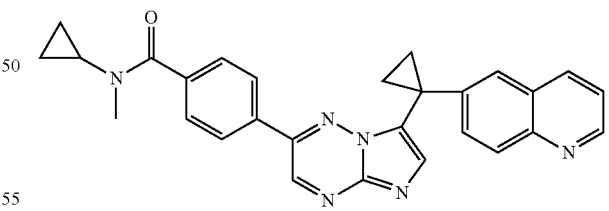

Sodium hydride (0.54 mg, 0.013 mmol) was added to a solution of N-cyclopropyl-4-[7-(1-quinolin-6-ylcyclopropyl)imidazo[1,2-b][1,2,4]triazin-2-yl]benzamide (3.0 mg, 0.0067 mmol) in THF (0.5 mL) at RT. The mixture was stirred for 10 min, and then methyl iodide (1.2 μL, 0.020 mmol) was added. The mixture was stirred for 2 h at RT. LCMS showed the reaction was complete. The mixture was diluted with methanol, and purified by RP-HPLC (pH 2) to give the desired product as a TFA salt. LCMS: (M+H)=461.1.

Example 115: N-[1-(Methoxymethyl)cyclopropyl]-4-[7-(1-quinolin-6-ylcyclopropyl)imidazo[1,2-b][1,2,4]triazin-2-yl]benzamide

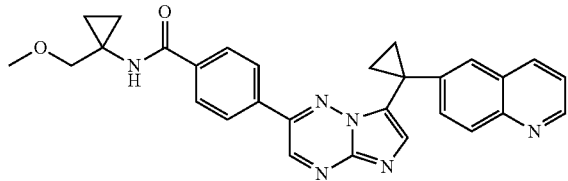 [SMILES: COCC1(NC(=O)c2ccc(-c3cnc4ncc(C5(c6ccc7ncccc7c6)CC5)n4n3)cc2)CC1]

Step 1. benzyl [1-(hydroxymethyl)cyclopropyl]carbamate

Ethyl chloroformate (0.17 mL, 0.0018 mol) was added to a solution of 1-[(benzyloxy)carbonyl]aminocyclopropanecarboxylic acid (0.35 g, 0.0015 mol) and triethylamine (0.25 mL, 0.0018 mol) in THF (5.0 mL) at −10° C. The mixture was stirred at RT for 30 min., filtered, and washed with THF. Sodium tetrahydroborate (0.11 g, 0.0030 mol) in water (1.0 mL) was added to the filtrate at 0° C., and stirred at RT for 2 h. The reaction mixture was carefully quenched with 1N HCl, and extracted with EtOAc. The extract was washed with saturated NaHCO$_3$, brine, dried over MgSO$_4$, filtered, and concentrated to give the crude product (0.32 g, 97%). LCMS: (M+H)=222.0, (M+Na)=244.0.

Step 2. Benzyl [1-(methoxymethyl)cyclopropyl]carbamate

To a solution of benzyl [1-(hydroxymethyl)cyclopropyl]carbamate (0.32 g, 0.0014 mol) in methylene chloride (5.0 mL) was added sequentially powdered MS 4 Å, N,N,N',N'-tetramethyl-1,8-naphthalenediamine (0.77 g, 0.0036 mol), and trimethyloxonium tetrafluoroborate (0.43 g, 0.0029 mol) at RT. The mixture was stirred for 5 h, filtered through a pad of Celite, and washed with EtOAc. The filtrate was washed with 1N HCl, water, brine, dried over MgSO$_4$, filtered, and concentrated. The residue was purified by chromatography on silica gel with EtOAc in hexanes (0-30%) to afford the desired product (140 mg, 41%). LCMS: (M+H)=236.1.

Step 3. 1-(Methoxymethyl)cyclopropanamine

To a solution of benzyl [1-(methoxymethyl)cyclopropyl]carbamate (400.0 mg, 1.700 mmol) in methanol (5.0 mL) was added Pd/C (50.0 mg) and stirred under hydrogen (balloon) for 1 h. The mixture was filtered through a pad of Celite. The solvent was evaporated under reduced pressure to provide the desired product. LCMS: (M+H)=102.1.

Step 4. N-[1-(methoxymethyl)cyclopropyl]-4-[7-(1-quinolin-6-ylcyclopropyl)imidazo-[1,2-b][1,2,4]triazin-2-yl]benzamide This compound was prepared as a TFA salt starting from 4-[7-(1-quinolin-6-ylcyclopropyl)imidazo[1,2-b][1,2,4]triazin-2-yl]benzoic acid using procedures analogous to those for Example 105, Step 8. LCMS: (M+H)=491.1.

Example 116: N-[1-(Methoxymethyl)cyclobutyl]-4-[7-(1-quinolin-6-ylcyclopropyl)imidazo[1,2-b][1,2,4]triazin-2-yl]benzamide

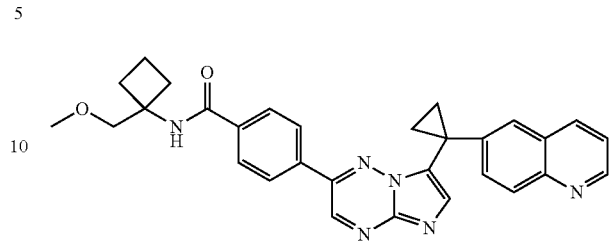

This compound was prepared as a TFA salt starting from 4-[7-(1-quinolin-6-ylcyclopropyl)imidazo[1,2-b][1,2,4]triazin-2-yl]benzoic acid using procedures analogous to those for Example 115. LCMS: (M+H)=505.3.

Example 117: N-[(1S)-1-(Methoxymethyl)-2-methylpropyl]-4-[7-(1-quinolin-6-ylcyclopropyl)imidazo[1,2-b][1,2,4]triazin-2-yl]benzamide

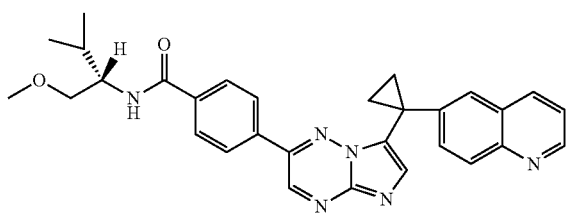 [SMILES: COC[C@@H](NC(=O)c1ccc(-c2cnc3ncc(C4(c5ccc6ncccc6c5)CC4)n3n2)cc1)C(C)C]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 115. LCMS: (M+H)=507.1.

Example 118: N-[4-(Methoxymethyl)tetrahydro-2H-pyran-4-yl]-4-[7-(1-quinolin-6-ylcyclopropyl)imidazo[1,2-b][1,2,4]triazin-2-yl]benzamide

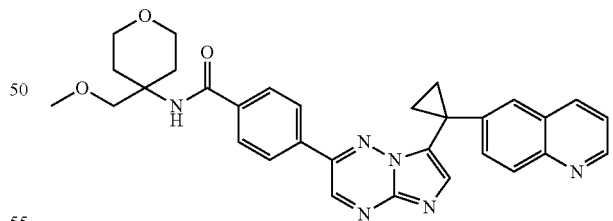

Step 1. tert-butyl [4-(hydroxymethyl)tetrahydro-2H-pyran-4-yl]carbamate

Ethyl chloroformate (0.234 mL, 0.00245 mol) was added to a solution of 4-[(tert-butoxycarbonyl)amino]tetrahydro-2H-pyran-4-carboxylic acid (0.5 g, 2.0 mmol) and triethylamine (0.341 mL, 2.45 mmol) in THF (6.8 mL) at −10° C. The mixture was stirred at RT for 30 min., filtered, and washed with THF. Sodium tetrahydroborate (0.15 g, 4.1 mmol) in water (1.0 mL) was added to the filtrate at 0° C., and then stirred at RT for 2 h. The reaction mixture was quenched with saturated NH$_4$Cl solution, extracted with EtOAc. The extract was washed with saturated NaHCO$_3$, brine, dried over MgSO$_4$, filtered, and concentrated to give the crude product which was directly used in next step without further purification. LCMS: (M+Na)=254.1; (M–100+H)=132.1.

Step 2. tert-butyl [4-(methoxymethyl)tetrahydro-2H-pyran-4-yl]carbamate

To a solution of tert-butyl [4-(hydroxymethyl)tetrahydro-2H-pyran-4-yl]carbamate (0.89 g, 3.8 mmol) in methylene chloride (19.2 mL) was added sequentially powdered MS 4 Å, N,N,N',N'-tetramethyl-1,8-naphthalenediamine (2.0 g, 9.6 mmol), and trimethyloxonium tetrafluoroborate (1.1 g, 7.7 mmol) at RT. The mixture was stirred for 5 h., filtered through a pad of Celite, and washed with EtOAc. The filtrate was washed with aqueous CuSO$_4$, water, brine, dried over MgSO$_4$, filtered, and concentrated. The residue was purified by chromatography on silica gel with EtOAc in hexanes (0-30%) to afford the desired product. LCMS: (M+Na)=268.0

Step 3. 4-(methoxymethyl)tetrahydro-2H-pyran-4-amine hydrochloride

To a solution of tert-butyl [4-(methoxymethyl)tetrahydro-2H-pyran-4-yl]carbamate (0.45 g, 0.0018 mol) in EtOAc (0.2 mL) was added 4M of hydrogen chloride in 1,4-dioxane (3 mL) and stirred for 2 h. The volatiles were removed under reduced pressure to give the desired compound which was directly used in next step without further purification. LCMS: (M+H)=146.2.

Step 4. N-[4-(methoxymethyl)tetrahydro-2H-pyran-4-yl]-4-[7-(1-quinolin-6-ylcyclopropyl) imidazo[1,2-b][1,2,4]triazin-2-yl]benzamide This compound was prepared as a TFA salt starting from 4-[7-(1-quinolin-6-ylcyclopropyl)imidazo[1,2-b][1,2,4]triazin-2-yl]benzoic acid using procedures analogous to those for Example 105, Step 8. LCMS: (M+H)=535.2.

Example 119: 4-[7-(1-Quinolin-6-ylcyclopropyl) imidazo[1,2-b][1,2,4]triazin-2-yl]-N-1,3-thiazol-2-ylbenzamide

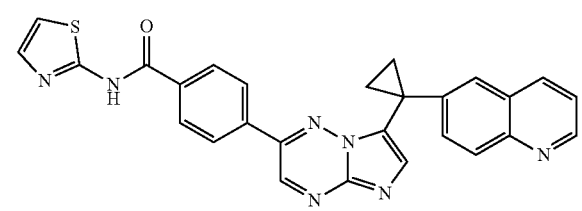 [SMILES: O=C(Nc1nccs1)c1ccc(-c2cnc3ncc(C4(c5ccc6ncccc6c5)CC4)n3n2)cc1]

N,N-Diisopropylethylamine (6.4 µL, 0.037 mmol) was added to a mixture of 4-[7-(1-quinolin-6-ylcyclopropyl) imidazo[1,2-b][1,2,4]triazin-2-yl]benzoic acid (5.0 mg, 0.012 mmol), 1,3-thiazol-2-amine (2.3 mg, 0.024 mmol), and N,N,N',N'-tetramethyl-O-(7-azabenzotriazol-1-yl)uronium hexafluorophosphate (7.0 mg, 0.018 mmol) in N,N-dimethylformamide (0.6 mL) at 0° C. The mixture was stirred for 4 h at RT, and purified by RP-HPLC (pH 2) to afford the desired product as a TFA salt. LCMS: (M+H)=490.0.

Example 120: N-Pyrimidin-4-yl-4-[7-(1-quinolin-6-ylcyclopropyl)imidazo[1,2-b][1,2,4]triazin-2-yl]benzamide

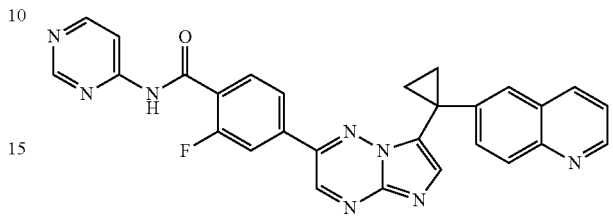

This compound was prepared as a TFA salt starting from 2-fluoro-4-[7-(1-quinolin-6-ylcyclopropyl)imidazo[1,2-b][1,2,4]triazin-2-yl]benzoic acid using procedures analogous to those for Example 119. LCMS: (M+H)=485.1.

Example 121: N-[4-(Methoxymethyl)tetrahydro-2H-pyran-4-yl]-4-[7-(1-quinolin-6-ylcyclopropyl)imidazo[1,2-b][1,2,4]triazin-2-yl]benzamide

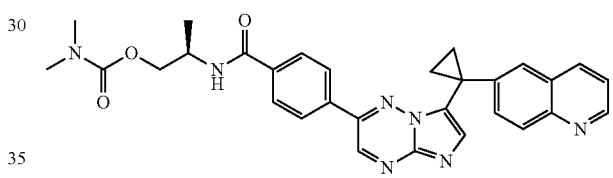

Step 1. (2R)-2-[(tert-butoxycarbonyl)amino]propyl dimethylcarbamate

N,N-Dimethylcarbamoyl chloride (0.12 mL, 0.0013 mol) was added to a solution of tert-butyl [(1R)-2-hydroxy-1-methylethyl]carbamate (0.150 g, 0.856 mmol), 4-dimethylaminopyridine (0.02 g, 0.2 mmol) and pyridine (0.14 g, 1.7 mmol) in methylene chloride (3.0 mL). The mixture was stirred overnight, diluted with EtOAc and washed with 1N HCl, saturated NaHCO$_3$ and brine. The organic layers were dried over Na$_2$SO$_4$, filtered, and concentrated. The residue was purified by chromatography on silica gel with EtOAc in hexanes (0-30%) to afford the desired product.

Step 2. (2R)-2-aminopropyl dimethylcarbamate hydrochloride

To a solution of (2R)-2-[(tert-Butoxycarbonyl)amino]propyl dimethylcarbamate (16.0 mg, 0.0650 mmol) in EtOAc (0.2 mL) was added 4M of hydrogen chloride in 1,4-dioxane (0.5 mL) and stirred for 1 h. The volatiles were removed under reduce pressure to give the desired compound. LCMS: (M+H)=147.1.

Step 3. N-[4-(methoxymethyl)tetrahydro-2H-pyran-4-yl]-4-[7-(1-quinolin-6-ylcyclopropyl)imidazo[1,2-b][1,2,4]triazin-2-yl]benzamide This compound was prepared as a TFA salt starting from 4-[7-(1-quinolin-6-ylcyclopropyl)imidazo[1,2-b][1,2,4]triazin-2-yl]benzoic acid using procedures analogous to those for Example 105, Step 8. LCMS: (M+H)=536.2

Example 122: N-{(1R)-1-[(Dimethylamino)carbonyl]-2-methylpropyl}-4-[7-(1-quinolin-6-ylethyl)imidazo[1,2-b]i[1,2,4]triazin-2-yl]benzamide

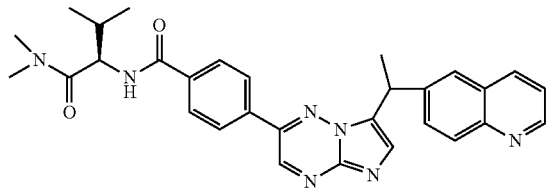 [SMILES: CC(c1ccc2ncccc2c1)c1cnc2ncc(-c3ccc(C(=O)N[C@@H](C(=O)N(C)C)C(C)C)cc3)nn12]

Step 1. 3-quinolin-6-ylbut-3-en-1-ol

Palladium acetate (100 mg, 0.6 mmol) was added to a solution of 6-(4,4,5,5-tetramethyl-1,3,2-dioxaborolan-2-yl)quinoline (8.0 g, 31 mmol) and 3-bromo-3-buten-1-ol (6.2 g, 41 mmol) in toluene (118 mL) and water (12 mL) followed by addition of 2-(dicyclohexylphosphino)-2',6'-dimethoxy-1,1'-biphenyl (500 mg, 1 mmol). The mixture was stirred at 100° C. for 6 h. After cooling to RT, the mixture was diluted with EtOAc, washed with water and brine. The organic layers were dried over Na2SO4, filtered, and concentrated. The residue was purified by chromatography on silica gel with EtOAc in methylene chloride (0-50%) to afford the desired product.

Step 2. 3-quinolin-6-ylbutan-1-ol

A mixture of 3-quinolin-6-ylbut-3-en-1-ol (1.0 g, 0.0050 mol), platinum on carbon (5 wt. % supported on activated carbon, wet, Degussa type F101 ra/w, 0.20 g) in methanol (15.0 mL) was stirred under hydrogen (with a balloon) at RT for 5 h. The mixture was filtered and the filtrate was concentrated to give the desired product (1.0 g, 99%). LCMS: (M+H)=202.1.

Step 3. 3-quinolin-6-ylbutanal

To a solution of 3-quinolin-6-ylbutan-1-ol (0.060 g, 0.30 mmol) in methylene chloride (3.0 mL) was added 2,2,6,6-tetramethyl-1-piperidinyloxy free radical (0.005 g, 0.03 mmol) and iodobenzene diacetate (0.10 g, 0.33 mmol). The reaction was stirred overnight at RT. The mixture was purified by chromatography on silica gel with EtOAc in hexanes (0-40%) to afford the desired product (0.050 g, 84%). LCMS: (M+H)=200.0.

Step 4. 2-chloro-3-quinolin-6-ylbutanal

L-Proline (5.8 mg, 0.050 mmol) was added to a solution of 3-quinolin-6-ylbutanal (50 mg, 0.25 mmol) in chloroform (0.5 mL) at 0° C. followed by addition of N-chlorosuccinimide (36.9 mg, 0.276 mmol). The mixture was stirred at RT for 2 h, diluted with hexanes and filtered. The filtrate was concentrated and purified by chromatography on silica gel with EtOAc in methylene chloride (0-10%) to afford the desired product (0.048 g, 82%). LCMS: (M+H)=234.1/236.1.

Step 4. Methyl 4-[7-(1-quinolin-6-ylethyl)imidazo[1,2-b][1,2,4]triazin-2-yl]benzoate A mixture of methyl 4-(3-amino-1,2,4-triazin-6-yl)benzoate (50 mg, 0.217 mmol) and 2-chloro-3-quinolin-6-ylbutanal (61 mg, 0.26 mmol) in isopropyl alcohol (3.0 mL) was heated at 110° C. for 48 h. The mixture was adjusted to pH 9 by adding triethylamine. The volatiles were removed under reduced pressure and the residue was purified by chromatography on silica gel with EtOAc in methylene chloride (0-60%) to afford the desired product (0.020 g, 22%). LCMS: (M+H)=410.0.

Step 5. 4-[7-(1-Quinolin-6-ylethyl)imidazo[1,2-b][1,2,4]triazin-2-yl]benzoic acid Lithium hydroxide monohydrate (24 mg, 0.57 mmol) was added to a solution of methyl 4-[7-(1-quinolin-6-ylethyl)imidazo[1,2-b][1,2,4]triazin-2-yl]benzoate (47 mg, 0.115 mmol) in THF (0.5 mL) and methanol (0.5 mL) and water (0.2 mL). The mixture was stirred at RT for 2 h. LCMS showed the reaction was complete. The mixture was adjusted with conc. HCl to pH 2. The volatiles were removed under reduced pressure to provide the crude product which was directly used in next step. LCMS: (M+H)=396.1.

Step 6. N-(JR)-1-[(Dimethylamino)carbonyl]-2-methylpropyl-4-[7-(1-quinolin-6-ylethyl)imidazo[1,2-b][1,2,4]triazin-2-yl]benzamide N,N-Diisopropylethylamine (13 µL, 0.074 mmol) was added to the mixture of 4-[7-(1-quinolin-6-ylethyl)imidazo[1,2-b][1,2,4]triazin-2-yl]benzoic acid (9.70 mg, 0.0245 mmol), (2R)-2-amino-N,N,3-trimethylbutanamide (5.3 mg, 0.037 mmol) and benzotriazol-1-yloxytris(dimethylamino)phosphonium hexafluorophosphate (16 mg, 0.037 mmol) in N,N-dimethylformamide (0.6 mL) at 0° C. The mixture was stirred overnight at RT, purified by RP-HPLC (pH 2) to afford the desired compound as a TFA salt. LCMS: (M+H)=522.1.

Example 123: N-Cyclopropyl-2-fluoro-4-[7-(quinolin-6-ylmethyl)imidazo[1,2-b][1,2,4]triazin-2-yl]benzamide

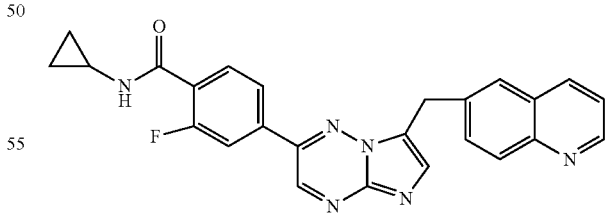

N,N-Diisopropylethylamine (6.4 µL, 0.037 mmol) was added to a mixture of 4-[7-(1-quinolin-6-ylcyclopropyl)imidazo[1,2-b][1,2,4]triazin-2-yl]benzoic acid (4.9 mg, 0.012 mmol, prepared as described in Example 7, Steps 1-10), cyclopropylamine (1.4 mg, 0.024 mmol) and benzotriazol-1-yloxytris(dimethylamino)phosphonium hexafluorophosphate (9.6 mg, 0.018 mmol) in N,N-dimethylformamide (0.6 mL) at 0'C. The mixture was stirred at RT for 3 h, Example 124: 2-Fluoro-N-[1-(methoxymethyl)cyclopropyl]-4-[7-(quinolin-6-ylmethyl)imidazo[1,2-b][1,2,4]triazin-2-yl]benzamide

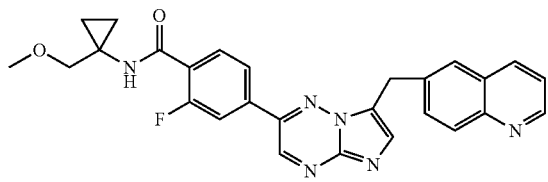 [SMILES: COCC1(NC(=O)c2ccc(-c3cnc4ncc(Cc5ccc6ncccc6c5)n4n3)cc2F)CC1]

This compound was prepared as a TFA salt starting from 4-[7-(1-quinolin-6-ylcyclopropyl)imidazo[1,2-b][1,2,4]triazin-2-yl]benzoic acid procedures analogous to those for Example 123. LCMS: (M+H)=483.1.

Example 125: 2-Fluoro-4-[7-(quinolin-6-ylmethyl)imidazo[1,2-b][1,2,4]triazin-2-yl]-N-(tetrahydro-2H-pyran-4-yl)benzamide

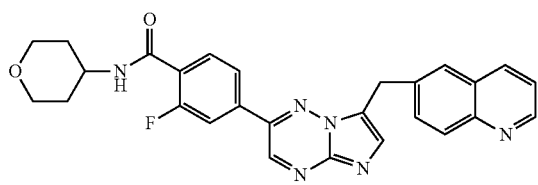 [SMILES: O=C(NC1CCOCC1)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=483.1.

Example 126: (3R)-1-{2-Fluoro-4-[7-(quinolin-6-ylmethyl)imidazol[1,2-b][1,2,4]triazin-2-yl]benzoyl}pyrrolidin-3-ol

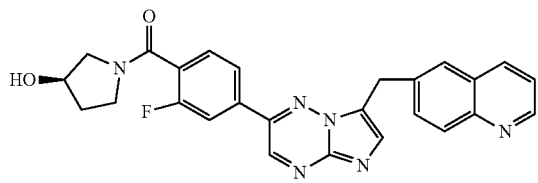 [SMILES: O=C(c1ccc(-c2cnc3ncc(Cc4ccc5ncccc5c4)n3n2)cc1F)N1CC[C@@H](O)C1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=469.1.

Example 127: 2-Fluoro-4-[7-(quinolin-6-ylmethyl)imidazo[1,2-b][1,2,4]triazin-2-yl]benzamide

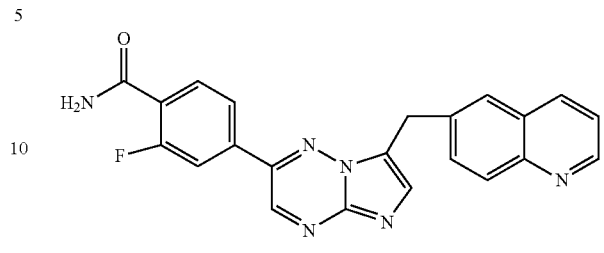

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=399.0.

Example 128: 2-Fluoro-N-(trans-4-hydroxycyclohexyl)-4-[7-(quinolin-6-ylmethyl)imidazo[1,2-b][1,2,4]triazin-2-yl]benzamide

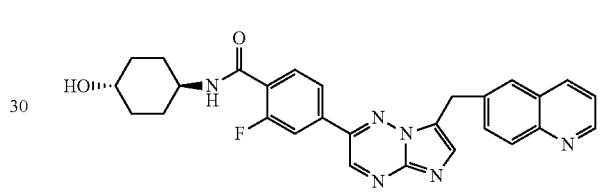

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=497.1.

Example 129: 6-{2-[3-Fluoro-4-(1H-imidazol-1-yl)phenyl]imidazo[1,2-b][1,2,4]triazin-7-ylmethyl}quinoline

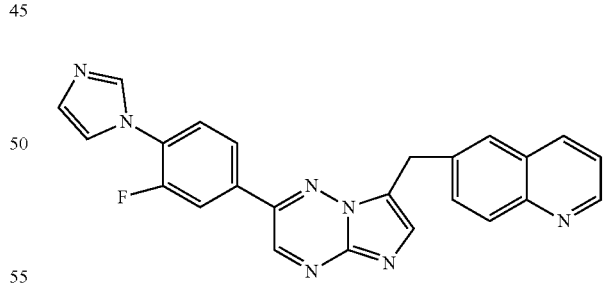

To a solution of 6-[2-(4-bromo-3-fluorophenyl)imidazo[1,2-b][1,2,4]triazin-7-yl]methylquinoline (6.5 mg, 0.015 mmol) in 1,4-dioxane (0.5 mL) was added (1S,2S)—N,N'-dimethylcyclohexane-1,2-diamine (0.42 mg, 0.0030 mmol), copper(I) iodide (0.28 mg, 0.0015 mmol), 1H-imidazole (2.0 mg, 0.030 mmol) and potassium carbonate (4.34 mg, 0.0314 mmol). The mixture was stirred at 100° C. overnight. After cooling to RT, the mixture was purified by RP-HPLC (pH 2) to give the desired product as a TFA salt. LCMS: (M+H)=422.0 and purified by RP-HPLC (pH 2) to afford the desired product as a TFA salt. LCMS: (M+H)=439.0.

Example 130: 3-{2-Fluoro-4-[7-(quinolin-6-ylmethyl)imidazo[1,2-b][1,2,4]triazin-2-yl]phenyl}-1,3-oxazolidin-2-one

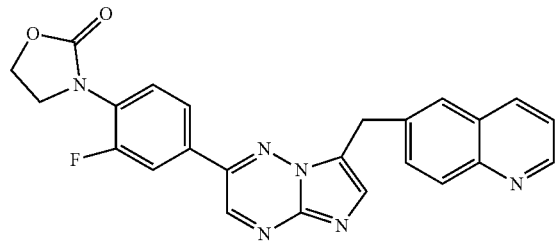 [SMILES: O=C1OCCN1c1ccc(-c2cnc3ncc(Cc4ccc5ncccc5c4)n3n2)cc1F]

This compound was prepared as a TFA salt starting from 6-[2-(4-bromo-3-fluorophenyl)imidazo[1,2-b][1,2,4]triazin-7-yl]methylquinoline using procedures analogous to those for Example 129. LCMS: (M+H)=441.1.

Example 131: N-(1S)-2,2-Dimethyl-1-[(methylamino)carbonyl]propyl-2-fluoro-4-[7-(quinolin-6-ylmethyl)imidazo[1,2-b][1,2,4]triazin-2-yl]benzamide

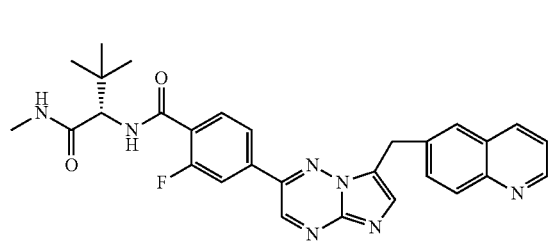 [SMILES: CNC(=O)[C@@H](NC(=O)c1ccc(-c2cnc3ncc(Cc4ccc5ncccc5c4)n3n2)cc1F)C(C)(C)C]

Step 1. tert-Butyl (2S)-2-(2-fluoro-4-[7-(quinolin-6-ylmethyl)imidazo[1,2-b][1,2,4]triazin-2-yl]benzoylamino)-3,3-dimethylbutanoate N,N-Diisopropylethylamine (160 µL, 0.90 mmol) was added to the mixture of 2-fluoro-4-[7-(quinolin-6-ylmethyl)imidazo[1,2-b][1,2,4]triazin-2-yl]benzoic acid (90.0 mg, 0.225 mmol), tert-butyl (2S)-2-amino-3,3-dimethylbutanoate hydrochloride (63 mg, 0.281 mmol) and benzotriazol-1-yloxytris(dimethylamino)phosphonium hexafluorophosphate (150 mg, 0.34 mmol) in N,N-dimethylformamide (2.0 mL) at 0'C. The mixture was stirred overnight at RT and was added to aqueous acetonitrile. The precipitates were filtered, dried to give the desired product (0.093 g, 72%). LCMS: (M+H)=569.5.

Step 2. (2S)-2-(2-Fluoro-4-[7-(quinolin-6-ylmethyl)imidazo[1,2-b][1,2,4]triazin-2-yl]benzoylamino)-3,3-dimethylbutanoic acid Trifluoroacetic acid (1.0 mL, 0.013 mol) was added to a solution of tert-butyl (2S)-2-(2-fluoro-4-[7-(quinolin-6-ylmethyl)imidazo[1,2-b][1,2,4]triazin-2-yl]benzoylamino)-3,3-dimethylbutanoate (0.092 g, 0.16 mmol) in methylene chloride (1.0 mL) and stirred at RT for 2 h. The volatiles were removed under reduced pressure to give the desired product as a TFA salt. LCMS: (M+H)=513.4.

Step 3. N-(1S)-2,2-dimethyl-1-[(methylamino)carbonyl]propyl-2-fluoro-4-[7-(quinolin-6-ylmethyl)imidazo[1,2-b][1,2,4]triazin-2-yl]benzamide N,N-Diisopropylethylamine (20 µL, 0.11 mmol) was added to the mixture of (2S)-2-(2-fluoro-4-[7-(quinolin-6-ylmethyl)imidazo[1,2-b][1,2,4]triazin-2-yl]benzoylamino) 3,3-dimethylbutanoic acid TFA salt (19.2 mg, 0.0376 mmol), methylamine (2M in THF, 0.2 mL, 0.4 mmol) and benzotriazol-1-yloxytris(dimethylamino)phosphonium hexafluorophosphate (25 mg, 0.056 mmol) in N,N-dimethylformamide (0.5 mL) at 0'C. The mixture was stirred at RT for 2 h and purified by RP-HPLC (pH 2) to afford the desired product as a TFA salt. LCMS: (M+H)=526.4.

Example 132: N-(1S)-1-[(Dimethylamino)carbonyl]-2,2-dimethylpropyl-2-fluoro-4-[7-(quinolin-6-ylmethyl)imidazo[1,2-b][1,2,4]triazin-2-yl]benzamide

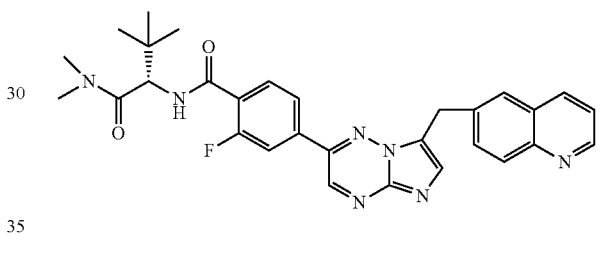

This compound was prepared as a TFA salt starting from (2S)-2-(2-fluoro-4-[7-(quinolin-6-ylmethyl)imidazo[1,2-b][1,2,4]triazin-2-yl]benzoylamino) 3,3-dimethylbutanoic acid TFA salt using procedures analogous to those for Example 131. LCMS: (M+H)=540.4.

Example 133: N-[(1S)-1-(Azetidin-1-ylcarbonyl)-2,2-dimethylpropyl]-2-fluoro-4-[7-(quinolin-6-ylmethyl)imidazo[1,2-b][1,2,4]triazin-2-yl]benzamide

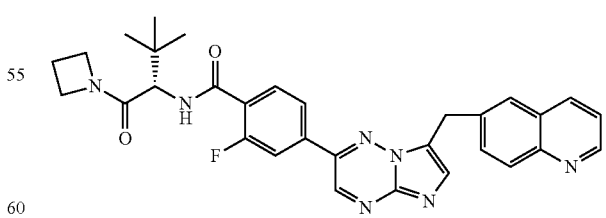

This compound was prepared as a TFA salt starting from (2S)-2-(2-fluoro-4-[7-(quinolin-6-ylmethyl)imidazo[1,2-b][1,2,4]triazin-2-yl]benzoylamino) 3,3-dimethylbutanoic acid TFA salt using procedures analogous to those for Example 131. LCMS: (M+H)=552.5.

Example 134: N-{(1S)-1-[(Dimethylamino)carbonyl]-3-methylbutyl}-2-fluoro-4-[7-(quinolin-6-ylmethyl)imidazo[1,2-b][1,2,4]triazin-2-yl]benzamide

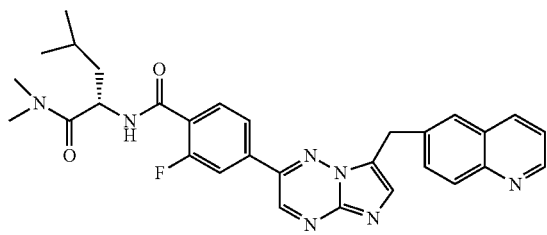 [SMILES: CC(C)C[C@H](NC(=O)c1ccc(-c2cnc3ncc(Cc4ccc5ncccc5c4)n3n2)cc1F)C(=O)N(C)C]

This compound was prepared as a TFA salt starting from 2-fluoro-4-[7-(quinolin-6-ylmethyl)imidazo[1,2-b][1,2,4]triazin-2-yl]benzoic acid using procedures analogous to those for Example 131. LCMS: (M+H)=540.4.

Example 135: 2-Fluoro-N-{(1R)-3-methyl-1-[(methylamino)carbonyl]butyl}-4-[7-(quinolin-6-ylmethyl)imidazo[1,2-b][1,2,4]triazin-2-yl]benzamide

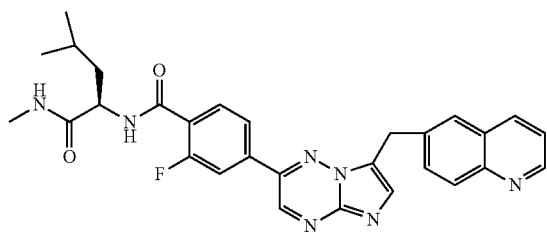 [SMILES: CNC(=O)[C@@H](CC(C)C)NC(=O)c1ccc(-c2cnc3ncc(Cc4ccc5ncccc5c4)n3n2)cc1F]

This compound was prepared as a TFA salt starting from 2-fluoro-4-[7-(quinolin-6-ylmethyl)imidazo[1,2-b][1,2,4]triazin-2-yl]benzoic acid using procedures analogous to those for Example 131. LCMS: (M+H)=526.4.

Example 136: N-{(1R)-1-[(Dimethylamino)carbonyl]-3-methylbutyl}-2-fluoro-4-[7-(quinolin-6-ylmethyl)imidazo[1,2-b][1,2,4]triazin-2-yl]benzamide

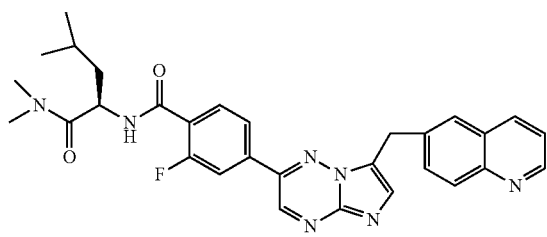 [SMILES: CC(C)C[C@@H](NC(=O)c1ccc(-c2cnc3ncc(Cc4ccc5ncccc5c4)n3n2)cc1F)C(=O)N(C)C]

This compound was prepared as a TFA salt starting from 2-fluoro-4-[7-(quinolin-6-ylmethyl)imidazo[1,2-b][1,2,4]triazin-2-yl]benzoic acid using procedures analogous to those for Example 131. LCMS: (M+H)=540.4.

Example 137: N-[(1R)-1-(Azetidin-1-ylcarbonyl)-3-methylbutyl]-2-fluoro-4-[7-(quinolin-6-ylmethyl)imidazo[1,2-b][1,2,4]triazin-2-yl]benzamide

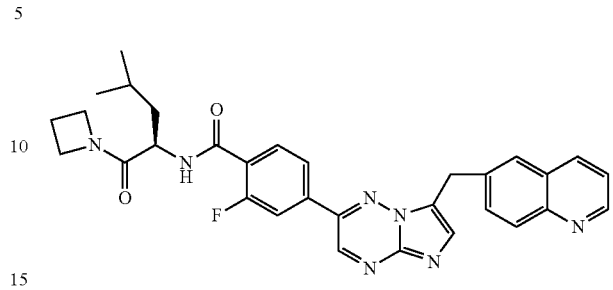

This compound was prepared as a TFA salt starting from 2-fluoro-4-[7-(quinolin-6-ylmethyl)imidazo[1,2-b][1,2,4]triazin-2-yl]benzoic acid using procedures analogous to those for Example 131. LCMS: (M+H)=552.5.

Example 138: 3-{4-[7-(Quinolin-6-ylmethyl)imidazo[1,2-b][1,2,4]triazin-2-yl]-1H-pyrazol-1-yl}propanenitrile

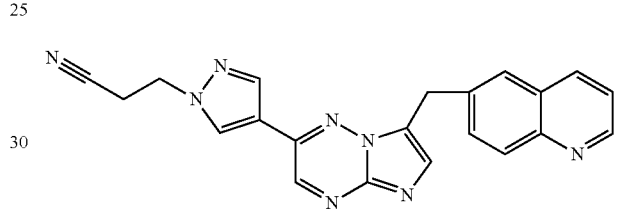

Step 1. 6-bromo-1,2,4-triazin-3-amine

Bromine (3.8 g, 24 mmol) in chloroform (20 mL) was added to a suspension of 1,2,4-triazin-3-amine (1.92 g, 20.0 mmol) in chloroform (100 mL). The reaction mixture was stirred at RT for 60 h. The mixture was washed with saturated NaHCO$_3$. The organic layer was separated, dried over MgSO$_4$, filtered, and concentrated. The residue was washed with acetone/hexanes (1/1) and filtered, to give the product (0.78 g, 22%) as a solid. $^1$H-NMR (400 MHz, DMSO-d$_6$): δ in ppm, 8.40 (s, 1H), 7.42 (br, 2H); LCMS: (M+H)=175.2/177.2; (M+H+H$_2$O)=193.2/195.2.

Step 2. 6-[1-(1-Ethoxyethyl)-1H-pyrazol-4-yl]-1,2,4-triazin-3-amine

Sodium carbonate (510 mg, 4.8 mmol) in water (1 mL) was added to a mixture of 6-bromo-1,2,4-triazin-3-amine (0.420 g, 2.40 mmol), 1-(1-ethoxyethyl)-4-(4,4,5,5-tetramethyl-1,3,2-dioxaborolan-2-yl)-1H-pyrazole (0.766 g, 2.88 mmol), and tetrakis(triphenylphosphine)palladium (100 mg, 0.1 mmol) in toluene (7 mL) and ethanol (5 mL). The resulting mixture was heated at 110° C. for 2 h. The mixture was cooled to RT, diluted with water, and extracted with chloroform. The combined organic layers were dried over Na$_2$SO$_4$, filtered, and concentrated. The residue was treated with CH$_2$Cl$_2$/Et$_2$O and filtered to give the desired product (0.39 g, 69%). LCMS: (M+H)=235.4.

Step 3. 6-[2-(1H-pyrazol-4-yl)imidazo[1,2-b][1,2,4]triazin-7-yl]methylquinoline

A mixture of 6-[1-(1-ethoxyethyl)-1H-pyrazol-4-yl]-1,2,4-triazin-3-amine (390.0 mg, 1.665 mmol) and 2-chloro-3- quinolin-6-ylpropanal (480 mg, 2.2 mmol) in isopropyl alcohol (20 mL) was heated at 110° C. for 2 days. After cooling to RT, 0.2 mL of concentrated HCl was added and stirred until completely deprotected. The solid formed was collected by filtration to give the desired product (0.35 g, 64%). LCMS: (M+H)=328.3.

Step 4. 3-{4-[7-(Quinolin-6-ylmethyl)imidazo[1,2-b][1,2,4]triazin-2-yl]-1H-pyrazol-1-yl}propanenitrile 1,8-Diazabicyclo[5.4.0]undec-7-ene (14 μL, 0.092 mmol) was added to a mixture of 6-[2-(1H-pyrazol-4-yl)imidazo[1,2-b][1,2,4]triazin-7-yl]methylquinoline (10.0 mg, 0.0305 mmol) and 2-propenenitrile (4.0 μL, 0.061 mmol) in acetonitrile (0.2 mL). The mixture was stirred at 60° C. overnight. The mixture was purified by RP-HPLC (pH 2) to give the desired product as a TFA salt. LCMS: (M+H)=381.3.

Example 139: 4-[7-(Quinolin-6-ylmethyl)imidazo[1,2-b][1,2,4]triazin-2-yl]-1H-pyrazol-1-ylacetonitrile

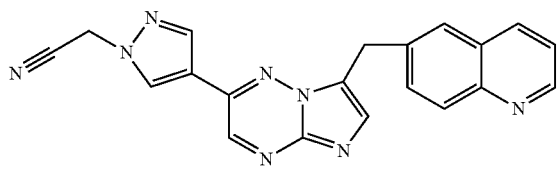 [SMILES: N#CCn1cc(-c2cnc3ncc(Cc4ccc5ncccc5c4)n3n2)cn1]

Sodium hydride (2.4 mg, 0.061 mmol) was added to a solution of 6-[2-(1H-pyrazol-4-yl)imidazo[1,2-b][1,2,4]triazin-7-yl]methylquinoline (10.0 mg, 0.0305 mmol) in N,N-dimethylformamide (0.2 mL) at RT and stirred for 5 min. Bromoacetonitrile (4.1 μL, 0.061 mmol) was then added and the reaction mixture stirred for 2 h. The reaction mixture was then purified by RP-HPLC (pH 2) to give the desired product as a TFA salt. LCMS: (M+H)=367.1.

Example 140: 2-{4-[7-(Quinolin-6-ylmethyl)imidazo[1,2-b][1,2,4]triazin-2-yl]-1H-pyrazol-1-yl}acetamide

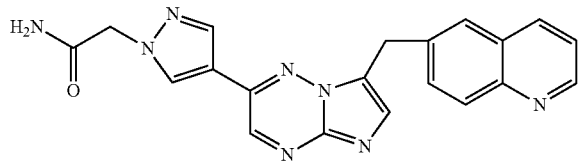 [SMILES: NC(=O)Cn1cc(-c2cnc3ncc(Cc4ccc5ncccc5c4)n3n2)cn1]

Cesium carbonate (40 mg, 0.12 mmol) was added to a solution of 6-[2-(1H-pyrazol-4-yl)imidazo[1,2-b][1,2,4]triazin-7-yl]methylquinoline (10 mg, 0.0305 mmol) and 2-bromoacetamide (0.0084 g, 0.061 mmol) in N,N-dimethylformamide (0.5 mL). The mixture was stirred at 60° C. overnight, and purified by RP-HPLC (pH 2) to give the desired product as a TFA salt. LCMS: (M+H)=385.3.

Example 141: Methyl 4-{4-[7-(quinolin-6-ylmethyl)imidazo[1,2-b][1,2,4]triazin-2-yl]-1H-pyrazol-1-yl}piperidine-1-carboxylate

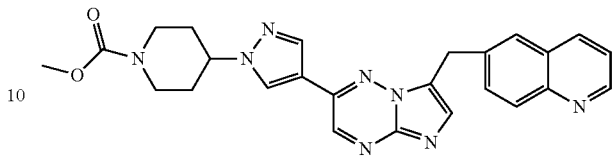

Step 1. tert-Butyl 4-[(methylsulfonyl)oxy]piperidine-1-carboxylate

To a solution of tert-butyl 4-hydroxypiperidine-1-carboxylate (0.30 g, 1.5 mmol) in methylene chloride (4 mL) and triethylamine (0.42 mL, 3.0 mmol), cooled with an ice bath, was added methanesulfonyl chloride (0.14 mL, 1.8 mmol). The mixture was stirred for 2 h, and partitioned between EtOAc and water. The organic layer was washed with 1N HCl, brine, dried over MgSO$_4$, filtered, and concentrated to give the desired product as a solid (0.41 g, 98%). LCMS: (M+Na)=302.3.

Step 2. tert-Butyl 4-{4-[7-(quinolin-6-ylmethyl)imidazo[1,2-b][1,2,4]triazin-2-yl]-H-pyrazol-1-yl}piperidine-1-carboxylate A mixture of 6-[2-(1H-pyrazol-4-yl)imidazo[1,2-b][1,2,4]triazin-7-yl]-methylquinoline (101 mg, 0.308 mmol), tert-butyl 4-[(methylsulfonyl)oxy]piperidine-1-carboxylate (0.17 g, 0.62 mmol) and cesium carbonate (0.30 g, 0.92 mmol) in N,N-dimethylformamide (2 mL) was stirred at 90° C. overnight. The mixture was purified by RP-HPLC (pH=10) to give the desired product (14 mg). LCMS: (M+H)=511.2.

Step 3. 6-[2-(1-Piperidin-4-yl-H-pyrazol-4-yl)imidazo[1,2-b][1,2,4]triazin-7-yl]methylquinoline Trifluoroacetic Acid (0.5 mL) was added to a solution of tert-butyl 4-{4-[7-(quinolin-6-ylmethyl)imidazo[1,2-b][1,2,4]triazin-2-yl]-1H-pyrazol-1-yl}piperidine-1-carboxylate (0.014 g, 0.027 mmol) in methylene chloride (0.5 mL) and stirred at RT for 1 h. The volatiles were removed under reduced pressure and the residue was purified by RP-HPLC (pH 10) to give the desired product. LCMS: (M+H)=411.1.

Step 4. Methyl 4-{4-[7-(quinolin-6-ylmethyl)imidazo[1,2-b][1,2,4]triazin-2-yl]-1H-pyrazol-1-yl}piperidine-1-carboxylate Methyl chloroformate (4.0 μL, 0.051 mmol) was added to a solution of 6-[2-(1-piperidin-4-yl-1H-pyrazol-4-yl)imidazo[1,2-b][1,2,4]triazin-7-yl]methylquinoline (7.0 mg, 0.017 mmol) and triethylamine (9.5 μL, 0.068 mmol) in methylene chloride (0.5 mL). The mixture was stirred for 1 h, and then purified by RP-HPLC (pH 2) to give the desired product as a TFA salt. LCMS: (M+H)=469.1.

Example 142: 2-Fluoro-N-[(1S,2S)-2-hydroxycyclopentyl]-4-[7-(quinolin-6-ylmethyl)imidazo[1,2-b][1,2,4]triazin-2-yl]benzamide

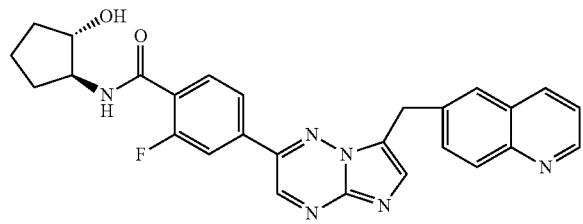 [SMILES: O=C(N[C@H]1CCC[C@@H]1O)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=483.4.

Example 143: 2-Fluoro-N-(2-hydroxyethyl)-4-[7-(quinolin-6-ylmethyl)imidazo[1,2-b][1,2,4]triazin-2-yl]benzamide

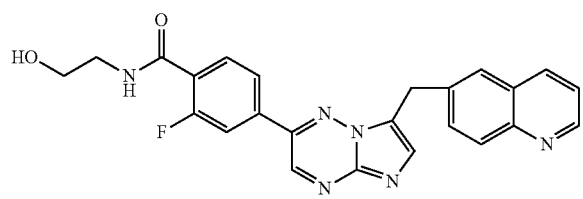 [SMILES: O=C(NCCO)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=443.2.

Example 144: 2-Fluoro-N-[1-(methoxymethyl)cyclobutyl]-4-[7-(quinolin-6-ylmethyl)imidazo[1,2-b][1,2,4]triazin-2-yl]benzamide

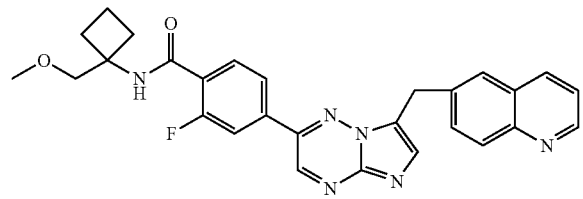 [SMILES: COCC1(NC(=O)c2ccc(-c3cnc4ncc(Cc5ccc6ncccc6c5)n4n3)cc2F)CCC1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=497.2.

Example 145: 2-Fluoro-N-[4-(methoxymethyl)tetrahydro-2H-pyran-4-yl]-4-[7-(quinolin-6-ylmethyl)imidazo[1,2-b][1,2,4]triazin-2-yl]benzamide

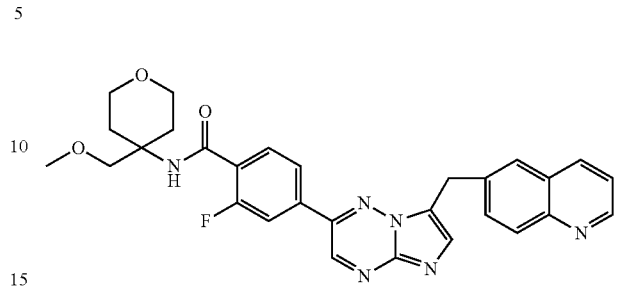

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=527.4.

Example 146: N-(Cyclopropylmethyl)-2-fluoro-4-[7-(quinolin-6-ylmethyl)imidazo[1,2-b][1,2,4]triazin-2-yl]benzamide

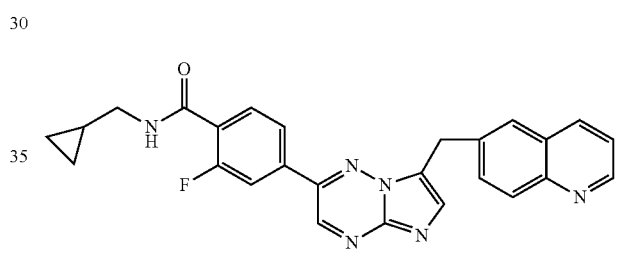

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=453.2.

Example 147: 2-Fluoro-4-[7-(quinolin-6-ylmethyl)imidazo[1,2-b][1,2,4]triazin-2-yl]-N-(tetrahydro-2H-pyran-4-ylmethyl)benzamide

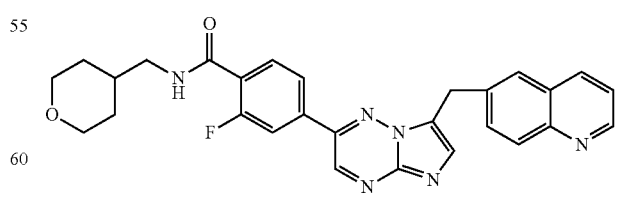

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=497.4.

Example 148: N-[2-(Dimethylamino)ethyl]-2-fluoro-4-[7-(quinolin-6-ylmethyl)imidazo[1,2-b][1,2,4]triazin-2-yl]benzamide

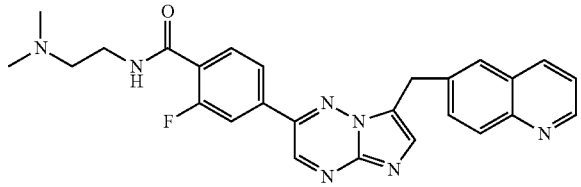 [SMILES: CN(C)CCNC(=O)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=470.4.

Example 149: 2-Fluoro-N-(2-piperidin-1-ylethyl)-4-[7-(quinolin-6-ylmethyl)imidazo[1,2-b][1,2,4]triazin-2-yl]benzamide

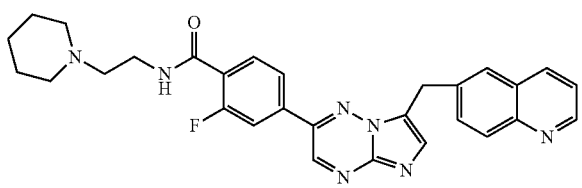 [SMILES: O=C(NCCN1CCCCC1)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=510.2.

Example 150: 2-Fluoro-N-[2-(1-methylpyrrolidin-2-yl)ethyl]-4-[7-(quinolin-6-ylmethyl)imidazo[1,2-b][1,2,4]triazin-2-yl]benzamide

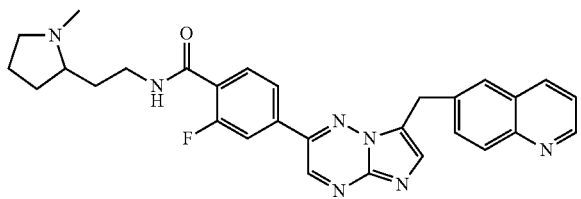 [SMILES: CN1CCCC1CCNC(=O)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=510.4.

Example 151: 2-Fluoro-N-(pyridin-2-ylmethyl)-4-[7-(quinolin-6-ylmethyl)imidazo[1,2-b][1,2,4]triazin-2-yl]benzamide

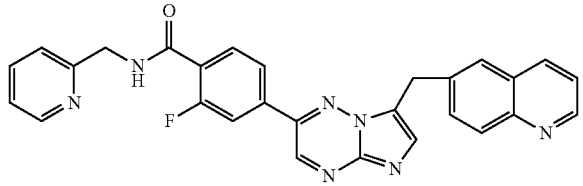 [SMILES: O=C(NCc1cccnc1)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=490.4.

Example 152: 2-Fluoro-N-(pyridin-3-ylmethyl)-4-[7-(quinolin-6-ylmethyl)imidazo[1,2-b][1,2,4]triazin-2-yl]benzamide

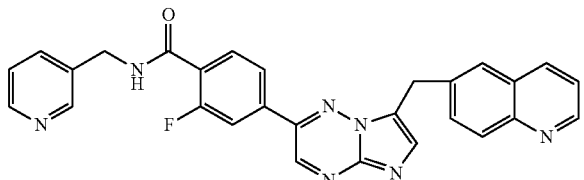

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=490.4.

Example 153: 2-Fluoro-N-(pyridin-4-ylmethyl)-4-[7-(quinolin-6-ylmethyl)imidazo[1,2-b][1,2,4]triazin-2-yl]benzamide

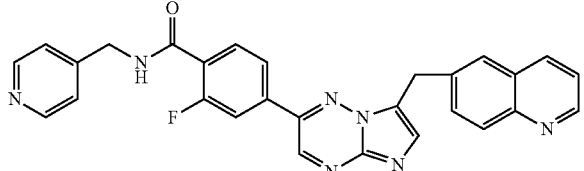

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=490.4.

Example 154: 2-Fluoro-N-(2-pyridin-2-ylethyl)-4-[7-(quinolin-6-ylmethyl)imidazo[1,2-b][1,2,4]triazin-2-yl]benzamide

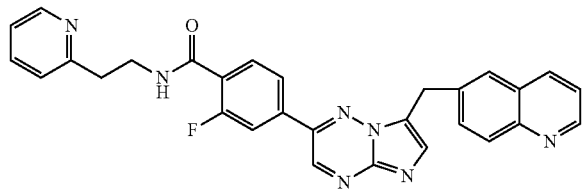 [SMILES: O=C(NCCc1ccccn1)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=504.1.

Example 155: 2-Fluoro-N-(1-pyridin-3-ylethyl)-4-[7-(quinolin-6-ylmethyl)imidazo[1,2-b][1,2,4]triazin-2-yl]benzamide

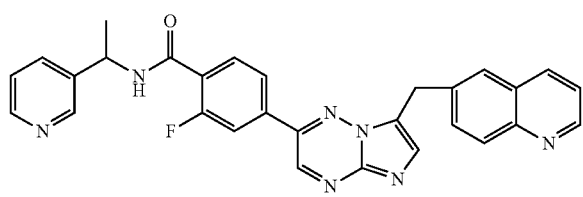 [SMILES: CC(NC(=O)c1ccc(-c2cnc3ncc(Cc4ccc5ncccc5c4)n3n2)cc1F)c1cccnc1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=504.3.

Example 156: 2-Fluoro-N-(1-pyridin-4-ylethyl)-4-[7-(quinolin-6-ylmethyl)imidazo[1,2-b][1,2,4]triazin-2-yl]benzamide

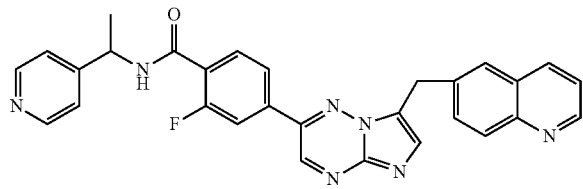 [SMILES: CC(NC(=O)c1ccc(-c2cnc3ncc(Cc4ccc5ncccc5c4)n3n2)cc1F)c1ccncc1]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=504.3.

Example 157: 2-Fluoro-N-[(1S)-1-(hydroxymethyl)-2,2-dimethylpropyl]-4-[7-(quinolin-6-ylmethyl)imidazo[1,2-b][1,2,4]triazin-2-yl]benzamide

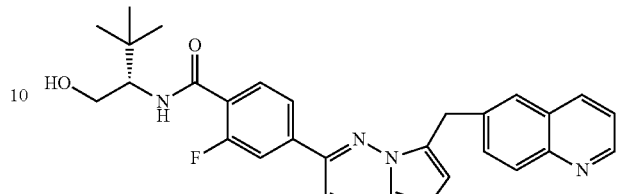

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=499.3.

Example 158: 2-Fluoro-N-[1-(hydroxymethyl)cyclopentyl]-4-[7-(quinolin-6-ylmethyl)imidazo[12-b][1,2,4]triazin-2-yl]benzamide

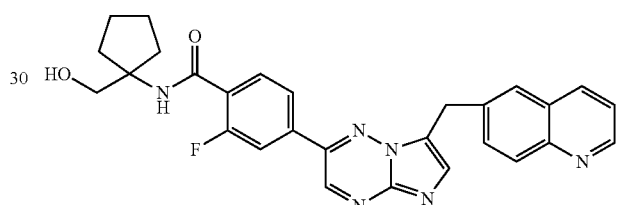

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=497.2.

Example 159: 2-Fluoro-N-(trans-4-hydroxycyclohexyl)-4-[7-(1-quinolin-6-ylethyl)imidazo[1,2-b][1,2,4]triazin-2-yl]benzamide

Step 1. 6-1-[2-(4-Bromo-3-fluorophenyl)imidazo[1,2-b][1,2,4]triazin-7-yl]ethylquinoline A mixture of 6-(4-bromo-3-fluorophenyl)-1,2,4-triazin-3-amine (100.0 mg, 0.3716 mmol, prepared as described for Example 7, Steps 1-5) and 2-chloro-3-quinolin-6-ylbutanal (0.10 g, 0.44 mmol, prepared as described for Example 122, Steps 1-4) in isopropyl alcohol (3 mL) was heated at 110° C. for 48 h. The mixture was adjusted to pH 9 by adding triethylamine. The volatiles were removed under reduced pressure and the residue was purified by chromatography on silica gel with MeOH in methylene chloride (0-8%) to afford the desired product (0.10 g, 60%). LCMS: (M+H)=448/450.0.

Step 2. 2-Fluoro-4-[7-(1-quinolin-6-ylethyl)imidazo[1,2-b][1,2,4]triazin-2-yl]benzonitrile A mixture of 6-1-[2-(4-bromo-3-fluorophenyl)imidazo[1,2-b][1,2,4]triazin-7-yl]ethylquinoline (0.100 g, 0.223 mmol), potassium hexacyanoferrate(II) trihydrate (30 mg, 0.06 mmol), sodium carbonate (0.047 g, 0.45 mmol) and palladium acetate (2 mg, 0.01 mmol) in N,N-dimethylacetamide (1.2 mL) was stirred at 120° C. for 2 h. LCMS showed the reaction was complete. The reaction was diluted with EtOAc, washed with water, brine, dried over MgSO$_4$, filtered, and concentrated. The residue was purified by chromatography on silica gel with MeOH in methylene chloride (0-10%) to afford the desired product (0.10 g, 60%). LCMS: (M+H)=395.0.

Step 3. 2-Fluoro-4-[7-(1-quinolin-6-ylethyl)imidazo[1,2-b][1,2,4]triazin-2-yl]benzoic acid 2-Fluoro-4-[7-(1-quinolin-6-ylethyl)imidazo[1,2-b][1,2,4]triazin-2-yl]benzonitrile (50.0 mg, 0.127 mmol) in conc. hydrochloric acid (0.6 mL) was stirred at 110° C. overnight. The solvent was removed (w/toluene) to give the desired product. LCMS: (M+H)=414.0.

Step 4. 2-Fluoro-N-(trans-4-hydroxycyclohexyl)-4-[7-(1-quinolin-6-ylethyl)imidazo[,2-b][1,2,4]triazin-2-yl]benzamide N,N-Diisopropylethylamine (6.4 µL, 0.037 mmol) was added to the mixture of 2-fluoro-4-[7-(1-quinolin-6-ylethyl)imidazo[1,2-b][1,2,4]triazin-2-yl]benzoic acid (5.1 mg, 0.012 mmol), trans-4-aminocyclohexanol hydrochloride (3.7 mg, 0.024 mmol) and benzotriazol-1-yloxytris(dimethylamino)phosphonium hexafluorophosphate (8.1 mg, 0.018 mmol) in N,N-dimethylformamide (0.6 mL) at 0° C. The mixture was stirred at RT for 4 h, and purified by RP-HPLC (pH 2) to give the desired product as a TFA salt. LCMS: (M+H)=511.0.

Example 160: 2-Fluoro-N-methyl-4-[7-(1-quinolin-6-ylethyl)imidazo[1,2-b][1,2,4]triazin-2-yl]benzamide

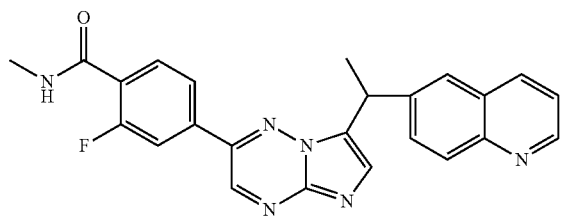 [SMILES: CNC(=O)c1ccc(-c2cnc3ncc(C(C)c4ccc5ncccc5c4)n3n2)cc1F]

This compound was prepared as a TFA salt starting from 2-fluoro-4-[7-(1-quinolin-6-ylethyl)imidazo[1,2-b][1,2,4]triazin-2-yl]benzoic acid using procedures analogous to those for Example 159. LCMS: (M+H)=427.1.

Example 161: N-Cyclopropyl-2-fluoro-4-[7-(1-quinolin-6-ylethyl)imidazo[1,2-b][1,2,4]triazin-2-yl]benzamide

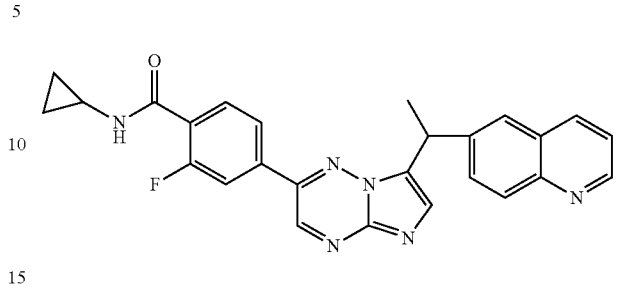

This compound was prepared as a TFA salt starting from 2-fluoro-4-[7-(1-quinolin-6-ylethyl)imidazo[1,2-b][1,2,4]triazin-2-yl]benzoic acid using procedures analogous to those for Example 159. LCMS: (M+H)=453.0.

Example 162: 2-Fluoro-N-[1-(methoxymethyl)cyclopropyl]-4-[7-(1-quinolin-6-ylethyl)imidazo[12-b][1,2,4]triazin-2-yl]benzamide

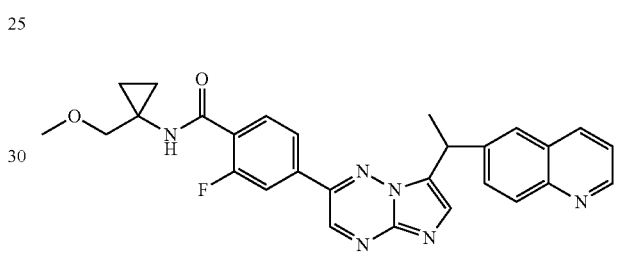

This compound was prepared as a TFA salt starting from 2-fluoro-4-[7-(1-quinolin-6-ylethyl)imidazo[1,2-b][1,2,4]triazin-2-yl]benzoic acid using procedures analogous to those for Example 159. LCMS: (M+H)=497.0.

Example 163: 2-Fluoro-N-(2-methoxy-1-methylethyl)-4-[3-(1-quinolin-6-ylcyclopropyl)imidazo[1,2-a]pyrimidin-6-yl]benzamide

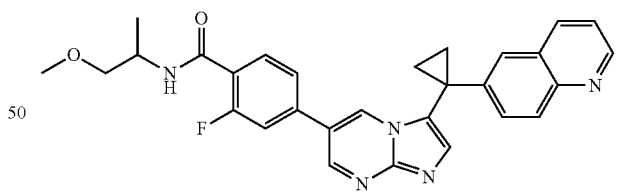

Step 1. 4-(2-aminopyrimidin-5-yl)-2-fluorobenzoic acid

A solution of sodium carbonate (1.4 g, 0.014 mol) in water (8 mL) was added to a mixture of 4-bromo-2-fluorobenzoic acid (1.0 g, 0.0046 mol), 5-(4,4,5,5-tetramethyl-1,3,2-dioxaborolan-2-yl)pyrimidin-2-amine (1.5 g, 6.8 mmol), and tetrakis(triphenylphosphine)palladium (0.3 g, 0.2 mmol) in toluene (16 mL) and ethanol (8 mL). The resulting mixture was heated at 120° C. for 15 min. The reaction mixture was washed with ether (3×10 mL) to remove impurity. The aqueous layer was adjusted with 1N HCl to pH 7.0, and purified by RP-HPLC (pH 10) to afford the desired product. LCMS: (M+H)=234.1.

Step 2. 2-fluoro-4-[3-(1-quinolin-6-ylcyclopropyl) imidazo[1,2-a]pyrimidin-6-yl]benzoic acid A mixture of 4-(2-aminopyrimidin-5-yl)-2-fluorobenzoic acid (0.20 g, 0.86 mmol) and chloro(1-quinolin-6-ylcyclopropyl)acetaldehyde (0.21 g, 0.86 mol) in ethanol (8 mL) was stirred at 100° C. overnight. The reaction mixture was purified by RP-HPLC to afford the desired product. LCMS: (M+H)=425.0.

Step 3. 2-fluoro-N-(2-methoxy-1-methylethyl)-4-[3-(1-quinolin-6-ylcyclopropyl)imidazo[1,2-a]pyrimidin-6-yl]benzamide A mixture of 2-fluoro-4-[3-(1-quinolin-6-ylcyclopropyl) imidazo[1,2-a]pyrimidin-6-yl]benzoic acid (19 mg, 0.045 mmol), 1-methoxypropan-2-amine (8 mg, 0.090 mmol), benzotriazol-1-yloxytris(dimethylamino)phosphonium hexafluorophosphate (40 mg, 0.090 mmol), and N,N-diisopropylethylamine (31 µL, 0.18 mmol) in N,N-dimethylformamide (0.5 mL) was stirred at RT for 2 h. The reaction mixture was purified by RP-HPLC (pH 10) to afford the desired product. LCMS: (M+H)=496.1

Example 164: 6-{1-[6-(3-Fluoro-4-[(3S)-3-fluoropyrrolidin-1-yl]carbonylphenyl)imidazo[1,2-a]pyrimidin-3-yl]cyclopropyl}quinoline

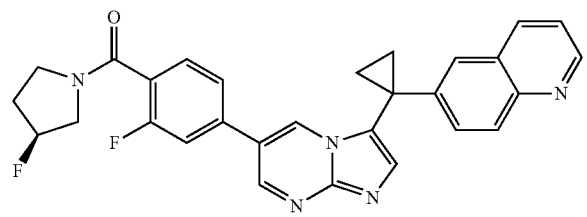 [SMILES: O=C(c1ccc(-c2cnc3ncc(C4(c5ccc6ncccc6c5)CC4)n3c2)cc1F)N1CC[C@H](F)C1]

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=496.1.

Example 165: 2-Fluoro-N-(pyridin-2-ylmethyl)-4-[3-(1-quinolin-6-ylcyclopropyl)imidazo[1,2-a]pyrimidin-6-yl]benzamide

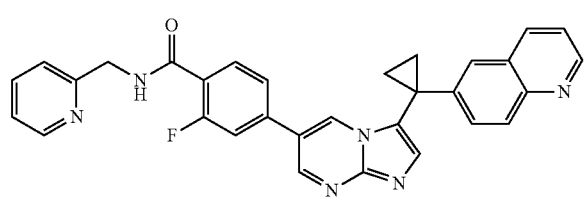 [SMILES: O=C(NCc1ccccn1)c1ccc(-c2cnc3ncc(C4(c5ccc6ncccc6c5)CC4)n3c2)cc1F]

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=515.1.

Example 166: 2-Fluoro-N-(1-pyridin-2-ylcyclopropyl)-4-[3-(1-quinolin-6-ylcyclopropyl)imidazo[1,2-a]pyrimidin-6-yl]benzamide

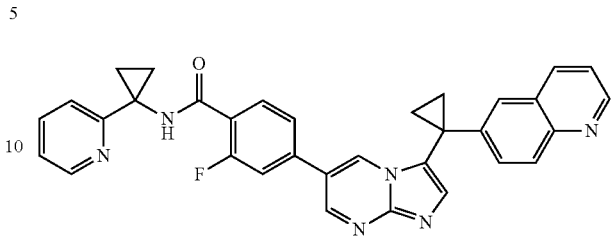

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=541.1.

Example 167: 2-Fluoro-N-(1-pyridin-2-ylpyrrolidin-3-yl)-4-[3-(1-quinolin-6-ylcyclopropyl)imidazo[1,2-a]pyrimidin-6-yl]benzamide

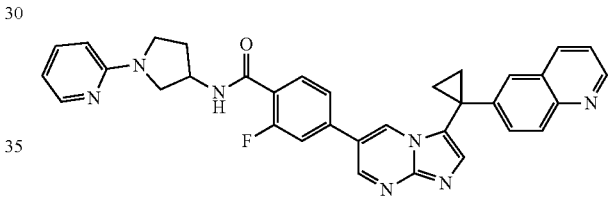

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=570.2.

Example 168: 2-Fluoro-4-[3-(1-quinolin-6-ylcyclopropyl)imidazo[1,2-a]pyrimidin-6-yl]-N-[(3R)-tetrahydrofuran-3-yl]benzamide

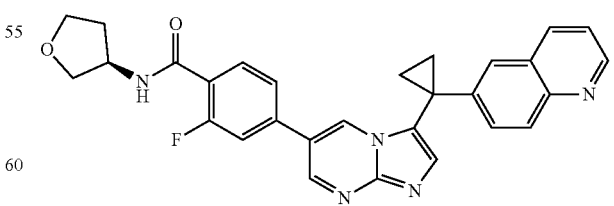

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=494.2.

Example 169: 2-Fluoro-4-[3-(1-quinolin-6-ylcyclopropyl)imidazo[1,2-a]pyrimidin-6-yl]-N-(tetrahydrofuran-2-ylmethyl)benzamide

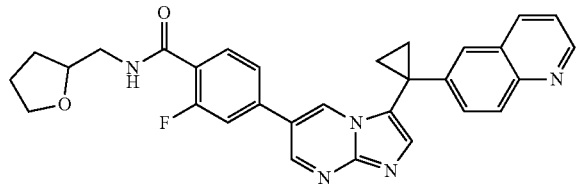 [SMILES: O=C(NCC1CCCO1)c1ccc(-c2cnc3ncc(C4(c5ccc6ncccc6c5)CC4)n3c2)cc1F]

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=508.2.

Example 170: N-Cyclopropyl-2-fluoro-4-[3-(1-quinolin-6-ylcyclopropyl)imidazo[1,2-a]pyrimidin-6-yl]benzamide

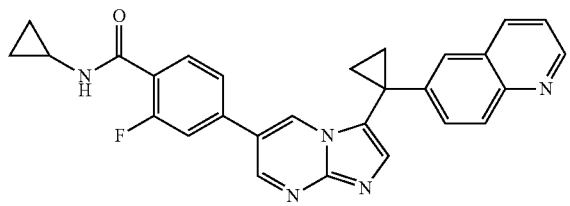 [SMILES: O=C(NC1CC1)c1ccc(-c2cnc3ncc(C4(c5ccc6ncccc6c5)CC4)n3c2)cc1F]

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=464.1.

Example 171: 2-Fluoro-N-[(1S)-1-(methoxymethyl)-2-methylpropyl]-4-[3-(1-quinolin-6-ylcyclopropyl)imidazo[1,2-a]pyrimidin-6-yl]benzamide

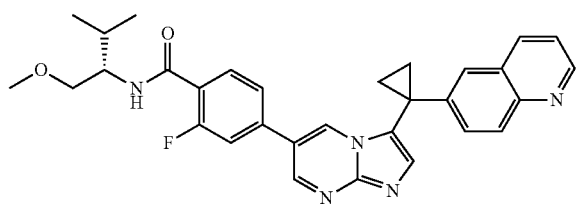 [SMILES: COC[C@@H](NC(=O)c1ccc(-c2cnc3ncc(C4(c5ccc6ncccc6c5)CC4)n3c2)cc1F)C(C)C]

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=524.1.

Example 172: 2-Fluoro-4-[3-(1-quinolin-6-ylcyclopropyl)imidazo[12-a]pyrimidin-6-yl]benzamide

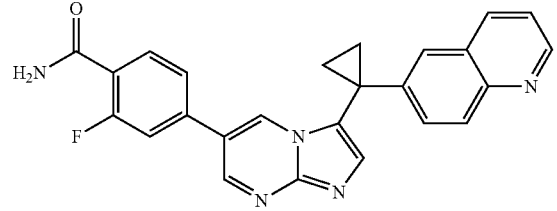 [SMILES: NC(=O)c1ccc(-c2cnc3ncc(C4(c5ccc6ncccc6c5)CC4)n3c2)cc1F]

This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=424.0.

Example 173: 2-Fluoro-N-methyl-N-2-[methyl(pyridin-2-yl)amino]ethyl-4-[3-(1-quinolin-6-ylcyclopropyl)imidazo[1,2-a]pyrimidin-6-yl]benzamide

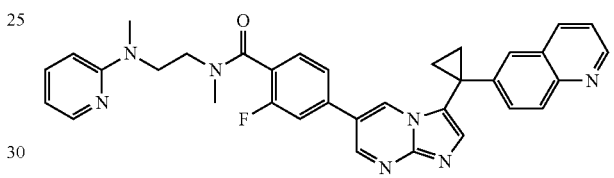

Step 1. N,N'-dimethyl-N-pyridin-2-ylethane-1,2-diamine

A mixture of 2-fluoropyridine (0.485 g, 5 mmol), N,N'-dimethyl-1,2-ethanediamine (1.32 g, 15 mmol) and sodium carbonate (1.59 g, 15 mmol) in 1,4-dioxane (5 mL) was heated under reflux overnight. The mixture was filtered and the filtrate was concentrated. The residue was co-evaporated with 1,4-dioxane (×2), and then dried to give the desired product (810 mg, 98%).

Step 2. 2-Fluoro-N-methyl-N-2-[methyl(pyridin-2-yl)amino]ethyl-4-[3-(1-quinolin-6-ylcyclopropyl)imidazo[1,2-a]pyrimidin-6-yl]benzamide This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=572.3.

Example 174: 2-Chloro-N-methyl-4-[3-(1-quinolin-6-ylcyclopropyl)imidazo[1,2-a]pyrimidin-6-yl]benzamide

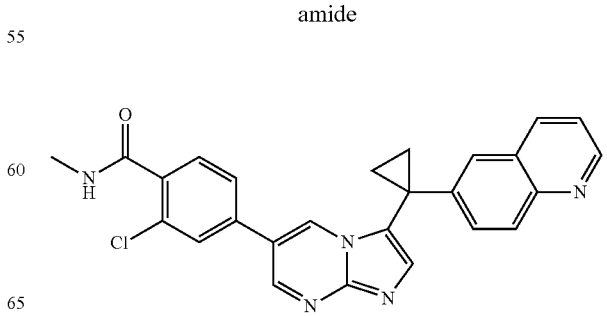

Step 1. methyl 4-(2-aminopyrimidin-5-yl)-2-chlorobenzoate

A solution of potassium carbonate (0.39 g, 2.8 mmol) in water (3 mL) was added to a mixture of methyl 4-bromo-2-chlorobenzoate (0.49 g, 2.0 mmol), 5-(4,4,5,5-tetramethyl-1,3,2-dioxaborolan-2-yl)pyrimidin-2-amine (0.31 g, 1.4 mmol), and tetrakis(triphenylphosphine)palladium (0.08 g, 0.07 mmol) in toluene (5.3 mL) and ethanol (3 mL). The resulting mixture was heated at 120° C. for 15 min. The reaction mixture was extracted with EtOAc (3×20 mL). The combined organic layers were washed with brine, dried over anhydrous $Na_2SO_4$, filtered, and concentrated. The residue was recrystallized from methanol and ether. The precipitate was collected by filtration, and washed with ether to afford the desired product (0.22 g, 59%). LCMS: (M+H)=264.0/266.0.

Step 2. methyl 2-chloro-4-[3-(1-quinolin-6-ylcyclopropyl)imidazo[1,2-a]pyrimidin-6-yl]benzoate A mixture of methyl 4-(2-aminopyrimidin-5-yl)-2-chlorobenzoate (0.22 g, 0.83 mmol) and chloro(1-quinolin-6-ylcyclopropyl)acetaldehyde (0.20 g, 0.83 mmol) in ethanol (6 mL) was stirred at 100° C. overnight. The reaction mixture was concentrated to afford the crude product which was directly used for next step. LCMS: (M+H)=455.1/457.1.

Step 3. 2-chloro-4-[3-(1-quinolin-6-ylcyclopropyl)imidazo[1,2-a]pyrimidin-6-yl]benzoic acid A mixture of methyl 2-chloro-4-[3-(1-quinolin-6-ylcyclopropyl)imidazo[1,2-a]pyrimidin-6-yl]benzoate (180.4 mg, 0.41 mmol) and lithium hydroxide monohydrate (34 mg, 0.82 mol) in methanol (0.99 mL) and water (0.33 mL) was stirred at 40° C. for about 3 h. The mixture was adjusted to pH 5 by adding 4N HCl in 1,4-dioxane. The volatiles were removed under reduced pressure. The residue was dried to give a crude product which was contaminated with LiCl and was directly used for next step without further purification. LCMS: (M+H)=441.0/443.0.

Step 4. 2-chloro-N-methyl-4-[3-(1-quinolin-6-ylcyclopropyl)imidazo[1,2-a]pyrimidin-6-yl]benzamide N,N-Diisopropylethylamine (14 µL, 0.081 mmol) was added to a mixture of 2-chloro-4-[3-(1-quinolin-6-ylcyclopropyl)imidazo[1,2-a]pyrimidin-6-yl]benzoic acid (0.027 mmol), methylamine (2M in THF, 0.2 mL, 0.4 mmol), benzotriazol-1-yloxytris(dimethylamino)phosphonium hexafluorophosphate (14 mg, 0.032 mmol) in N,N-dimethylformamide (0.5 mL). The mixture was stirred at RT for 2 h, and then purified by RP-HPLC (pH 10) to afford the desired product. LCMS: (M+H)=454.1/456.0.

Example 175: 2-Chloro-N-cyclopropyl-4-[3-(1-quinolin-6-ylcyclopropyl)imidazo[1,2-a]pyrimidin-6-yl]benzamide

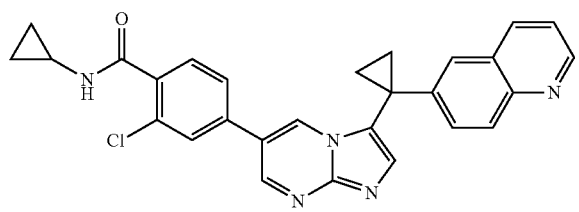

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=480.1/482.0.

Example 176: 2-Chloro-4-[3-(1-quinolin-6-ylcyclopropyl)imidazo[1,2-a]pyrimidin-6-yl]-N-(tetrahydrofuran-3-yl)benzamide

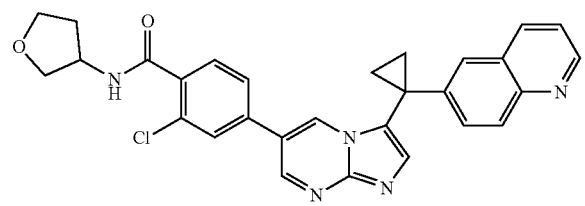 [SMILES: O=C(NC1CCOC1)c1ccc(-c2cnc3ncc(C4(c5ccc6ncccc6c5)CC4)n3c2)cc1Cl]

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=510.0/512.1.

Example 177: 2-Chloro-N-(1-pyridin-2-ylethyl)-4-[3-(1-quinolin-6-ylcyclopropyl)imidazo[1,2-a]pyrimidin-6-yl]benzamide

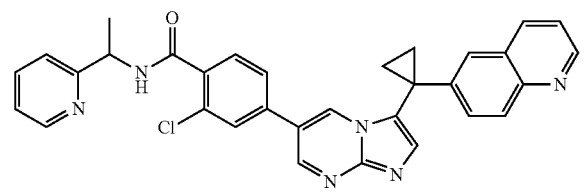 [SMILES: CC(NC(=O)c1ccc(-c2cnc3ncc(C4(c5ccc6ncccc6c5)CC4)n3c2)cc1Cl)c1ccccn1]

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=545.1/547.1.

Example 178: 6-(1-{6-[4-(Azetidin-1-ylcarbonyl)-3-chlorophenyl]imidazo[1,2-a]pyrimidin-3-yl}cyclopropyl)quinoline

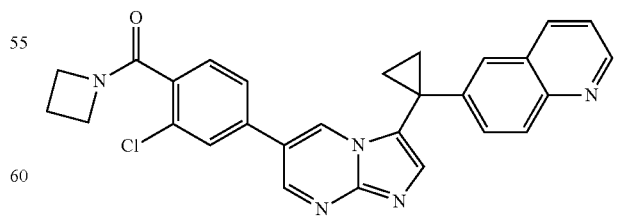

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=480.1/482.0.

Example 179: 2-Chloro-N-(1-pyridin-2-ylpyrrolidin-3-yl)-4-[3-(1-quinolin-6-ylcyclopropyl)imidazo[1,2-a]pyrimidin-6-yl]benzamide

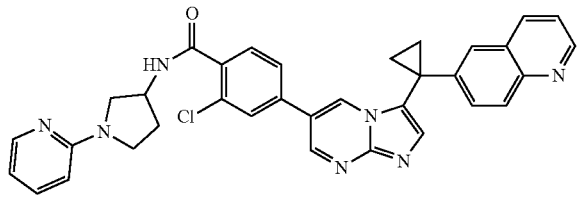 [SMILES: O=C(NC1CCN(c2ccccn2)C1)c1ccc(-c2cnc3ncc(C4(c5ccc6ncccc6c5)CC4)n3c2)cc1Cl]

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=586.0/588.1.

Example 180: 2-Chloro-N-[1-methyl-2-(pyridin-2-yloxy)ethyl]-4-[3-(1-quinolin-6-ylcyclopropyl)imidazo[1,2-a]pyrimidin-6-yl]benzamide

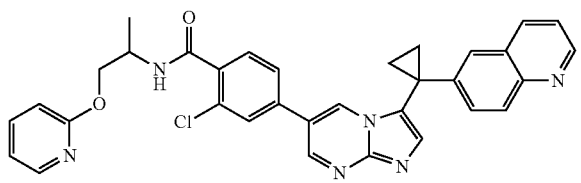 [SMILES: CC(COc1ccccn1)NC(=O)c1ccc(-c2cnc3ncc(C4(c5ccc6ncccc6c5)CC4)n3c2)cc1Cl]

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=575.1/577.1.

Example 181: 2-Chloro-N-(1S)-1-[(dimethylamino)carbonyl]-2-methylpropyl-4-[3-(1-quinolin-6-ylcyclopropyl)imidazo[1,2-a]pyrimidin-6-yl]benzamide

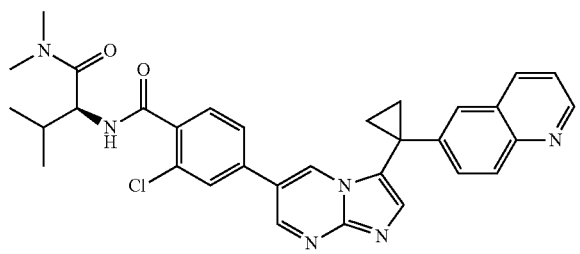 [SMILES: CC(C)[C@H](NC(=O)c1ccc(-c2cnc3ncc(C4(c5ccc6ncccc6c5)CC4)n3c2)cc1Cl)C(=O)N(C)C]

This compound was prepared from 2-chloro-4-[3-(1-quinolin-6-ylcyclopropyl)imidazo[1,2-a]pyrimidin-6-yl]benzoic acid using procedures analogous to those for Example 174. LCMS: (M+H)=567.1/569.1.

Example 182: 2-Cyclopropyl-5-[3-(1-quinolin-6-ylcyclopropyl)imidazo[1,2-a]pyrimidin-6-yl]isoindolin-1-one

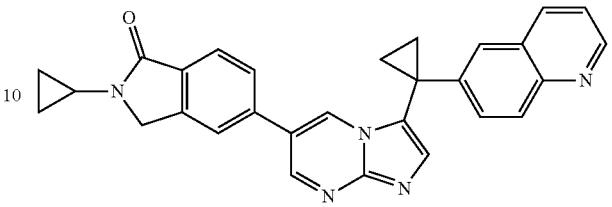

Step 1. methyl 4-bromo-2-(bromomethyl)benzoate

A mixture of methyl 4-bromo-2-methylbenzoate (0.7 g, 0.003 mol), N-bromosuccinimide (0.65 g, 0.0037 mol) and benzoyl peroxide (0.038 g, 0.00016 mol) in carbon tetrachloride (30 mL) was refluxed under an atmosphere of nitrogen for 2 h. The mixture was cooled to RT, and filtered through silica gel eluting with dichloromethane followed by diethyl ether. The mixture was concentrated and the residue was purified by chromatography on silica gel with 30% EtOAc in hexanes to afford the desired product (0.86 g, 90%).

Step 2. 5-bromo-2-cyclopropylisoindolin-1-one

A mixture of methyl 4-bromo-2-(bromomethyl)benzoate (0.13 g, 0.42 mmol), cyclopropylamine (0.034 mL, 0.49 mmol) and potassium carbonate (0.090 g, 0.65 mmol) in ethanol (0.9 mL) was stirred at 40° C. for 3 h. The reaction mixture was quenched with saturated sodium bicarbonate and extracted with EtOAc (3×20 mL). The combined organic layers were washed with brine, dried over anhydrous $Na_2SO_4$, filtered, and concentrated. The residue was purified by chromatography on silica gel with 30% EtOAc in hexanes to afford the desired product (0.10 g, 94%). LCMS: (M+H)=252.0/254.0.

Step 3. 5-(2-aminopyrimidin-5-yl)-2-cyclopropylisoindolin-1-one

A solution of potassium carbonate (0.10 g, 0.75 mmol) in water (0.7 mL) was added to a mixture of 5-bromo-2-cyclopropylisoindolin-1-one (0.095 g, 0.38 mmol), 5-(4,4,5,5-tetramethyl-1,3,2-dioxaborolan-2-yl)pyrimidin-2-amine (0.12 g, 0.56 mmol), and tetrakis(triphenylphosphine)palladium (0.02 g, 0.02 mmol) in toluene (1.4 mL) and ethanol (0.7 mL). The resulting mixture was heated at 120° C. for 15 min. The reaction mixture was then quenched with saturated sodium bicarbonate (5 mL) and extracted with EtOAc. The organic layers were washed with brine, dried with anhydrous $Na_2SO_4$, filtered, and concentrated. The residue was purified by chromatography on silica gel with 10% methanol in dichloromethane to afford the desired product (0.046 g, 46%). LCMS: (M+H)=267.1.

Step 4. 2-cyclopropyl-5-[3-(1-quinolin-6-ylcyclopropyl) imidazo[1,2-a]pyrimidin-6-yl]isoindolin-1-one A mixture of 5-(2-aminopyrimidin-5-yl)-2-cyclopropylisoindolin-1-one (20 mg, 0.075 mmol) and chloro(1-quinolin-6-ylcyclopropyl)acetaldehyde (18 mg, 0.075 mmol) in isopropyl alcohol (0.5 mL) was stirred at 90° C. overnight. The reaction mixture was purified by RP-HPLC (pH 10) to afford the desired product. LCMS: (M+H)=458.1.

Example 183: 2-Ethyl-5-[3-(1-quinolin-6-ylcyclopropyl)imidazo[1,2-a]pyrimidin-6-yl]isoindolin-1-one

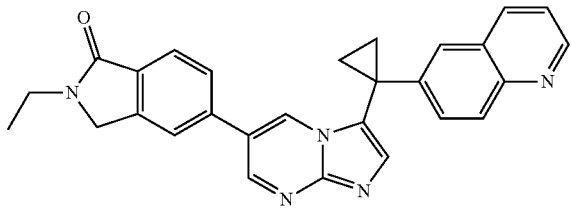 [SMILES: CCN1Cc2cc(-c3cnc4ncc(C5(c6ccc7ncccc7c6)CC5)n4c3)ccc2C1=O]

This compound was prepared from methyl 4-bromo-2-(bromomethyl)benzoate using procedures analogous to those for Example 182. LCMS: (M+H)=446.1.

Example 184: 2-(2-Methoxy-1-methylethyl)-5-[3-(1-quinolin-6-ylcyclopropyl)imidazo[1,2-a]pyrimidin-6-yl]isoindolin-1-one

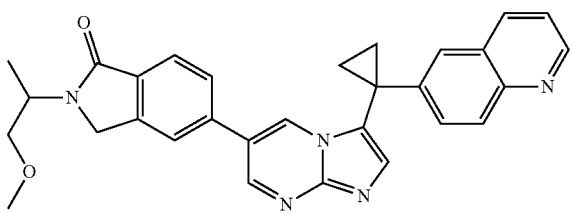 [SMILES: COCC(C)N1Cc2cc(-c3cnc4ncc(C5(c6ccc7ncccc7c6)CC5)n4c3)ccc2C1=O]

This compound was prepared from methyl 4-bromo-2-(bromomethyl)benzoate using procedures analogous to those for Example 182. LCMS: (M+H)=490.2.

Example 185: 2-(Pyridin-2-ylmethyl)-5-[3-(1-quinolin-6-ylcyclopropyl)imidazo[1,2-a]pyrimidin-6-yl]isoindolin-1-one

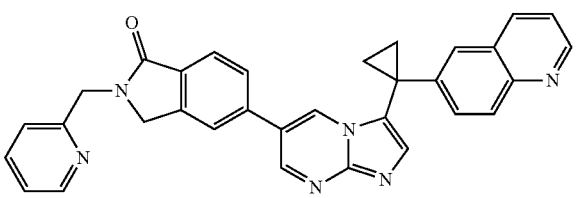 [SMILES: O=C1c2ccc(-c3cnc4ncc(C5(c6ccc7ncccc7c6)CC5)n4c3)cc2CN1Cc1ccccn1]

This compound was prepared from methyl 4-bromo-2-(bromomethyl)benzoate using procedures analogous to those for Example 182. LCMS: (M+H)=509.1.

Example 186: 2-Methyl-5-[3-(1-quinolin-6-ylcyclopropyl)imidazo[1,2-a]pyrimidin-6-yl]isoindolin-1-one

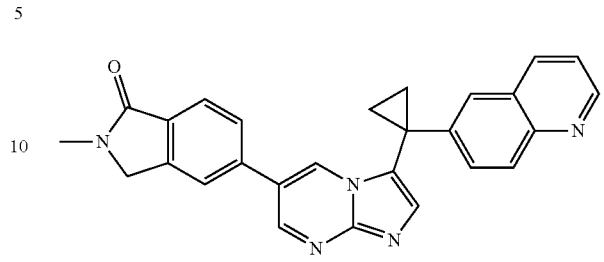

This compound was prepared from methyl 4-bromo-2-(bromomethyl)benzoate using procedures analogous to those for Example 182. LCMS: (M+H)=432.1.

Example 187: N-Ethyl-1-{4-[3-(1-quinolin-6-ylcyclopropyl)imidazo[1,2-a]pyrimidin-6-yl]phenyl}cyclopropanecarboxamide

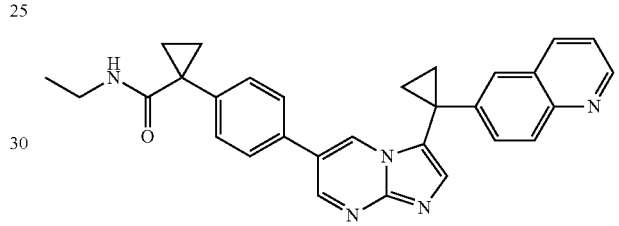

Step 1. 1-[4-(2-aminopyrimidin-5-yl)phenyl]cyclopropanecarboxylic acid

A solution of sodium carbonate (0.56 g, 0.0052 mol) in water (5.0 mL) was added to a mixture of tert-butyl 1-(4-bromophenyl)cyclopropanecarboxylate (0.78 g, 0.0026 mol), 5-(4,4,5,5-tetramethyl-1,3,2-dioxaborolan-2-yl)pyrimidin-2-amine (0.87 g, 0.0039 mol), and tetrakis(triphenylphosphine)palladium (0.2 g, 0.0001 mol) in toluene (10 mL) and ethanol (5 mL). The resulting mixture was heated at 120° C. for 15 min, quenched with water (5 mL), and washed with ether (3×10 mL). The precipitate in the aqueous layer was filtered, washed with water, and dried to afford the desired product (0.40 g, 60%). LCMS: (M+H)=256.1.

Step 2. 1-{4-[3-(1-quinolin-6-ylcyclopropyl)imidazo[1,2-a]pyrimidin-6-yl]phenyl}cyclopropanecarboxylic acid A mixture of 1-[4-(2-aminopyrimidin-5-yl)phenyl]cyclopropanecarboxylic acid (0.22 g, 0.86 mmol) and chloro(1-quinolin-6-ylcyclopropyl)acetaldehyde (0.21 g, 0.86 mmol) in ethanol (8 mL) was stirred at 100° C. overnight. The reaction mixture was purified by RP-HPLC (pH 10) to afford the desired product (0.12 g, 31%). LCMS: (M+H)=447.1.

Step 3. N-ethyl-1-{4-[3-(1-quinolin-6-ylcyclopropyl)imidazo[1,2-a]pyrimidin-6-yl]phenyl}cyclopropanecarboxamide A mixture of 1-{4-[3-(1-quinolin-6-ylcyclopropyl)imidazo[1,2-a]pyrimidin-6-yl]phenyl}cyclopropanecarboxylic acid (20 mg, 0.045 mmol), ethylamine (2.4 mg, 0.054 mmol), benzotriazol-1-yloxytris(dimethylamino)phosphonium hexafluorophosphate (24 mg, 0.054 mmol), and N,N-diisopropylethylamine (23 µL, 0.13 mmol) in N,N-dimethylformamide (0.5 mL) was stirred at RT for 2 h. The reaction mixture was purified by RP-HPLC (pH 10) to afford the desired product. LCMS: (M+H)=474.1.

Example 188: N-(1-Pyridin-2-ylethyl)-1-{4-[3-(1-quinolin-6-ylcyclopropyl)imidazo[1,2-a]pyrimidin-6-yl]phenyl}cyclopropanecarboxamide

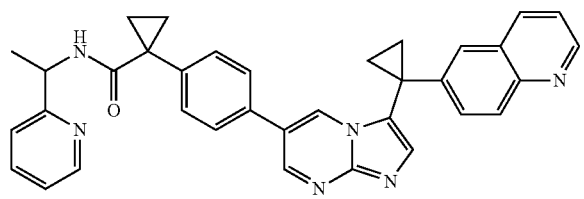 [SMILES: CC(NC(=O)C1(c2ccc(-c3cnc4ncc(C5(c6ccc7ncccc7c6)CC5)n4c3)cc2)CC1)c1ccccn1]

This compound was prepared from 1-{4-[3-(1-quinolin-6-ylcyclopropyl)imidazo[1,2-a]pyrimidin-6-yl]phenyl}cyclopropanecarboxylic acid using procedures analogous to those for Example 187. LCMS: (M+H)=551.2.

Example 189: N-[1-Methyl-2-(pyridin-2-yloxy)ethyl]-1-{4-[3-(1-quinolin-6-ylcyclopropyl)imidazo[1,2-a]pyrimidin-6-yl]phenyl}cyclopropanecarboxamide

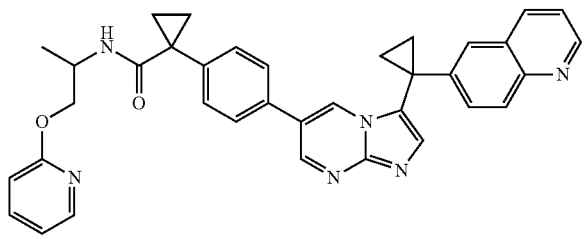 [SMILES: CC(COc1ccccn1)NC(=O)C1(c2ccc(-c3cnc4ncc(C5(c6ccc7ncccc7c6)CC5)n4c3)cc2)CC1]

This compound was prepared from 1-{4-[3-(1-quinolin-6-ylcyclopropyl)imidazo[1,2-a]pyrimidin-6-yl]phenyl}cyclopropanecarboxylic acid using procedures analogous to those for Example 187. LCMS: (M+H)=581.2.

Example 190: 2-{2-Fluoro-4-[3-(1-quinolin-6-ylcyclopropyl)imidazo[1,2-a]pyrimidin-6-yl]phenyl}-2-hydroxy-N-methylacetamide

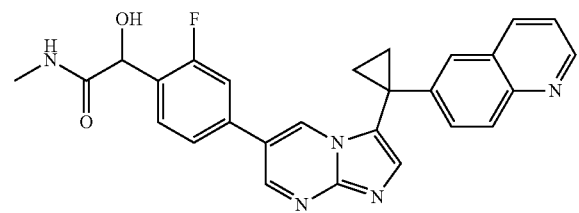 [SMILES: CNC(=O)C(O)c1ccc(-c2cnc3ncc(C4(c5ccc6ncccc6c5)CC4)n3c2)cc1F]

Step 1. 2-(4-bromo-2-fluorophenyl)-2-hydroxy-N-methylacetamide

N,N-Diisopropylethylamine (0.2 mL, 0.001 mol) was added to a mixture of (4-bromo-2-fluorophenyl)(hydroxy)acetic acid (0.1 g, 0.4 mmol), methylamine (2M in THF, 0.24 mL, 0.48 mmol) and benzotriazol-1-yloxytris(dimethylamino)phosphonium hexafluorophosphate (0.21 g, 0.00048 mol) in methylene chloride (2 mL). The mixture was stirred at RT for 2 h. The reaction mixture was concentrated. The residue was purified by chromatography on silica gel with 10% methanol in dichloromethane to afford the desired product. LCMS: (M+H)=261.9/263.9.

Step 2. 2-[4-(2-aminopyrimidin-5-yl)-2-fluorophenyl]-2-hydroxy-N-methylacetamide A mixture of 2-(4-bromo-2-fluorophenyl)-2-hydroxy-N-methylacetamide (0.4 mmol), 5-(4,4,5,5-tetramethyl-1,3,2-dioxaborolan-2-yl)pyrimidin-2-amine (0.11 g, 0.48 mmol), tetrakis(triphenylphosphine)palladium (0.01 g, 0.01 mmol) and potassium carbonate (0.16 g, 1.2 mmol) in toluene (0.6 mL) and 1,4-dioxane (0.6 mL) was heated at 100° C. for 1.5 h. After cooling to RT, the mixture was filtered through a pad of silica gel, washed with 10% methanol in dichloromethane. The filtrate was concentrated under reduced pressure and the residue purified by chromatography on silica gel with 10% methanol in dichloromethane to afford the desired product. LCMS: (M+H)=277.0.

Step 3. 2-2-fluoro-4-[3-(1-quinolin-6-ylcyclopropyl)imidazo[1,2-a]pyrimidin-6-yl]phenyl-2-hydroxy-N-methylacetamide A mixture of 2-[4-(2-aminopyrimidin-5-yl)-2-fluorophenyl]-2-hydroxy-N-methylacetamide (18 mg, 0.066 mmol) and chloro(1-quinolin-6-ylcyclopropyl)acetaldehyde (19 mg, 0.079 mmol) in ethanol (0.4 mL) was stirred at 90° C. overnight. The reaction mixture was purified by RP-HPLC (pH 10) to afford the desired product. LCMS: (M+H)=468.1.

Example 191: 2-{2-fluoro-4-[3-(1-quinolin-6-ylcyclopropyl)imidazo[1,2-a]pyrimidin-6-yl]phenyl}-2-hydroxy-N,N-dimethylacetamide

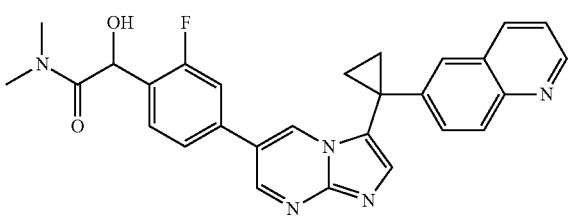 [SMILES: CN(C)C(=O)C(O)c1ccc(-c2cnc3ncc(C4(c5ccc6ncccc6c5)CC4)n3c2)cc1F]

This compound was prepared from (4-bromo-2-fluorophenyl)(hydroxy)acetic acid using procedures analogous to those for Example 190. LCMS: (M+H)=482.1.

Example 192: N-(3-[2-(4-Bromo-3-fluorophenyl)imidazo[1,2-b][1,2,4]triazin-7-yl]methylphenyl)-N'-ethylurea

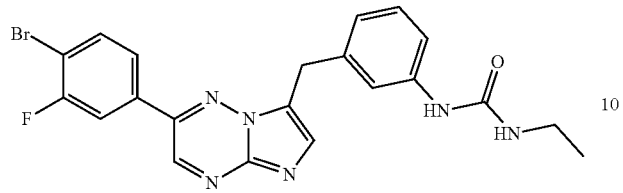

Step 1. tert-butyl [3-(3-oxopropyl)phenyl]carbamate

Tris(dibenzylideneacetone)dipalladium (0.10 g, 0.00011 mol) and tri-tert-butylphosphonium tetrafluoroborate (0.064 g, 0.00022 mol) in a flask was evacuated and refilled with $N_2$ (3 times). Then 1,4-dioxane (7.0 mL) was added followed by consecutive addition of tert-butyl (3-bromophenyl)carbamate (2.00 g, 0.00735 mol), 2-propen-1-ol (0.854 g, 0.0147 mol), N-cyclohexyl-N-methyl-cyclohexanamine (1.7 g, 0.0088 mol). The reaction mixture was stirred at 40° C. overnight, filtered, and washed with dichloromethane. The filtrate was concentrated and purified by chromatography on silica gel with 40% EtOAc in hexanes to afford the desired product (0.5 g, 30%).

Step 2. tert-butyl [3-(2-chloro-3-oxopropyl)phenyl]carbamate

N-Chlorosuccinimide (0.27 g, 0.0020 mol) was added to a mixture of tert-butyl [3-(3-oxopropyl)phenyl]carbamate (0.50 g, 0.0020 mol) and D-proline (0.05 g, 0.0004 mol) in methylene chloride (5 mL) at 0° C. The reaction mixture was stirred at RT for 2 h and concentrated. The residue was purified by chromatography on silica gel with 30% EtOAc in hexanes to afford the desired product (0.50 g, 88%). LCMS: (M+H)=209.9/211.9.

Step 3. tert-butyl (3-[2-(4-bromo-3-fluorophenyl)imidazo[1,2-b][1,2,4]triazin-7-yl]methylphenyl)carbamate A mixture of 6-(4-bromo-3-fluorophenyl)-1,2,4-triazin-3-amine (19 mg, 0.070 mmol) and tert-butyl [3-(2-chloro-3-oxopropyl)phenyl]carbamate (20 mg, 0.070 mmol) in ethanol (0.4 mL) was stirred overnight at 105° C. The reaction mixture was purified by RP-HPLC (pH 10) to afford the desired product. LCMS: (M+H)=498.0/500.0.

Step 4. 3-[2-(4-bromo-3-fluorophenyl)imidazo[1,2-b][1,2,4]triazin-7-yl]methylaniline A mixture of tert-butyl (3-[2-(4-bromo-3-fluorophenyl)imidazo[1,2-b][1,2,4]triazin-7-yl]methylphenyl)carbamate (10 mg, 0.02 mmol) in trifluoroacetic acid (0.5 mL) and methylene chloride (0.5 mL) was stirred overnight at RT. The mixture was concentrated to afford the desired product as a TFA salt which was directly used for next step. LCMS: (M+H)=397.9/399.9.

Step 5. N-(3-[2-(4-bromo-3-fluorophenyl)imidazo[1,2-b][1,2,4]triazin-7-yl]methylphenyl)-N'-ethylurea Isocyanatoethane (1.3 µL, 0.019 mmol) were added to a mixture of 3-[2-(4-bromo-3-fluorophenyl)imidazo[1,2-b][1,2,4]triazin-7-yl]methylaniline (5 mg, 0.01 mmol) and triethylamine (7.0 µL, 0.050 mmol) in acetonitrile (0.5 mL). After the reaction mixture was stirred at RT for 30 min, it was purified by RP-HPLC (pH 10) to afford the desired product (2 mg, 30%). LCMS: (M+H)=469.0/470.8.

Example 193: 2-(2,3-Dichlorophenyl)-7-(1-quinolin-6-ylcyclopropyl)imidazo[1,2-][1,2,4]triazin-3-amine

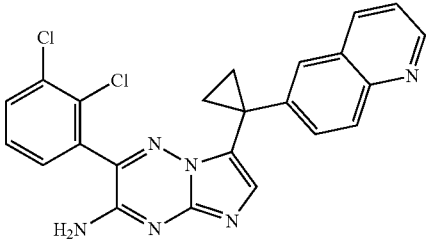 [SMILES: Nc1nc2ncc(C3(c4ccc5ncccc5c4)CC3)n2nc1-c1cccc(Cl)c1Cl]

A mixture of 6-(2,3-dichlorophenyl)-1,2,4-triazine-3,5-diamine (19 mg, 0.076 mmol) and chloro(1-quinolin-6-ylcyclopropyl)acetaldehyde (22 mg, 0.091 mmol) in ethanol (0.50 mL) was stirred at 105° C. overnight. The reaction mixture was purified by RP-HPLC (pH 10) to afford the desired product (12 mg, 35%). LCMS: (M+H)=447.3/449.2/451.2.

Example 194: 2,3-Difluoro-N-methyl-4-[3-(1-quinolin-6-ylcyclopropyl)imidazo[1,2-a]pyrimidin-6-yl]benzamide

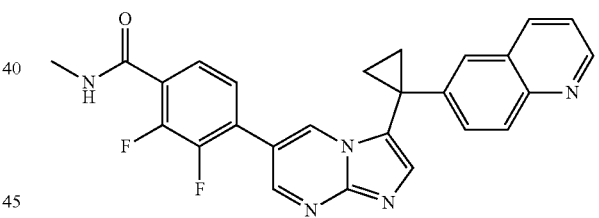

Step 1. 1-[2-chloro-1-hydroxy-2-(1-quinolin-6-ylcyclopropyl)ethyl]pyrrolidine-2,5-dione To a cooled (0° C.) mixture of (1-quinolin-6-ylcyclopropyl)acetaldehyde (9.9 g, 47 mmol), D-proline (1.1 g, 9.4 mmol) in chloroform (200 mL) was added N-chlorosuccinimide (6.26 g, 46.9 mmol). The mixture was stirred at 0° C. for 30 min and then gradually warmed to RT for 2 h. The reaction mixture was quenched with saturated sodium bicarbonate (25 mL) and extracted with EtOAc (3×100 mL). The combined organic layers were washed with brine, dried over $Na_2SO_4$, filtered, and concentrated. The precipitate formed was filtered to give the desired product. The filtrate was chromatographed on silica gel with EtOAc in methylene chloride (10%) to afford chloro(1-quinolin-6-ylcyclopropyl)acetaldehyde which was contaminated with pyrrolidine-2,5-dione (13.0 g), and automatically converted to the desired product after a few days. The total desired product obtained is 16 g. LCMS: (M+H)=345.0/347.0.

Step 2. 4-(2-aminopyrimidin-5-yl)-2,3-difluorobenzoic acid

A mixture of 4-(dihydroxyboryl)-2,3-difluorobenzoic acid (0.47 g, 2.3 mmol), 5-bromopyrimidin-2-amine (0.44 g, 2.6 mmol), tetrakis(triphenylphosphine)palladium (0.1 g, 0.1 mmol), and potassium carbonate (0.96 g, 7.0 mmol) in toluene (4.0 mL), ethanol (2.0 mL) and water (2.0 mL) was heated at 110° C. for 3 h. After cooling to RT, the mixture was washed with ether to remove impurity. The aqueous layer was adjusted to pH 6 with 1N HCl. The solid was filtered, washed with water and ether to give the desired product. LCMS: (M+H)=252.9.

Step 3. 2,3-difluoro-4-[3-(1-quinolin-6-ylcyclopropyl)imidazo[1,2-a]pyrimidin-6-yl]benzoic acid A mixture of 4-(2-aminopyrimidin-5-yl)-2,3-difluorobenzoic acid (15 mg, 0.060 mmol) and 1-[2-chloro-1-hydroxy-2-(1-quinolin-6-ylcyclopropyl)ethyl]pyrrolidine-2,5-dione (20 mg, 0.058 mmol) in ethanol (1.0 mL) was stirred at 100° C. overnight. The reaction mixture was purified by RP-HPLC (pH 10) to afford the desired product (9 mg, 40%). LCMS: (M+H)=443.0.

Step 4. 2,3-difluoro-N-methyl-4-[3-(1-quinolin-6-ylcyclopropyl)imidazo[, 2-a]pyrimidin-6-yl]benzamide A mixture of 2,3-difluoro-4-[3-(1-quinolin-6-ylcyclopropyl)imidazo[1,2-a]pyrimidin-6-yl]benzoic acid (9.0 mg, 0.020 mmol), methylamine (2M in THF, 0.02 mL, 0.041 mmol), benzotriazol-1-yloxytris(dimethylamino)phosphonium hexafluorophosphate (11 mg, 0.024 mmol) and N,N-diisopropylethylamine (11 μL, 0.061 mmol) in N,N-dimethylformamide (0.5 mL) was stirred at RT for 4 h. The reaction mixture was purified by RP-HPLC (pH 10) to afford the desired product. LCMS: (M+H)=456.0.

Example 195: 6-Difluoro-N-methyl-4-[3-(1-quinolin-6-ylcyclopropyl)imidazo[1,2-a]pyrimidin-6-yl]benzamide This compound was prepared from 4-(dihydroxyboryl)-2,6-difluorobenzoic acid using procedures analogous to those for Example 194. LCMS: (M+H)=456.0.

Example 196: 2-Fluoro-N-methyl-4-[3-(1-quinolin-6-ylcyclopropyl)imidazo[1,2-a]pyrimidin-6-yl]benzenesulfonamide

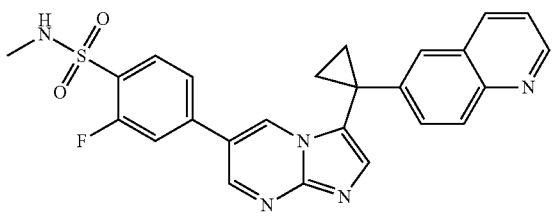 [SMILES: CNS(=O)(=O)c1ccc(-c2cnc3ncc(C4(c5ccc6ncccc6c5)CC4)n3c2)cc1F]

Step 1. 4-(2-aminopyrimidin-5-yl)-2-fluoro-N-methylbenzenesulfonamide

4-Bromo-2-fluorobenzenesulfonyl chloride (100 mg, 0.36 mmol) was added to a mixture of methylamine (2M in THF, 0.275 mL, 0.55 mmol) and triethylamine (0.10 mL, 0.73 mmol) in methylene chloride (2.0 mL). The reaction mixture was quenched with saturated NaHCO$_3$ (1.0 mL) and concentrated to afford the crude intermediate in water. A mixture of the intermediate in water, 5-(4,4,5,5-tetramethyl-1,3,2-dioxaborolan-2-yl)pyrimidin-2-amine (81 mg, 0.36 mmol), tetrakis(triphenylphosphine)palladium (20 mg, 0.02 mmol), potassium carbonate (150 mg, 1.1 mmol) in toluene (2.0 mL) and ethanol (1.0 mL) was heated at 110° C. for 2 h. After cooling to RT, ether was added to the mixture and the solid was filtered, washed with water and ether to afford the desired product (0.086 g, 83%). LCMS: (M+H)=282.9.

Step 2. 2-fluoro-N-methyl-4-[3-(1-quinolin-6-ylcyclopropyl)imidazo[1,2-a]pyrimidin-6-yl]benzenesulfonamide A mixture of 4-(2-aminopyrimidin-5-yl)-2-fluoro-N-methylbenzenesulfonamide (20 mg, 0.07 mmol) and 1-[2-chloro-1-hydroxy-2-(1-quinolin-6-ylcyclopropyl)ethyl]pyrrolidine-2,5-dione (24 mg, 0.07 mmol) in ethanol (0.4 mL) was stirred overnight at 105° C. The reaction mixture was purified by RP-HPLC (pH 10) to afford the desired product. LCMS: (M+H)=474.0.

Example 197: N,N-Dimethyl-2-{3-[3-(1-quinolin-6-ylcyclopropyl)imidazo[1,2-a]pyrimidin-6-yl]-1H-pyrazol-1-yl}acetamide

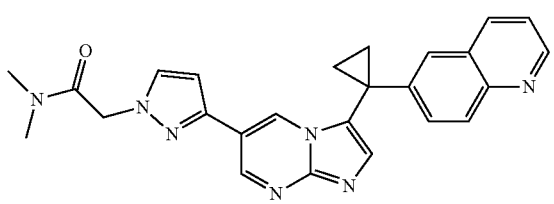 [SMILES: CN(C)C(=O)Cn1ccc(-c2cnc3ncc(C4(c5ccc6ncccc6c5)CC4)n3c2)n1]

Step 1. tert-butyl [3-(2-aminopyrimidin-5-yl)-1H-pyrazol-1-yl]acetate

To a solution of 1H-pyrazol-5-ylboronic acid (0.2 g, 2 mmol) in N,N-dimethylformamide (1.0 mL) were added 1,1-dimethylethyl bromoacetate (0.38 g, 2 mmol) and potassium carbonate (0.74 g, 0.0054 mol). The reaction mixture was stirred overnight at RT. To the reaction mixture was added 5-bromopyrimidin-2-amine (0.40 g, 2.3 mmol) and tetrakis(triphenylphosphine)palladium (0.1 g, 0.09 mmol). The resulting mixture was stirred at 100° C. for 2 h. After cooling to RT, the reaction mixture was extracted with EtOAc (3×30 mL). The combined organic layers were washed with brine, dried over anhydrous $Na_2SO_4$, filtered, and concentrated. The residue was purified by RP-HPLC to afford the desired product. LCMS: (M+H)=276.0.

Step 2. tert-butyl 3-[3-(1-quinolin-6-ylcyclopropyl)imidazo[, 2-a]pyrimidin-6-yl]-1H-pyrazol-1-ylacetate A mixture of tert-butyl [3-(2-aminopyrimidin-5-yl)-1H-pyrazol-1l-yl]acetate (16 mg, 0.058 mmol) and 1-[2-chloro-1-hydroxy-2-(1-quinolin-6-ylcyclopropyl)ethyl]pyrrolidine-2,5-dione (20 mg, 0.058 mmol) in ethanol (0.3 mL) was stirred overnight at 105° C. The reaction mixture was purified by RP-HPLC (pH 10) to afford the desired product (10 mg, 37%). LCMS: (M+H)=467.0.

Step 3. N,N-dimethyl-2-{3-[3-(1-quinolin-6-ylcyclopropyl)imidazo[1,2-a]pyrimidin-6-yl]-1H-pyrazol-1-yl}acetamide A mixture of tert-butyl 3-[3-(1-quinolin-6-ylcyclopropyl)imidazo[1,2-a]pyrimidin-6-yl]-1H-pyrazol-1-ylacetate (10 mg, 0.02 mmol) in trifluoroacetic acid (0.5 mL) and methylene chloride (0.5 mL) was stirred overnight at RT. The volatiles were removed under reduced pressure. The residue [LCMS: (M+H)=411.0] was dissolved in N,N-dimethylformamide (0.5 mL) and treated with dimethylamine (2M in THF, 0.016 mL, 0.032 mmol), benzotriazol-1-yloxytris(dimethylamino)phosphonium hexafluorophosphate (11 mg, 0.026 mmol), and N,N-diisopropylethylamine (11 μL, 0.064 mmol). The reaction mixture was stirred overnight at RT, and then purified by RP-HPLC (pH 10) to afford the desired product. LCMS: (M+H)=438.1.

Example 198: N-[(1S)-1-(Azetidin-1-ylcarbonyl)-2,2-dimethylpropyl]-2-fluoro-4-[3-(1-quinolin-6-ylcyclopropyl)imidazo[1,2-a]pyrimidin-6-yl]benzamide

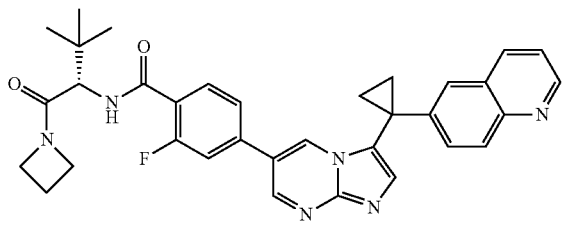 [SMILES: CC(C)(C)[C@H](NC(=O)c1ccc(-c2cnc3ncc(C4(c5ccc6ncccc6c5)CC4)n3c2)cc1F)C(=O)N1CCC1]

Step 1. tert-butyl (2S)-2-(2-fluoro-4-[3-(1-quinolin-6-ylcyclopropyl)imidazo[1,2-a]pyrimidin-6-yl]benzoylamino)-3,3-dimethylbutanoate This compound was prepared from 2-fluoro-4-[3-(1-quinolin-6-ylcyclopropyl)imidazo[1,2-a]pyrimidin-6-yl]benzoic acid using procedures analogous to those for Example 163. LCMS: (M+H)=594.2.

Step 2. (2S)-2-(2-fluoro-4-[3-(1-quinolin-6-ylcyclopropyl)imidazo[1,2-a]pyrimidin-6-yl]benzoylamino)-3,3-dimethylbutanoic acid A mixture of tert-butyl (2S)-2-(2-fluoro-4-[3-(1-quinolin-6-ylcyclopropyl)imidazo[1,2-a]pyrimidin-6-yl]benzoylamino)-3,3-dimethylbutanoate (60 mg, 0.1 mmol) in 2.0 ml of 4N HCl in 1,4-dioxane was stirred for 1 h. The mixture was concentrated to give the desired product as an HCl salt. LCMS: (M+H)=538.1.

Step 3. N-[(1S)-1-(azetidin-1-ylcarbonyl)-2,2-dimethylpropyl]-2-fluoro-4-[3-(1-quinolin-6-ylcyclopropyl)imidazo[1,2-a]pyrimidin-6-yl]benzamide N,N-Diisopropylethylamine (14 μL, 0.084 mmol) was added to a mixture of (2S)-2-(2-fluoro-4-[3-(1-quinolin-6-ylcyclopropyl)imidazo[1,2-a]pyrimidin-6-yl]benzoylamino)-3,3-dimethylbutanoic acid (15 mg, 0.028 mmol), azetidine hydrochloride (3.9 mg 0.042 mmol), and benzotriazol-1-yloxytris(dimethylamino)phosphonium hexafluorophosphate (18 mg, 0.042 mmol) in N,N-dimethylformamide (0.5 mL). After stirring at RT overnight, the reaction mixture was purified by RP-HPLC (pH 10) to afford the desired product. LCMS: (M+H)=577.2.

Example 199: N-[2-(Dimethylamino)-1-methyl-2-oxoethyl]-2-fluoro-4-[3-(1-quinolin-6-ylcyclopropyl)imidazo[1,2-a]pyrimidin-6-yl]benzamide

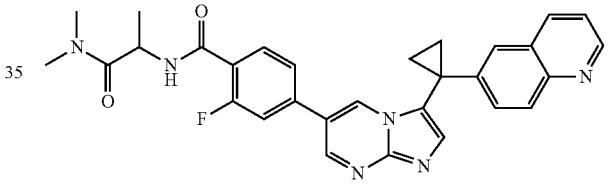

Step 1. methyl 2-[(4-bromo-2-fluorobenzoyl)amino]propanoate

N,N-Diisopropylethylamine (2.0 mL, 0.011 mol) was added to a mixture of methyl 2-aminopropanoate hydrochloride (0.64 g, 0.0046 mol), 4-bromo-2-fluorobenzoic acid (1.0 g, 0.0046 mol) and benzotriazol-1-yloxytris(dimethylamino)phosphonium hexafluorophosphate (2.12 g, 0.00479 mol) in N,N-dimethylformamide (10.0 mL, 0.129 mol). The reaction mixture was stirred overnight at RT, quenched with saturated sodium bicarbonate (25 mL) and extracted with EtOAc (3×40 mL). The combined organic layers were washed with brine, dried over anhydrous $Na_2SO_4$, filtered, and concentrated. The residue was purified by chromatography on silica gel with 60% EtOAc in hexanes to afford the desired product (1.33 g, 96%). LCMS: (M+H)=303.9/305.9.

Step 2. 2-{[4-(2-aminopyrimidin-5-yl)-2-fluorobenzoyl]amino}propanoic acid

A solution of potassium carbonate (0.35 g, 2.5 mmol) in water (2 mL) was added to a mixture of methyl 2-[(4-bromo-2-fluorobenzoyl)amino]propanoate (0.5 g, 1.6 mmol), 5-(4,4,5,5-tetramethyl-1,3,2-dioxaborolan-2-yl)pyrimidin-2-amine (0.28 g, 1.3 mmol), and tetrakis(triphenylphosphine)palladium (0.07 g, 0.06 mmol) in toluene (4 mL) and ethanol (2 mL). The resulting mixture was heated at 120° C. for 15 min. The reaction mixture was extracted with ether (3×10 mL) to remove impurity. The aqueous layer was adjusted to pH 7 with aqueous HCl and purified by RP-HPLC (pH 10) to afford the desired product (0.40 g, 100%). LCMS: (M+H)= 305.0.

Step 3. 2-(2-fluoro-4-[3-(1-quinolin-6-ylcyclopropyl)imidazo[1,2-a]pyrimidin-6-yl]benzoylamino) propanoic acid A mixture of 2-[4-(2-aminopyrimidin-5-yl)-2-fluorobenzoyl]aminopropanoic acid (0.20 g, 0.66 mmol) and chloro (1-quinolin-6-ylcyclopropyl)acetaldehyde (0.19 g, 0.79 mmol) in ethanol (4.0 mL) was stirred overnight at 90° C. The mixture was concentrated to afford the crude product. LCMS: (M+H)=496.1.

Step 4. N-[2-(dimethylamino)-1-methyl-2-oxoethyl]-2-fluoro-4-[3-(1-quinolin-6-ylcyclopropyl) imidazo[1,2-a]pyrimidin-6-yl]benzamide N,N-Diisopropylethylamine (31 µL, 0.18 mmol) was added to a mixture of 2-(2-fluoro-4-[3-(1-quinolin-6-ylcyclopropyl)imidazo[1,2-a]pyrimidin-6-yl]benzoylamino)propanoic acid (29.7 mg, 0.06 mmol), dimethylamine (4.0 mg, 0.09 mmol) and benzotriazol-1-yloxytris(dimethylamino) phosphonium hexafluorophosphate (40 mg, 0.09 mmol) in N,N-dimethylformamide (0.5 mL). The reaction mixture was stirred overnight at RT and purified by RP-HPLC (pH 10) to afford the desired product. LCMS: (M+H)=523.1.

Example 200: N-(2-Azetidin-1-yl-1-methyl-2-oxoethyl)-2-fluoro-4-[3-(1-quinolin-6-ylcyclopropyl) imidazo[1,2-a]pyrimidin-6-yl]benzamide This compound was prepared from 2-(2-fluoro-4-[3-(1-quinolin-6-ylcyclopropyl)imidazo[1,2-a]pyrimidin-6-yl] benzoylamino)propanoic acid using procedures analogous to those for Example 199. LCMS: (M+H)=535.1.

Example 201: 2-Fluoro-N-2-[(3R)-3-methoxypyrrolidin-1-yl]-1-methyl-2-oxoethyl-4-[3-(1-quinolin-6-ylcyclopropyl)imidazo[1,2-a]pyrimidin-6-yl]benzamide This compound was prepared from 2-(2-fluoro-4-[3-(1-quinolin-6-ylcyclopropyl)imidazo[1,2-a]pyrimidin-6-yl] benzoylamino)propanoic acid using procedures analogous to those for Example 199. LCMS: (M+H)=579.2.

Example 202: 2-Fluoro-N-[(1-hydroxycyclopropyl) methyl]-4-[7-(quinolin-6-ylmethyl)imidazo[1,2-b][1, 2,4]triazin-2-yl]benzamide

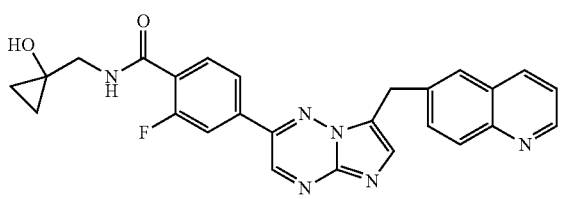 [SMILES: O=C(NCC1(O)CC1)c1ccc(-c2cnc3ncc(Cc4ccc5ncccc5c4)n3n2)cc1F]

This compound was prepared as a TFA salt starting from 4-[7-(1-quinolin-6-ylcyclopropyl)imidazo[1,2-b][1,2,4]triazin-2-yl]benzoic acid using procedures analogous to those for Example 123. LCMS: (M+H)=469.1.

Example 203: Methyl 4-(cyanomethyl)-4-{4-[7-(quinolin-6-ylmethyl)imidazo[1,2-b][1,2,4]triazin-2-yl]-1H-pyrazol-1-yl}piperidine-1-carboxylate

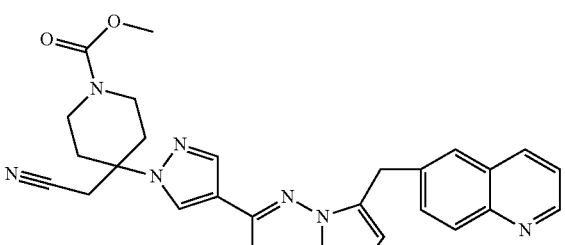

Step 1. tert-butyl 4-(cyanomethylene)piperidine-1-carboxylate

To a solution of 1.0 M of potassium tert-butoxide in THF (26.3 mL) at 0° C. was added drop wise a solution of diethyl cyanomethylphosphonate (4.47 mL, 0.0276 mol) in THF (33.6 mL). The reaction was warmed to RT and then cooled at 0° C. again. To the reaction mixture was then added a solution of tert-butyl 4-oxo-1-piperidinecarboxylate (5.0 g, 0.025 mol) in THF (6.72 mL). The reaction was allowed to warm up to RT and stirred overnight. After being quenched with water, the mixture was extracted with EtOAc. The combined organic layers were washed with brine, dried, and concentrated. The crude mixture was purified on silica gel eluting with EtOAc in hexanes (0-60%) to give the desired product (5.4 g, 96.81%). LCMS: (M+Na)=244.9, (M−56+H)=167.0.

Step 2. tert-butyl 4-(cyanomethyl)-4-{4-[7-(quinolin-6-ylmethyl)imidazo[1,2-b][1,2,4]triazin-2-yl]-1H-pyrazol-1-yl}piperidine-1-carboxylate 1,8-Diazabicyclo[5.4.0]undec-7-ene (68 µL, 0.46 mmol) was added to a mixture of 6-[2-(1H-pyrazol-4-yl)imidazo

[1,2-b][1,2,4]triazin-7-yl]methylquinoline (50.0 mg, 0.153 mmol) and tert-butyl 4-(cyanomethylene)piperidine-1-carboxylate (0.068 g, 0.30 mmol) in acetonitrile (1 mL). The reaction was stirred at 60° C. overnight. After cooling to RT, the mixture was purified by chromatography on silica gel with EtOAc in $CH_2Cl_2$ (0-70%) to give the desired product (30 mg, 35.7%). LCMS: (M+H)=550.5.

Step 3. (4-{4-[7-(quinolin-6-ylmethyl)imidazo[1,2-b][1,2,4]triazin-2-yl]-1H-pyrazol-1-yl}piperidin-4-yl)acetonitrile Trifluoroacetic Acid (0.5 mL) was added to a solution of tert-butyl 4-(cyanomethyl)-4-{4-[7-(quinolin-6-ylmethyl)imidazo[1,2-b][1,2,4]triazin-2-yl]-1H-pyrazol-1-yl}piperidine-1-carboxylate (0.015 g, 0.000027 mol) in methylene chloride (0.5 mL). The mixture was stirred at RT for 0.5 h. The volatiles were removed under reduced pressure to give the desired product as a TFA salt which was directly used in the next step without further purification. LCMS: (M+H)=450.5.

Step 4. Methyl 4-(cyanomethyl)-4-{4-[7-(quinolin-6-ylmethyl)imidazo[1,2-b][1,2,4]triazin-2-yl]-1H-pyrazol-1-yl}piperidine-1-carboxylate Methyl chloroformate (2.6 µL, 0.033 mmol) was added to a solution of (4-{4-[7-(quinolin-6-ylmethyl)imidazo[1,2-b][1,2,4]triazin-2-yl]-1H-pyrazol-1-yl}piperidin-4-yl)acetonitrile (5.0 mg, 0.011 mmol) and triethylamine (6.2 µL, 0.044 mmol) in methylene chloride (0.5 mL). The mixture was stirred at RT for 1 h, and then purified by RP-HPLC (pH=2) to give the desired product as a TFA salt. LCMS: (M+H)=508.5.

Example 204: Ethyl 4-(cyanomethyl)-4-{4-[7-(quinolin-6-ylmethyl)imidazo[1,2-b][1,2,4]triazin-2-yl]-1H-pyrazol-1-yl}piperidine-1-carboxylate

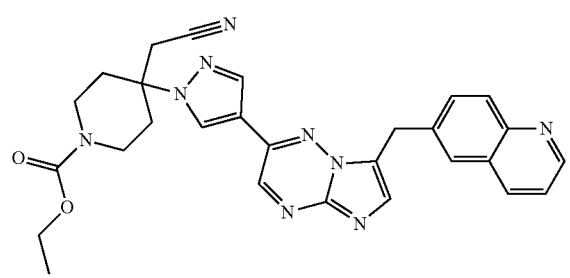 [SMILES: CCOC(=O)N1CCC(CC#N)(n2cc(-c3cnc4ncc(Cc5ccc6ncccc6c5)n4n3)cn2)CC1]

This compound was prepared as a TFA salt starting from (4-{4-[7-(quinolin-6-ylmethyl)imidazo[1,2-b][1,2,4]triazin-2-yl]-1H-pyrazol-1-yl}piperidin-4-yl)acetonitrile using procedures analogous to those for Example 203, Step 4. LCMS: (M+H)=522.4.

Example 205: (1-Acetyl-4-{4-[7-(quinolin-6-ylmethyl)imidazo[1,2-b][1,2,4]triazin-2-yl]-1H-pyrazol-1-yl}piperidin-4-yl)acetonitrile

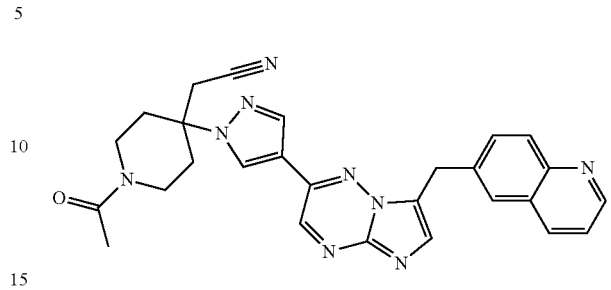

This compound was prepared as a TFA salt starting from (4-{4-[7-(quinolin-6-ylmethyl)imidazo[1,2-b][1,2,4]triazin-2-yl]-1H-pyrazol-1-yl}piperidin-4-yl)acetonitrile using procedures analogous to those for Example 203, Step 4. LCMS: (M+H)=492.4.

Example A

In Vitro c-Met Kinase Enzyme Assays

Compounds were screened in vitro for their ability to inhibit c-Met kinase activity. The $IC_{50}$ values of compounds for the inhibition of c-Met kinase were determined as described in the literature with some modifications (Wang, X. et al, Mol. Cancer Ther. 2003, 2(11):1085-1092; Calic, M. et al., *Croatica* Chemical ACTA. 2005, 78(3):367-374). Briefly, histidine-tagged c-Met catalytic domain fusion protein (Invitrogen, # PV3143) was used for the assay. $IC_{50}$ measurements were based on the degree of phosphorylation of poly Glu-Tyr (Sigma-Aldrich, # P0275) that was coated (0.01 mg/per well) on 96-well microplates (R&D systems, # DY990). The reaction was carried out in a 50 µL solution containing 50 mM HEPES (pH 7.5), 10 mM $MnCl_2$, 10 mM $MgCl_2$, 0.5 mM DTT, 100 µM $Na_3VO_4$, 5 µM ATP (Cell Signaling Technology, #9804) and serial dilutions of individual compounds. The reaction lasted for 25 minutes at 30° C. After the reaction was completed, the contents of the plates was discarded. Plates were then washed with TBS-T (250 µL/well, 5×) and then blocked with TBS-T containing 1% BSA for 2 hours. The contents of the plates was discarded, and 100 µL (per well) of peroxidase-labeled anti-phospho-tyrosine antibody (Sigma, # A5964) diluted (1:60,000) in 1% BSA containing TBS-T were then added and incubated for 1 hour. Plates were washed with TBS-T (250 µL/well, 5×) and followed by the color reaction using 100 µL (1:1 mixture) of $H_2O_2$ and tetramethylbenzidine (R&D Systems, # DY999). The reaction was stopped in minutes with 100 µL of 2 N $H_2SO_4$. The optical density was measured immediately using a microplate reader at 450 nm with wavelength correction at 540 nm. $IC_{50}$ values were calculated with the GraphPad Prism software. The linear range (i.e., the time period over which the rate remained equivalent to the initial rate) was determined for the kinase and $IC_{50}$ determinations were performed within this range.

Wang, X., et al. Potent and selective inhibitors of the Met [hepatocyte growth factor/scatter factor (HGF/SF) receptor] tyrosine kinase block HGF/SF-induced tumor cell growth and invasion. Mol. Cancer Ther. 2003, 2(11):1085-1092.

Calic, M., et al. Flavonoids as inhibitors of Lck and Fyn kinases. Croatica Chemica ACTA. 2005, 78(3):367-374.

$IC_{50}$ data for certain compounds of the invention is provided below.

| Example | h-Met IC$_{50}$ (nM) |
|---|---|
| 1 | <500 |
| 2 | <500 |
| 3 | <500 |
| 4 | <500 |
| 5 | <500 |
| 6 | <500 |
| 7 | <500 |
| 8 | <500 |
| 9 | <500 |
| 10 | <500 |
| 11 | <500 |
| 12 | <500 |
| 13 | <500 |
| 14 | <500 |
| 15 | <500 |
| 16 | <3000 |
| 17 | <500 |
| 18 | <500 |
| 19 | <500 |
| 20 | <500 |
| 21 | <500 |
| 22 | <500 |
| 23 | <500 |
| 24 | <500 |
| 25 | <500 |
| 26 | <500 |
| 27 | <500 |
| 28 | <500 |
| 29 | <500 |
| 30 | <500 |
| 31 | <500 |
| 32 | <500 |
| 33 | <500 |
| 34 | <500 |
| 35 | <500 |
| 36 | <500 |
| 37 | <500 |
| 38 | <500 |
| 39 | <500 |
| 40 | <500 |
| 41 | <500 |
| 42 | <500 |
| 43 | <500 |
| 44 | <500 |
| 45 | <500 |
| 46 | <500 |
| 47 | <500 |
| 48 | <500 |
| 49 | <500 |
| 50 | <500 |
| 51 | <500 |
| 52 | <500 |
| 53 | <500 |
| 54 | <500 |
| 55 | <500 |
| 56 | <500 |
| 57 | <500 |
| 58 | <500 |
| 59 | <500 |
| 60 | <500 |
| 61 | <500 |
| 62 | <500 |
| 63 | <500 |
| 64 | <500 |
| 65 | <500 |
| 66 | <500 |
| 67 | <500 |
| 68 | <500 |
| 69 | <500 |
| 70 | <500 |
| 71 | <500 |
| 72 | <500 |
| 73 | <500 |
| 74 | <500 |
| 75 | <500 |
| 76 | <500 |
| 77 | <500 |
| 78 | <500 |
| 79 | <500 |
| 80 | <500 |
| 81 | <2000 |
| 82 | <500 |
| 83 | <500 |
| 84 | <500 |
| 85 | <500 |
| 86 | <500 |
| 87 | <500 |
| 88 | <500 |
| 89 | <3000 |
| 90 | <500 |
| 91 | <500 |
| 92 | <500 |
| 93 | <500 |
| 94 | <500 |
| 95 | <500 |
| 96 | <500 |
| 97 | <500 |
| 98 | <500 |
| 99 | <500 |
| 100 | <500 |
| 101 | <500 |
| 102 | <500 |
| 103 | <500 |
| 104 | <500 |
| 105 | <500 |
| 106 | <500 |
| 107 | <500 |
| 108 | <500 |
| 109 | <500 |
| 110 | <500 |
| 111 | <500 |
| 112 | <500 |
| 113 | <500 |
| 114 | <500 |
| 115 | <500 |
| 116 | <500 |
| 117 | <500 |
| 118 | <500 |
| 119 | <500 |
| 120 | <500 |
| 121 | <500 |
| 122 | <500 |
| 123 | <500 |
| 124 | <500 |
| 125 | <500 |
| 126 | <500 |
| 127 | <500 |
| 128 | <500 |
| 129 | <500 |
| 130 | <500 |
| 131 | <500 |
| 132 | <500 |
| 133 | <500 |
| 134 | <500 |
| 135 | <500 |
| 136 | <500 |
| 137 | <500 |
| 138 | <500 |
| 139 | <500 |
| 140 | <500 |
| 141 | <500 |
| 142 | <500 |
| 143 | <500 |
| 144 | <500 |
| 145 | <500 |
| 146 | <500 |
| 147 | <500 |
| 148 | <500 |
| 149 | <500 |
| 150 | <500 |
| 151 | <500 |
| 152 | <500 |
| 153 | <500 |
| 154 | <500 |

-continued

| Example | h-Met IC$_{50}$ (nM) |
|---|---|
| 155 | <500 |
| 156 | <500 |
| 157 | <500 |
| 158 | <500 |
| 159 | <500 |
| 160 | <500 |
| 161 | <500 |
| 162 | <500 |
| 163 | <500 |
| 164 | <500 |
| 165 | <500 |
| 166 | <500 |
| 167 | <500 |
| 168 | <500 |
| 169 | <500 |
| 170 | <500 |
| 171 | <500 |
| 172 | <500 |
| 173 | <500 |
| 174 | <500 |
| 175 | <500 |
| 176 | <500 |
| 177 | <500 |
| 178 | <500 |
| 179 | <500 |
| 180 | <500 |
| 181 | <500 |
| 182 | <500 |
| 183 | <500 |
| 184 | <500 |
| 185 | <500 |
| 186 | <500 |
| 187 | <500 |
| 188 | <500 |
| 189 | <500 |
| 190 | <500 |
| 191 | <500 |
| 192 | <500 |
| 193 | <500 |
| 194 | <500 |
| 195 | <500 |
| 196 | <500 |
| 197 | <500 |
| 198 | <500 |
| 199 | <500 |
| 200 | <500 |
| 201 | <500 |
| 202 | <500 |
| 203 | <500 |
| 204 | <500 |
| 205 | <500 |

Example B

Cell Proliferation/Survival Assays

Cell lines representing various human cancers (SNU-1 and SUN-5 gastric, A549 and NCI-H441 lung, U-87 glioblastoma, HT-29 colon, 786-0 kidney, PC-3 pancreatic) can be obtained from American Type Culture Collection and routinely maintained in culture media and conditions recommended by ATCC. Optimal cell density used in proliferation/survival assay can be predetermined for individual cell lines. Compounds are screened for their ability to inhibit cell proliferation/survival, and IC$_{50}$ values are determined. Below are the sample protocols for SNU-5 and SNU-1 cell proliferation/survival assays. SNU-5 and SNU-1 cells are seeded into 96 well cell culture plates at 4000 cells/well and 2000 cells/well respectively in appropriate media containing 2% FBS and supplemented with serial dilutions of individual compounds in a final volume of 100 µL/well. After 72 hour incubation, 24 µL of CellTiter 96® AQueous One Solution reagent (Promega, # G3581) are added to each well (final concentration=333 g/mL), and the plates are incubated for 2 more hours in a 37° C. incubator. The optical density is measured in the linear range using a microplate reader at 490 nm with wavelength correction at 650 nm. IC$_{50}$ values are calculated with the GraphPad Prism software. For proliferation assays using A549, NCI-H441, U-87, HT-29, 786-0 and PC-3 cells, the cells are first starved for 48 hours in low serum condition (0.1-0.5% FBS in appropriate culture media), then treated with different concentrations of compounds for 2 hours. After the cells are treated with HGF (50 ng/mL) (R&D, #294-HGN) for 24 hours, CellTiter 96® AQueous One Solution reagent is added and plates are incubated for 2 hours. The results are recorded with a plate reader. Compounds having an IC$_{50}$ of 10 µM or less are considered active.

Example C

Cell-Based c-Met Phosphorylation Assays

The inhibitory effect of compounds on c-Met phosphorylation in relevant cell lines (SNU-5 gastric, A549 and NCI-H441 lung, U-87 glioblastoma, HT-29 colon, 786-O kidney and PC-3 pancreatic cancer cell lines and HUVEC cell line) can be assessed using immunoblotting analysis and ELISA-based c-Met phosphorylation assays. Cells are grown in appropriate culture media and treated with various concentrations of individual compounds. For SNU-5, HT-29, 786-0 cells, cells are grown in appropriated media supplemented with 0.2% or 2% FBS and treated with compounds for 3-4 hours. Whole cell protein extracts are prepared using reagents and a protocol (# FNN0011) obtained from Biosource International with slight modifications. Briefly, protein extracts are made by incubation in lysis buffer with protease and phosphatase inhibitors [50 mM HEPES (pH 7.5), 100 mM NaCl, 1.5 mM MgCl$_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 20 minutes. For A549, H441, U-87 and PC-3 cells, cells are serum (0.2% FBS) starved for at least 24 hours, then pretreated with various concentrations of compounds for 1 hour. Whole cell extracts are prepared after the cells were treated with HGF (50 ng/mL) for 10 minutes.

Immunoblotting Analysis

Relevant antibodies are obtained from commercial sources: rabbit polyclonal antibodies included anti-human c-Met (Santa Cruz Biotechnology, # sc-161) and anti-phosphorylated-c-Met (Biosource International, pY1230/4/5 and pY1003). For immunoblotting, 10-20 µg of protein extracts from individual treatment conditions are resolved by electrophoresis on 10% SDS-PAGE gel, and electrotransferred to a nitrocellulose (or PVDF) membrane. The membrane is blocked in PBS containing 3% milk and 0.1% Tween-20 for 1 hour, and then incubated with primary anti-c-Met antibodies in blocking solution for 1 hour. After 3 washes, the membrane is incubated with appropriate horseradish-conjugated secondary antibodies for 1 hour. After final wash, the blot is incubated with chemiluminescence detection reagent for 5 minutes and exposed to X-ray film. The images are scanned, quantified and corrected with total c-Met, and IC$_{50}$ values are calculated. Compounds having an IC$_{50}$ of 10 µM or less are considered active.

ELISA

Cell protein extracts are analyzed using a human phospho-c-Met ELISA kit according to the manufacturer's instructions (R&D Systems, # DYC2480). Optimal amounts of protein extracts are predetermined for individual cell lines. Briefly, for the assay, appropriate amounts of protein extracts are captured with a capture anti-human c-Met antibody for 2 hours in a 96 well microplate. After washes, a detection antibody (HRP-conjugated anti-phospho-tyrosine antibody) is added and incubated for 2 hours. After additional washes, 100 µL of substrate solution (1:1 mixture of $H_2O_2$ and tetramethylbenzidine) are added into each well and the reaction is stopped with 2 N $H_2SO_4$ within an appropriate amount of time during color development. The optical density is measured in the linear range using a microplate reader at 450 nm with wavelength correction at 540 nm. $IC_{50}$ values are calculated with the GraphPad Prism software. Compounds having an $IC_{50}$ of 10 µM or less are considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating gastric cancer, cancer of the kidney, liver cancer, lung cancer, or glioblastoma in a patient comprising administering to said patient a therapeutically effective amount of a compound of Formula I:

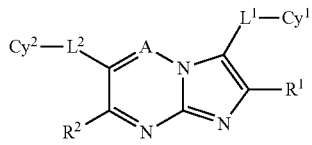

I or pharmaceutically acceptable salt thereof, wherein:
  A is $CR^3$;
  $Cy^1$ is aryl, heteroaryl, cycloalkyl, or heterocycloalkyl, each optionally substituted by 1, 2, 3, 4, or 5 —W—X—Y—Z;
  $Cy^2$ is aryl, heteroaryl, cycloalkyl, or heterocycloalkyl, each optionally substituted by 1, 2, 3, 4, or 5 —W'—X'—Y'—Z';
  $L^1$ is $(CR^4R^5)_m$, $(CR^4R^5)_p$-(cycloalkylene)-$(CR^4R^5)_q$, $(CR^4R^5)_p$-(arylene)-$(CR^4R^5)_q$, $(CR^4R^5)_p$-(heterocycloalkylene)-$(CR^4R^5)_q$, $(CR^4R^5)_p$-(heteroarylene)-$(CR^4R^5)_q$, $(CR^4R^5)_p O(CR^4R^5)_q$, $(CR^4R^5)_p S(CR^4R^5)_q$, $(CR^4R^5)_p C(O)(CR^4R^5)_q$, $(CR^4R^5)_p C(O)NR^6(CR^4R^5)_q$, $(CR^4R^5)_p C(O)O(CR^4R^5)_q$, $(CR^4R^5)_p OC(O)(CR^4R^5)_q$, $(CR^4R^5)_p OC(O)NR^6(CR^4R^5)_q$, $(CR^4R^5)_p NR^6(CR^4R^5)_q$, $(CR^4R^5)_p NR^6C(O)NR^6(CR^4R^5)_q$, $(CR^4R^5)_p S(O)(CR^4R^5)_q$, $(CR^4R^5)_p S(O)NR^6(CR^4R^5)_q$, $(CR^4R^5)_p S(O)_2(CR^4R^5)_q$, or $(CR^4R^5)_p S(O)_2NR^6(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^a$, $SR^a$, C(O)$R^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, NR$^c$C(O)OR$^a$, C(=NR$^g$)NR$^c$R$^d$, NR$^c$C(=NR$^g$)NR$^c$R$^d$, P(R$^f$)$_2$, P(OR$^e$)$_2$, P(O)R$^e$R$^f$, P(O)OR$^e$OR$^f$, S(O)R$^b$, S(O)NR$^c$R$^d$, S(O)$_2$R$^b$, NR$^c$S(O)$_2$R$^b$, and S(O)$_2$NR$^c$R$^d$;

$L^2$ is $(CR^7R^8)_r$, $(CR^7R^8)_s$-(cycloalkylene)-$(CR^7R^8)_t$, $(CR^7R^8)_s$-(arylene)-$(CR^7R^8)_t$, $(CR^7R^8)_s$-(heterocycloalkylene)-$(CR^7R^8)_t$, $(CR^7R^8)_s$-(heteroarylene)-$(CR^7R^8)_t$, $(CR^7R^8)_s O(CR^7R^8)_t$, $(CR^7R^8)_s S(CR^7R^8)_t$, $(CR^7R^8)_s C(O)(CR^7R^8)_t$, $(CR^7R^8)_s C(O)NR^9(CR^7R^8)_t$, $(CR^7R^8)_s C(O)O(CR^7R^8)_t$, $(CR^7R^8)_s OC(O)(CR^7R^8)_t$, $(CR^7R^8)_s OC(O)NR^9(CR^7R^8)_t$, $(CR^7R^8)_s NR^9(CR^7R^8)_t$, $(CR^7R^8)_s NR^9C(O)NR^9(CR^7R^8)_t$, $(CR^7R^8)_s S(O)(CR^7R^8)_t$, $(CR^7R^8)_s S(O)NR^7(CR^8R^9)_t$, $(CR^7R^8)_s S(O)_2(CR^7R^8)_t$, or $(CR^7R^8)_s S(O)_2NR^9(CR^7R^8)_t$, wherein said cycloalkylene, arylene, heterocycloalkylene, or heteroarylene is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$;

$R^1$ is H or —W"—X"—Y"—Z";
  $R^2$ is H, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, C(O)$R^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, or S(O)$_2$NR$^C$R$^D$;
  $R^3$ is H, cycloalkyl, aryl, heterocycloalkyl, heteroaryl, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, C(O)$R^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^{c1}$S(O)$_2$R$^B$, and S(O)$_2$NR$^C$R$^D$; wherein said cycloalkyl, aryl, heterocycloalkyl, heteroaryl, or $C_{1-6}$ alkyl is optionally substituted with 1, 2, or 3 substituents independently selected from $Cy^5$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, C(=NR$^g$)NR$^{c1}$R$^{d1}$, NR$^{c1}$C(=NR$^g$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)NR$^{c1}$R$^{d1}$, S(O)$_2$R$^{b1}$, NR$^{c1}$S(O)$_2$R$^{b1}$, and S(O)$_2$NR$^{c1}$R$^{d1}$;
  or $R^2$ and -$L^2$-$Cy^2$ are linked together to form a group of formula:

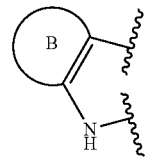

wherein ring B is a fused aryl or fused heteroaryl ring, each optionally substituted with 1, 2, or 3 —W'—X'—Y'—Z';
  $R^4$ and $R^5$ are independently selected from H, halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;
  or $R^4$ and $R^5$ together with the C atom to which they are attached form a 3, 4, 5, 6, or 7-membered cycloalkyl or heterocycloalkyl ring, each optionally substituted by 1, 2, or 3 substituents independently selected from halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;

$R^6$ is H, $C_{1-6}$ alkyl, $C_{2-6}$ alkenyl, or $C_{2-6}$ alkynyl;

$R^7$ and $R^8$ are independently selected from H, halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

or $R^7$ and $R^8$ together with the C atom to which they are attached form a 3, 4, 5, 6, or 7-membered cycloalkyl or heterocycloalkyl ring, each optionally substituted by 1, 2, or 3 substituent independently selected from halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

$R^9$ is H, $C_{1-6}$ alkyl, $C_{2-6}$ alkenyl, or $C_{2-6}$ alkynyl;

W, W', and W" are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$ and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

X, X', and X" are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^j$, $C(O)NR^hR^i$, amino, $C_{1-6}$ alkylamino, and $C_{2-8}$ dialkylamino;

Y, Y', and Y" are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$, and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z, Z', and Z" are independently selected from H, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

wherein two adjacent —W—X—Y—Z, together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR)NR^{c3}R^{d3}$, $S(O)R^{b3}$, $S(O)NR^{c3}R^{d3}$, $S(O)_2R^{b3}$, $NR^{c3}S(O)_2R^{b3}$, $S(O)_2NR^{c3}R^{d3}$, aryl, cycloalkyl, heteroaryl, and heterocycloalkyl;

wherein two adjacent —W'—X'—Y'—Z', together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR)NR^{c3}R^{d3}$ $S(O)R^{b3}$, $S(O)NR^{c3}R^{d3}$, $S(O)_2R^{b3}$, $NR^{c3}S(O)_2R^{b3}$, $S(O)_2NR^{c3}R^{d3}$, aryl, cycloalkyl, heteroaryl, and heterocycloalkyl;

$Cy^3$, $Cy^4$, and $Cy^5$ are independently selected from aryl, cycloalkyl, heteroaryl, and heteorcycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^g)NR^{c4}R^{d4}$, $NR^{c4}C(=NR^g)NR^{c4}R^{d4}$, $P(R^{f4})_2$, $P(OR^4)_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$;

$R^A$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, $C_{2-4}$ alkynyl, cycloalkyl, heterocycloalkyl, aryl or heteroaryl is optionally substituted with 1, 2, or 3 substituents independently selected from OH, CN, amino, halo, and $C_{1-4}$alkyl;

$R^B$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, or $C_{2-4}$ alkynyl, cycloalkyl, heterocycloalkyl, aryl, or heteroaryl is optionally substituted with 1, 2, or 3 substituents independently selected from OH, CN, amino, halo, and $C_{1-4}$ alkyl;

$R^C$ and $R^D$ are independently selected from H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

or $R^C$ and $R^D$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, and $C_{1-4}$ alkyl;

$R^a$, $R^{a1}$, $R^{a2}$, $R^{a3}$, and $R^{a4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^b$, $R^{b1}$, $R^{b2}$, $R^{b3}$, and $R^{b4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^c$ and $R^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2 R^{b3}$, alkoxyalkyl, and alkoxyalkoxy;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c3}$ and $R^{d3}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c4}$ and $R^{d4}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^e$, $R^{e1}$, $R^{e2}$, and $R^{e4}$ are independently selected from H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, and heterocycloalkylalkyl;

$R^f$, $R^{f1}$, $R^{f2}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl;

$R^g$ is H, CN, and $NO_2$;

$R^h$ and $R^i$ are independently selected from H and $C_{1-6}$ alkyl;

$R^j$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl;

m is 0, 1, 2, 3, 4, 5, or 6;

p is 0, 1, 2, 3, or 4;

q is 0, 1, 2, 3, or 4;

r is 0, 1, 2, 3, 4, 5, or 6;

s is 0, 1, 2, 3, or 4; and t is 0, 1, 2, 3, or 4, with the proviso that when A is CH, then L¹ is other than CO or (CR⁴R⁵)ᵤ wherein u is 1.

2. The method of claim 1, wherein Cy¹ is heteroaryl optionally substituted by 1, 2, 3, 4, or 5 —W—X—Y—Z.

3. The method of claim 1, wherein Cy² is aryl optionally substituted by 1, 2, 3, 4, or 5 —W'—X'—Y'—Z'.

4. The method of claim 1, wherein L¹ is CH₂ or CH₂CH₂ or cycloalkylene.

5. The method of claim 1, wherein L² is cycloalkylene or arylene.

6. The method of claim 1, wherein R¹ is H.

7. The method of claim 1, wherein R² is H.

8. The method of claim 1, wherein —W—X—Y—Z is halo, $C_{1-6}$ alkyl, $C_{1-6}$ haloalkyl, CN, NO₂, N₃, or $OR^{a2}$.

9. The method of claim 1 wherein —W'—X'—Y'—Z' is halo, $C_{1-6}$ alkyl, $C_{1-6}$ haloalkyl, CN, NO₂, N₃, or $OR^{a2}$.

10. The method of claim 1, wherein the compound of Formula I is Formula III:

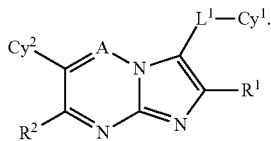

III

11. The method of claim 1, wherein the compound of Formula I is Formula VIII:

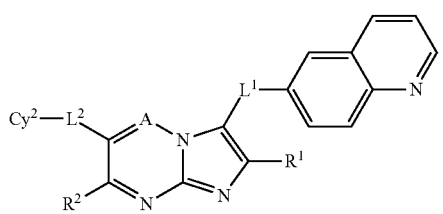

VIII

12. The method of claim 1, wherein the compound of Formula I is selected from:
- 6-(4-Fluorophenyl)-3-(4-methoxybenzyl)imidazo[1,2-a]pyrimidine;
- 6-(4-Fluorophenyl)-3-(1-(4-methoxyphenyl)cyclopropyl)imidazo[1,2-a]pyrimidine;
- 6-(1-(6-(4-Fluorophenyl)imidazo[1,2-a]pyrimidin-3-yl)cyclopropyl)quinoline;
- 2-Fluoro-4-(3-[(4-methoxyphenyl)thio]imidazo[1,2-a]pyrimidin-6-yl)-N-methylbenzamide;
- 2-chloro-4-3-[(4-methoxyphenyl)thio]imidazo[1,2-a]pyrimidin-6-yl-N-methylbenzamide;
- 2-Fluoro-N-methyl-4-[3-(quinolin-6-ylthio)imidazo[1,2-a]pyrimidin-6-yl]benzamide;
- 2-chloro-N-methyl-4-[3-(quinolin-6-ylthio)imidazo[1,2-a]pyrimidin-6-yl]benzamide;
- 3-(4-Methoxyphenoxy)-6-(4-methyl-1H-pyrazol-1-yl)imidazo[1,2-a]pyrimidine;
- 6-(4-Bromophenyl)-3-(4-methoxyphenoxy)imidazo[1,2-a]pyrimidine;
- 2-chloro-N-methyl-4-[3-(quinolin-6-yloxy)imidazo[1,2-a]pyrimidin-6-yl]benzamide;
- 2-Fluoro-N-methyl-4-[3-(1-quinolin-6-ylcyclopropyl)imidazo[1,2-a]pyrimidin-6-yl]benzamide;
- 6-(4-bromophenyl)-3-[(4-methoxyphenyl)thio]imidazo[1,2-a]pyrimidine;
- 6-(1-{6-[3-Fluoro-4-(1-methyl-2-oxo-2-pyrrolidin-1-ylethoxy)phenyl]imidazo[1,2-a]pyrimidin-3-yl}cyclopropyl)quinoline;
- 6-{1-[6-(1H-Pyrazol-1-yl)imidazo[1,2-a]pyrimidin-3-yl]cyclopropyl}quinoline;
- 6-{1-[6-(4-Methyl-1H-pyrazol-1-yl)imidazo[1,2-a]pyrimidin-3-yl]cyclopropyl}quinoline;
- N,N-Dimethyl-1-[3-(1-quinolin-6-ylcyclopropyl)imidazo[1,2-a]pyrimidin-6-yl]-1H-pyrazole-4-carboxamide;
- N-[1-(4-Methyl-1,3-thiazol-2-yl)ethyl]-1-[3-(1-quinolin-6-ylcyclopropyl)imidazo[1,2-a]pyrimidin-6-yl]-1H-pyrazole-4-carboxamide;
- N-Cyclohexyl-3-(1-quinolin-6-ylcyclopropyl)imidazo[1,2-a]pyrimidine-6-carboxamide;
- 3-(1-Quinolin-6-ylcyclopropyl)-N-(tetrahydrofuran-2-ylmethyl) imidazo[1,2-a]pyrimidine-6-carboxamide;
- N-Cyclobutyl-4-[3-(1-quinolin-6-ylcyclopropyl)imidazo[1,2-a]pyrimidin-6-yl]benzamide;
- 6-(1-{6-[4-(Azetidin-1-ylcarbonyl) phenyl]imidazo[1,2-a]pyrimidin-3-yl}cyclopropyl)quinoline;
- N,N-Dimethyl-4-[3-(1-quinolin-6-ylcyclopropyl)imidazo[1,2-a]pyrimidin-6-yl]benzamide;
- 4-[3-(1-Quinolin-6-ylcyclopropyl)imidazo[1,2-a]pyrimidin-6-yl]-N-(tetrahydrofuran-2-ylmethyl)benzamide;
- N-(1-Benzylpyrrolidin-3-yl)-N-methyl-4-[3-(1-quinolin-6-ylcyclopropyl)imidazo[1,2-a]pyrimidin-6-yl]benzamide;
- N-(1-Pyridin-2-ylpiperidin-4-yl)-4-[3-(1-quinolin-6-ylcyclopropyl)imidazo[1,2-a]pyrimidin-6-yl]benzamide;
- N-(1-Pyridin-2-ylethyl)-4-[3-(1-quinolin-6-ylcyclopropyl)imidazo[1,2-a]pyrimidin-6-yl]benzamide;
- 6-{1-[6-(4-[(3S)-3-Fluoropyrrolidin-1-yl]carbonylphenyl)imidazo[1,2-a]pyrimidin-3-yl]cyclopropyl}quinoline;
- N-[1-(Methoxymethyl)cyclobutyl]-4-[3-(1-quinolin-6-ylcyclopropyl)imidazo[1,2-a]pyrimidin-6-yl]benzamide;
- N-(1-Pyridin-2-ylpyrrolidin-3-yl)-4-[3-(1-quinolin-6-ylcyclopropyl) imidazo[1,2-a]pyrimidin-6-yl]benzamide;
- 6-[1-(6-{4-[(3-Pyridin-2-ylpyrrolidin-1-yl)carbonyl]phenyl}imidazo[1,2-a]pyrimidin-3-yl)cyclopropyl]quinoline;
- 6-{1-[6-(4-[(3S)-3-(Pyridin-2-yloxy)pyrrolidin-1-yl]carbonylphenyl)imidazo[1,2-a]pyrimidin-3-yl]cyclopropyl}quinoline;
- N-[2-(Pyridin-2-yloxy)ethyl]-4-[3-(1-quinolin-6-ylcyclopropyl)imidazo[1,2-a]pyrimidin-6-yl]benzamide;
- N-[1-Methyl-2-(pyridin-2-yloxy)ethyl]-4-[3-(1-quinolin-6-ylcyclopropyl)imidazo[1,2-a]pyrimidin-6-yl]benzamide;
- N-(2-Phenoxyethyl)-4-[3-(1-quinolin-6-ylcyclopropyl)imidazo[1,2-a]pyrimidin-6-yl]benzamide;
- N-(1S)-2,2-Dimethyl-1-[(methylamino)carbonyl]propyl-4-[3-(1-quinolin-6-ylcyclopropyl)imidazo[1,2-a]pyrimidin-6-yl]benzamide;
- N-(1S)-1-[(Dimethylamino)carbonyl]-2,2-dimethylpropyl-4-[3-(1-quinolin-6-ylcyclopropyl)imidazo[1,2-a]pyrimidin-6-yl]benzamide;
- N-[(1S)-1-(Azetidin-1-ylcarbonyl)-2,2-dimethylpropyl]-4-[3-(1-quinolin-6-ylcyclopropyl)imidazo[1,2-a]pyrimidin-6-yl]benzamide;
- N-Cyclopropyl-3-[3-(1-quinolin-6-ylcyclopropyl)imidazo[1,2-a]pyrimidin-6-yl]benzamide;
- N-(Pyridin-2-ylmethyl)-3-[3-(1-quinolin-6-ylcyclopropyl)imidazo[1,2-a]pyrimidin-6-yl]benzamide;

N,N-Dimethyl-3-[3-(1-quinolin-6-ylcyclopropyl)imidazo[1,2-a]pyrimidin-6-yl]benzamide;
N-Methyl-3-[3-(1-quinolin-6-ylcyclopropyl)imidazo[1,2-a]pyrimidin-6-yl]benzamide;
N-[(1S)-1-Methyl-2-(methylamino)-2-oxoethyl]-4-[3-(1-quinolin-6-ylcyclopropyl)imidazo[1,2-a]pyrimidin-6-yl]benzamide;
N-[(1R)-1-Methyl-2-(methylamino)-2-oxoethyl]-4-[3-(1-quinolin-6-ylcyclopropyl)imidazo[1,2-a]pyrimidin-6-yl]benzamide;
(3R)-1-{4-[3-(1-Quinolin-6-ylcyclopropyl) imidazo[1,2-a]pyrimidin-6-yl]benzoyl}pyrrolidine-3-carbonitrile;
Methyl 4-{5-[3-(1-quinolin-6-ylcyclopropyl)imidazo[1,2-a]pyrimidin-6-yl]pyridin-2-yl}-piperazine-1-carboxylate;
6-[1-(6-{6-[4-(Methylsulfonyl)piperazin-1-yl]pyridin-3-yl}imidazo[1,2-a]pyrimidin-3-yl)cyclopropyl]quinoline;
N,N-Dimethyl-4-{5-[3-(1-quinolin-6-ylcyclopropyl)imidazo[1,2-a]pyrimidin-6-yl]pyridin-2-yl}piperazine-1-carboxamide;
N-(1S)-1-[(Dimethylamino)carbonyl]-2-methylpropyl-4-[3-(1-quinolin-6-ylcyclopropyl)imidazo[1,2-a]pyrimidin-6-yl]benzamide;
N-1-[(Dimethylamino)carbonyl]cyclobutyl-4-[3-(1-quinolin-6-ylcyclopropyl)imidazo[1,2-a]pyrimidin-6-yl]benzamide;
N-[(1S)-1-(Azetidin-1-ylcarbonyl)-2,2-dimethylpropyl]-5-[3-(1-quinolin-6-ylcyclopropyl)imidazo[1,2-a]pyrimidin-6-yl]pyridine-2-carboxamide;
N-(1S)-2,2-Dimethyl-1-[(methylamino)carbonyl]propyl-5-[3-(1-quinolin-6-ylcyclopropyl)imidazo[1,2-a]pyrimidin-6-yl]pyridine-2-carboxamide;
N-(1S)-1-[(Cyclopropylamino)carbonyl]-2,2-dimethylpropyl-5-[3-(1-quinolin-6-ylcyclopropyl)imidazo[1,2-a]pyrimidin-6-yl]pyridine-2-carboxamide;
N-[(1S)-2-(Dimethylamino)-1-methyl-2-oxoethyl]-5-[3-(1-quinolin-6-ylcyclopropyl)imidazo[1,2-a]pyrimidin-6-yl]pyridine-2-carboxamide;
N-[(1R)-2-(Dimethylamino)-1-methyl-2-oxoethyl]-5-[3-(1-quinolin-6-ylcyclopropyl)imidazo[1,2-a]pyrimidin-6-yl]pyridine-2-carboxamide;
6-(1-{6-[4-(2-Oxo-2-pyrrolidin-1-ylethoxy)phenyl]imidazo[1,2-a]pyrimidin-3-yl}cyclopropyl)quinoline;
1-{4-[3-(1-Quinolin-6-ylcyclopropyl)imidazo[1,2-a]pyrimidin-6-yl]phenyl}cyclopropanecarbonitrile;
N,N-Dimethyl-4-[3-(1-quinolin-6-ylcyclopropyl)imidazo[1,2-a]pyrimidin-6-yl]benzenesulfonamide;
Methyl 2-fluoro-4-[3-(1-quinolin-6-ylcyclopropyl)imidazo[1,2-a]pyrimidin-6-yl]benzylcarbamate;
N'-2-Fluoro-4-[3-(1-quinolin-6-ylcyclopropyl)imidazo[1,2-a]pyrimidin-6-yl]benzyl-N,N-dimethylurea;
(3R)-1-{2-Fluoro-4-[3-(1-quinolin-6-ylcyclopropyl)imidazo[1,2-a]pyrimidin-6-yl]benzyl}pyrrolidin-3-ol;
6-(1-{6-[3-Fluoro-4-(1H-pyrazol-1-ylmethyl)phenyl]imidazo[1,2-a]pyrimidin-3-yl}cyclopropyl)quinoline;
3-{2-Fluoro-4-[3-(1-quinolin-6-ylcyclopropyl)imidazo[1,2-a]pyrimidin-6-yl]benzyl}-1,3-oxazolidin-2-one;
6-{1-[6-(4-Chloro-1H-pyrazol-1-yl)imidazo[1,2-a]pyrimidin-3-yl]cyclopropyl}quinoline;
6-{1-[6-(2-Methyl-1,3-thiazol-4-yl)imidazo[1,2-a]pyrimidin-3-yl]cyclopropyl}quinoline;
6-{1-[6-(1,3-Thiazol-4-yl)imidazo[1,2-a]pyrimidin-3-yl]cyclopropyl}quinoline;
3-Fluoro-N-methyl-4-[3-(1-quinolin-6-ylcyclopropyl)imidazo[1,2-a]pyrimidin-6-yl]benzamide;
(3S)-1-{3-Fluoro-4-[3-(1-quinolin-6-ylcyclopropyl)imidazo[1,2-a]pyrimidin-6-yl]benzoyl}pyrrolidin-3-ol;
2,5-Difluoro-N-methyl-4-[3-(1-quinolin-6-ylcyclopropyl)imidazo[1,2-a]pyrimidin-6-yl]benzamide;
2,5-Difluoro-4-[3-(1-quinolin-6-ylcyclopropyl)imidazo[1,2-a]pyrimidin-6-yl]benzamide;
N-Cyclopropyl-2,5-difluoro-4-[3-(1-quinolin-6-ylcyclopropyl)imidazo[1,2-a]pyrimidin-6-yl]benzamide;
2,5-Difluoro-N-(trans-4-hydroxycyclohexyl)-4-[3-(1-quinolin-6-ylcyclopropyl)imidazo[1,2-a]pyrimidin-6-yl]benzamide;
1-{2-Fluoro-4-[3-(1-quinolin-6-ylcyclopropyl)imidazo[1,2-a]pyrimidin-6-yl]phenyl}pyrrolidin-2-one;
3-{2-Fluoro-4-[3-(1-quinolin-6-ylcyclopropyl)imidazo[1,2-a]pyrimidin-6-yl]phenyl}-1,3-oxazolidin-2-one;
Ethyl 4-{4-[3-(1-quinolin-6-ylcyclopropyl)imidazo[1,2-a]pyrimidin-6-yl]-1H-pyrazol-1-yl}piperidine-1-carboxylate;
2-(4-{2-Fluoro-4-[3-(1-quinolin-6-ylcyclopropyl)imidazo[1,2-a]pyrimidin-6-yl]phenyl}-1H-pyrazol-1-yl)-N,N-dimethylacetamide;
5-{2-Fluoro-4-[3-(1-quinolin-6-ylcyclopropyl)imidazo[1,2-a]pyrimidin-6-yl]phenyl}-N-methylpyridine-2-carboxamide;
5-{2-Fluoro-4-[3-(1-quinolin-6-ylcyclopropyl)imidazo[1,2-a]pyrimidin-6-yl]phenyl}-N,N-dimethylpyridine-2-carboxamide;
6-(1-{6-[3-Fluoro-4-(1-methyl-1H-pyrazol-4-yl)phenyl]imidazo[1,2-a]pyrimidin-3-yl}cyclopropyl)quinoline;
6-(1-{6-[1-(Tetrahydrofuran-3-yl)-1H-pyrazol-4-yl]imidazo[1,2-a]pyrimidin-3-yl}cyclopropyl)quinoline;
6-(1-{6-[1-(1-Benzylpyrrolidin-3-yl)-1H-pyrazol-4-yl]imidazo[1,2-a]pyrimidin-3-yl}cyclopropyl)quinoline;
6-{1-[6-(1-Methyl-1H-pyrazol-4-yl)imidazo[1,2-a]pyrimidin-3-yl]cyclopropyl}quinoline;
N,N-Dimethyl-4-{4-[3-(1-quinolin-6-ylcyclopropyl)imidazo[1,2-a]pyrimidin-6-yl]-1H-pyrazol-1-yl}piperidine-1-carboxamide;
4-{4-[3-(1-Quinolin-6-ylcyclopropyl)imidazo[1,2-a]pyrimidin-6-yl]-1H-pyrazol-1-yl}cyclohexanol;
{4-[3-(1-Quinolin-6-ylcyclopropyl)imidazo[1,2-a]pyrimidin-6-yl]-1H-pyrazol-1-yl}acetonitrile;
2-Fluoro-N-(2-methoxy-1-methylethyl)-4-[3-(1-quinolin-6-ylcyclopropyl)imidazo[1,2-a]pyrimidin-6-yl]benzamide;
6-{1-[6-(3-Fluoro-4-[(3S)-3-fluoropyrrolidin-1-yl]carbonylphenyl)imidazo[1,2-a]pyrimidin-3-yl]cyclopropyl}quinoline;
2-Fluoro-N-(pyridin-2-ylmethyl)-4-[3-(1-quinolin-6-ylcyclopropyl)imidazo[1,2-a]pyrimidin-6-yl]benzamide;
2-Fluoro-N-(1-pyridin-2-ylcyclopropyl)-4-[3-(1-quinolin-6-ylcyclopropyl)imidazo[1,2-a]pyrimidin-6-yl]benzamide;
2-Fluoro-N-(1-pyridin-2-ylpyrrolidin-3-yl)-4-[3-(1-quinolin-6-ylcyclopropyl)imidazo[1,2-a]pyrimidin-6-yl]benzamide;
2-Fluoro-4-[3-(1-quinolin-6-ylcyclopropyl)imidazo[1,2-a]pyrimidin-6-yl]-N-[(3R)-tetrahydrofuran-3-yl]benzamide;
2-Fluoro-4-[3-(1-quinolin-6-ylcyclopropyl)imidazo[1,2-a]pyrimidin-6-yl]-N-(tetrahydrofuran-2-ylmethyl) benzamide;
N-Cyclopropyl-2-fluoro-4-[3-(1-quinolin-6-ylcyclopropyl)imidazo[1,2-a]pyrimidin-6-yl]benzamide;
2-Fluoro-N-[(1S)-1-(methoxymethyl)-2-methylpropyl]-4-[3-(1-quinolin-6-ylcyclopropyl)imidazo[1,2-a]pyrimidin-6-yl]benzamide;

2-Fluoro-4-[3-(1-quinolin-6-ylcyclopropyl)imidazo[1,2-a]pyrimidin-6-yl]benzamide;
2-Fluoro-N-methyl-N-2-[methyl(pyridin-2-yl)amino]ethyl-4-[3-(1-quinolin-6-ylcyclopropyl)imidazo[1,2-a]pyrimidin-6-yl]benzamide;
2-Chloro-N-methyl-4-[3-(1-quinolin-6-ylcyclopropyl)imidazo[1,2-a]pyrimidin-6-yl]benzamide;
2-Chloro-N-cyclopropyl-4-[3-(1-quinolin-6-ylcyclopropyl)imidazo[1,2-a]pyrimidin-6-yl]benzamide;
2-Chloro-4-[3-(1-quinolin-6-ylcyclopropyl)imidazo[1,2-a]pyrimidin-6-yl]-N-(tetrahydrofuran-3-yl)benzamide;
2-Chloro-N-(1-pyridin-2-ylethyl)-4-[3-(1-quinolin-6-ylcyclopropyl)imidazo[1,2-a]pyrimidin-6-yl]benzamide;
6-(1-{6-[4-(Azetidin-1-ylcarbonyl)-3-chlorophenyl]imidazo[1,2-a]pyrimidin-3-yl}cyclopropyl)quinoline;
2-Chloro-N-(1-pyridin-2-ylpyrrolidin-3-yl)-4-[3-(1-quinolin-6-ylcyclopropyl)imidazo[1,2-a]pyrimidin-6-yl]benzamide;
2-Chloro-N-[1-methyl-2-(pyridin-2-yloxy)ethyl]-4-[3-(1-quinolin-6-ylcyclopropyl)imidazo[1,2-a]pyrimidin-6-yl]benzamide;
2-Chloro-N-(1S)-1-[(dimethylamino)carbonyl]-2-methylpropyl-4-[3-(1-quinolin-6-ylcyclopropyl)imidazo[1,2-a]pyrimidin-6-yl]benzamide;
2-Cyclopropyl-5-[3-(1-quinolin-6-ylcyclopropyl)imidazo[1,2-a]pyrimidin-6-yl]isoindolin-1-one;
2-Ethyl-5-[3-(1-quinolin-6-ylcyclopropyl)imidazo[1,2-a]pyrimidin-6-yl]isoindolin-1-one;
2-(2-Methoxy-1-methylethyl)-5-[3-(1-quinolin-6-ylcyclopropyl)imidazo[1,2-a]pyrimidin-6-yl]isoindolin-1-one;
2-(Pyridin-2-ylmethyl)-5-[3-(1-quinolin-6-ylcyclopropyl)imidazo[1,2-a]pyrimidin-6-yl]isoindolin-1-one;
2-Methyl-5-[3-(1-quinolin-6-ylcyclopropyl)imidazo[1,2-a]pyrimidin-6-yl]isoindolin-1-one;
N-Ethyl-1-{4-[3-(1-quinolin-6-ylcyclopropyl)imidazo[1,2-a]pyrimidin-6-yl]phenyl}cyclopropanecarboxamide;
N-(1-Pyridin-2-ylethyl)-1-{4-[3-(1-quinolin-6-ylcyclopropyl)imidazo[1,2-a]pyrimidin-6-yl]phenyl}cyclopropanecarboxamide;
N-[1-Methyl-2-(pyridin-2-yloxy)ethyl]-1-{4-[3-(1-quinolin-6-ylcyclopropyl)imidazo[1,2-a]pyrimidin-6-yl]phenyl}cyclopropanecarboxamide;
2-{2-Fluoro-4-[3-(1-quinolin-6-ylcyclopropyl)imidazo[1,2-a]pyrimidin-6-yl]phenyl}-2-hydroxy-N-methylacetamide;
2-{2-fluoro-4-[3-(1-quinolin-6-ylcyclopropyl)imidazo[1,2-a]pyrimidin-6-yl]phenyl}-2-hydroxy-N,N-dimethylacetamide;
2,3-Difluoro-N-methyl-4-[3-(1-quinolin-6-ylcyclopropyl)imidazo[1,2-a]pyrimidin-6-yl]benzamide;
6-Difluoro-N-methyl-4-[3-(1-quinolin-6-ylcyclopropyl)imidazo[1,2-a]pyrimidin-6-yl]benzamide;
2-Fluoro-N-methyl-4-[3-(1-quinolin-6-ylcyclopropyl)imidazo[1,2-a]pyrimidin-6-yl]benzenesulfonamide;
N,N-Dimethyl-2-{3-[3-(1-quinolin-6-ylcyclopropyl)imidazo[1,2-a]pyrimidin-6-yl]-1H-pyrazol-1-yl}acetamide;
N-[(1S)-1-(Azetidin-1-ylcarbonyl)-2,2-dimethylpropyl]-2-fluoro-4-[3-(1-quinolin-6-ylcyclopropyl)imidazo[1,2-a]pyrimidin-6-yl]benzamide;
N-[2-(Dimethylamino)-1-methyl-2-oxoethyl]-2-fluoro-4-[3-(1-quinolin-6-ylcyclopropyl)imidazo[1,2-a]pyrimidin-6-yl]benzamide;
N-(2-Azetidin-1-yl-1-methyl-2-oxoethyl)-2-fluoro-4-[3-(1-quinolin-6-ylcyclopropyl)imidazo[1,2-a]pyrimidin-6-yl]benzamide;
2-Fluoro-N-2-[(3R)-3-methoxypyrrolidin-1-yl]-1-methyl-2-oxoethyl-4-[3-(1-quinolin-6-ylcyclopropyl)imidazo[1,2-a]pyrimidin-6-yl]benzamide;

or pharmaceutically acceptable salt thereof.

13. The method of claim 1, comprising administering to said patient a therapeutically effective amount of a composition comprising a compound of claim 1, or pharmaceutically acceptable salt thereof, and at least one pharmaceutically acceptable carrier.

14. The method of claim 1, wherein said cancer is gastric cancer.

15. The method of claim 1, wherein said cancer is cancer of the kidney.

16. The method of claim 1, wherein said cancer is liver cancer.

17. The method of claim 1, wherein said cancer is lung cancer.

18. The method of claim 1, wherein said cancer is glioblastoma.

* * * * *

UNITED STATES PATENT AND TRADEMARK OFFICE
CERTIFICATE OF CORRECTION

PATENT NO. : 10,738,052 B2  
APPLICATION NO. : 15/925996  
DATED : August 11, 2020  
INVENTOR(S) : Jincong Zhuo et al.

Page 1 of 1

It is certified that error appears in the above-identified patent and that said Letters Patent is hereby corrected as shown below:

On the Title Page

Item (54), and In the Specification, Column 1, Lines 1-3, should read:  
IMIDAZOTRIAZINES AND IMIDAZOPYRIMIDINES AS KINASE INHIBITORS Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*